US008975264B2

(12) United States Patent
Shin et al.

(10) Patent No.: US 8,975,264 B2
(45) Date of Patent: Mar. 10, 2015

(54) COMPOUND ACTING AS A CANNABINOID RECEPTOR-1 INHIBITOR

(75) Inventors: Song Seok Shin, Yongin-si (KR); Yong Deog Hong, Gunpo-si (KR); Kyoung Hee Byoun, Yongin-si (KR); Mi Young Park, Gwacheon-si (KR); Jin Kyu Choi, Suwon-si (KR); Yang Hui Park, Seongnam-si (KR); Il Hong Bae, Yongin-si (KR); Yung Hyup Joo, Yongin-si (KR); Kyung Min Lim, Hwaseong-si (KR); Young Ho Park, Seoul (KR)

(73) Assignee: Amorepacific Corporation (KR)

( * ) Notice: Subject to any disclaimer, the term of this patent is extended or adjusted under 35 U.S.C. 154(b) by 66 days.

(21) Appl. No.: 13/819,601

(22) PCT Filed: Aug. 31, 2011

(86) PCT No.: PCT/KR2011/006474
§ 371 (c)(1),
(2), (4) Date: Feb. 27, 2013

(87) PCT Pub. No.: WO2012/030170
PCT Pub. Date: Mar. 8, 2012

(65) Prior Publication Data
US 2013/0158025 A1    Jun. 20, 2013

(30) Foreign Application Priority Data

Aug. 31, 2010   (KR) .................. 10-2010-0085042

(51) Int. Cl.
| | | |
|---|---|---|
| A01N 43/90 | (2006.01) |
| A61K 31/519 | (2006.01) |
| C07D 487/00 | (2006.01) |
| C07D 487/04 | (2006.01) |

(52) U.S. Cl.
CPC ............. *C07D 487/04* (2013.01); *A61K 31/519* (2013.01)
USPC ...................... 514/259.3; 544/281

(58) Field of Classification Search
None
See application file for complete search history.

(56) References Cited

FOREIGN PATENT DOCUMENTS

| WO | 2004069838 A1 | 8/2004 |
| WO | 2008004698 A2 | 1/2008 |

OTHER PUBLICATIONS

Graeme Griffin et al., Evaluation of Cannabinoid Receptor Agonists and Antagonists Using the Guanosine-5'-O-(3-[35 S]thio)-triphoshate Binding Assay in Rat Cerebellar Membranes1, The Journal of Pharmacology and Experimental Therapeutics, vol. 285, No. 2, 1998, pp. 553-560.
Murielle Rinaldi et al., "Biochemical and Pharmacological Characterisation of SR141716A, the First Potent and Selective Brain Cannabinoid Receptor Antagonist," Life Sciences, vol. 56, Nos. 23/24, 1995, pp. 1941-1947.
Roger Pertwee et al., AM630, A Competitive Cannabinoid Receptor Antagonist, Life Sciences, vol. 56, Nos. 23/24, 1995, pp. 1949-1955.
International Search Report—PCT/KR2011/006474 dated May 1, 2012.
Written Opinion—PCT/KR2011/006474 dated May 1, 2012.
Carlo Mustazza et al.; "Synthesis of Pyrazolol [1,5-a]-, 1-2,4-Triazolo [1,5-a]- and Imidazol [ 1,2-a] pyrimidines Related to Zaleplon, a New Drug for the Treatment of Insomnia," Journal of Heterocyclic Chemistry, vol. 38, No. 5, 2001, pp. 1119-1129.
European Search Report Application No. 11822145.6-1462/2617723 dated Jun. 4, 2014.
G.N. Lipunova et al., "Fluoro-containing Heterocycles: V.* Cyclization of 3-Azolylamino-2-potyfluorobenzoylacrylates," Russian Journal of Organic Chemistry, vol. 37, No. 4, 2001, pp. 570-576.
Dan Zhou, et al., "Voluntary exercise augments acute effects of CB1-receptor inverse agonist on body weight loss in obese and lean mice," Pharmacology, Biochemistry and Behavior, vol. 77, 2004, pp. 117-125.
Monsif Bouaboula, et al., "Stimulation of Cannabinoid Receptor CB1 Induces krox-24 Expression in Human Astrocytoma Cells", The Journal of Biological Chemistry, vol. 270, No. 23, Jun. 9, 1995, pp. 13973-13980.
Paul Consroe, "Brain Cannabinoid Systems as Targets for the Therapy of Neurological Disorders," Neurobiology of Disease, vol. 5, 1998, p. 534-551.
Sándor Bátkai, et al., "Endocannabinoids Acting at Cannabinoid-1 Receptors Regulate Cardiovascular Function in Hypertension", Downloaded from http://circ.ahajourln9al9s6.org/ by guest on Dec. 18, 2014, pp. 1997-2002.

*Primary Examiner* — Jeffrey H Murray
(74) *Attorney, Agent, or Firm* — Cantor Colburn LLP

(57) ABSTRACT

Disclosed is a novel compound acting as a cannabinoid receptor 1 inhibitor, the compound being a pyrazolo[1,5-a]pyrimidine derivative, a prodrug thereof, an isomer thereof, a pharmaceutically acceptable salt thereof, a hydrate thereof or a solvate thereof. The novel compound or the like is useful for preventing or treating diseases mediated by the cannabinoid receptor-1.

14 Claims, 2 Drawing Sheets

COMPOUND ACTING AS A CANNABINOID RECEPTOR-1 INHIBITOR

TECHNICAL FIELD

The present disclosure relates to a novel compound acting as a cannabinoid receptor 1 inhibitor, a prodrug thereof, an isomer thereof, a pharmaceutically acceptable salt thereof, a hydrate thereof or a solvate thereof.

BACKGROUND ART

Obesity in general refers to a fat state, but more accurately it means a medical condition in which excess fat has accumulated in the body. Since it is known that overweight and obesity are known to cause various health problems including chronic diseases such as hypertension, type 2 diabetes, cardiovascular diseases, fatty liver and hyperlipidemia, various drugs for treating obesity are being developed worldwide.

At present, only two drugs, Reductil® (Sibutramine) and Xenical® (Orlistat) are approved by the FDA. However, Reductil has been withdrawn from the market in Europe by the because the recent SCOUT clinical study with 9,880 patients with cardiovascular diseases revealed higher incidence of side effects in the patients who took Reductil (11.4%) than those who received placebo (10%), and use of Xenical is recommended to be stopped if symptoms of liver damage occur after taking the drug due to the risk of severe liver damage.

Accordingly, development of an obesity-drug exhibiting excellent effect without side effects is necessary.

DISCLOSURE

Technical Problem

The present disclosure is directed to providing a novel compound acting as an cannabinoid receptor 1 inhibitor, which is a pyrazolo[1,5-a]pyrimidine derivative, a prodrug thereof, an isomer thereof, a pharmaceutically acceptable salt thereof, a hydrate thereof or a solvate thereof.

Technical Solution

In a general aspect, there is provided a compound represented by Chemical Formula 1:

[Chemical Formula 1]

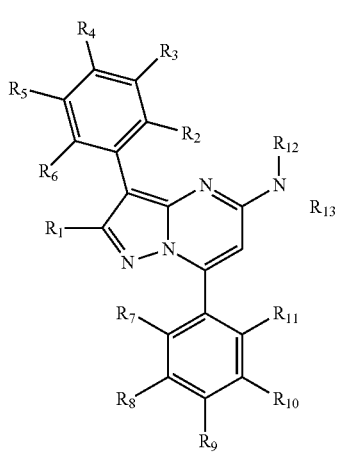

wherein $R_1$ is selected from a group consisting of hydrogen, $C_1$-$C_5$ alkyl, haloalkyl, $C_1$-$C_5$ cycloalkyl and $C_1$-$C_5$ alkoxyalkyl;

each of $R_2$, $R_3$, $R_4$, $R_5$ and $R_6$ is independently selected from a group consisting of hydrogen, fluoro, chloro, bromo, iodo, nitro, cyano, $C_1$-$C_5$ alkyl, hydroxy $C_1$-$C_5$ alkyl, $C_1$-$C_5$ alkoxy, $C_1$-$C_5$ alkoxy alkyl, halo $C_1$-$C_3$ alkyl, halo $C_1$-$C_5$ alkoxy, haloalkoxy $C_2$-$C_5$ alkenyl, $C_2$-$C_5$ alkenyl, alkynyl, carboxyl, $C_1$-$C_5$ alkylcarbonyl, $C_1$-$C_5$ alkoxycarbonyl, $C_1$-$C_5$ alkylcarbonylamino, $C_1$-$C_5$ alkylaminocarbonyl, $C_1$-$C_5$ alkylsulfanyl, $C_1$-$C_5$ alkylsulfonyl, $C_1$-$C_5$ alkoxysulfonyl, $C_1$-$C_5$ alkylsulfamoyl, aryl, aryl $C_1$-$C_3$ alkyl, aryl $C_1$-$C_5$ alkoxy, aminosulfonyl, $C_1$-$C_5$ alkylamino, $C_1$-$C_5$ alkylaminosulfonyl, $C_1$-$C_5$ alkylsulfonylamino, $C_1$-$C_5$ alkylthio, $C_3$-$C_7$ cycloalkylsulfonylaminophenyl,

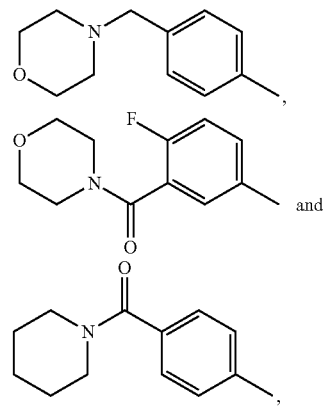

or two selected from $R_2$ through $R_6$ form a 5- to 7-membered ring fused with an aryl group together with the carbon atoms to which they are bound and the ring includes 0-2 double bonds and contains 0-2 N, O or S atoms;

each of $R_7$, $R_8$, $R_9$, $R_{10}$ and $R_{11}$ is independently selected from a group consisting of hydrogen, fluoro, chloro, bromo, iodo, nitro, cyano, $C_1$-$C_5$ alkyl, $C_1$-$C_5$ alkoxy, halo $C_1$-$C_3$ alkyl, haloalkoxy $C_2$-$C_5$ alkenyl, $C_2$-$C_5$ alkenyl and alkynyl; and each of $R_{12}$ and $R_{13}$ is independently selected from a group consisting of hydrogen, $C_1$-$C_5$ alkyl, hydroxy $C_1$-$C_5$ alkyl, $C_3$-$C_7$ cycloalkyl and halo $C_1$-$C_5$ alkyl, or $R_{12}$ and $R_{13}$ form a 5- to 7-membered ring together with the nitrogen atom which they are bound and the ring contains 0-2 N, O or S atoms or at least one substituent selected from a group consisting of hydrogen, hydroxy, hydroxy $C_1$-$C_5$ alkyl, $C_1$-$C_5$ alkoxy, $C_1$-$C_5$ alkoxy alkyl, halo $C_1$-$C_5$ alkyl, halo $C_1$-$C_5$ alkoxy and carboxyl, a prodrug thereof, an isomer thereof, a pharmaceutically acceptable salt thereof, a hydrate thereof or a solvate thereof.

In another general aspect, there is provided a pharmaceutical composition containing the compound, the prodrug thereof, the isomer thereof, the pharmaceutically acceptable salt thereof, the hydrate thereof or the solvate thereof.

In another general aspect, there is provided a method for preparing pyrazolo[1,5-a]pyrimidine having an aryl substituent bound at 7-position, including reacting aminopyrazole and a diketoester in a pyridine solvent, wherein at least one of the aminopyrazole and the diketoester contains an aryl group.

In another general aspect, there is provided a pyrazolo[1,5-a]pyrimidine compound having an aryl substituent bound at 7-position prepared by the method for preparing pyrazolo[1,5-a]pyrimidine having an aryl substituent bound at 7-position, an isomer thereof, a pharmaceutically acceptable salt thereof, a hydrate thereof or a solvate thereof.

Advantageous Effects

A compound, a prodrug thereof, an isomer thereof, a pharmaceutically acceptable salt thereof, a hydrate thereof or a solvate thereof according to an aspect of the present disclosure may act as a cannabinoid receptor 1 inhibitor. Accordingly, the compound, the prodrug thereof, the isomer thereof, the pharmaceutically acceptable salt thereof, the hydrate thereof or the solvate thereof according to an aspect of the present disclosure may be used to prevent or treat diseases mediated by the cannabinoid receptor. Specifically, the compound, the prodrug thereof, the isomer thereof, the pharmaceutically acceptable salt thereof, the hydrate thereof or the solvate thereof according to an aspect of the present disclosure is useful for prevention or treatment of inflammatory diseases, immune diseases, neurological and mental disorders, cancers of the immune system, respiratory diseases or cardiovascular disease. More specifically, the compound, the prodrug thereof, the isomer thereof, the pharmaceutically acceptable salt thereof, the hydrate thereof or the solvate thereof according to an aspect of the present disclosure may be used to prevent or treat inflammatory pain, psycopathy, anxiety, depression, attention deficiency, memory or cognitive disorder, neuropathic pain disorder, sexual dysfunction, impulse control disorder, obesity, neurological or obsessive eating disorder, metabolic disorder such as morning sickness, nausea, gastric ulcer, diabetes, hypertension and hyperlipidemia or cardiac dysfunction such as valvular heart disease, myocardial infarction, cardiomegaly or congestive heart failure.

BEST MODE

Figure 1:
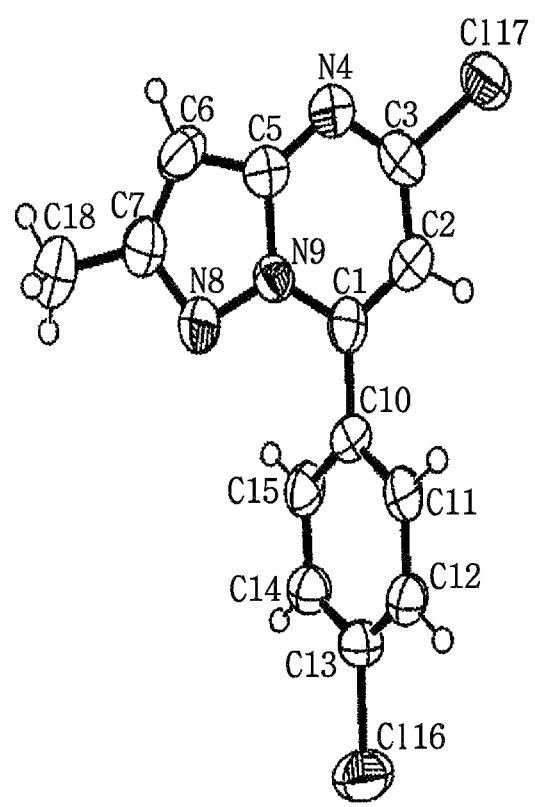
FIG. 1 shows a structure of 5-chloro-7-(4-chlorophenyl)-2-methylpyrazolo[1,5-a]pyrimidine solid crystal obtained from X-ray analysis.

Obesity may be prevented or treated by drugs participating in various mechanisms, including suppression of appetite, promotion of energy metabolism through enhanced thermogenesis, control of metabolism through inhibition or alteration of fat absorption, inhibition of fat biosynthesis, facilitation of fat breakdown, or the like.

In particular, the endocannabinoid system is known to play an important role in regulation of appetite and energy metabolism. This system includes a variety of enzymes, endocannabinoids and cannabinoid receptors involved in the synthesis and breakdown of endogenous ligands. There are two cannabinoid (CB) receptors CB1 and CB2 consisting of 7 transmembrane domains.

The CB1 receptor is distributed in several parts of the brain that regulate energy homeostasis and in peripheral parts including the liver, adipose tissue, gastrointestinal tract, pancreas and muscle tissue. An antagonist, inhibitor or modulator of the CB1 receptor is known to have various potentially therapeutic effects for treatment of neurological or mental disorders including psycopathy, anxiety, depression, attention deficiency, memory or cognitive disorder, etc., metabolic disorders or related conditions such as obesity, neurological or obsessive eating disorder, diabetes, hypertension and hyperlipidemia, cardiac dysfunctions such as valvular heart disease, myocardial infarction, cardiomegaly or congestive heart failure, neuropathic pain disorder, cancer, morning sickness, nausea, gastric ulcer, sexual dysfunction, impulse control disorder, and so forth. The CB2 receptor is primarily expressed in the spleen, tonsils, B cells, T cells, monocytes, etc. of the immune system and is involved in the recognition of inflammatory and neuropathic pain as well as allergy, asthma, multiple sclerosis, osteoporosis and inflammatory conditions.

As described above, the CB1 receptor is directly involved in various metabolic diseases including obesity through facilitation of energy metabolism, control of appetite, regulation of processes related with fat metabolism, or the like. Indeed, it is known that CB1 receptor-deficient mice are resistant against obesity induced with high-fat diet and maintain body weight similarly to the control group fed with normal diet. The effect of suppression of appetite and reduction of body weight is also achieved when the CB1 receptor is inhibited with drugs. Specifically, CB1 receptor inhibitors such as rimonabant are known to have an excellent effect of suppressing appetite and reducing body weight also in human. However, since the CB1 receptor inhibitors may cause vomiting and mental side effects depression and anxiety in some people, many drugs were ceased to be developed during clinical stages.

Therefore, if a CB1 receptor inhibitor is to be developed for treatment of obesity, development of a drug having a pharmacological and clinical profile different from that of the first-generation drug rimonabant will be necessary to avoid side effects. As a strategy for developing a safe CB1 receptor inhibitor without adversely affecting the central nervous system (CNS), development of an inhibitor targeting only the CB1 receptors in the peripheral tissues such as the adipose tissue, liver, muscle and gastrointestinal tract without acting on the brain may be conceived. A drug chemically modified not to pass the blood-brain barrier may ensure both safety and efficacy since it can be distributed only in the peripheral tissues without acting on the CB1 receptors existing in the brain. The peripheral effect of the CB1 receptor can be controlled according to various target tissues with different mechanisms. Examples include: i) liver: inhibition of fat biosynthesis, ii) muscle: promotion of glucose absorption, iii) adipose tissue: facilitation of expression and secretion of adiponectin and inhibition of fat biosynthesis and iv) gastrointestinal tract: secretion of signals inducing satiety.

DEFINITION

As used herein, "alkyl" refers to a saturated, monovalent aliphatic hydrocarbon chain. The hydrocarbon chain may be straight or branched. In an exemplary embodiment of the present disclosure, "alkyl" may have 1-5 carbon atoms ("$C_1$-$C_5$ alkyl"). In another exemplary embodiment, it may have 1-4 carbon atoms ("$C_1$-$C_4$ alkyl"). In another exemplary embodiment, it may have 1-3 carbon atoms ("$C_1$-$C_3$ alkyl"). Specifically, "alkyl" includes methyl, ethyl, n-propyl, isopropyl, n-butyl, isobutyl, tert-butyl or t-amyl, but is not limited thereto.

As used herein, "alkoxy" refers to an —OR group wherein R is an alkyl group defined above. Specifically, "alkoxy" includes methoxy, ethoxy, n-propoxy, isopropoxy, n-butoxy, tert-butoxy, sec-butoxy, n-pentoxy or 1,2-dimethylbutoxy, but is not limited thereto.

As used herein, "alkoxyalkyl" refers to an —ROR' wherein R and R' are alkyl groups defined above and may be identical or different.

As used herein, "alkenyl" refers to an unsaturated, monovalent olefin-based hydrocarbon group having at least one double bond and may be straight or branched. In an exemplary embodiment of the present disclosure, "alkenyl" has 2-5 carbon atoms ("$C_2$-$C_5$ alkenyl"). Specifically, the alkenyl group includes ethenyl (—CH=$CH_2$), n-propenyl (—$CH_2$CH=$CH_2$) or isopropenyl (—C($CH_3$)=$CH_2$).

As used herein, "vinyl" may also be referred to as "ethenyl" and refers to —CH=$CH_2$.

As used herein, "alkynyl" refers to an unsaturated hydrocarbon group having at least one triple bond. In an exemplary embodiment of the present disclosure, "alkynyl" may have 2-5 carbon atoms ("$C_2$-$C_5$ alkynyl"). In another exemplary embodiment, it may be ethynyl (acetylenyl). As used herein, "ethynyl" refers to —C≡CH.

As used herein, "cycloalkyl" refers to a saturated, cyclic aliphatic hydrocarbon group. A number attached to C means the number of carbon atoms forming the ring. For example, "$C_3$-$C_6$ cycloalkyl" means cycloalkyl having 3-6 ring-forming C atoms. In an exemplary embodiment of the present disclosure, "cycloalkyl" includes cyclopropyl, cyclobutyl, cyclopentyl or cyclohexyl, but is not limited thereto. In another exemplary embodiment of the present disclosure, "cycloalkyl" may be substituted with at least one alkyl group, for example, a $C_1$-$C_6$ alkyl group, specifically a $C_1$-$C_3$ alkyl group, more specifically methyl. When "cycloalkyl" has more than one substituents, these substituent may be identical or different.

As used herein, "cycloalkoxy" refers to an —OR group wherein R is a "cycloalkyl" group defined above.

As used herein, "halo" or "halogen" includes fluoro, chloro, bromo or iodo. In an exemplary embodiment of the present disclosure, a halo group may be fluoro or chloro.

As used herein, "haloalkyl" refers to an "alkyl" group defined above which is substituted with at least one halogen that are identical (e.g., trifluoromethyl or pentafluoroethyl) or different.

As used herein, "hydroxy" refers to an —OH radical.

As used herein, "hydroxyalkyl" refers to an "alkyl" group defined above which is substituted with at least one hydroxy group.

As used herein, "amino" refers to an —$NH_2$ radical.

As used herein, "cyano" refers to a —C≡N radical.

As used herein, "nitro" refers to an —$NO_2$ radical.

As used herein, "alkylamino" refers to an —NHR group wherein R is the "alkyl" group defined above.

As used herein, "dialkylamino" refers to an —NRR' group wherein R and R' are the alkyl groups defined above and may be identical or different.

As used herein, "aryl" refers to an aromatic hydrocarbon radical. Examples of the "aryl" group include phenyl, naphthyl, indenyl, azulenyl or anthracenyl. Phenyl may be preferred among them.

As used herein, "arylamino" refers to an —NHAr group wherein Ar is the aryl group defined above.

As used herein, "alkoxycarbonyl" refers to a —C(=O)—O—R radical wherein R is the alkyl group defined above.

As used herein, "carboxy(I)" refers to a —C(=O)OH radical.

As used herein, "alkylsulfonyl" refers to an —$SO_2$R radical wherein R is the alkyl group defined above. In an exemplary embodiment of the present disclosure, "alkylsulfonyl" includes methylsulfonyl, ethylsulfonyl, propylsulfonyl or butylsulfonyl, but is not limited thereto.

As used herein, "alkylthio" refers to an —S—R radical wherein R is the alkyl group defined above. In an exemplary embodiment of the present disclosure, "alkylthio" includes methylthio, ethylthio or propylthio, but is not limited thereto.

As used herein, "isomer" includes not only optical isomers (e.g., essentially pure enantiomers, essentially pure diastereomers or a mixture thereof) but also conformational isomers (i.e., isomers that can be interconverted by rotations about single bonds), positional isomers (particularly, tautomers) or geometric isomers (e.g., cis-trans isomers).

As used herein, "essentially pure" means, when used, for example, with regard to enantiomers or diastereomers, that specific compounds, e.g. enantiomers or diastereomers, are present in an amount of about 90% (w/w) or more, specifically about 95% or more, more specifically about 97% or more or about 98% or more, more specifically about 99% or more, more specifically about 99.5% or more.

As used herein, "pharmaceutically acceptable" means being devoid of substantial toxic effects when used in a usually employed medicinal dosage and thereby being approvable or approved by the government or an international organization comparable thereto for use in animals, and more particularly in humans or being listed in the pharmacopeia.

As used herein, "pharmaceutically acceptable salt" refers to a salt according to an aspect of the present disclosure that is pharmaceutically acceptable and possesses the desired pharmacological activity of the parent compound. Such salts include: (1) acid addition salts formed with inorganic acids such as hydrochloric acid, hydrobromic acid, sulfuric acid, nitric acid, phosphoric acid, etc. or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tert-butylacetic acid, lauryl sulfuric acid, gluconic acid, glutamic acid, hydroxynaphthoic acid, salicylic acid, stearic acid and muconic acid; or (2) salts formed when an acidic proton present in the parent compound is replaced.

As used herein, "pharmaceutically acceptable carrier" refers to a pharmaceutically acceptable carrier that can be administered together with the compound of the present disclosure.

As used herein, "subject" includes human. The terms "human", "patient" and "subject" may be used interchangeably.

As used herein, "preventing" or "prevention" refers to a reduction in the risk of acquiring a disease or disorder (i.e., causing at least one of the clinical symptoms of the disease not to develop in a subject that is exposed to or predisposed to the disease but does not yet experience or display the symptoms of the disease).

As used herein, "therapeutically effective amount" refers to an amount of a compound that, when administered to a patient for treatment of a disease, is sufficient to effect such treatment of the disease. The "therapeutically effective amount" can vary depending on the compound, the disease and severity thereof, the age, body weight, etc. of the patient to be treated, or the like. In an exemplary embodiment of the present disclosure, "treating" or "treatment" of a disease or a disorder refers to ameliorating at least one of the clinical symptoms of the disease or disorder (i.e., arresting or reducing the development of the disease or at least one of the clinical symptoms of the disease). In another exemplary embodiment of the present disclosure, "treating" or "treatment" refers to ameliorating at least one physical parameter, which may not be discernible by the patient. In another exemplary embodiment of the present disclosure, "treating" or "treatment" refers to modulating the disease or disorder physically (e.g., stabilization of a discernible symptom), physiologically (e.g., stabilization of a physical parameter) or both. In another exemplary embodiment of the present disclosure, "treating" or "treatment" refers to delaying the onset of the disease or disorder.

As used herein, "prodrug" refers to a drug whose physical and chemical properties have been changed chemically such that it does not exhibit a physiological activity as it is but is converted to an active drug through chemical or enzymatic processes after being administered.

As used herein, "hydrate" refers to a compound to which water is bound. The binding between water and the compound includes non-covalent binding.

As used herein, "solvate" refers to a complex formed by a solute molecule or ion and a solvent molecule or ion.

DETAILED DESCRIPTION

Formerly, 2-methyl-5-arylpyrazolo[1,5-a]pyridin-7(4H)-one was synthesized by reacting 5-aminopyrazole with an arylketoester in an acetic acid, alcohol or toluene solvent to which an acid has been added under heating (*Bioorg. Med. Chem. Lett.*, 2004, 14, 3669-3673). Then, 2-methyl-5-arylpyrazolo[1,5-a]pyridin-7(4H)-one was chlorinated in a POCl₃ solvent to synthesize a pyrimidine in which a substituent is attached at 5-position (see Scheme 1).

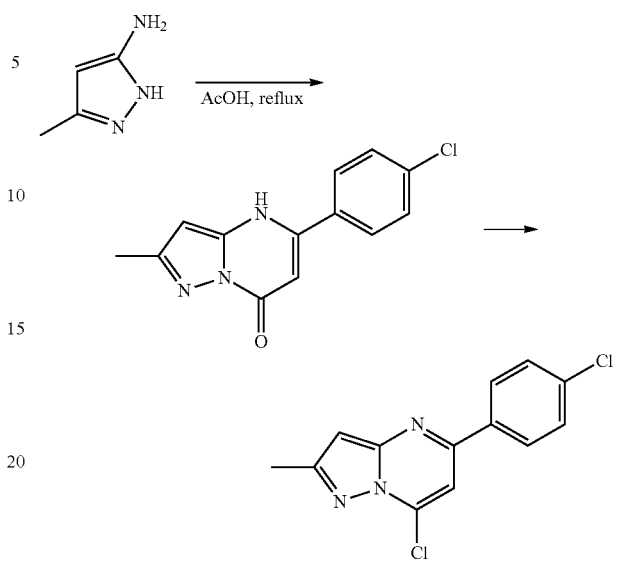

In contrast, the inventors of the present disclosure have found that 2-methyl-7-arylpyrazolo[1,5-a]pyrimidin-5(4H)-one can be synthesized by reacting 2-methyl-5-aminopyrazole with a 4-chlorophenylketoester in a pyridine solvent by stirring overnight at 90-95° C. (see Scheme 2).

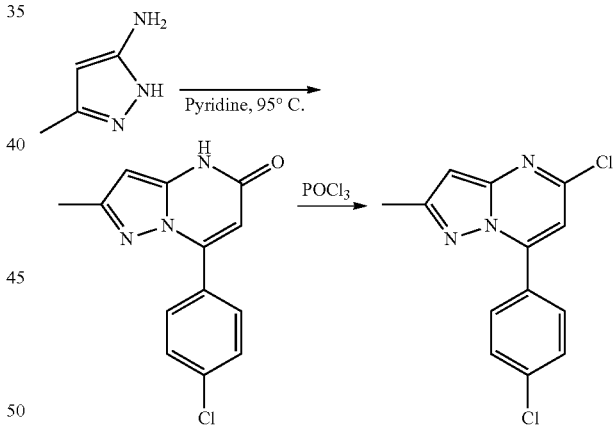

That is to say, by changing the solvent, arylpyrazolo[1,5-a]pyridinpyrimidine-5(4H)-one in which an aryl is substituted at 7-position, not at the 5-position, can be synthesized in accordance with the method of the inventors of the present disclosure. In other words, an isomer having the aryl substituent at different position is obtained from that prepared by the previously known method in an organic solvent or under an acidic condition. The inventors of the present disclosure have identified the structure of the synthesized compound by X-ray crystallography. From the compound, a novel compound 3-aryl-7-aryl-5-dialkylaminopyrazolo[1,5-a]pyrimidine can be synthesized.

The synthesis method will be described in further detail.

Scheme 3 describes a method for synthesizing pyrazolo[1,5]pyridine pyrimidine of Chemical Formula 1.

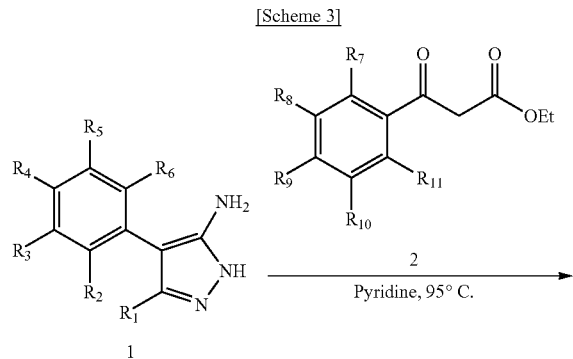

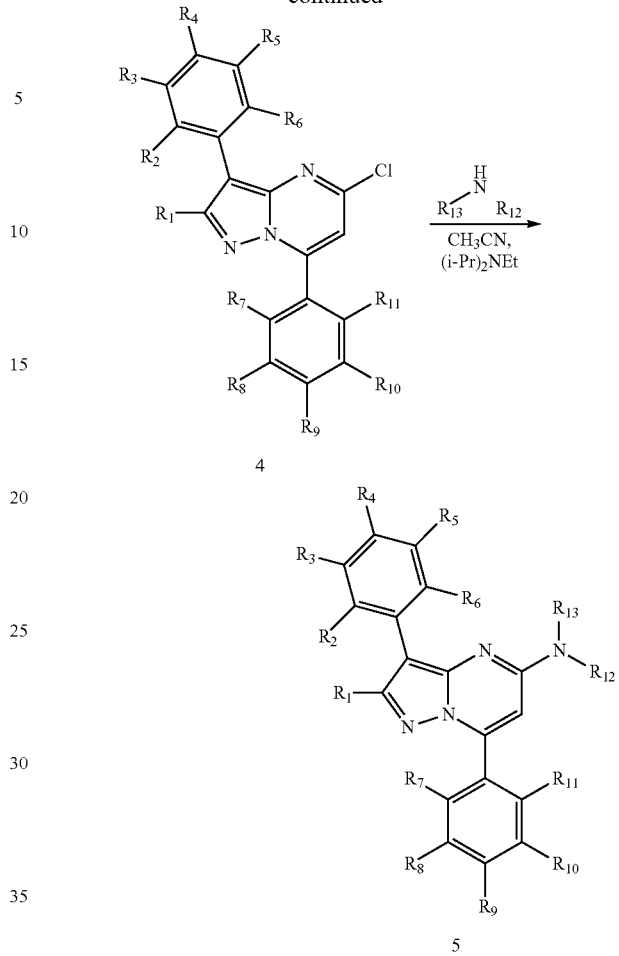

5-Aminopyrazole (1) is a starting material that can be easily obtained in the art. First, 5-aminopyrazole (1) and an arylketoester (2) are reacted in a pyridine solvent to synthesize pyrazolopyridinpyrazolopyrimidine-5(4H)-one (3). The compound (3) is reacted in a POCl₃ solvent to synthesize 5-chloro-pyrazolopyridinepyrazolopyrimidine-5(4H) (4), which is then reacted with a secondary amine in an acetonitrile solvent to prepare a novel compound pyrazolo[1,5]pyridine pyrimidine (5). Most of the synthesis procedure is based on the known organic synthesis methods.

Scheme 4 describes another method for synthesizing novel pyrazolo[1,5]pyridinepyrimidine.

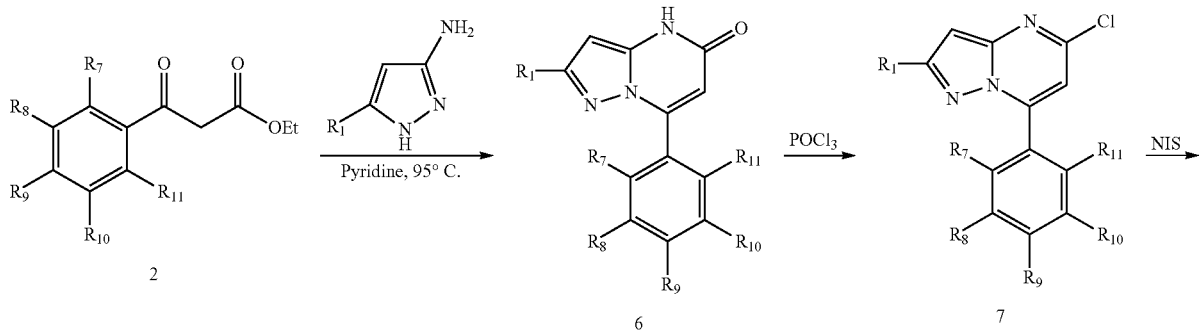

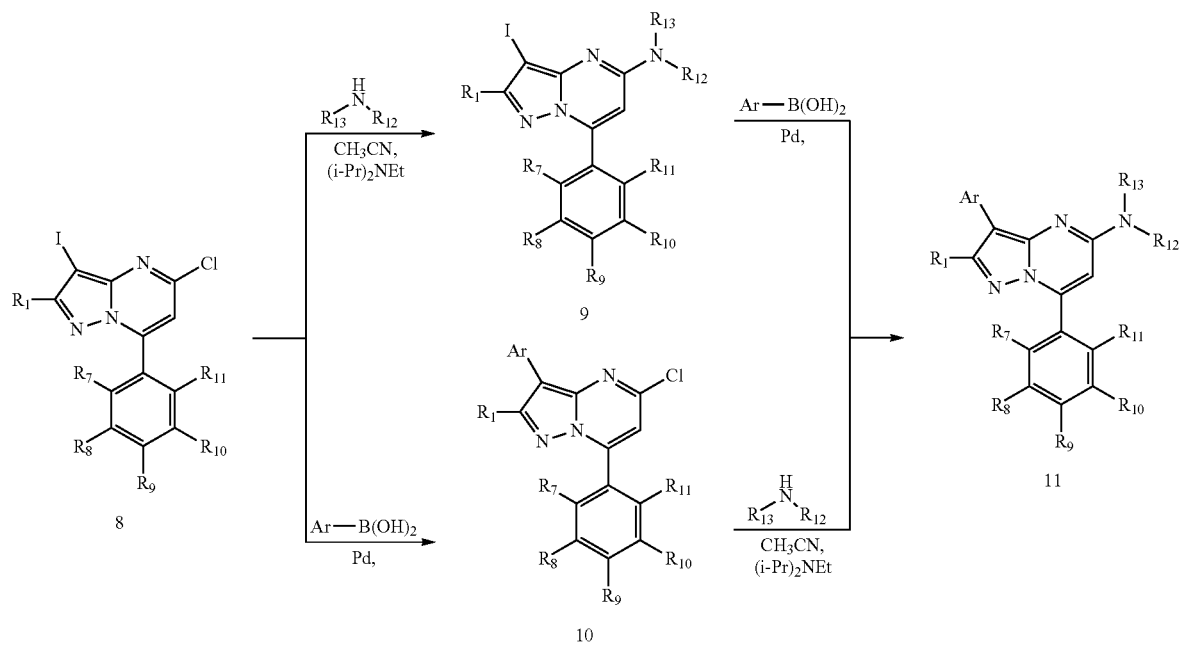

According to Scheme 4, novel pyrazolo[1,5]pyridine pyrimidine can be synthesized more easily using the Suzuki cross-coupling reaction (*J. Org. Chem.*, 1995, 60, 7508). An arylketoester (2) is reacted with aminopyrazole in a pyridine solvent to synthesize a compound (6). The compound (6) is reacted in a $POCl_3$ solvent under heating to synthesize 5-chloro-pyrazolopyridinepyrazolopyrimidine-5(4H) (7). The compound (7) is halogenated with N-iodosuccinimide (NIS) in a dichloromethane solvent by stirring at room temperature to synthesize iodo-5-chloro-pyrazolopyridinepyrazolopyrimidine-5(4H) (8). The compound (8) is reacted with a secondary amine to synthesize a compound (9). The compound (9) is Suzuki cross-coupled to synthesize aryl-substituted pyrazolopyridinepyrazolopyrimidine-5(4H) (11). Alternatively, iodo-5-chloro-pyrazolopyridinepyrazolopyrimidine-5(4H) (8) may be Suzuki cross-coupled to synthesize a compound (10) and then it may be aminated to obtain the novel pyrazolopyridinepyrazolopyrimidine-5(4H) compound (11).

Scheme 5 describes another method for synthesizing novel pyrazolopyridinepyrazolopyrimidine-5(4H) (5).

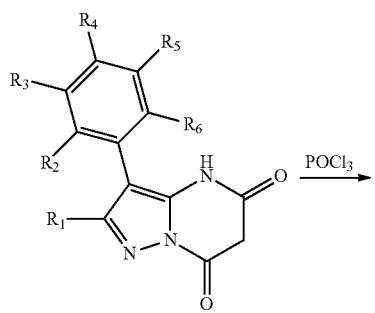

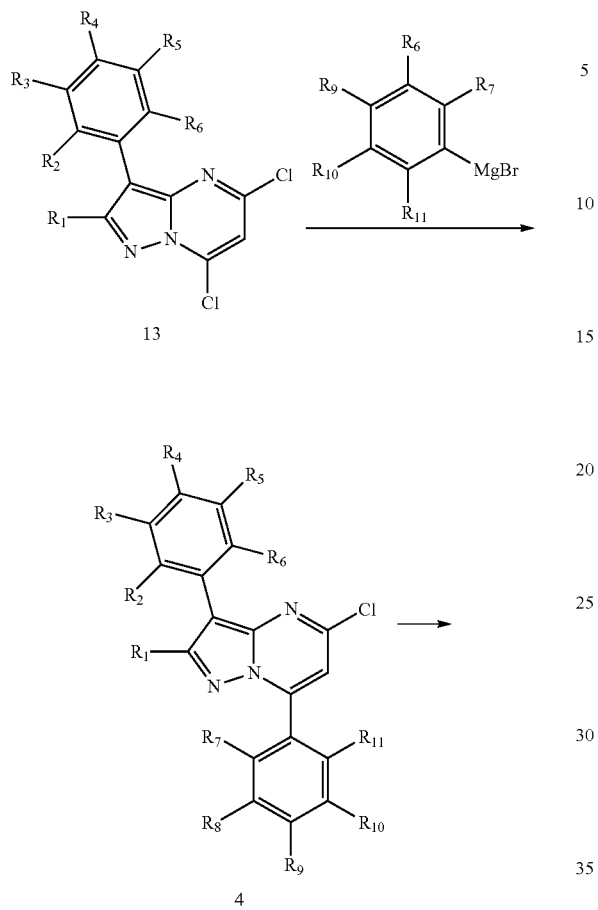
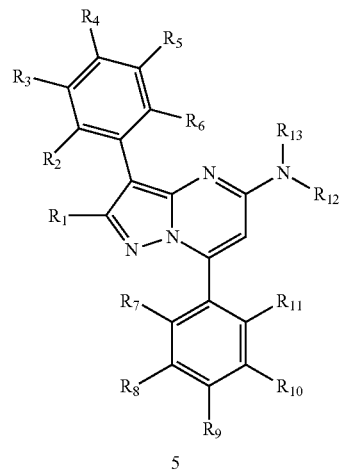

Aminopyrazole (1) is reacted with diethylmalonate to synthesize pyrazolo[1,5-a]pyrimidin-5,7(4H,6H)-dione (12). The compound (12) is reacted in POCl₃ to obtain a compound (13). The compound (13) is reacted with an aryl Grignard reagent under anhydrous condition to obtain a compound (4). As described in Scheme 3, the compound (4) may be aminated to obtain novel pyrazolopyridinepyrazolopyrimidine-5(4H) (5). This procedure may be more suited for large-scale preparation.

Scheme 6 describes a method for synthesizing a compound having a pyrrolidinemethanol or secondary amine group as a preferred compound among derivatives of novel pyrazolopyridinepyrazolopyrimidine-5(4H).

[Scheme 6]

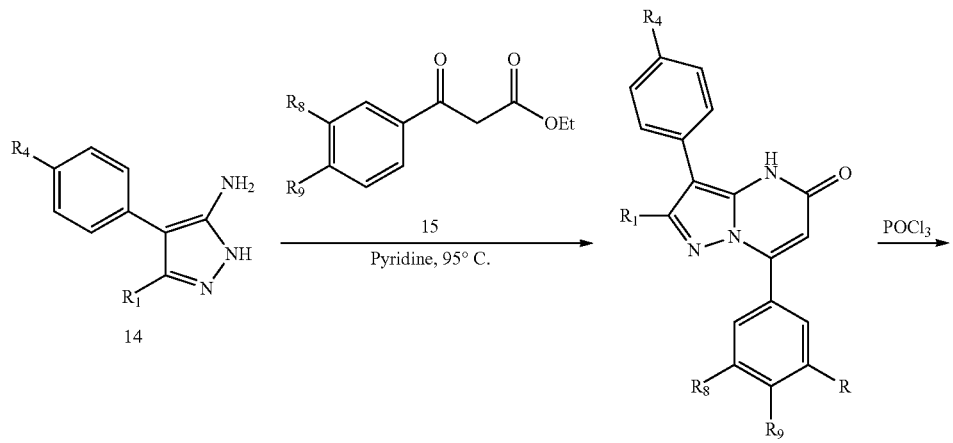

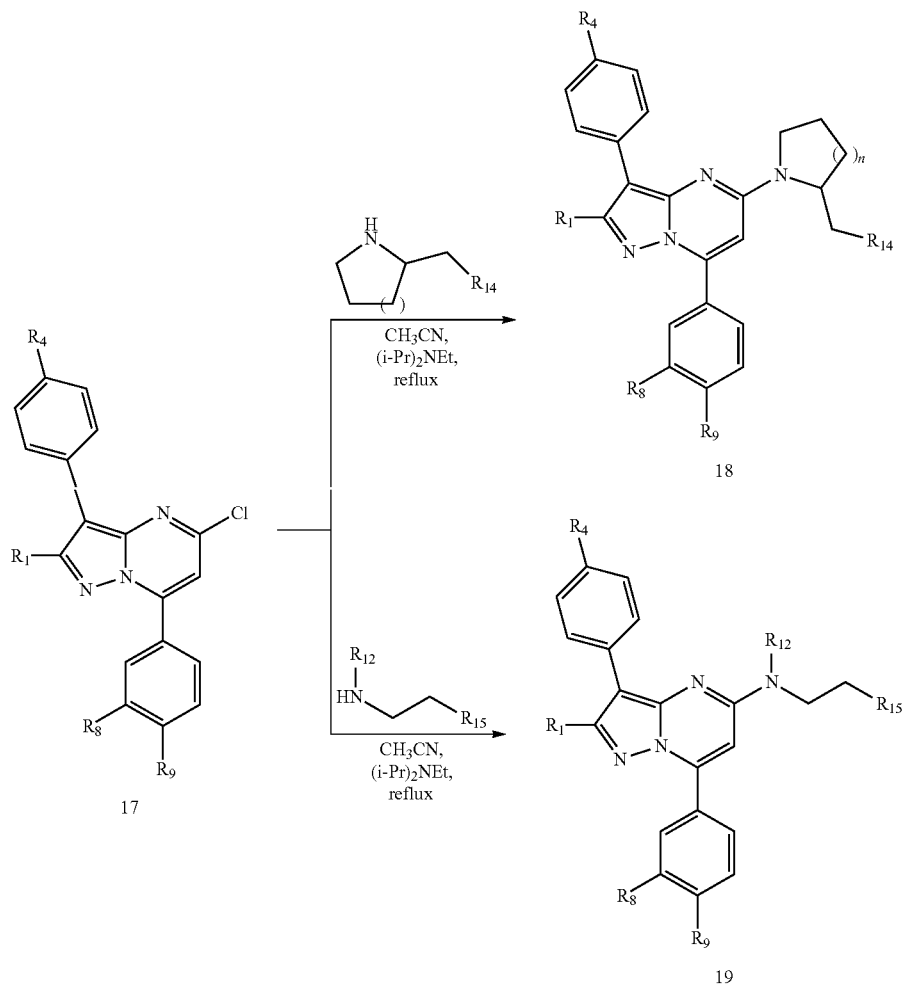

Aminopyrazole (14) with aryl substituted at 3-position is reacted with arylketoester to synthesize diarylpyrazolo[1,5-a]pyrimidin-5(4H)-one (16). The compound (16) is converted to a compound (17) by heating in POCl₃. A substituted cyclic amine is reacted with the compound (17) to obtain a novel pyrazolopyridinepyrazolopyrimidine-5(4H) compound (18).

Alternatively, the compound (17) may be reacted with a linear secondary amine to obtain a compound (19).

Scheme 7 describes a method for synthesizing novel diarylpyrazolo[1,5-a]pyrimidine having various substituents at 2-position of pyrazole.

[Scheme 7]

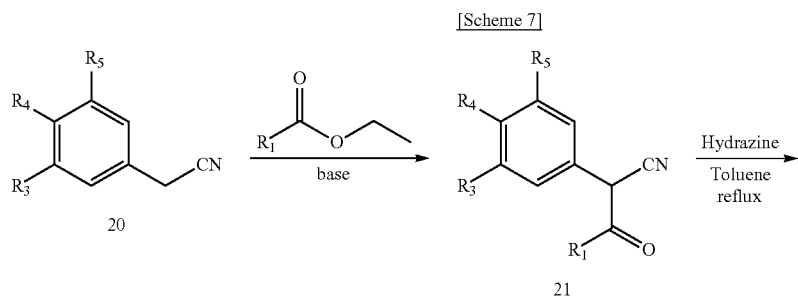

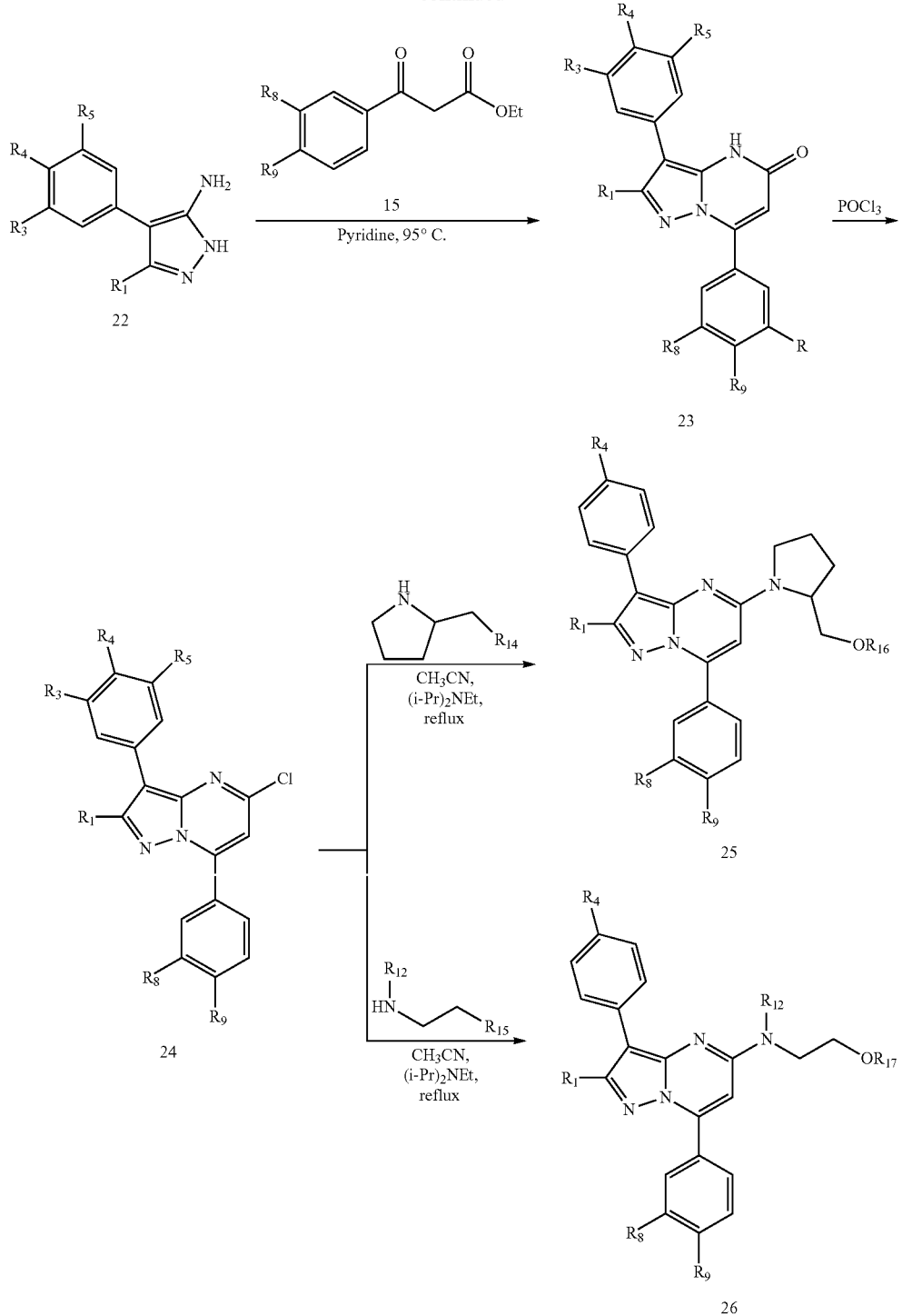

Diarylpyrazolo[1,5-a]pyrimidine having various substituents is synthesized using aminopyrazole having an alkyl or alkoxyalkyl substituent at 3-position as a starting material (Bioorg. Med. Chem., 2000, 8, 181-189). The substituent $R_1$ may be $C_1$-$C_5$ alkyl, halo $C_1$-$C_5$ alkyl, $C_1$-$C_5$ alkoxy or $C_1$-$C_5$ alkoxy $C_1$-$C_5$ alkyl, more specifically methyl, ethyl, propyl, butyl, methoxy methyl, ethoxyethyl, ethoxymethyl or trifluoromethyl. A substituted phenylacetonitrile (20) is stirred with an ester in the presence of NaH at room temperature to synthesize a compound (21). Alternatively, the compound (21) may be synthesized by stirring with an ester in the presence of EtONa and another base in an ethanol solvent. The compound (21) is reacted with hydrazine to synthesize aminopyrazole (22) having various $C_1$-$C_5$ alkyl or $C_1$-$C_5$ alkoxy $C_1$-$C_5$ alkyl substituents at 3-position. From the aminopyrazole having various substituents at 3-position, compounds (25) and (26) are synthesized under conditions similar to those of Schemes 3-5.

In an aspect, the present disclosure provides a compound represented by Chemical Formula 1, a prodrug thereof, an isomer thereof, a pharmaceutically acceptable salt thereof, a hydrate thereof or a solvate thereof.

In Chemical Formula 1, $R_1$ is selected from a group consisting of hydrogen, $C_1$-$C_5$ alkyl, haloalkyl, $C_1$-$C_5$ cycloalkyl and $C_1$-$C_5$ alkoxyalkyl;

each of $R_2$, $R_3$, $R_4$, $R_5$ and $R_6$ is independently selected from a group consisting of hydrogen, fluoro, chloro, bromo, iodo, nitro, cyano, $C_1$-$C_5$ alkyl, hydroxy $C_1$-$C_5$ alkyl, $C_1$-$C_5$ alkoxy, $C_1$-$C_5$ alkoxy alkyl, halo $C_1$-$C_3$ alkyl, halo $C_1$-$C_5$ alkoxy, haloalkoxy $C_2$-$C_5$ alkenyl, $C_2$-$C_5$ alkenyl, alkynyl, carboxyl, $C_1$-$C_5$ alkylcarbonyl, $C_1$-$C_5$ alkoxycarbonyl, $C_1$-$C_5$ alkylcarbonylamino, $C_1$-$C_5$ alkylaminocarbonyl, $C_1$-$C_5$ alkylsulfanyl, $C_1$-$C_5$ alkylsulfonyl, $C_1$-$C_5$ alkoxysulfonyl, $C_1$-$C_5$ alkylsulfamoyl, aryl, aryl $C_1$-$C_3$ alkyl, aryl $C_1$-$C_5$ alkoxy, aminosulfonyl, $C_1$-$C_5$ alkylamino, $C_1$-$C_5$ alkylaminosulfonyl, $C_1$-$C_5$ alkylsulfonylamino, $C_1$-$C_5$ alkylthio, $C_3$-$C_7$ cycloalkylsulfonylaminophenyl,

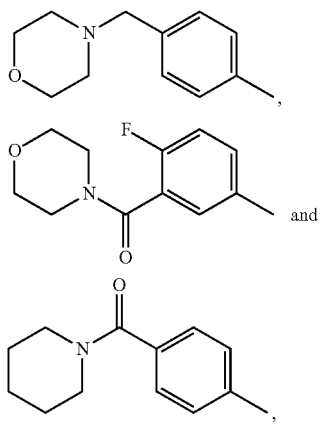

or two selected from $R_2$ through $R_6$ form a 5- to 7-membered ring fused with an aryl group together with the carbon atoms to which they are bound and the ring includes 0-2 double bonds and contains 0-2 N, O or S atoms;

each of $R_7$, $R_8$, $R_9$, $R_{10}$ and $R_{11}$ is independently selected from a group consisting of hydrogen, fluoro, chloro, bromo, iodo, nitro, cyano, $C_1$-$C_5$ alkyl, $C_1$-$C_5$ alkoxy, halo $C_1$-$C_3$ alkyl, haloalkoxy $C_2$-$C_5$ alkenyl, $C_2$-$C_5$ alkenyl and alkynyl; and each of $R_{12}$ and $R_{13}$ is independently selected from a group consisting of hydrogen, $C_1$-$C_5$ alkyl, hydroxy $C_1$-$C_5$ alkyl, $C_3$-$C_7$ cycloalkyl and halo $C_1$-$C_5$ alkyl, or $R_{12}$ and $R_{13}$ form a 5- to 7-membered ring together with the nitrogen atom which they are bound and the ring contains 0-2 N, O or S atoms or at least one substituent selected from a group consisting of hydrogen, hydroxy, hydroxy $C_1$-$C_5$ alkyl, $C_1$-$C_5$ alkoxy, $C_1$-$C_5$ alkoxy alkyl, halo $C_1$-$C_5$ alkyl, halo $C_1$-$C_5$ alkoxy and carboxyl.

The compound may be prepared based on Schemes 3-7.

In another aspect, the present disclosure provides a compound represented by Chemical Formula 2, as a compound related with the compound of Chemical Formula 1, a prodrug thereof, an isomer thereof, a pharmaceutically acceptable salt thereof, a hydrate thereof or a solvate thereof.

[Chemical Formula 2]

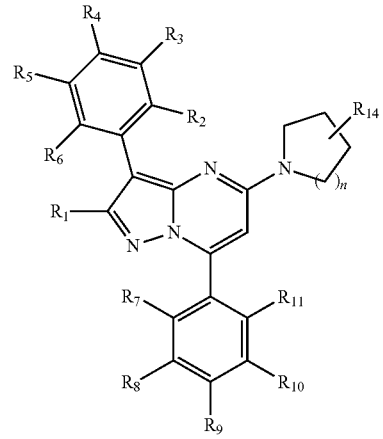

In Chemical Formula 2, $R_1$ is selected from a group consisting of hydrogen, $C_1$-$C_5$ alkyl, haloalkyl, $C_1$-$C_5$ cycloalkyl and $C_1$-$C_5$ alkoxyalkyl;

each of $R_2$, $R_3$, $R_4$, $R_5$ and $R_6$ is independently selected from a group consisting of hydrogen, fluoro, chloro, bromo, iodo, nitro, cyano, $C_1$-$C_5$ alkyl, hydroxy $C_1$-$C_5$ alkyl, $C_1$-$C_5$ alkoxy, $C_1$-$C_5$ alkoxy alkyl, halo $C_1$-$C_3$ alkyl, halo $C_1$-$C_5$ alkoxy, haloalkoxy $C_2$-$C_5$ alkenyl, $C_2$-$C_5$ alkenyl, alkynyl, carboxyl, $C_1$-$C_5$ alkylcarbonyl, $C_1$-$C_5$ alkoxycarbonyl, $C_1$-$C_5$ alkylcarbonylamino, $C_1$-$C_5$ alkylaminocarbonyl, $C_1$-$C_5$ alkylsulfanyl, $C_1$-$C_5$ alkylsulfonyl, $C_1$-$C_5$ alkoxysulfonyl, $C_1$-$C_5$ alkylsulfamoyl, aryl, aryl $C_1$-$C_3$ alkyl, aryl $C_1$-$C_5$ alkoxy, aminosulfonyl, $C_1$-$C_5$ alkylamino, $C_1$-$C_5$ alkylaminosulfonyl, $C_1$-$C_5$ alkylsulfonylamino, $C_1$-$C_5$ alkylthio, $C_3$-$C_7$ cycloalkylsulfonylaminophenyl,

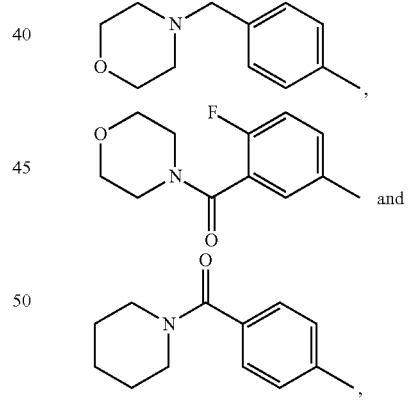

or two selected from $R_2$ through $R_6$ form a 5- to 7-membered ring fused with an aryl group together with the carbon atoms to which they are bound and the ring includes 0-2 double bonds and contains 0-2 N, O or S atoms;

each of $R_7$, $R_8$, $R_9$, $R_{10}$ and $R_{11}$ is independently selected from a group consisting of hydrogen, fluoro, chloro, bromo, iodo, nitro, cyano, $C_1$-$C_5$ alkyl, $C_1$-$C_5$ alkoxy, halo $C_1$-$C_3$ alkyl, haloalkoxy $C_2$-$C_5$ alkenyl, $C_2$-$C_5$ alkenyl and alkynyl;

$R_{14}$ is selected from a group consisting of hydrogen, hydroxy, hydroxy $C_1$-$C_5$ alkyl, $C_1$-$C_5$ alkoxy, $C_1$-$C_5$ alkoxy alkyl, halo $C_1$-$C_5$ alkyl, halo $C_1$-$C_5$ alkoxy and carboxyl; and n is an integer selected from 1 to 3.

In another aspect, the present disclosure provides a compound represented by Chemical Formula 3, as a compound related with the compound of Chemical Formula 1, a prodrug thereof, an isomer thereof, a pharmaceutically acceptable salt thereof, a hydrate thereof or a solvate thereof.

[Chemical Formula 3]

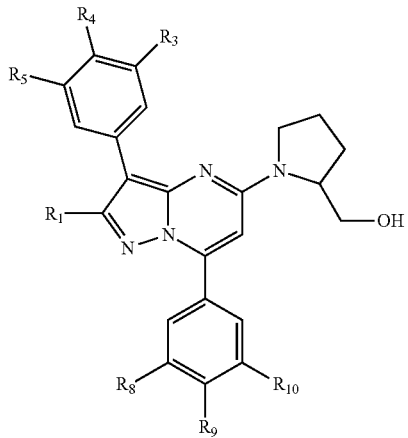

In Chemical Formula 3,

R₁ is selected from a group consisting of methyl, ethyl, propyl, butyl, isobutyl, difluoromethyl, trifluoromethyl, cyclopropyl, ethoxymethyl, methoxymethyl and ethoxyethyl;

each of R₃, R₄ and R₅ is independently selected from a group consisting of hydrogen, fluoro, chloro, bromo, iodo, nitro, cyano, methyl, ethyl, propyl, isopropyl, butyl, tert-butyl, methoxy, ethoxy, propoxy, isopropoxy, butoxy, hydroxymethyl, hydroxyethyl, trifluoromethyl, difluoromethyl, fluoromethyl, trifluoromethoxyvinyl, acetylenyl, carboxyl, methoxycarbonyl, ethoxycarbonyl, acetyl, methylsulfanyl, ethylsulfanyl, methylsulfonyl, methylsulfonylamino, cyclopropylaminosulfonyl, methylaminosulfonyl, ethylaminosulfonyl, dimethylaminocarbonyl, diethylaminocarbonyl, methylcarbonylamino, methylsulfamoyl, phenylmethyl, phenylethyl, phenylmethoxy, phenylacetyl, aminosulfonyl, methylaminosulfonyl, ethylaminosulfonyl, dimethylamino, diethylamino, cyclopropylamino and methylthio, or two selected from R₃ through R₅ form a 5- to 7-membered ring fused with an aryl group together with the carbon atoms to which they are bound and the ring includes 0-2 double bonds and contains 0-2 N, O or S atoms; and each of R₈, R₉ and R₁₀ is independently selected from a group consisting of hydrogen, fluoro, chloro, bromo, iodo, nitro, cyano, methyl, ethyl, propyl, butyl, isopropyl, methoxy, ethoxy, propoxy, isopropoxy, hydroxymethyl, trifluoromethyl, difluoromethyl, fluoromethyl, trifluoromethoxyvinyl and acetylenyl.

In another aspect, the present disclosure provides a compound represented by Chemical Formula 3, a prodrug thereof, an isomer thereof, a pharmaceutically acceptable salt thereof, a hydrate thereof or a solvate thereof, wherein:

R₁ is selected from a group consisting of methyl, ethyl, propyl, butyl, isobutyl, trifluoromethyl, cyclopropyl, ethoxymethyl, methoxymethyl and ethoxyethyl;

each of R₃, R₄ and R₅ is independently selected from a group consisting of hydrogen, fluoro, chloro, nitro, cyano, methyl, ethyl, propyl, isopropyl, butyl, tert-butyl, methoxy, ethoxy, propoxy, methylenedioxy, isopropoxy, hydroxymethyl, hydroxyethyl, trifluoromethyl, difluoromethyl, fluoromethyl, trifluoromethoxyvinyl, acetylenyl, carboxyl, methoxycarbonyl, ethoxycarbonyl, acetyl, methylsulfonyl, methylsulfamoyl, phenylmethyl, phenylethyl and methylthio, or two selected from R₃ through R₅ form a 5- to 7-membered ring fused with an aryl group together with the carbon atoms to which they are bound and the ring includes 0-2 double bonds and contains 0-2 N, O or S atoms; and each of R₈, R₉ and R₁₀ is independently selected from a group consisting of hydrogen, fluoro, chloro, bromo, iodo, nitro, cyano, methyl, ethyl, propyl, butyl, isopropyl, methoxy, ethoxy, propoxy, isopropoxy, butoxy, hydroxymethyl, trifluoromethyl, difluoromethyl, fluoromethyl, trifluoromethoxyvinyl and acetylenyl.

In another aspect, the present disclosure provides a compound selected from the followings, an isomer thereof, a pharmaceutically acceptable salt thereof, a hydrate thereof or a solvate thereof:

{1-[7-(3-chloro-4-fluorophenyl)-2-methyl-3-p-tolyl-pyrazolo[1,5-a]pyrimidin-5-yl]-pyrrolidin-2-yl}-methanol, {1-[7-(3-chloro-4-fluorophenyl)-3-(4-fluorophenyl)-2-methyl-pyrazolo[1,5-a]pyrimidin-5-yl]-pyrrolidin-2-yl}-methanol, {1-[3-(3-fluoro-4-methylphenyl)-7-(3-methoxyphenyl)-2-methyl-pyrazolo[1,5-a]pyrimidin-5-yl]-pyrrolidin-2-yl}-methanol, {1-[3-(2,4-difluorophenyl)-7-(3-methoxyphenyl)-2-methyl-pyrazolo[1,5-a]pyrimidin-5-yl]pyrrolidin-2-yl}-methanol, {1-[3-(3-fluoro-4-methylphenyl)-2-methyl-7-(3-trifluoromethylphenyl)-pyrazolo[1,5-a]pyrimidin-5-yl]-pyrrolidin-2-yl}-methanol, {1-[3-(2,4-difluorophenyl)-2-methyl-7-(3-trifluoromethylphenyl)-pyrazolo[1,5-a]pyrimidin-5-yl]-pyrrolidin-2-yl}-methanol, {1-[7-(3-chloro-4-fluorophenyl)-3-(4-methoxyphenyl)-2-methyl-pyrazolo[1,5-a]pyrimidin-5-yl]-pyrrolidin-2-yl}-methanol, {1-[7-(3,4-difluorophenyl)-3-(3-fluoro-4-methyl-phenyl)-2-methyl-pyrazolo[1,5-a]pyrimidin-5-yl]-pyrrolidin-2-yl}-methanol, {1-[7-(3-ethylphenyl)-2-methyl-3-p-tolyl-pyrazolo[1,5-a]pyrimidin-5-yl]-pyrrolidin-2-yl}-methanol, {1-[3-(4-chlorophenyl)-7-(3-ethylphenyl)-2-methyl-pyrazolo[1,5-a]pyrimidin-5-yl]-pyrrolidin-2-yl}-methanol, {1-[7-(3,5-difluorophenyl)-3-(4-methoxyphenyl)-2-methyl-pyrazolo[1,5-a]pyrimidin-5-yl]-pyrrolidin-2-yl}-methanol, {1-[3-(3,4-difluorophenyl)-2-methyl-7-(3-trifluoromethylphenyl)-pyrazolo[1,5-a]pyrimidin-5-yl]-pyrrolidin-2-yl}-methanol, {1-[3-(4-fluorophenyl)-2-methyl-7-(3-trifluoromethylphenyl)-pyrazolo[1,5-a]pyrimidin-5-yl]-pyrrolidin-2-yl}-methanol, {1-[3-(3,4-difluorophenyl)-2-methyl-7-(3-trifluoromethylphenyl)-pyrazolo[1,5-a]pyrimidin-5-yl]-pyrrolidin-2-yl}-methanol, {1-[3-benzo-1,3]dioxol-5-yl-7-(3,5-difluorophenyl)-2-methyl-pyrazolo[1,5-a]pyrimidin-5-yl]-pyrrolidin-2-yl}-methanol, {1-[2-ethoxymethyl-3-(4-methoxyphenyl)-7-(3-trifluoromethylphenyl)-pyrazolo[1,5-a]pyrimidin-5-yl]-pyrrolidin-2-yl}-methanol, {1-[7-(3,5-difluorophenyl)-3-(4-methoxyphenyl)-2-methyl-pyrazolo[1,5-a]pyrimidin-5-yl]-pyrrolidin-2-yl}-methanol, {1-[3-(4-methoxyphenyl)-2-trifluoromethyl-7-(3-trifluoromethylphenyl)-pyrazolo[1,5-a]pyrimidin-5-yl]-pyrrolidin-2-yl}-methanol, {1-[2-ethoxymethyl-3-(4-methoxyphenyl)-7-(3-methoxyphenyl)-pyrazolo[1,5-a]pyrimidin-5-yl]-pyrrolidin-2-yl}-methanol, {1-[2-ethoxymethyl-7-(4-fluorophenyl)-3-(4-methoxyphenyl)-pyrazolo[1,5-a]pyrimidin-5-yl]-pyrrolidin-2-yl}-methanol, {1-[2-difluoromethyl-3-(4-methoxyphenyl)-7-(3-trifluoromethylphenyl)-pyrazolo[1,5-a]pyrimidin-5-yl]-pyrrolidin-2-yl}-methanol, {1-[3-benzo-[1,3]dioxol-5-yl-2-ethoxymethyl-7-(3-fluorophenyl)-pyrazolo[1,5-a]pyrimidin-5-yl]-pyrrolidin-2-yl}-methanol, {1-[2-ethyl-7-(4-fluorophenyl)-3-p-tolyl-pyrazolo[1,5-a]pyrimidin-5-yl]-pyrrolidin-2-yl}-methanol, {1-[7-(3-chlorophenyl)-2-ethyl-3-p-tolyl-pyrazolo[1,5-a]pyrimidin-5-yl]-pyrrolidin-2-yl]-methanol, {1-[2-ethyl-7-(3-fluorophenyl)-3-p-tolylpyrazolo[1,5-a]pyrimidin-5-yl]-pyrrolidin-2-yl}-methanol, {1-[3-benzo[1,3]dioxol-5-yl-2-ethoxymethyl-7-(3-trifluoromethylphenyl)-pyrazolo[1,5-a]pyrimidin-5-yl]-pyrrolidin-2-yl}-methanol, {1-[3-benzo[1,3]dioxol-5-yl-7-(3-chlorophenyl)-2-ethoxymethyl-pyrazolo[1,5-a]pyrimidin-5-yl]-pyrrolidin-2-yl}-methanol, {1-[2-ethoxymethyl-3-p-tolyl-7-(3-trifluoromethylphenyl)-pyrazolo[1,5-a]pyrimidin-5-yl]-pyrrolidin-2-yl}-methanol, {1-[2-ethoxymethyl-7-(3-fluorophenyl)-3-p-tolyl-pyrazolo[1,5-a]pyrimidin-5-yl]-pyrrolidin-2-yl}-methanol, {1-[2-ethoxymethyl-3-p-tolyl-7-(3-trifluoromethylphenyl)-pyrazolo[1,5-a]pyrimidin-5-yl]-pyrrolidin-2-yl}methanol, {1-[2-ethoxymethyl-7-m-tolyl-3-p-tolyl-pyrazolo[1,5-a]pyrimidin-5-yl]-pyrrolidin-2-yl}-methanol, {1-[2-ethoxymethyl-7-(3-fluorophenyl)-3-(4-methoxyphenyl)-pyrazolo[1,5-a]pyrimidin-5-yl]pyrrolidin-2-yl}-methanol, {1-[2-ethoxymethyl-7-(4-fluorophenyl)-3-(4-methoxyphenyl)-pyrazolo[1,5-a]pyrimidin-5-yl]-pyrrolidin-2-yl}-methanol, {1-[2-methoxymethyl-3-(4-methoxyphenyl)-7-(3-trifluoromethylphenyl)-pyrazolo[1,5-a]pyrimidin-5-yl]-pyrrolidin-2-yl}-methanol, {1-[2-butyl-3-p-tolyl-7-(3-trifluoromethylphenyl)-pyrazolo[1,5-a]pyrimidin-5-yl]-pyrrolidin-2-yl}-methanol, {1-[2-ethoxymethyl-7-(3-methoxyphenyl)-3-p-tolyl-pyrazolo[1,5-a]pyrimidin-5-yl]-pyrrolidin-2-yl}-methanol, {1-[3-(4-chlorophenyl)-2-ethoxymethyl-7-(3-trifluoromethylphenyl)-pyrazolo[1,5-a]pyrimidin-5-yl]-pyrrolidin-2-yl}-methanol, {1-[3-(4-chlorophenyl)-2-ethoxymethyl-7-(4-fluorophenyl)-pyrazolo[1,5-a]pyrimidin-5-yl]-pyrrolidin-2-yl}methanol, {1-[3-(4-chlorophenyl)-2-ethoxymethyl-7-(3-fluorophenyl)-pyrazolo[1,5-a]pyrimidin-5-yl]-pyrrolidin-2-yl}-methanol, {1-[3-(4-chlorophenyl)-2-ethoxymethyl-7-(3-trifluoromethylphenyl)-pyrazolo[1,5-a]pyrimidin-5-yl]-pyrrolidin-2-yl}-methanol, 2-{[3-(4-chlorophenyl)-2-methoxymethyl-7-(3-trifluoromethylphenyl)-pyrazolo[1,5-a]pyrimidin-5-yl]-pyrrolidin-2-yl}-methanol, {1-[3-(4-chlorophenyl)-7-(4-fluorophenyl)-2-methoxymethyl-pyrazolo[1,5-a]pyrimidin-5-yl]-pyrrolidin-2-yl}methanol, {1-[3-(4-chlorophenyl)-7-(3-fluorophenyl)-2-methoxymethyl-pyrazolo[1,5-a]pyrimidin-5-yl]-pyrrolidin-2-yl}-methanol, 2-{[2-methoxymethyl-3-(4-methoxyphenyl)-7-(3-trifluoromethylphenyl)-pyrazolo[1,5-a]pyrimidin-5-yl]-pyrrolidin-2-yl}-methanol, {1-[7-(4-fluorophenyl)-2-methoxymethyl-3-(4-methoxyphenyl)-pyrazolo[1,5-a]pyrimidin-5-yl]-pyrrolidin-2-yl}-methanol, {1-[3-benzo[1,3]dioxol-5-yl-7-(3-fluorophenyl)-2-methoxymethyl-pyrazolo[1,5-a]pyrimidin-5-yl]-pyrrolidin-2-yl}-methanol, {1-[3-benzo[1,3]dioxol-5-yl-7-(4-fluorophenyl)-2-methoxymethyl-pyrazolo[1,5-a]pyrimidin-5-yl]-pyrrolidin-2-yl}-methanol, {1-[3-benzo[1,3]dioxol-5-yl-2-methoxymethyl-7-(3-trifluoromethylphenyl)-pyrazolo[1,5-a]pyrimidin-5-yl]-pyrrolidin-2-yl}-methanol, (s)-3-(5-(2-hydroxymethyl)pyrrolidin-1-yl)-2-(methoxymethyl)-3(4-methoxyphenyl)-pyrazolo[1,5-a]pyrimidin-7-yl)benzonitrile, (S)-[{1-(2-methoxymethyl)-3-(methoxyphenyl)-7-(m-tolyl)-pyrazolo[1,5-a]-pyridinpyrimidine-5-yl}-pyrrolidin-2-yl]-methanol, (S)-{[1-(2-methoxymethyl)-7-(3-methoxyphenyl)-3-(4-methoxyphenyl)-pyrazolo[1,5-a]pyrimidin-5-yl]-pyrrolidin-2-yl]-methanol, {1-[3-(4-chlorophenyl)-7-(2,4-difluorophenyl)-2-methyl-pyrazolo[1,5-a]pyrimidin-5-yl]-pyrrolidin-2-yl}-methanol,

[1-(3-benzo[1,3]dioxol-5-yl-2-methyl-7-phenyl-pyrazolo[1,5-a]pyrimidin-5-yl)-pyrrolidin-2-yl]methanol, {1-[3-(4-ethoxyphenyl)-2-methyl-7-phenyl-pyrazolo[1,5-a]pyrimidin-5-yl]-pyrrolidin-2-yl}-methanol, {1-[3-(4-methoxyphenyl)-2-methyl-7-phenyl-pyrazolo[1,5-a]pyrimidin-5-yl]-pyrrolidin-2-yl}-methanol, (S)-(1-(7-(3,4-difluorophenyl)-3-(4-ethoxyphenyl)-2-methyl-pyrazolo[1,5-a]pyrimidin-5-yl)-pyrrolidin-2-yl)-methanol, {1-[2-methyl-3-(4-methylsulfanylphenyl)-7-(3-trifluoromethylphenyl)-pyrazolo[1,5-a]pyrimidin-5-yl]-pyrrolidin-2-yl}-methanol, {1-[7-(3,4-difluorophenyl)-3-(4-methoxyphenyl)-2-methyl-pyrazolo[1,5-a]pyrimidin-5-yl]-pyrrolidin-2-yl}-methanol, {1-[7-(3,4-difluorophenyl)-2-methyl-3-p-tolyl-pyrazolo[1,5-a]pyrimidin-5-yl]-pyrrolidin-2-yl}-methanol, {1-[7-(3,4-difluorophenyl)-2-methyl-3-p-tolyl-pyrazolo[1,5-a]pyrimidin-5-yl]-pyrrolidin-2-yl}-methanol, {1-[7-(3,4-difluorophenyl)-2-methyl-3-p-tolyl-pyrazolo[1,5-a]pyrimidin-5-yl]-pyrrolidin-2-yl}-methanol, {1-[3-(4-chlorophenyl)-7-(3,4-difluorophenyl)-2-methyl-pyrazolo[1,5-a]pyrimidin-5-yl]-pyrrolidin-2-yl}-methanol, {1-[7-(4-fluorophenyl)-2-methyl-3-p-tolyl-pyrazolo[1,5-a]pyrimidin-5-yl]-pyrrolidin-2-yl}-methanol,

[1-(2-methyl-7-phenyl-3-p-tolyl-pyrazolo[1,5-a]pyrimidin-5-yl)-pyrrolidin-2-yl]-methanol,

[1-[3-(4-difluoromethylphenyl)-7-(3-fluorophenyl)-2-methyl-pyrazolo[1,5-a]pyrimidin-5-yl]-pyrrolidin-2-yl]-methanol, {1-[3-(4-difluoromethylphenyl)-7-(3-methoxyphenyl)-2-methyl-pyrazolo[1,5-a]pyrimidin-5-yl]-pyrrolidin-2-yl}-methanol, {1-[3-(4-difluoromethylphenyl)-2-methyl-7-(3-trifluoromethylphenyl)-pyrazolo[1,5-a]pyrimidin-5-yl]-pyrrolidin-2-yl}-methanol, {1-[3-(4-difluoromethylphenyl)-7-(4-fluorophenyl)-2-methyl-pyrazolo[1,5-a]pyrimidin-5-yl]-pyrrolidin-2-yl}-methanol, {1-[3-(4-difluoromethylphenyl)-2-methyl-7-m-tolyl-pyrazolo[1,5-a]pyrimidin-5-yl]-pyrrolidin-2-yl}-methanol, {1-[7-(4-chlorophenyl)-3-(4-methoxyphenyl)-2-methyl-pyrazolo[1,5-a]pyrimidin-5-yl]-pyrrolidin-2-yl}-methanol, {1-[7-(3-methoxyphenyl)-2-methyl-3-(4-trifluoromethylphenyl)-pyrazolo[1,5-a]pyrimidin-5-yl]-pyrrolidin-2-yl}methanol, {1-[3-(4-ethylphenyl)-2-methyl-7-(3-trifluoromethylphenyl)-pyrazolo[1,5-a]pyrimidin-5-yl]-pyrrolidin-2-yl}-methanol, {1-[3-(4-ethylphenyl)-2-methyl-7-(3-trifluoromethylphenyl)-pyrazolo[1,5-a]pyrimidin-5-yl]-pyrrolidin-2-yl}-methanol, {1-[2-methyl-3-(4-trifluoromethylphenyl)-7-(3-trifluoromethylphenyl)-pyrazolo[1,5-a]pyrimidin-5-yl]-pyrrolidin-2-yl}-methanol, {1-[7-(4-chlorophenyl)-2-methyl-3-p-tolyl-pyrazolo[1,5-a]pyrimidin-5-yl]-pyrrolidin-2-yl}-methanol,

[1-(2-methyl-3,7-di-p-tolyl-pyrazolo[1,5-a]pyrimidin-5-yl)-pyrrolidin-2-yl]-methanol, {1-[7-(3-chlorophenyl)-2-methyl-3-p-tolyl-pyrazolo[1,5-a]pyrimidin-5-yl]-pyrrolidin-2-yl}-methanol, {1-[7-(3-chlorophenyl)-2-methyl-3-p-tolyl-pyrazolo[1,5-a]pyrimidin-5-yl]-pyrrolidin-2-yl}-methanol,

[1-(2-methyl-7-m-tolyl-3-p-tolyl-pyrazolo[1,5-a]pyrimidin-5-yl)-pyrrolidin-2-yl]-methanol, {1-[7-(3-methoxyphenyl)-2-methyl-3-p-tolyl-pyrazolo[1,5-a]pyrimidin-5-yl]-pyrrolidin-2-yl}-methanol, {1-[7-(4-methoxyphenyl)-2-methyl-3-p-tolyl-pyrazolo[1,5-a]pyrimidin-5-yl]-pyrrolidin-2-yl}-methanol, {1-[7-(2-fluorophenyl)-2-methyl-3-p-tolyl-pyrazolo[1,5-a]pyrimidin-5-yl]-pyrrolidin-2-yl}-methanol, {1-[3-benzo[1,3]dioxol-5-yl-7-(3-fluorophenyl)-2-methyl-pyrazolo[1,5-a]pyrimidin-5-yl]-pyrrolidin-2-yl}-methanol, {1-[7-(3-fluorophenyl)-3-(4-methoxyphenyl)-2-methyl-pyrazolo[1,5-a]pyrimidin-5-yl]-pyrrolidin-2-yl}-methanol, {1-[3-(4-ethoxyphenyl)-7-(3-fluoromethylphenyl)-2-methyl-pyrazolo[1,5-a]pyrimidin-5-yl]-pyrrolidin-2-yl}-methanol, {1-[2-methyl-3-p-tolyl-7-(3-trifluoromethylphenyl)-pyrazolo[1,5-a]pyrimidin-5-yl]-pyrrolidin-2-yl}-methanol, {1-[3-(4-methoxyphenyl)-2-methyl-7-(3-trifluoromethylphenyl)-pyrazolo[1,5-a]pyrimidin-5-yl]-pyrrolidin-2-yl}-methanol, {1-[7-(3-chlorophenyl)-3-(4-methoxyphenyl)-2-methyl-pyrazolo[1,5-a]pyrimidin-5-yl]-pyrrolidin-2-yl}-methanol, {1-[3-benzo[1,3]dioxol-5-yl-7-(3-chloro-phenyl)-2-methyl-pyrazolo[1,5-a]pyrimidin-5-yl]-pyrrolidin-2-yl}-methanol, {1-[7-(4-fluorophenyl)-2-methyl-3-(4-vinylphenyl)-pyrazolo[1,5-a]-pyrrolidin-2-yl]-methanol, {1-[3-(4-ethoxyphenyl)-2-methyl-7-(3-trifluoromethylphenyl)-pyrazolo[1,5-a]pyrimidin-5-yl]-pyrrolidin-2-yl}-methanol, {1-[3-benzo[1,3]dioxol-5-yl-2-methyl-7-(3-trifluoromethylphenyl)-pyrazolo[1,5-a]pyrimidin-5-yl]-pyrrolidin-2-yl}-methanol, {1-[3-(4-fluoro-3-methylphenyl)-7-(4-fluorophenyl)-2-methyl-pyrazolo[1,5-a]pyrimidin-5-yl]-pyrrolidin-2-yl}-methanol, {1-[3-(3-fluoro-4-methylphenyl)-7-(4-fluorophenyl)-2-methyl-pyrazolo[1,5-a]pyrimidin-5-yl]-pyrrolidin-2-yl}-methanol, {1-[3-(4-ethoxyphenyl)-7-(4-fluorophenyl)-2-methyl-pyrazolo[1,5-a]pyrimidin-5-yl]-pyrrolidin-2-yl}-methanol, {1-[7-(4-fluorophenyl)-2-methyl-3-p-tolyl-pyrazolo[1,5-a]pyrimidin-5-yl]-pyrrolidin-2-yl}methanol, {1-[7-(4-fluorophenyl)-2-methyl-3-(4-propoxyphenyl)-pyrazolo[1,5-a]pyrimidin-5-yl]-pyrrolidin-2-yl}methanol, {1-[3-biphenyl-4-yl-7-(4-fluorophenyl)-2-methyl-pyrazolo[1,5-a]pyrimidin-5-yl]-pyrrolidin-2-yl}methanol, {1-[3-(2,4-difluorophenyl)-7-(4-fluorophenyl)-2-methyl-pyrazolo[1,5-a]pyrimidin-5-yl]-pyrrolidin-2-yl}methanol, {1-[3-(4-ethylsulfanylphenyl)-7-(4-fluorophenyl)-2-methyl-pyrazolo[1,5-a]pyrimidin-5-yl]-pyrrolidin-2-yl}methanol, {1-[3-(4-butoxyphenyl)-7-(4-fluorophenyl)-2-methyl-pyrazolo[1,5-a]pyrimidin-5-yl]-pyrrolidin-2-yl}methanol, {1-[7-(4-fluorophenyl)-2-methyl-3-(4-methylsulfanylphenyl)-pyrazolo[1,5-a]pyrimidin-5-yl]-pyrrolidin-2-yl}methanol, {1-[3-(4-benzoyloxyphenyl)-7-(4-fluorophenyl)-2-methyl-pyrazolo[1,5-a]pyrimidin-5-yl]-pyrrolidin-2-yl}methanol, {1-[7-(4-fluorophenyl)-2-methyl-3-(3-trifluoromethoxyphenyl)-pyrazolo[1,5-a]pyrimidin-5-yl]-pyrrolidin-2-yl}methanol, {1-[7-(4-fluorophenyl)-2-methyl-3-(4-trifluoromethoxyphenyl)-pyrazolo[1,5-a]pyrimidin-5-yl]-pyrrolidin-2-yl}-methanol, {1-[3-(4-ethylphenyl)-7-(4-fluorophenyl)-2-methyl-pyrazolo[1,5-a]pyrimidin-5-yl]-pyrrolidin-2-yl}-methanol, {1-[7-(4-fluorophenyl)-2-methyl-3-(4-trifluoromethylphenyl)-pyrazolo[1,5-a]pyrimidin-5-yl]-pyrrolidin-2-yl}-methanol, 1-{4-[7-(4-fluorophenyl)-5-(2-hydroxymethyl-pyrrolidin-1-yl)-2-methyl-pyrazolo[1,5-a]pyrimidin-3-yl]phenyl}-ethanol, {1-[3-(4-tert-butylphenyl)-7-(4-fluorophenyl)-2-methyl-pyrazolo[1,5-a]pyrimidin-5-yl]pyrrolidin-2-yl}-methanol,

[1-(2-methyl-7-phenyl-3-p-tolyl-pyrazolo[1,5-a]pyrimidin-5-yl)-pyrrolidin-2-yl]-methanol, {1-[7-(3-fluorophenyl)-2-methyl-3-p-tolyl-pyrazolo[1,5-a]pyrimidin-5-yl]-pyrrolidin-2-yl}-methanol, {1-[3-(4-chlorophenyl)-2-methyl-7-m-tolyl-pyrazolo[1,5-a]pyrimidin-5-yl]-pyrrolidin-2-yl}-methanol, {1-[3-benzo[1,3]dioxol-5-yl-7-(4-fluorophenyl)-2-methyl-pyrazolo[1,5-a]pyrimidin-5-yl]-pyrrolidin-2-yl}-methanol, {1-[7-(4-fluorophenyl)-3-(4-methoxyphenyl)-2-methyl-pyrazolo[1,5-a]pyrimidin-5-yl]-pyrrolidin-2-yl}-methanol, {1-[3-(4-chlorophenyl)-7-(4-fluorophenyl)-2-methyl-pyrazolo[1,5-a]pyrimidin-5-yl]-pyrrolidin-2-yl}methanol, {1-[3-(4-chlorophenyl)-2-cyclopropyl-7-(3-fluorophenyl)-pyrazolo[1,5-a]pyridinpyrimidine-5-yl]-pyrrolidin-2-yl}-methanol, {1-[3-(4-chlorophenyl)-2-methyl-7-(3-trifluoromethylphenyl)-pyrazolo[1,5-a]pyridinpyrimidine-5-yl]pyrrolidin-2-yl}-methanol, {1-[3-(4-chlorophenyl)-7-(3-fluorophenyl)-2-methyl-pyrazolo[1,5-a]pyrimidin-5-yl]-pyrrolidin-2-yl}-methanol, {1-[3-(4-chlorophenyl)-7-(3-chlorophenyl)-2-methyl-pyrazolo[1,5-a]pyrimidin-5-yl]-pyrrolidin-2-yl}-methanol, {1-[3,7-bis-(4-chlorophenyl)-2-methyl-pyrazolo[1,5-a]pyrimidin-5-yl]-pyrrolidin-2-yl}-methanol, {1-[3-(2,4-dichlorophenyl)-2-cyclopropyl-7-(2-fluorophenyl)-pyrazolo[1,5-a]pyrimidin-5-yl]-pyrrolidin-2-yl}methanol, {1-[3-(2,4-dichlorophenyl)-2-cyclopropyl-7-(4-fluorophenyl)-pyrazolo[1,5-a]pyrimidin-5-yl]-pyrrolidin-2-yl}-methanol, (S)-{1-[3-(4-chlorophenyl)-2-methyl-7-phenyl-pyrazolo[1,5-a]pyrimidin-5-yl]-pyrrolidin-2-yl}-methanol, (S)-{1-[7-(2-fluorophenyl)-2-(methoxymethyl)-3-(4-methoxyphenyl)-pyrazolo[1,5-a]pyrimidin-5-yl]-pyrrolidin-2-yl}-methanol, (S)-{1-[2-ethoxymethyl-3-(4-methoxyphenyl)-7-(3-tolyl)-pyrazolo[1,5-a]pyrimidin-5-yl]-pyrrolidin-2-yl}-methanol, (S)-{1-[7-(3-chlorophenyl)-2-(methoxymethyl)-3-(4-methoxyphenyl)-pyrazolo[1,5-a]pyridinpyrimidine-5-yl]-pyrrolidin-2-yl}-methanol, (S)-{1-[7-(4-chlorophenyl)-2-(methoxymethyl)-3-(4-methoxyphenyl)-pyrazolo[1,5-a]pyrimidin-5-yl]-pyrrolidin-2-yl}-methanol, (S)-{1-[3-(4-chlorophenyl)-2-(methoxymethyl)-7-(3-fluorophenyl)-pyrazolo[1,5-a]pyrimidin-5-yl]-pyrrolidin-2-yl}-methanol, (S)-{1-[3-(4-chlorophenyl)-2-(methoxymethyl)-7-(3-methylphenyl)-pyrazolo[1,5-a]pyrimidin-5-yl]-pyrrolidin-2-yl}-methanol, (S)-{1-[2-butyl-7-(3-tolyl)-3-(4-tolyl)-pyrazolo[1,5-a]pyrimidin-5-yl]-pyrrolidin-2-yl}-methanol, (S)-{1-[2-butyl-3-(p-tolyl)-7-(3-trifluoromethylphenyl)-pyrazolo[1,5-a]pyrimidin-5-yl]-pyrrolidin-2-yl}-methanol, (S)-{1-[2-propyl-3-(p-tolyl)-7-(3-trifluoromethylphenyl)-pyrazolo[1,5-a]pyridinpyrimidine-5-yl]-pyrrolidin-2-yl}-methanol and (S)-{1-[2-propyl-7-(m-tolyl)-3-(p-tolyl)-pyrazolo[1,5-a]pyrimidin-5-yl]-pyrrolidin-2-yl}-methanol.

In another aspect, the present disclosure provides a compound represented by Chemical Formula 4, as a compound related with the compound of Chemical Formula 1, a prodrug thereof, an isomer thereof, a pharmaceutically acceptable salt thereof, a hydrate thereof or a solvate thereof.

[Chemical Formula 4]

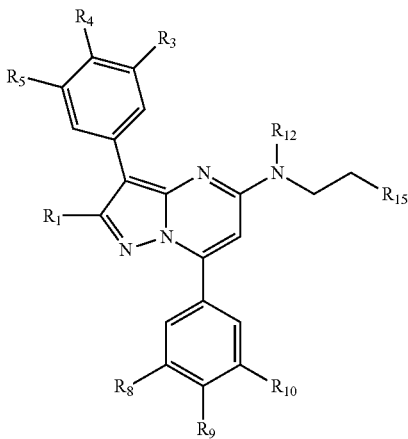

In Chemical Formula 4, $R_1$ is selected from a group consisting of methyl, ethyl, propyl, butyl, isobutyl, difluoromethyl, trifluoromethyl, cyclopropyl, ethoxymethyl, methoxymethyl and ethoxyethyl;

each of $R_3$, $R_4$ and $R_5$ is independently selected from a group consisting of hydrogen, fluoro, chloro, bromo, iodo, nitro, cyano, methyl, ethyl, propyl, isopropyl, butyl, tert-butyl, methoxy, ethoxy, propoxy, isopropoxy, butoxy, hydroxymethyl, hydroxyethyl, trifluoromethyl, difluoromethyl, fluoromethyl, trifluoromethoxyvinyl, vinyl, acetylenyl, carboxyl, methoxycarbonyl, ethoxycarbonyl, acetyl, methylsulfanyl, ethylsulfanyl, methylsulfonyl, methylsulfonylamino, cyclopropylaminosulfonyl, methylaminosulfonyl, ethylaminosulfonyl, dimethylaminocarbonyl, diethylaminocarbonyl, methylcarbonylamino, methylsulfamoyl, phenylmethyl, phenylethyl, phenylmethoxy, phenylacetyl, aminosulfonyl, methylaminosulfonyl, ethylaminosulfonyl, dimethylamino, diethylamino, cyclopropylamino and methylthio, or two selected from $R_3$ through $R_5$ form a 5- to 7-membered ring fused with an aryl group together with the carbon atoms to which they are bound and the ring includes 0-2 double bonds and contains 0-2 N, O or S atoms;

each of $R_8$, $R_9$ and $R_{10}$ is independently selected from a group consisting of hydrogen, fluoro, chloro, bromo, iodo, nitro, cyano, methyl, ethyl, propyl, butyl, isopropyl, methoxy, ethoxy, propoxy, isopropoxy, hydroxymethyl, trifluoromethyl, difluoromethyl, fluoromethyl, trifluoromethoxyvinyl and acetylenyl; and each of $R_{12}$ and $R_{15}$ is independently selected from a group consisting of hydrogen, methyl, ethyl, propyl, methoxy, ethoxy and hydroxy.

In another aspect, the present disclosure provides a compound represented by Chemical Formula 4, a prodrug thereof, an isomer thereof, a pharmaceutically acceptable salt thereof, a hydrate thereof or a solvate thereof, wherein:

$R_1$ is selected from a group consisting of methyl, ethyl, propyl, butyl, isobutyl, trifluoromethyl, cyclopropyl, ethoxymethyl, methoxymethyl and ethoxyethyl;

each of $R_3$, $R_4$ and $R_5$ is independently selected from a group consisting of hydrogen, fluoro, chloro, nitro, cyano, methyl, ethyl, propyl, isopropyl, butyl, tert-butyl, methoxy, ethoxy, propoxy, methylenedioxy, isopropoxy, hydroxymethyl, hydroxyethyl, trifluoromethyl, difluoromethyl, fluoromethyl, trifluoromethoxyvinyl, acetylenyl, carboxyl, methoxycarbonyl, ethoxycarbonyl, acetyl, methylsulfonyl, methylsulfamoyl, phenylmethyl, phenylethyl and methylthio, or two selected from $R_3$ through $R_5$ form a 5- to 7-membered ring fused with an aryl group together with the carbon atoms to which they are bound and the ring includes 0-2 double bonds and contains 0-2 N, O or S atoms; and each of $R_8$, $R_9$ and $R_{10}$ is independently selected from a group consisting of hydrogen, fluoro, chloro, bromo, iodo, nitro, cyano, methyl, ethyl, propyl, butyl, isopropyl, methoxy, ethoxy, propoxy, isopropoxy, butoxy, hydroxymethyl, trifluoromethyl, difluoromethyl, fluoromethyl, trifluoromethoxyvinyl and acetylenyl.

In another aspect, the present disclosure provides a compound selected from the followings, an isomer thereof, a pharmaceutically acceptable salt thereof, a hydrate thereof or a solvate thereof:

2-{[3-(4-methoxyphenyl)-2-methyl-7-(3-trifluoromethylphenyl)-pyrazolo[1,5-a]pyrimidin-5-yl]-methylamino}-ethanol, 2-{[3-benzo[1,3]dioxol-5-yl-2-ethoxymethyl-7-(3-methoxyphenyl)-pyrazolo[1,5-a]pyrimidin-5-yl]-methylamino}-ethanol, 2-{[7-(3-fluorophenyl)-2-methyl-3-p-tolyl-pyrazolo[1,5-a]pyrimidin-5-yl]-methylamino}-ethanol, 2-{[7-(4-fluorophenyl)-2-methyl-3-p-tolyl-pyrazolo[1,5-a]pyrimidin-5-yl]-methylamino}-ethanol, 2-{[7-(3-chlorophenyl)-2-methyl-3-p-tolyl-pyrazolo[1,5-a]pyrimidin-5-yl]-amino}-ethanol, 2-[2-ethoxymethyl-3-(4-methoxyphenyl)-7-(3-trifluoromethylphenyl)-pyrazolo[1,5-a]pyrimidin-5-yl]-methylamino}-ethanol, 2-{[2-ethoxymethyl-7-(4-fluorophenyl)-3-p-tolyl-pyrazolo[1,5-a]pyrimidin-5-yl]-amino}-ethanol, 2-{3-benzo[1,3]dioxol-5-yl-2-ethoxymethyl-7-(3-trifluoromethylphenyl)-pyrazolo[1,5-a]pyrimidin-5-yl]-methylamino}-ethanol, 2-{[3-benzo[1,3]dioxol-5-yl-7-(3-chlorophenyl)-2-ethoxymethyl-pyrazolo[1,5-a]pyrimidin-5-yl]-methylamino}-ethanol, 2-{[2-ethoxymethyl-7-(3-fluorophenyl)-3-p-tolyl-pyrazolo[1,5-a]pyrimidin-5-yl]-methylamino}-ethanol, 2-{[2-ethoxymethyl-3-p-tolyl-7-(3-trifluoromethylphenyl)-pyrazolo[1,5-a]pyrimidin-5-yl]-methylamino}-ethanol, {2-[2-butyl-3-p-tolyl-7-(3-trifluoromethylphenyl)-pyrazolo[1,5-a]pyrimidin-5-yl]-methylamino}-ethanol, 2-{[3-(4-chlorophenyl)-2-ethoxymethyl-7-(4-fluorophenyl)-pyrazolo[1,5-a]pyrimidin-5-yl]-methylamino}-ethanol, 2-{[3-(4-chlorophenyl)-2-ethoxymethyl-7-(3-fluorophenyl)-pyrazolo[1,5-a]pyrimidin-5-yl]-methylamino}-ethanol, 2-{[3-(4-chlorophenyl)-2-ethoxymethyl-7-(3-trifluoromethylphenyl)-pyrazolo[1,5-a]pyrimidin-5-yl]-methylamino}-ethanol, 2-{[3-(4-chlorophenyl)-2-methoxymethyl-7-(3-trifluoromethylphenyl)-pyrazolo[1,5-a]pyrimidin-5-yl]-methylamino}-ethanol, 2-{[3-(4-chlorophenyl)-7-(4-fluorophenyl)-2-methoxymethyl-pyrazolo[1,5-a]pyrimidin-5-yl]-methylamino}-ethanol, 2-{[3-(4-chlorophenyl)-7-(3-fluorophenyl)-2-methoxymethyl-pyrazolo[1,5-a]pyrimidin-5-yl]-methylamino}-ethanol, 2-{[2-methoxymethyl-3-(4-methoxyphenyl)-7-(3-trifluoromethylphenyl)-pyrazolo[1,5-a]pyrimidin-5-yl]-methylamino}-ethanol, 2-{[3-(4-chlorophenyl)-2-ethoxymethyl-7-(4-fluorophenyl)-pyrazolo[1,5-a]pyrimidin-5-yl]-ethylamino}-ethanol and 2-{[3-(4-chlorophenyl)-2-methoxymethyl-7-(m-tolyl)-pyrazolo[1,5-a]pyrimidin-5-yl]-methylamino}-ethanol.

The arylpyrazolo[1,5-a]pyrimidin-5(4H)-one compound having an aryl group substituted at 7-position have an effect of inhibiting the cannabinoid receptor 1 and the effect is very superior to the existing compound having an aryl group substituted at 5-position.

In another aspect, the present disclosure provides a pharmaceutical composition containing the compound, the prodrug thereof, the isomer thereof, the pharmaceutically acceptable salt thereof, the hydrate thereof or the solvate thereof.

In an exemplary embodiment of the present disclosure, the pharmaceutical composition may be used for prevention or treatment of a disease mediated by the cannabinoid receptor-1. In another exemplary embodiment of the present disclosure, the pharmaceutical composition may be used for prevention or treatment of inflammatory pain, psycopathy, anxiety, depression, attention deficiency, memory or cognitive disorder, neuropathic pain disorder, sexual dysfunction, impulse control disorder, metabolic disorders such as obesity, neurological or obsessive eating disorder, morning sickness, nausea, gastric ulcer, diabetes, hypertension and hyperlipidemia or cardiac dysfunctions such as valvular heart disease, myocardial infarction, cardiomegaly or congestive heart failure.

In another exemplary embodiment of the present disclosure, the pharmaceutical composition may be used for prevention or treatment of obesity and this effect may be achieved through facilitation of energy metabolism, control of appetite or regulation of processes related with fat metabolism.

The pharmaceutical composition may further contain a pharmaceutical adjuvant such as an antiseptic, a stabilizer, a hydrating agent, an emulsifying accelerator, a salt for control of osmotic pressure, a buffer, etc. and other therapeutically useful substance. The pharmaceutical composition may be prepared into various formulations for oral or parenteral administration according to commonly employed methods.

The formulation for oral administration may include, for example, tablet, pill, hard or soft capsule, liquid, suspension, emulsion, syrup, powder, dust, fine granule, granule, pellet, elixir, or the like, without being limited thereto. These formulations may include, in addition to the active ingredient, a diluent (e.g., lactose, dextrose, sucrose, mannitol, sorbitol, cellulose and glycine), a lubricant (e.g., silica, talc, stearic acid or its magnesium, calcium, and polyethylene glycol). The tablet may further include a binder such as magnesium aluminum silicate, starch paste, gelatin, tragacanth, methyl cellulose, sodium carboxymethyl cellulose and polyvinylpyrrolidine. As occasion demands, it may further include a pharmaceutical additive such as a disintegrant, e.g., starch, agar, alginic acid or its sodium salt, an absorbent, a colorant, a flavor, a sweetener, or the like. The tablet may be prepared according to the commonly employed mixing, granulation or coating methods.

The formulation for parenteral administration may include, for example, injection, medicinal drop, ointment, lotion, gel, cream, spray, suspension, emulsion, suppository, patch, or the like, without being limited thereto.

The pharmaceutical composition according to the present disclosure may be administered orally or parenterally, for example, rectally, topically, transdermally, intravenously, intramuscularly, intraperitoneally or subcutaneously.

A pharmaceutically acceptable dosage, i.e. an administration dosage, of the active ingredient will vary depending on the age, gender and body weight of the subject to be treated, particular disease or pathological condition to be treated, or severity of the disease or pathological condition, administration route and discretion of a diagnoser. Determination of the administration dosage considering these factors is in the level of those skilled in the art. A general dosage may be 0.01-2000 mg/kg/day, specifically 1-100 mg/kg/day. However, the scope of the present disclosure is not limited by the administration dosage by any means.

[Mode for Invention]

Hereinafter, the present disclosure will be described in detail through preparation example, examples and test examples. However, the following preparation example, examples and test examples are for illustrative purposes only and it will be apparent to those of ordinary skill in the art that the scope of the present disclosure is not limited by thereby.

PREPARATION EXAMPLE

Preparation of pyrazolo[1,5-a]pyrimidine

Aminopyrazole was reacted with a diketoester in a pyridine solvent according to one of Schemes 3-7 to prepare pyrazolo[1,5-a]pyrimidine having an aryl group substituent at 7-position, which was used in Examples described below. At least one of the aminopyrazole and the diketoester had the aryl group.

Test Example 1

The solid crystal structure of the pyrazolo[1,5-a]pyrimidine prepared in Preparation Example was identified by X-ray crystallography. The X-ray data and structure are summarized in Table 1. FIG. 1 shows the solid crystal structure of the pyrazolo[1,5-a]pyrimidine.

TABLE 1

| | |
|---|---|
| Empirical formula | $C_{13}H_9Cl_2N_3$ |
| Formula weight | 278.14 |
| Temperature | 296(2) K |
| Wavelength | 0.71073 Å |
| Crystal system/space group | Orthorhombic/Pca2$_1$ |
| Unit cell diameter | a = 27.779(10) Å, α = 90 deg. |
| | b = 3.9341(15) Å, β = 90 deg. |
| | c = 11.195(4) Å, γ = 90 deg. |
| Volume | 1223.5(8) Å$^3$ |
| Z, calculated density | 4, 1.510 Mg/m$^3$ |
| Absorption coefficient | 0.513 mm$^{-1}$ |
| F(000) | 568 |
| Crystal size | 0.14 × 0.04 × 0.04 mm |
| Theta range for data collection | 3.64-25.50 deg. |
| Index ranges | −32 ≤ h ≤ 29, −4 ≤ k ≤ 1, −10 ≤ l ≤ 13 |
| Reflections collected/unique | 4220/1955 [R(int) = 0.0574] |
| Completeness to theta = 28.34 deg. | 94.9% |
| Absorption correction | Semi-empirical from equivalents |
| Max. and min. transmission | 0.980 and 0.976 |
| Refinement method | Full-matrix least-squares on F$_2$ |
| Data/restraints/parameters | 1955/1/164 |
| Goodness-of-fit on F$_2$ | 0.999 |
| Final R indices [I > 2sigma(I)] | R$_1$ = 0.0513, wR$_2$ = 0.1070 |
| R indices (all data) | R$_1$ = 0.1055, wR$_2$ = 0.1333 |
| Largest diff. peak and hole | 0.232 and −0.227 e.Å$^{-3}$ |

As seen from Table 1, the pyrazolo[1,5-a]pyrimidine prepared in Preparation Example was identified as 5-chloro-7-(4-chlorophenyl)-2-methylpyrazolo[1,5-a]pyrimidine (Chemical Formula 5) having an aryl group at 7-position. That is to say, the pyrazolo[1,5-a]pyrimidine having an aryl group at 7-position could be prepared by the above method.

[Chemical Formula 5]

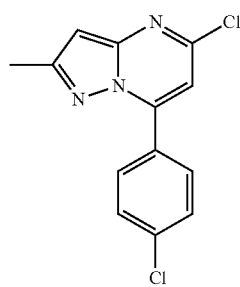

Example 1

Preparation of (S)-(1-(3-(4-chlorophenyl)-7-(4-methoxyphenyl)-2-methylpyrazolo[1,5-a]pyrimidin-5-yl) pyrrolidin-yl)methanol (Chemical Formula 6)

[Chemical Formula 6]

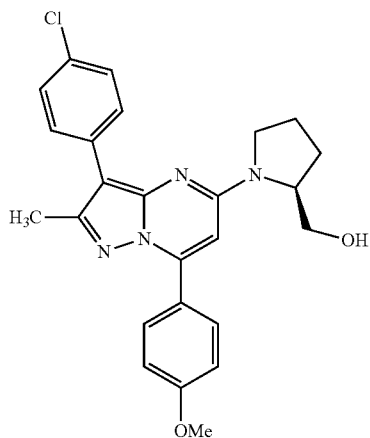

Step 1: Preparation of 3-(4-chlorophenyl)-7-(4-methoxyphenyl)-2-methylpyrazolo[1,5-a]pyrimidin-5 (4H)-one (Chemical Formula 7)

[Chemical Formula 7]

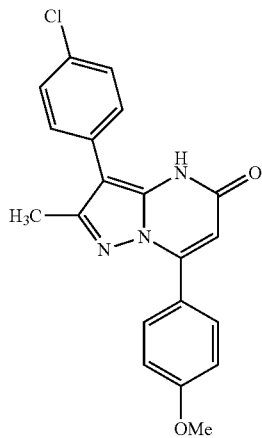

3-Methyl-4-(4-chlorophenyl)-1H-pyrazol-5-amine (166 mg) and ethyl 3-(4-methoxyphenyl)-3-oxopropanoate (266 mg) are stirred overnight at 95° C. in a pyridine (10 mL) solvent. After lowering reaction temperature to room temperature, the reaction solvent is removed by distillation under reduced pressure. The remainder is extracted with ethyl acetate and water. The extracted organic layer is washed with brine and dehydrated with anhydrous MgSO$_4$. The dehydrated organic layer is distilled under reduced pressure and 141 mg of the target compound is obtained by column chromatography. $^1$H NMR (CDCl$_3$, 300 MHz) δ 11.40 (br, 1H), 7.98 (d, J=8.7 Hz, 2H), 7.44 (m, 4H), 6.97 (d, J=8.7 Hz, 2H), 4.06 (br, 1H), 3.89 (s, 3H), 2.17 (s, 3H), 2.25 (s, 1H).

Step 2: Preparation of 5-chloro-3-(4-chlorophenyl)-7-(4-methoxyphenyl)-2-methylpyrazolo[1,5-a]pyridine pyrimidine (Chemical Formula 8)

[Chemical Formula 8]

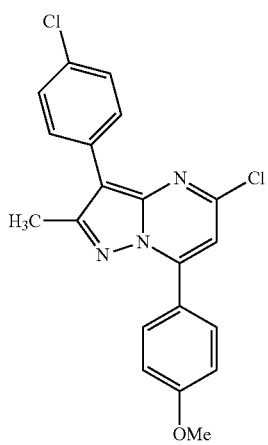

3-(4-Chlorophenyl)-7-(4-methoxyphenyl)-2-methylpyrazolo[1,5-a]pyrimidin-5(4H)-one (200 mg) is added to POCl₃ (3 mL) and pyridine (0.1 mL) and stirred for 2 hours while heating. The reaction mixture is cooled to room temperature and POCl₃ is removed by distillation under reduced pressure. After the distillation, ethyl acetate (20 mL) and ice are added to the remainder. After the organic layer is extracted, it is extracted once again with water and ethyl acetate. The organic layer is washed with 1 M NaHCO₃ aqueous solution and brine. The organic layer is dehydrated with anhydrous MgSO₄. The solvent is removed from the organic layer by distillation under reduced pressure. The remainder is purified by column chromatography to yield 160 mg of the target compound. ¹H NMR (CDCl₃, 300 MHz) δ 8.09 (m, 2H), 7.64 (m, 2H), 7.45 (m, 2H), 7.08 (m, 2H), 6.84 (s, 1H), 3.91 (s, 3H), 2.61 (s, 3H).

Step 3: Preparation of (S)-(1-(3-(4-chlorophenyl)-7-(4-methoxyphenyl)-2-methylpyrazolo[1,5-a]pyrimidin-5-yl)pyrrolidin-yl)methanol 5-Chloro-3-(4-chlorophenyl)-7-(4-methoxyphenyl)-2-methylpyrazolo[1,5-a]pyrimidine (50 mg), (S)-pyrrolin-2-ylmethanol (16 mg) and DIPEA (0.2 mL) are added to acetonitrile (10 mL) and stirred overnight at 80° C. After cooling to room temperature, the solvent and volatile substance are removed by distillation under reduced pressure. The remainder is extracted 3 times with ethyl acetate (20 mL) and water. The collected organic layer is washed with brine. The organic layer is dehydrated with anhydrous MgSO₄ and the solvent is removed by distillation under reduced pressure. The remainder is purified by column chromatography to yield 53 mg of the target compound. ¹H NMR (CDCl₃, 300 MHz) δ 7.91 (m, 2H), 7.52 (m, 2H), 7.40 (m, 2H), 7.03 (m, 2H), 6.12 (s, 1H), 4.43 (br, 1H), 3.89 (s, 3H), 3.78-3.52 (m, 4H), 2.45 (s, 3H), 2.15-1.99 (m, 3H), 1.78-1.69 (m, 1H).

Example 2

Preparation of (S)-(1-(3-(4-chlorophenyl)-7-(3-chlorophenyl)-2-methylpyrazolo[1,5-a]pyrimidin-5-yl)pyrrolidin-2-yl)methanol (Chemical Formula 9)

[Chemical Formula 9]

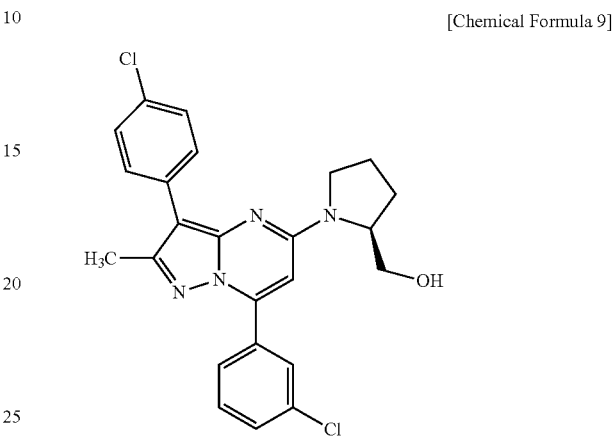

Step 1: Preparation of 3-(4-chlorophenyl)-7-(3-chlorophenyl)-2-methylpyrazolo[1,5-a]pyrimidin-5(4H)-one (Chemical Formula 10)

[Chemical Formula 10]

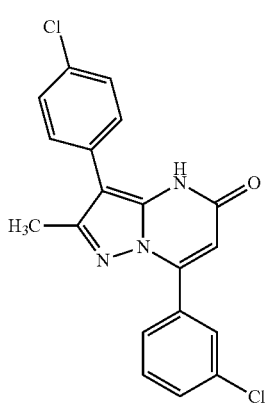

3-Methyl-4-(4-chlorophenyl)-1H-pyrazol-5-amine (578 mg) and ethyl 3-(3-chlorophenyl)-3-oxopropanoate (728 mg) are stirred overnight in a pyridine (30 mL) solvent at 95° C. After cooling to room temperature, the reaction solvent is removed by distillation under reduced pressure. The remainder is extracted with ethyl acetate and water. The extracted organic layer is washed with brine and dehydrated with anhydrous MgSO₄. The dehydrated organic layer is distilled under reduced pressure and concentrated and then 424 mg of the target compound is yielded by column chromatography. ¹H NMR (CDCl₃, 300 MHz) δ 9.90 (br, 1H), 7.88 (m, 1H), 7.75 (m, 1H), 7.53 (m, 1H), 7.33 (m, 5H), 3.99 (br, 1H), 2.23 (s, 3H).

Step 2: Preparation of 5-chloro-3-(4-chlorophenyl)-7-(4-methoxyphenyl)-2-methylpyrazolo[1,5-a]pyridinepyrimidine (Chemical Formula 11)

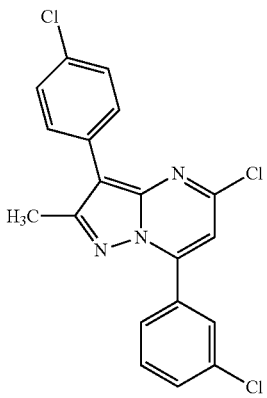

[Chemical Formula 11]

3-(4-Chlorophenyl)-7-(3-chlorophenyl)-2-methylpyrazolo[1,5-a]pyrimidin-5(4H)-one (382 mg) is added to POCl$_3$ (10 mL) and pyridine (0.2 mL) and stirred for 5 hours while heating. After cooling to room temperature, POCl$_3$ is removed by distillation under reduced pressure. After the distillation, ethyl acetate (20 mL) and ice water are added to the remainder. After the organic layer is extracted, it is extracted once again with water and ethyl acetate. The organic layer is washed with 1 M NaHCO$_3$ aqueous solution and brine. The organic layer is dehydrated with anhydrous MgSO$_4$. The solvent is removed from the organic layer by distillation under reduced pressure. The remainder is purified by column chromatography to yield the target compound (324 mg). $^1$H NMR (CDCl$_3$, 300 MHz) δ 8.04 (s, 1H), 7.94 (d, J=7.8 Hz, 1H), 7.65 (m, 2H), 7.52 (m, 2H), 7.46 (m, 2H), 6.86 (s, 1H), 2.61 (s, 3H).

Step 3: Preparation of (S)-(1-(3-(4-chlorophenyl)-7-(3-chlorophenyl)-2-methylpyrazolo[1,5-a]pyrimidin-pyrimidine-5-yl)pyrrolidin-2-yl)methanol 5-Chloro-3-(4-chlorophenyl)-7-(4-methoxyphenyl)-2-methylpyrazolo[1,5-a]pyrimidine (210 mg), (S)-pyrrolin-2-ylmethanol (254 mg) and DIPEA (0.6 mL) are added to acetonitrile (30 mL) and stirred overnight at 80° C. After cooling to room temperature, the solvent is removed by distillation under reduced pressure. The remainder is extracted 3 times with ethyl acetate (20 mL) and water. The collected organic layer is washed with brine. The organic layer is dehydrated with anhydrous MgSO$_4$ and the solvent is removed by distillation under reduced pressure. The remainder is purified by column chromatography to yield the target compound (235 mg). $^1$H NMR (CDCl$_3$, 300 MHz) δ 7.90 (m, 1H), 7.84 (m, 1H), 7.55-7.47 (m, 4H), 7.41 (d, J=8.4 Hz, 2H), 6.15 (s, 1H), 4.44 (br, 1H), 3.75-3.54 (m, 5H), 2.45 (s, 3H), 2.14-2.02 (m, 2H), 1.78 (m, 1H).

Examples 3-24

Compounds of Examples 3-24 are prepared in a similar manner as Examples 1 and 2.

Chemical formula and NMR analysis data for the compounds of Examples 1-24 are shown in Chemical Formula 12 and Table 2.

[Chemical Formula 12]

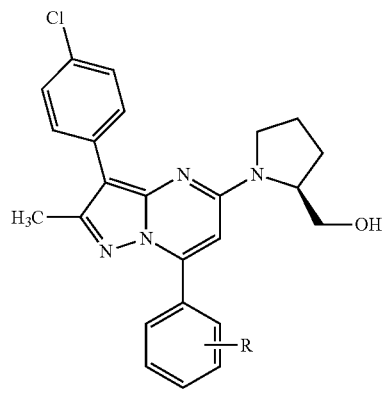

TABLE 2

| Ex. No. | R | $^1$H NMR (CDCl$_3$, 300 MHz) |
|---|---|---|
| 1 | 4-OMe | 7.91 (m, 2H), 7.52 (m, 2H), 7.40 (m, 2H), 7.03 (m, 2H), 6.12 (s, 1H), 4.43 (br, 1H), 3.89 (s, 3H), 3.78-3.52 (m, 4H), 2.45 (s, 3H), 2.15-1.99 (m, 3H), 1.78-1.69 (m, 1H) |
| 2 | 3-Cl | 7.90 (m, 1H), 7.84 (m, 1H), 7.55-7.47 (m, 4H), 7.41 (d, J = 8.4 Hz, 2H), 6.15 (s, 1H), 4.44 (br, 1H), 3.75-3.54 (m, 5H), 2.45 (s, 3H), 2.14-2.02 (m, 2H), 1.78 (m, 1H) |
| 3 | 3-F | 7.71 (d, J = 7.8 Hz, 2H), 7.53 (m, 3H), 7.40 (d, J = 7.8 Hz, 2H), 7.20 (m, 1H), 6.17 (s, 1H), 4.44 (br, 1H), 3.75-3.53 (m, 5H), 2.47 (s, 3H), 2.14-2.01 (m, 2H), 1.80 (m, 1H) |
| 4 | 2-F | 7.75 (m, 1H), 7.53 (m, 3H), 7.40 (d, J = 8.4 Hz, 2H), 7.29 (m, 2H), 6.21 (s, 1H), 4.45 (br, 1H), 3.78-3.52 (m, 4H), 2.44 (s, 3H), 2.15-1.99 (m, 3H), 1.78-1.69 (m, 1H) |
| 5 | H | 7.94 (m, 2H), 7.55 (m, 5H), 7.40 (d, J = 8.4 Hz, 2H), 6.17 (s, 1H), 4.46 (br, 1H), 3.78-3.52 (m, 4H), 2.47 (s, 3H), 2.15-1.99 (m, 3H), 1.78-1.69 (m, 1H) |
| 6 | 3-OMe | 7.51 (m, 4H), 7.38 (d, J = 8.4 Hz, 2H), 7.07 (m, 2H), 6.15 (s, 1H), 5.50 (bs, 1H), 4.40 (bs, 1H), 3.80 (s, 3H), 3.60 (m, 4H), 2.42 (s, 3H), 2.06 (m, 3H), 1.76 (m, 1H) |

TABLE 2-continued

| Ex. No. | R | $^1$H NMR (CDCl$_3$, 300 MHz) |
|---|---|---|
| 7 | 2-OMe | 7.53 (dd, J = 8.1, 6.3 Hz, 3H), 7.44 (d, J = 8.1 Hz, 2H), 7.38 (d, J = 8.4 Hz, 2H), 7.06 (m, 1H), 6.15 (s, 1H), 5.25 (bs, 1H), 4.42 (bs, 1H), 3.86 (s, 3H), 3.60 (m, 4H), 2.46 (s, 3H), 2.06 (m, 3H), 1.76 (m, 1H) |
| 8 | 4-CF$_3$ | 8.04 (d, J = 8.1 Hz, 2H), 7.78 (d, J = 8.4 Hz, 2H), 7.52 (d, J = 8.1 Hz, 2H), 7.37 (d, J = 8.4 Hz, 2H), 6.15 (s, 1H), 5.98 (bs, 1H), 4.43 (m, 1H), 3.63 (m, 4H), 2.43 (s, 3H), 2.06 (m, 3H), 1.78 (m, 1H) |
| 9 | 3-CF$_3$ | 8.17 (d, J = 8.4 Hz, 2H), 7.80 (d, J = 7.8 Hz, 1H), 7.67 (dd, J = 7.8, 7.5 Hz, 1H), 7.54 (d, J = 8.4 Hz, 2H), 7.40 (d, J = 8.4 Hz, 2H), 6.18 (s, 1H), 5.15 (bs, 1H), 4.44 (m, 1H), 3.63 (m, 4H), 2.46 (s, 3H), 2.06 (m, 3H), 1.81 (m, 1H) |
| 10 | 2-CF$_3$ | 7.85 (d, J = 7.5 Hz, 1H), 7.68 (dd, J = 8.1, 6.9 Hz, 2H), 7.56 (m, 3H), 7.40 (m, 2H), 6.09 (s, 1H), 5.29 (bs, 1H), 4.44 (m, 1H), 3.73 (m, 2H), 3.57 (m, 1H), 3.47 (m, 1H), 2.39 (s, 3H), 2.06 (m, 3H), 1.81 (m, 1H) |
| 11 | 4-Me | 7.80 (d, J = 7.8 Hz, 2H), 7.51 (d, J = 8.4 Hz, 2H), 7.36 (d, J = 8.7 Hz, 2H), 7.31 (d, J = 7.8 Hz, 2H), 6.12 (s, 1H), 4.41 (br, 1H), 3.78-3.52 (m, 4H), 2.44 (s, 3H), 2.42 (s, 3H), 2.15-1.99 (m, 3H), 1.78-1.69 (m, 1H) |
| 12 | 3-Me | 7.70 (m, 2H), 7.55 (d, J = 8.7 Hz, 2H), 7.44 (m, 4H), 6.14 (s, 1H), 4.44 (br, 1H), 3.89 (s, 3H), 3.78-3.52 (m, 4H), 2.47 (s, 3H), 2.46 (s, 3H), 2.15-1.99 (m, 3H), 1.78-1.69 (m, 1H) |
| 13 | 2-Me | 7.56 (d, J = 8.5 Hz, 2H), 7.47-7.33 (m, 6H), 6.06 (s, 1H), 4.47 (br, 1H), 3.77 (m, 1H), 3.69 (m, 1H), 3.60 (m, 1H), 3.51 (m, 1H), 2.42 (s, 3H), 2.25 (s, 3H), 2.15-1.99 (m, 3H), 1.79 (m, 1H) |
| 14 | 3-Et | 7.74 (d, J = 8.7 Hz, 2H), 7.55 (d, J = 8.4 Hz, 2H), 7.41 (m, 4H), 6.15 (s, 1H), 5.39 (bs, 1H), 4.45 (m, 1H), 3.66 (m, 4H), 2.76 (q, J = 7.5 Hz, 2H), 2.46 (s, 3H), 2.09 (m, 3H), 1.77 (m, 1H), 1.29 (dd, J = 7.5, 7.8 Hz, 3H) |
| 15 | 4-Cl | 7.90 (d, J = 8.7 Hz, 2H), 7.53 (m, 4H), 7.40 (d, J = 8.7 Hz, 2H), 6.15 (s, 1H), 4.44 (br, 1H), 3.75-3.56 (m, 5H), 2.47 (s, 3H), 2.13-2.02 (m, 2H), 1.78 (m, 1H) |
| 16 | 4-F | 7.96 (m, 2H), 7.54 (d, J = 8.7 Hz, 2H), 7.40 (d, J = 8.7 Hz, 2H), 7.22 (d, J = 8.7 Hz, 2H), 6.14 (s, 1H), 4.45 (br, 1H), 3.78-3.52 (m, 4H), 2.47 (s, 3H), 2.15-1.99 (m, 3H), 1.78-1.69 (m, 1H) |
| 17 | 2-Cl | 7.56-7.53 (m, 4H), 7.45-7.39 (m, 4H), 6.13 (s, 1H), 4.44 (br, 1H), 3.77-3.52 (m, 5H), 2.42 (s, 3H), 2.11-2.00 (m, 2H), 1.78 (m, 1H) |
| 18 | 4-Br | 7.91 (d, J = 8.1 Hz, 2H), 7.77 (d, J = 8.4 Hz, 2H), 7.58 (d, J = 8.7 Hz, 2H), 7.42 (d, J = 8.4 Hz, 2H), 6.27 (s, 1H), 5.77 (m, 1H), 4.45 (m, 1H), 3.80 (m, 2H), 3.67 (m, 2H), 2.58 (s, 3H), 2.13 (m, 3H), 1.94 (m, 1H) |
| 19 | 3-Br | 8.14 (s, 1H), 7.97 (d, J = 7.8 Hz, 1H), 7.77 (d, J = 8.4 Hz, 2H), 7.55 (d, J = 8.1 Hz, 1H), 7.44 (d, J = 8.1 Hz, 2H), 7.32 (t, J = 7.8 Hz, 1H), 6.24 (s, 1H), 5.77 (m, 1H), 4.45 (m, 1H), 3.80 (m, 2H), 3.67 (m, 2H), 2.58 (s, 3H), 2.13 (m, 3H), 1.94 (m, 1H) |
| 20 | 2-Br | 7.76 (m, 1H), 7.54 (m, 4H), 7.41 (m, 3H), 6.12 (s, 1H), 5.76 (m, 1H), 4.46 (m, 1H), 3.72 (m, 2H), 3.53 (m, 2H), 2.42 (s, 3H), 2.09 (m, 3H), 1.80 (m, 1H) |
| 21 | 3-F, 4-F | 7.89 (m, 1H), 7.69 (m, 1H), 7.54 (d, J = 8.1 Hz, 2H), 7.39 (d, J = 8.1 Hz, 2H), 7.31 (m, 1H), 6.15 (s, 1H), 4.45 (br, 1H), 3.75-3.56 (m, 4H), 2.47 (s, 3H), 2.13-2.02 (m, 2H), 1.77 (m, 1H) |
| 22 | 2-F, 4-F | 7.79 (m, 1H), 7.54 (d, J = 8.4 Hz, 2H), 7.26 (d, J = 8.4 Hz, 2H), 7.04 (m, 2H), 6.78 (m, 1H), 6.18 (s, 1H), 4.45 (bs, 1H), 3.64 (m, 4H), 2.44 (s, 3H), 2.03 (m, 3H), 1.80 (m, 1H) |
| 23 | 3-F, 5-F | 7.73 (d, J = 8.7 Hz, 2H), 7.54 (d, J = 6.6 Hz, 2H), 7.43 (d, J = 8.4 Hz, 2H), 6.84 (m, 1H), 6.19 (s, 1H), 5.77 (bs, 1H), 4.43 (m, 1H), 3.66 (m, 4H), 2.57 (s, 3H), 2.13 (m, 3H), 1.95 (m, 1H) |
| 24 | 3-MeO, 4-MeO | 7.59 (s, 1H), 7.54 (d, J = 8.1 Hz, 1H), 7.50 (t, J = 8.4 Hz, 2H), 7.38 (d, J = 8.1 Hz, 2H), 6.98 (d, J = 8.4 Hz, 1H), 6.13 (s, 1H), 5.36 (bs, 1H), 4.42 (bs, 1H), 3.94 (s, 6H), 3.61 (m, 4H), 2.46 (s, 3H), 2.06 (m, 3H), 1.76 (m, 1H) |

Example 25

Preparation of (S)-(1-(3-(4-methylphenyl)-7-(3-methoxyphenyl)-2-methylpyrazolo[1,5-a]pyrimidin-5-yl)pyrrolidin-2-yl)methanol (Chemical Formula 13)

[Chemical Formula 13]

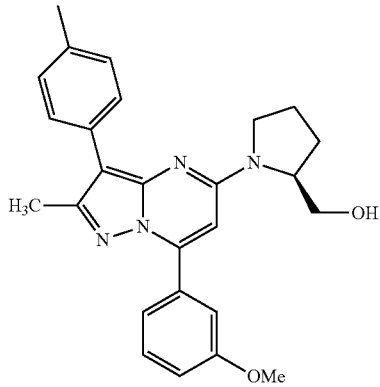

Step 1: Preparation of 3-(4-methylphenyl)-7-(3-methoxyphenyl)-2-methylpyrazolo[1,5-a]pyrimidin-5(4H)-one (Chemical Formula 14)

[Chemical Formula 14]

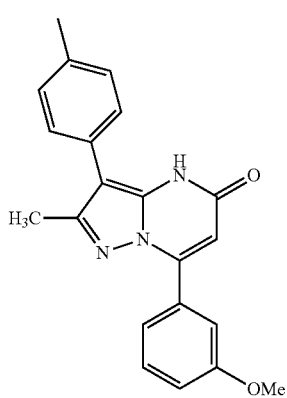

3-Methyl-4-(4-methylphenyl)-1H-pyrazol-5-amine and ethyl 3-(3-methoxyphenyl)-3-oxopropanoate are stirred overnight in a pyridine (10 mL) solvent at 95° C. After cooling to room temperature, the reaction solvent is removed by distillation under reduced pressure. The remainder is extracted with ethyl acetate and water. The extracted organic layer is washed with brine and dehydrated with anhydrous MgSO₄. The dehydrated organic layer is distilled under reduced pressure and the target compound is yielded by column chromatography.

Step 2: Preparation of 5-chloro-3-(4-methylphenyl)-7-(3-methoxyphenyl)-2-methylpyrazolo[1,5-a]pyridinepyrimidine (Chemical Formula 15)

[Chemical Formula 15]

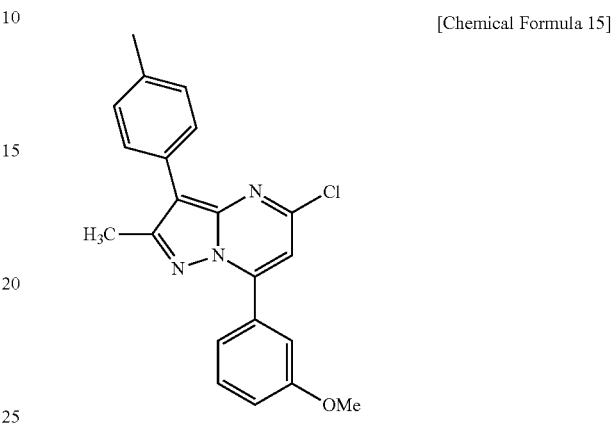

3-(4-Methylphenyl)-7-(3-methoxyphenyl)-2-methylpyrazolo[1,5-a]pyrimidin-5(4H)-one is added to POCl₃ (3 mL) and pyridine (0.1 mL) and stirred for 2 hours while heating. After cooling to room temperature, POCl₃ is removed by distillation under reduced pressure. After the distillation, ethyl acetate (20 mL) and ice are added to the remainder. The organic layer is extracted and it is extracted once again with water and ethyl acetate. The organic layer is washed with 1 M NaHCO₃ aqueous solution and brine. The organic layer is dehydrated with anhydrous MgSO₄. The solvent is removed from the organic layer by distillation under reduced pressure. The remainder is purified by column chromatography to yield the target compound.

Step 3: Preparation of (S)-(1-(3-(4-methylphenyl)-7-(3-methoxyphenyl)-2-methylpyrazolo[1,5-a]pyrimidin-5-yl)pyrrolidin-2-yl)methanol 5-Chloro-3-(4-methylphenyl)-7-(3-methoxyphenyl)-2-methylpyrazolo[1,5-a]pyridinepyrimidine, (S)-pyrrolin-2-ylmethanol and DIPEA (0.2 mL) are added to acetonitrile (10 mL) and stirred overnight at 80° C. After cooling to room temperature, the solvent and volatile substance are removed by distillation under reduced pressure. The remainder is extracted 3 times with ethyl acetate (20 mL) and water. The collected organic layer is washed with brine. The organic layer is dehydrated with anhydrous MgSO₄ and the solvent is removed by distillation under reduced pressure. The remainder is purified by column chromatography to yield the target compound.

Example 26

Preparation of (S)-(1-(3-(4-methylphenyl)-7-(3,4-difluorophenyl)-2-methylpyrazolo[1,5-a]pyrimidin-5-yl)pyrrolidin-2-yl)methanol (Chemical Formula 16)

[Chemical Formula 16]

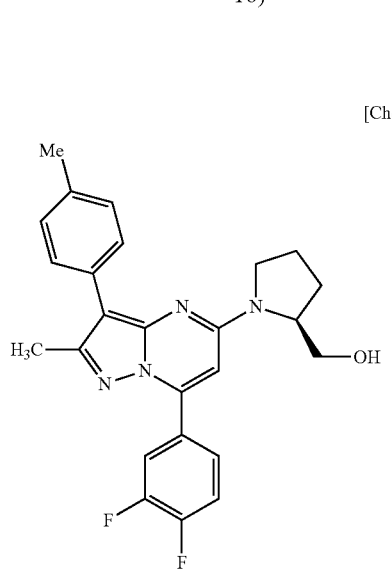

Step 1: Preparation of 7-(3,4-difluorophenyl)-2-methylpyrazolo[1,5-a]pyrimidin-5(4H)-one (Chemical Formula 17)

[Chemical Formula 17]

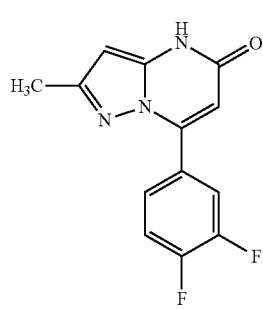

3-Methylpyrazol-5-amine (670 mg) and ethyl 3-(3,4-difluorophenyl)-3-oxopropanoate (1.12 g) are stirred overnight in a pyridine (30 mL) solvent at 85° C. After cooling to room temperature, the reaction solvent is removed by distillation under reduced pressure. The remainder is extracted with ethyl acetate and water. The extracted organic layer is washed with brine and dehydrated with anhydrous MgSO$_4$. The dehydrated organic layer is distilled under reduced pressure and the target compound (821 mg) is yielded by column chromatography. $^1$H NMR (CDCl$_3$, 300 MHz) δ 10.80 (br, 1H), 8.01 (m, 1H), 7.54 (m, 1H), 7.30 (m, 1H), 6.45 (s, 1H), 5.88 (s, 1H), 2.31 (s, 3H).

Step 2: Preparation of 5-chloro-7-(3,4-difluorophenyl)-2-methylpyrazolo[1,5-a]pyrimidine (Chemical Formula 18)

[Chemical Formula 18]

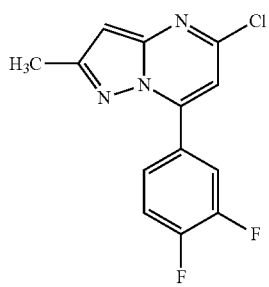

7-(3,4-Difluorophenyl)-2-methylpyrazolo[1,5-a]pyrimidin-5(4H)-one (821 mg) is dissolved in POCl$_3$ (15 mL) and pyridine (0.2 mL) and stirred overnight while heating. After cooling to room temperature, the reaction solvent is removed by distillation under reduced pressure. The remainder is extracted with ethyl acetate and water. The extracted organic layer is washed with 1 M NaHCO$_3$ aqueous solution and brine and dehydrated with anhydrous MgSO$_4$. The dehydrated organic layer is distilled under reduced pressure and the target compound (301 mg) is yielded by column chromatography. $^1$H NMR (CDCl$_3$, 300 MHz) δ 8.08 (m, 1H), 7.78 (m, 1H), 7.36 (q, J=8.7 Hz, 1H), 6.73 (s, 1H), 6.40 (s, 1H), 2.51 (s, 3H).

Step 3: Preparation of 5-chloro-7-(3,4-difluorophenyl)-3-iodo-2-methylpyrazolo[1,5-a]pyrimidine (Chemical Formula 19)

[Chemical Formula 19]

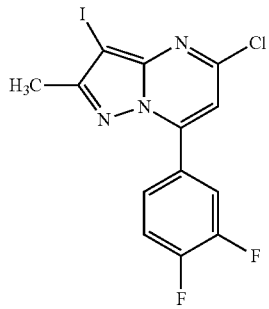

5-Chloro-7-(3,4-difluorophenyl)-2-methylpyrazolo[1,5-a]pyrimidine (301 mg) is dissolved in CH$_2$Cl$_2$ (50 mL). N-Iodosuccinimide (NIS, 500 mg) is added to the reaction solution. The reaction mixture is stirred at room temperature for about 16 hours. The reaction solvent is removed by distillation under reduced pressure. The remainder is extracted with ethyl acetate and water. The extracted organic layer is washed with 1 M NaHCO$_3$ aqueous solution and brine and dehydrated with anhydrous MgSO$_4$. The dehydrated organic layer is distilled under reduced pressure and the target compound (301 mg) is yielded by column chromatography. $^1$H NMR (CDCl$_3$, 300 MHz) δ 8.04 (m, 1H), 7.78 (m, 1H), 7.38 (q, J=8.7 Hz, 1H), 6.85 (s, 1H), 2.51 (s, 3H).

Step 4: Preparation of (S)-(1-(7-(3,4-difluorophenyl)-3-iodo-2-methylpyrazolo[1,5-a]pyrimidin-5-yl)pyrrolidin-2-yl)methanol (Chemical Formula 20)

[Chemical Formula 20]

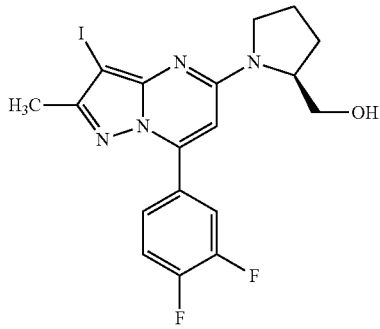

5-Chloro-7-(3,4-difluorophenyl)-3-iodo-2-methylpyrazolo[1,5-a]pyrimidine (401 mg), DIPEA (0.35 mL) and (S)-2-pyrrolidinemethanol (401 mg) are stirred for 2.5 hours in an acetonitrile (60 mL) solvent at 90° C. The reaction solvent is removed by distillation under reduced pressure. The remainder is purified by column chromatography to yield the target compound (395 mg). $^1$H NMR (CDCl$_3$, 300 MHz) δ 7.82 (m, 1H), 7.67 (m, 1H), 7.29 (q, J=8.7 Hz, 1H), 6.11 (s, 1H), 4.45 (br, 1H), 3.85 (m, 1H), 3.77 (m, 1H), 3.57 (m, 2H), 2.38 (s, 3H), 2.08-2.01 (m, 3H), 1.70 (m, 1H).

Step 5: Preparation of (S)-(1-(3-(4-methylphenyl)-7-(3,4-difluorophenyl)-2-methylpyrazolo[1,5-a]pyrimidin-5-yl)pyrrolidin-2-yl)methanol (S)-(1-(7-(3,4-Difluorophenyl)-3-iodo-2-methylpyrazolo[1,5-a]pyrimidin-5-yl)pyrrolidin-2-yl)methanol (74 mg), 4-methylphenylboronic acid (27 mg) and tetrakis(triphenylphosphine)palladium (10 mg) are added to toluene (7 mL), ethanol (3 mL) and 1 N NaHCO$_3$ aqueous solution (1.5 mL) and stirred overnight under argon atmosphere at 85° C. After cooling to room temperature, the reaction solvent is removed by distillation under reduced pressure. The remainder is extracted with ethyl acetate and water. The organic layer is washed with brine and dehydrated with anhydrous MgSO$_4$. The dehydrated organic layer is distilled under reduced pressure, concentrated and purified by column chromatography to yield the target compound (41 mg).

Examples 27-36

Compounds of Examples 27-36 are prepared in a similar manner as Examples 25 and 26.

Chemical formula and NMR analysis data for the compounds of Examples 25-36 are shown in Chemical Formula 21 and Table 3.

[Chemical Formula 21]

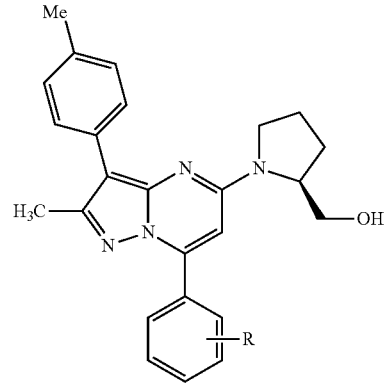

TABLE 3

| Ex. No. | R | $^1$H NMR (CDCl$_3$, 300 MHz) |
|---|---|---|
| 25 | 3-OMe | 7.47 (m, 4H), 7.26 (m, 3H), 7.07 (m, 1H), 6.15 (s, 1H), 5.60 (bs, 1H), 4.41 (m, 1H), 3.88 (s, 3H), 3.63 (m, 4H), 2.47 (s, 3H), 2.38 (s, 3H), 2.05 (m, 3H), 1.75 (m, 1H) |
| 26 | 3-F, 4-F | 7.94 (m, 1 H), 7.71 (m, 1 H), 7.47 (d, J = 7.8 Hz, 2H), 7.31 (m, 1 H), 7.27 (d, 2H), 6.11 (s, 1 H), 4.43 (br, 1 H), 3.74-3.52 (m, 4H), 2.47 (s, 3H), 2.38 (s, 3H), 2.10-1.97 (m, 2H), 1.75 (m, 1H) |
| 27 | 4-OMe | 7.96 (m, 1H), 7.48 (d, J = 7.8 Hz, 1H), 7.26 (m, 2H), 7.06 (m, 2H), 6.11 (s, 1H), 5.70 (bs, 1H), 4.41 (m, 1H), 3.89 (s, 3H), 3.63 (m, 4H), 2.48 (s, 3H), 2.38 (s, 3H), 2.05 (m, 3H), 1.75 (m, 1H) |
| 28 | H | 7.92 (m,2), 7.51 (m, 5H), 7.23 (bs, 2H), 6.11 (s, 1H), 5.60 (bs, 1H), 4.39 (m, 1H), 3.63 (m, 4H), 2.46 (s, 3H), 2.37 (s, 3H), 2.06 (m, 3H), 1.73 (m, 1H) |
| 29 | 4-CF$_3$ | 8.07 (d, J = 7.8 Hz, 2H), 7.80 (d, J = 8.1 Hz, 2H), 7.47 (d, J = 7.8 Hz, 2H), 7.25 (m, 2H), 6.15 (s, 1H), 5.42 (bs, 1H), 4.42 (m, 1H), 3.63 (m, 4H), 2.46 (s, 3H), 2.38 (s, 3H), 2.05 (m, 3H), 1.75 (m, 1H) |
| 30 | 4-Me | 7.84 (d, J = 7.8 Hz, 2H), 7.48 (d, J = 7.8 Hz, 2H), 7.33 (d, J = 8.1 Hz, 2H), 7.25 (m, 2H), 6.11 (s, 1H), 5.67 (bs, 1H), 4.40 (m, 1H), 3.63 (m, 4H), 2.46 (s, 3H), 2.44 (s, 3H) |
| 31 | 3-Et | 7.75 (d, J = 8.4 Hz, 2H), 7.45 (m, 3H), 7.37 (d, J = 7.5 Hz, 1H), 7.26 (d, J = 6.3 Hz, 2H), 6.12 (s, 1H), 5.70 (bs, 1H), 4.42 (m, 1H), 3.66 (m, 4H), 2.75 (dd, J = 7.5 Hz, 2H), 2.47 (s, 3H), 2.38 (s, 3H), 2.09 (m, 3H), 1.77 (m, 1 H), 1.28 (m, 3H) |
| 32 | 4-Cl | 7.91 (d, J = 8.7 Hz, 2H), 7.49 (dd, J = 8.7, 8.1 Hz, 4H), 7.25 (m, 2H), 6.11 (s, 1H), 5.49 (bs, 1H), 4.40 (m, 1H), 3.63 (m, 4H), 2.46 (s, 3H), 2.37 (s, 3H), 2.05 (m, 3H), 1.75 (m, 1H) |

TABLE 3-continued

| Ex. No. | R | $^1$H NMR (CDCl$_3$, 300 MHz) |
|---|---|---|
| 33 | 2-F | 7.77 (t, J = 7.2 Hz, 1H), 7.53 (m, 1H), 7.48 (d, J = 6.6 Hz, 2H), 7.26 (m, 4H), 6.18 (s, 1H), 5.55 (bs, 1H), 4.41 (m, 1H), 3.63 (m, 4H), 2.48 (s, 3H), 2.38 (s, 3H), 2.05 (m, 3H), 1.75 (m, 1H) |
| 34 | 2-F, 4-F | 7.57 (dd, J = 8.1, 6.9 Hz, 1 H), 7.47 (d, J = 7.8 Hz, 2H), 7.25 (d, J = 7.5 Hz, 2H), 6.78 (m, 2H), 6.15 (s, 1H), 5.71 (bs, 1H), 4.42 (m, 1H), 3.79 (m, 2H), 3.54 (m, 2H), 2.42 (s, 3H), 2.37 (s, 3H), 2.06 (m, 3H), 1.74 (m, 1H) |
| 35 | 3-F, 5-F | 7.68 (d, J = 7.8 Hz, 2H), 7.57 (d, J = 6.6 Hz, 2H), 7.29 (d, J = 7.8 Hz, 2H), 6.84 (m, 1H), 6.19 (s, 1H), 5.79 (bs, 1H), 4.63 (m, 1H), 3.66 (m, 4H), 2.59 (s, 3H), 2.41 (s, 3H), 2.13 (m, 3H), 1.93 (m, 1H) |
| 36 | 3-Cl, 4-F | 8.04 (m, 1H), 7.88 (m, 1H), 7.48 (m, 2H), 7.31 (m, 3H), 6.10 (s, 1H), 5.50 (br, 1H), 4.42 (br, 1H), 3.62 (m, 5H), 2,47 (s, 3H), 2.13 (s, 3H), 1.73 (m, 1H), |

Example 37

Preparation of (S)-(1-(3-(4-methoxyphenyl)-7-phenyl-2-methylpyrazolo[1,5-a]pyrimidin-5-yl)pyrrolidin-2-yl)methanol (Chemical Formula 22)

[Chemical Formula 22]

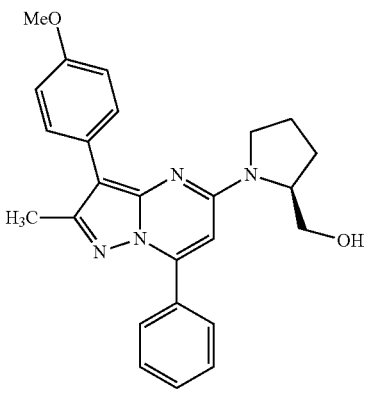

Step 1: Preparation 3-(4-methoxyphenyl)-7-phenyl-2-methylpyrazolo[1,5-a]pyrimidin-5(4H)-one (Chemical Formula 23)

[Chemical Formula 23]

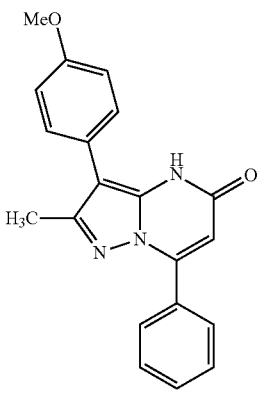

3-Methyl-4-(4-methoxyphenyl)-1H-pyrazol-5-amine (200 mg) and ethyl 3-phenyl-3-oxopropanoate (227 mg) are stirred overnight in a pyridine (10 mL) solvent at 95° C. After cooling to room temperature, the reaction solvent is removed by distillation under reduced pressure. The remainder is extracted with ethyl acetate and water. The extracted organic layer is washed with brine and dehydrated with anhydrous MgSO$_4$. The dehydrated organic layer is distilled under reduced pressure and 270 mg of the target compound is yielded by column chromatography.

Step 2: Preparation of 5-chloro-3-(4-methoxyphenyl)-7-phenyl-2-methylpyrazolo[1,5-a]pyridine pyrimidine (Chemical Formula 24)

[Chemical Formula 24]

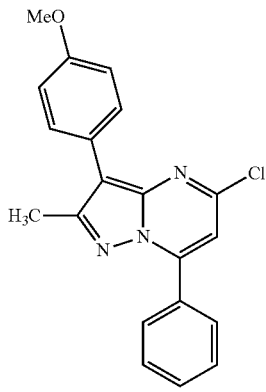

3-(4-Methoxyphenyl)-7-phenyl-2-methylpyrazolo[1,5-a]pyrimidin-5(4H)-one (150 mg) is added to POCl$_3$ (3 mL) and pyridine (0.1 mL) and stirred for 2 hours while heating. After cooling to room temperature, POCl$_3$ is removed by distillation under reduced pressure. After the distillation, ethyl acetate (20 mL) and ice are added to the remainder. The organic layer is extracted and it is extracted once again with water and ethyl acetate. The organic layer is washed with 1 M NaHCO$_3$ aqueous solution and brine. The organic layer is dehydrated with anhydrous MgSO$_4$. The solvent is removed from the organic layer by distillation under reduced pressure. The remainder is purified by column chromatography to yield 119 mg of the target compound. $^1$H NMR (CDCl$_3$, 300 MHz) δ 8.10 (m, 2H), 7.50 (m, 5H), 7.09 (m, 2H), 6.82 (s, 1H), 3.87 (s, 3H) 2.47 (s, 3H).

Step 3: Preparation of (S)-(1-(3-(4-methoxyphenyl)-7-phenyl-2-methylpyrazolo[1,5-a]pyrimidin-5-yl)pyrrolidin-2-yl)methanol 5-Chloro-3-(4-methoxyphenyl)-7-phenyl-2-methylpyrazolo[1,5-a]pyrimidine (50 mg), (S)-pyrrolin-2-ylmethanol (17 mg) and DIPEA (0.2 mL) are added to acetonitrile (10 mL) and stirred overnight at 80° C. After cooling to room temperature, the solvent and volatile substance are removed by distillation under reduced pressure. The remainder is extracted 3 times with ethyl acetate (20 mL) and water. The collected organic layer is washed with brine. The organic layer is dehydrated with anhydrous MgSO$_4$ and the solvent is removed by distillation under reduced pressure. The remainder is purified by column chromatography to yield 48 mg of the target compound.

Example 38

Preparation of (S)-{1-[7-(3,4-difluorophenyl)-3-(4-methoxyphenyl)-2-methylpyrazolo[1,5-a]pyrimidin-5-yl)pyrrolidin-2-yl)methanol (Chemical Formula 25)

(S)-(1-(7-(3,4-Difluorophenyl)-3-iodo-2-methylpyrazolo[1,5-a]pyrimidin-5-yl)pyrrolidin-2-yl)methanol (62 mg), 4-methoxyphenylboronic acid (27 mg) and tetrakis(triphenylphosphine)palladium (10 mg) are added to toluene (8 mL), ethanol (3 mL) and 1 N NaHCO$_3$ aqueous solution (1.5 mL) and stirred for 6 hours under argon atmosphere at 85° C. After cooling to room temperature, the reaction solvent is removed by distillation under reduced pressure. The remainder is extracted with ethyl acetate and water. The organic layer is washed with brine and dehydrated with anhydrous MgSO$_4$. The dehydrated organic layer is distilled under reduced pressure, concentrated and purified by column chromatography to yield the target compound (58 mg).

Examples 39-46

Compounds of Examples 39-46 are prepared in a similar manner as Examples 37 and 38.

Chemical formula and NMR analysis data for the compounds of Examples 37-46 are shown in Chemical Formula 26 and Table 4.

[Chemical Formula 25]

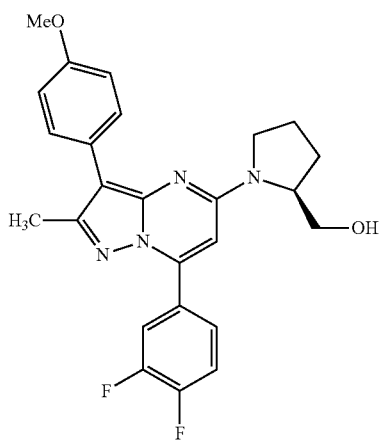

[Chemical Formula 26]

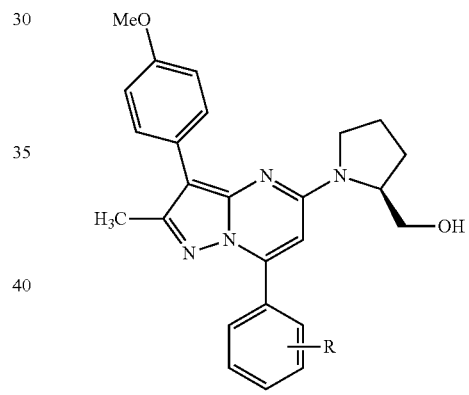

TABLE 4

| Ex. No. | R | $^1$H NMR (CDCl$_3$, 300 MHz) |
|---|---|---|
| 37 | H | 7.92 (m, 2H), 7.50 (m, 3H), 7.47 (d, J = 8.4 Hz, 2H), 6.98 (d, J = 8.4 Hz, 2H), 6.10 (s, 1H), 5.94 (s, 2H), 4.39 (br, 1H), 3.82 (s, 3H), 3.69-3.50 (m, 4H), 2.43 (s, 3H), 2.15-1.99 (m, 3H), 1.78-1.69 (m, 1H) |
| 38 | 3-F, 4-F | 7.90 (m, 1H), 7.70 (m, 1H), 7.51 (d, J = 8.7 Hz, 2H), 7.31 (m, 1H), 7.00 (d, J = 8.1 Hz, 2H), 6.11 (s, 1H), 4.42 (br, 1H), 3.84 (s, 3H), 3.74-3.50 (m, 4H), 2.45 (s, 3H), 2.13-2.00 (m, 2H), 1.77 (m, 1H) |
| 39 | 2-F | 8.12 (m, 1H), 7.37 (d, J = 7.8 Hz, 2H), 7.36 (m, 1H), 7.25 (m, 1H), 7.13 (dd, J = 11.7, 11.4 Hz, 1H), 7.01 (d, J = 8.4 Hz, 2H), 6.46 (s, 1H), 5.78 (bs, 1H), 4.81 (dd, J = 2.7, 7.8 Hz, 1H), 3.85 (s, 3H), 3.79 (m, 2H), 3.69 (m, 2H), 2.59 (s, 3H), 2.12 (m, 3H), 1.91 (m, 1H) |
| 40 | 4-OMe | 7.95 (d, J = 9.0 Hz, 2H), 7.50 (d, J = 8.4 Hz, 2H), 7.02 (dd, J = 9.0 Hz, 4H), 6.10 (s, 1H), 5.71 (bs, 1H), 4.42 (m, 1H), 3.89 (s, 3H), 3.84 (s, 3H), 3.63 (m, 4H), 2.46 (s, 3H), 2.05 (m, 3H), 1.75 (m, 1H) |
| 41 | 3-OMe | 7.49 (m, 5H), 7.02 (m, 1H), 6.97 (d, J = 8.7 Hz, 2H), 6.11 (s, 1H), 4.38 (br, 1H), 3.85 (s, 3H), 3.81 (s, 3H), 3.69-3.50 (m, 4H), 2.42 (s, 3H), 2.15-1.99 (m, 3H), 1.78-1.69 (m, 1H) |
| 42 | 4-Me | 7.84 (d, J = 8.1 Hz, 2H), 7.49 (d, J = 8.7 Hz, 2H), 7.33 (d, J = 7.8 Hz, 2H), 7.00 (d, J = 6.0 Hz, 2H), 6.12 (s, 1H), 4.42 (br, 1H), 3.84 (s, 3H), 3.43.74-3.49 (m, 4H), 2.45 (s, 3H), 2.10-1.97 (m, 3H), 1.78-1.69 (m, 1H) |

TABLE 4-continued

| Ex. No. | R | $^1$H NMR (CDCl$_3$, 300 MHz) |
|---|---|---|
| 43 | 3-Et | 7.74 (dd, J = 10.2, 6.6 Hz, 2H), 7.45 (m, 4H), 6.99 (d, J = 8.4 Hz, 2H), 6.12 (s, 1H), 5.71 (bs, 1H), 4.42 (m, 1H), 3.84 (s, 3H), 3.66 (m, 4H), 2.74 (m, 2H), 2.45 (s, 3H), 2.09 (m, 3H), 1.77 (m, 1H), 1.28 (m, 3H) |
| 44 | 4-Cl | 7.91 (d, J = 8.4 Hz, 2H), 7.50 (dd, J = 8.4, 7.8 Hz, 4H), 6.99 (d, J = 8.7 Hz, 4H), 6.11 (s, 1H), 5.51 (bs, 1H), 4.42 (m, 1H), 3.84 (s, 3H), 3.63 (m, 4H), 2.45 (s, 3H), 2.05 (m, 3H), 1.75 (m, 1H) |
| 45 | 3-F, 5-F | 7.54 (d, J = 6.0 Hz, 2H), 7.48 (d, J = 8.7 Hz, 2H), 6.99 (dd, J = 8.7, 6.0 Hz, 2H), 6.96 (m, 1H), 6.14 (s, 1H), 5.36 (bs, 1H), 4.42 (m, 1H), 3.84 (s, 3H), 3.66 (m, 4H), 2.46 (s, 3H), 2.09 (m, 3H), 1.80 (m, 1H) |
| 46 | 3-Cl, 4-F | 8.15 (m, 1H), 8.01 (m, 1H), 7.89 (m, 1H), 7.50 (m, 1H), 7.30 (m, 1H), 7.01 (m, 2H), 6.10 (s, 1H), 4.42 (br, 1H), 3.89 (s, 3H), 3.60 (m, 4H), 2.45 (s, 3H), 2.13 (m, 2H), 1.75 (m, 1H) |

Example 47

Preparation of (S)-(1-(3-(4-ethoxyphenyl)-7-phenyl-2-methylpyrazolo[1,5-a]pyrimidin-5-yl)pyrrolidin-2-yl)methanol (Chemical Formula 27)

[Chemical Formula 27]

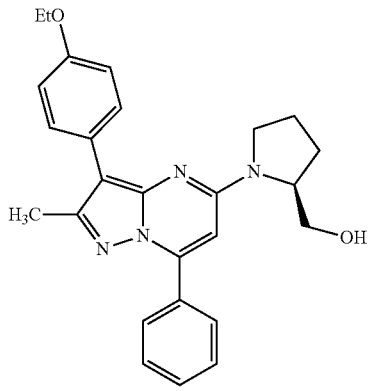

Step 1: Preparation of 3-(4-ethoxyphenyl)-7-phenyl-2-methylpyrazolo[1,5-a]pyrimidin-5(4H)-one (Chemical Formula 28)

[Chemical Formula 28]

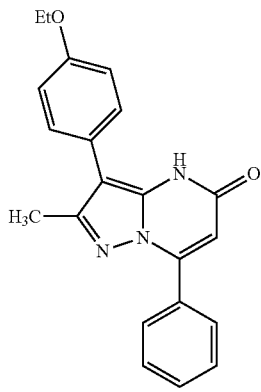

3-Methyl-4-(4-ethoxyphenyl)-1H-pyrazol-5-amine and ethyl 3-phenyl-3-oxopropanoate are stirred overnight in a pyridine (10 mL) solvent at 95° C. After cooling to room temperature, the reaction solvent is removed by distillation under reduced pressure. The remainder is extracted with ethyl acetate and water. The extracted organic layer is washed with brine and dehydrated with anhydrous MgSO$_4$. The dehydrated organic layer is distilled under reduced pressure and the target compound is yielded by column chromatography.

Step 2: Preparation of 5-chloro-3-(4-ethoxyphenyl)-7-phenyl-2-methylpyrazolo[1,5-a]pyridine pyrimidine (Chemical Formula 29)

[Chemical Formula 29]

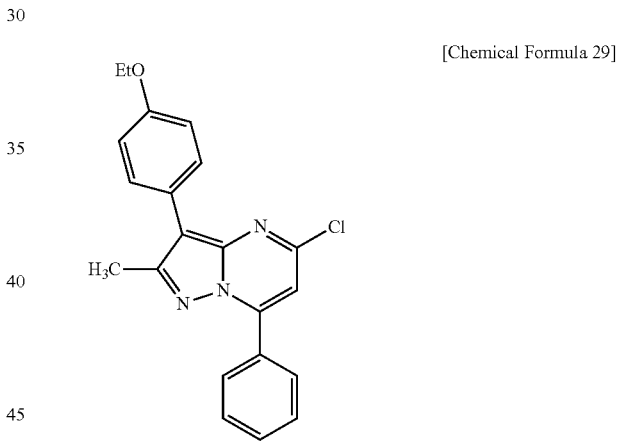

3-(4-Ethoxyphenyl)-7-phenyl-2-methylpyrazolo[1,5-a]pyrimidin-5(4H)-one is added to POCl$_3$ (3 mL) and pyridine (0.1 mL) and stirred for 2 hours while heating. After cooling to room temperature, POCl$_3$ is removed by distillation under reduced pressure. After the distillation, ethyl acetate (20 mL) and ice are added to the remainder. The organic layer is extracted and it is extracted once again with water and ethyl acetate. The organic layer is washed with 1 M NaHCO$_3$ aqueous solution and brine. The organic layer is dehydrated with anhydrous MgSO$_4$. The solvent is removed from the organic layer by distillation under reduced pressure. The remainder is purified by column chromatography to yield the target compound.

Step 3: Preparation of (S)-(1-(3-(4-ethoxyphenyl)-7-phenyl-2-methylpyrazolo[1,5-a]pyrimidin-5-yl)pyrrolidin-2-yl)methanol 5-Chloro-3-(4-ethoxyphenyl)-7-phenyl-2-methylpyrazolo[1,5-a]pyrimidine, (S)-pyrrolin-2-ylmethanol and DIPEA (0.2 mL) are added to acetonitrile (10 mL) and stirred overnight at 80° C. After cooling to room temperature, the solvent and volatile substance are removed by distillation under reduced pressure. The remainder is extracted 3 times with ethyl acetate (20 mL) and water. The collected organic layer is washed with brine. The organic layer is dehydrated with anhydrous $MgSO_4$ and the solvent is removed by distillation under reduced pressure. The remainder is purified by column chromatography to yield the target compound.

Example 48

Preparation of (S)-{1-[7-(3,4-difluorophenyl)-3-(4-ethoxyphenyl)-2-methylpyrazolo[1,5-a]pyrimidin-5-yl)pyrrolidin-2-yl)methanol (Chemical Formula 30)

[Chemical Formula 30]

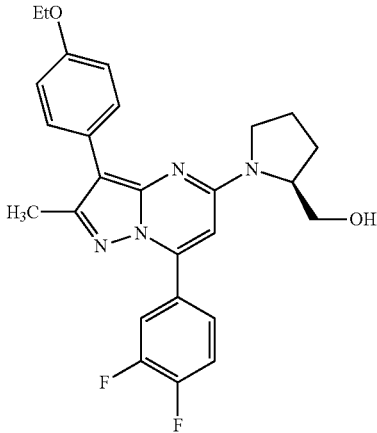

(S)-(1-(7-(3,4-Difluorophenyl)-3-iodo-2-methylpyrazolo[1,5-a]pyrimidin-5-yl)pyrrolidin-2-yl)methanol (27 mg), 4-ethoxyphenylboronic acid (16 mg) and tetrakis(triphenylphosphine)palladium (10 mg) are added to toluene (8 mL), ethanol (3 mL) and 1 N $NaHCO_3$ aqueous solution (1.5 mL) and stirred at 85° C. for 6 hours under argon atmosphere. After cooling to room temperature, the reaction solvent is removed by distillation under reduced pressure. The remainder is extracted with ethyl acetate and water. The organic layer is washed with brine and dehydrated with anhydrous $MgSO_4$. The dehydrated organic layer is distilled under reduced pressure, concentrated and purified by column chromatography to yield the target compound (20 mg).

Examples 49-55

Compounds of Examples 49-55 are prepared in a similar manner as Examples 47 and 48.
Chemical formula and NMR analysis data for the compounds of Examples 47-55 are shown in Chemical Formula 31 and Table 5.

[Chemical Formula 31]

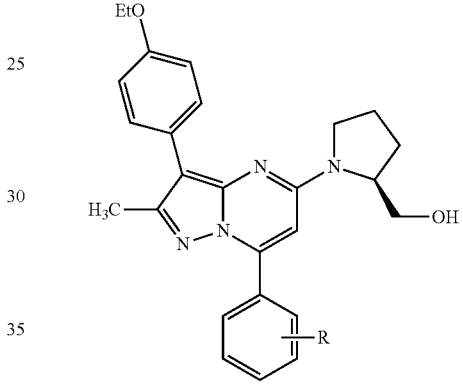

TABLE 5

| Ex. No. | R | $^1$H NMR ($CDCl_3$, 300 MHz) |
|---|---|---|
| 47 | H | 7.92 (m, 2H), 7.50 (m, 3H), 7.45 (d, J = 8.7 Hz, 1H), 6.98 (d, J = 8.7 Hz, 2H), 6.10 (s, 1H), 5.94 (s, 2H), 4.39 (br, 1H), 4.04 (q, J = 7.2 Hz, 2H), 3.69-3.50 (m, 4H), 2.43 (s, 3H), 2.15-1.99 (m, 3H), 1.78-1.69 (m, 1H), 1.40 (t, 6.9 Hz, 3H) |
| 48 | 3-F, 4-F | 7.91 (m, 1H), 7.70 (m, 1H), 7.45 (d, J = 8.4 Hz, 1H), 7.31 (m, 1H), 6.99 (d, J = 8.4 Hz, 2H), 6.11 (s, 1H), 5.74 (bs, 1H), 4.42 (br, 1H), 4.06 (d, J = 6.9 Hz, 2H), 3.73-3.68 (m, 4H), 2.50 (s, 3H), 2.09 (m, 2H), 1.77 (m, 1H), 1.43 (dd, J = 6.9 Hz, 3H) |
| 49 | 2-F | 8.12 (dt, J = 1.2, 7.8 Hz, 1 H), 7.71 (d, J = 8.7 Hz, 2H), 7.36 (m, 1H), 7.25 (m, 1H), 7.11 (dd, J = 11.4 Hz, 1H), 6.99 (d, J = 8.7 Hz, 2H), 6.45 (s, 1H), 5.74 (bs, 1H), 4.83 (bs, 1H), 4.07 (dd, J = 7.2, 6.9 Hz, 2H), 3.79 (m, 2H), 3.68 (m, 2H), 2.58 (s, 3H), 2.10 (m, 3H), 1.92 (m, 1H), 1.43 (dd, J = 7.2, 6.6 Hz, 3H) |
| 50 | 4-OMe | 8.07 (d, J = 9.0 Hz, 2H), 7.48 (d, J = 8.1 Hz, 2H), 7.04 (d, J = 8.4 Hz, 2H), 6.99 (d, J = 8.1 Hz, 2H), 6.09 (s, 1H), 5.65 (bs, 1H), 4.40 (m, 1H), 4.08 (q, J = 6.9 Hz, 2H), 3.88 (s, 3H), 3.63 (m, 4H), 2.46 (s, 3H), 2.04 (m, 3H), 1.73 (m, 1H), 1.42 (t, J = 6.9 Hz, 3H) |
| 51 | 3-OMe | 7.44 (m, 5H), 7.03 (m, 1H), 6.97 (d, J = 8.4 Hz, 2H), 6.11 (s, 1H), 4.38 (br, 1H), 4.06 (q, J = 7.5 Hz, 2H), 3.85 (s, 3H), 3.69-3.50 (m, 4H), 2.42 (s, 3H), 2.15-1.99 (m, 3H), 1.78-1.69 (m, 1H), 1.23 (t, J = 6.6 Hz, 3H) |
| 52 | 4-$CF_3$ | 8.07 (d, J = 8.1 Hz, 2H), 7.79 (d, J = 8.1 Hz, 2H), 7.48 (d, J = 8.7 Hz, 2H), 6.99 (d, J = 8.4 Hz, 2H), 6.14 (s, 1 H), 5.39 (bs, 1H), 4.41 (m, 1H), 4.08 (q, J = 6.9 Hz, 2H), 3.63 (m, 4H), 2.45 (s, 3H), 2.07 (m, 3H), 1.75 (m, 1H), 1.42 (m, 3H) |
| 53 | 4-Me | 7.85 (d, J = 8.1 Hz, 2H), 7.48 (d, J = 8.4 Hz, 2H), 7.33 (d, J = 7.8 Hz, 2H), 6.99 (d, J = 8.4 Hz, 2H), 6.11 (s, 1H), 4.41 (br, 1H), 4.07 (q, J = 6.9 Hz, 2H), 3.78-3.52 (m, 4H), 2.45 (s, 3H), 2.44 (s, 3H), 2.15-1.99 (m, 3H), 1.78-1.69 (m, 1H), 1.42 (t, J = 6.9 Hz, 3H) |

TABLE 5-continued

| Ex. No. | R | $^1$H NMR (CDCl$_3$, 300 MHz) |
|---|---|---|
| 54 | 4-Cl | 7.91 (d, J = 8.4 Hz, 2H), 7.49 (dd, J = 9.9, 8.4 Hz, 4H), 6.98 (d, J = 8.4 Hz, 2H), 6.11 (s, 1H), 5.47 (bs, 1H), 4.41 (m, 1H), 4.08 (dt, J = 6.6, 6.9 Hz, 2H), 3.63 (m, 4H), 2.45 (s, 3H), 2.05 (m, 3H), 1.75 (m, 1H), 1.42 (t, J = 6.9 Hz, 3H) |
| 55 | 3-F, 5-F | 7.73 (m, 2H), 7.48 (d, J = 8.4 Hz, 2H), 6.98 (d, J = 8.4 Hz, 3H), 6.14 (s, 1H), 5.29 (bs, 1H), 4.41 (m, 1H), 4.08 (m, 2H), 3.66 (m, 4H), 2.46 (s, 3H), 2.09 (m, 3H), 1.77 (m, 1H), 1.42 (t, J = 6.9 Hz, 3H) |

Example 56

Preparation of (S)-(1-(3-(3,4-methylenedioxyphenyl)-7-(phenyl)-2-methylpyrazolo[1,5-a]pyrimidin-5-yl)pyrrolidin-2-yl)methanol (Chemical Formula 32)

[Chemical Formula 32]

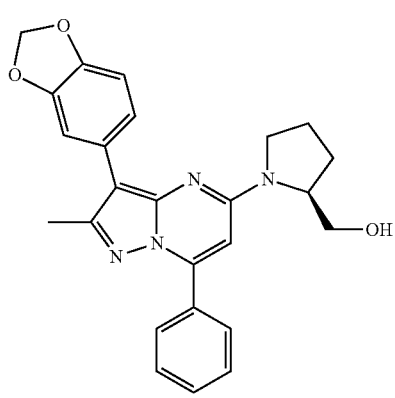

Step 1: Preparation of 3-(3,4-methylenedioxyphenyl)-7-phenyl-2-methylpyrazolo[1,5-a]pyrimidin-5(4H)-one (Chemical Formula 33)

[Chemical Formula 33]

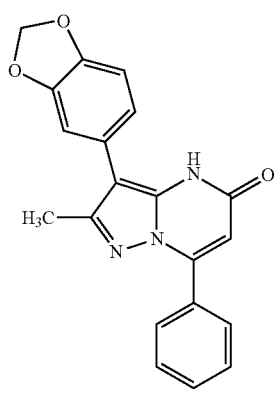

3-Methyl-4-(3,4-methylenedioxyphenyl)-1H-pyrazol-5-amine (300 mg) and ethyl 3-phenyl-3-oxopropanoate (318 mg) are stirred overnight in a pyridine (10 mL) solvent at 95° C. After cooling to room temperature, the reaction solvent is removed by distillation under reduced pressure. The remainder is extracted with ethyl acetate and water. The extracted organic layer is washed with brine and dehydrated with anhydrous MgSO$_4$. The dehydrated organic layer is distilled under reduced pressure 330 mg of the target compound is yielded by column chromatography.

Step 2: Preparation of 5-chloro-3-(3,4-methylenedioxyphenyl)-7-phenyl-2-methylpyrazolo[1,5-a]pyridine pyrimidine (Chemical Formula 34)

[Chemical Formula 34]

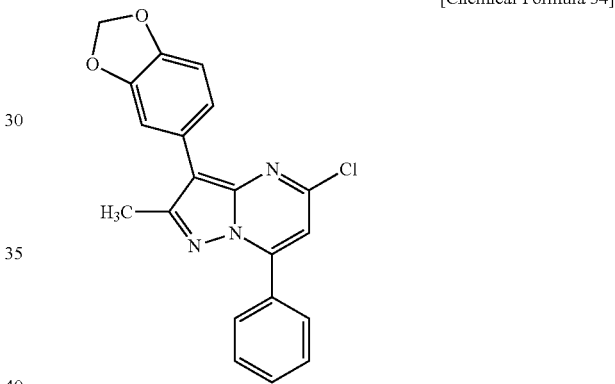

3-(3,4-Methylenedioxyphenyl)-7-phenyl-2-methylpyrazolo[1,5-a]pyrimidin-5(4H)-one (150 mg) is added to POCl$_3$ (3 mL) and pyridine (0.1 mL) and stirred for 2 hours while heating. After cooling to room temperature, POCl$_3$ is removed by distillation under reduced pressure. After the distillation, ethyl acetate (20 mL) and ice are added to the remainder. The organic layer is extracted and it is extracted once again with water and ethyl acetate. The organic layer is washed with 1 M NaHCO$_3$ aqueous solution and brine. The organic layer is dehydrated with anhydrous MgSO$_4$. The solvent is removed from the organic layer by distillation under reduced pressure. The remainder is purified by column chromatography to yield 115 mg of the target compound. $^1$H NMR (CDCl$_3$, 300 MHz) δ 7.92 (m, 2H), 7.50 (m, 5H), 7.05 (s, 1H), 6.85 (s, 1H), 5.94 (s, 2H), 2.40 (s, 3H).

Step 3: Preparation of (S)-(1-(3-(3,4-methylenedioxyphenyl)-7-(phenyl)-2-methylpyrazolo[1,5-a]pyrimidin-5-yl)pyrrolidin-2-yl)methanol 5-Chloro-3-(3,4-methylenedioxyphenyl)-7-phenyl-2-methylpyrazolo[1,5-a]pyrimidine (50 mg), (S)-pyrrolin-2-yl-methanol (16 mg) and DIPEA (0.2 mL) are added to acetonitrile (10 mL) and stirred overnight at 80° C. After cooling to room temperature, the solvent and volatile substance are removed by distillation under reduced pressure. The remainder is extracted 3 times with ethyl acetate (20 mL) and water. The collected organic layer is washed with brine. The organic layer is dehydrated with anhydrous MgSO₄ and the solvent is removed by distillation under reduced pressure. The remainder is purified by column chromatography to yield 45 mg of the target compound.

Examples 57-61

Compounds of Examples 57-61 are prepared in a similar manner as Example 56.

Example 62

Preparation of (S)-(1-(3-(3,4-methylenedioxyphenyl)-7-(3,5-difluorophenyl)-2-methylpyrazolo[1,5-a]pyrimidin-5-yl)pyrrolidin-2-yl)methanol (Chemical Formula 35)

[Chemical Formula 35]

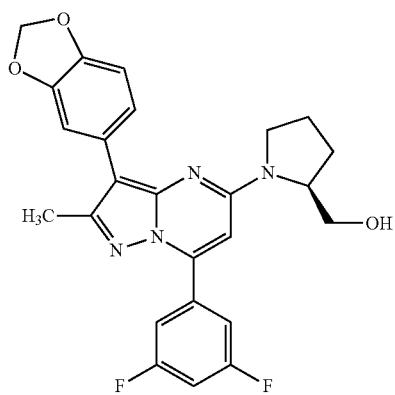

Step 1: Preparation of 7-(3,5-difluorophenyl)-2-methylpyrazolo[1,5-a]pyrimidin-5(4H)-one (Chemical Formula 36)

[Chemical Formula 36]

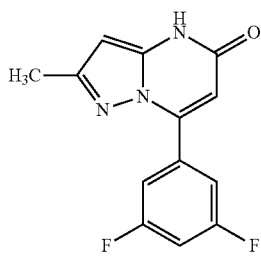

3-Methylpyrazol-5-amine (526 mg) and ethyl 3-(3,5-difluorophenyl)-3-oxopropanoate (879 g) are stirred overnight in a pyridine (30 mL) solvent at 85° C. After cooling to room temperature, the reaction solvent is removed by distillation under reduced pressure. The remainder is extracted with ethyl acetate and water. The extracted organic layer is washed with brine and dehydrated with anhydrous MgSO₄. The dehydrated organic layer is distilled under reduced pressure and purified by column chromatography to yield the target compound (521 mg).

Step 2: Preparation of 5-chloro-7-(3,5-difluorophenyl)-2-methylpyrazolo[1,5-a]pyrimidine (Chemical Formula 37)

[Chemical Formula 37]

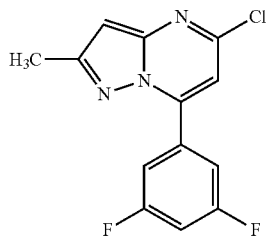

7-(3,5-Difluorophenyl)-2-methylpyrazolo[1,5-a]pyrimidin-5(4H)-one (521 mg) is dissolved in POCl₃ (15 mL) and pyridine (0.2 mL) and stirred overnight while heating at 100° C. After cooling to room temperature, the reaction solvent is removed by distillation under reduced pressure. The remainder is extracted with ethyl acetate and water. The extracted organic layer is washed with 1 M NaHCO₃ aqueous solution and brine and dehydrated with anhydrous MgSO₄. The dehydrated organic layer is distilled under reduced pressure and purified by column chromatography to yield the target compound (327 mg). ¹H NMR (CDCl₃, 300 MHz) δ 7.63 (m, 2H), 7.02 (m, 1H), 6.82 (m, 1H), 6.52 (m, 1H), 2.52 (s, 3H).

Step 3: Preparation of 5-chloro-7-(3,5-difluorophenyl)-3-iodo-2-methylpyrazolo[1,5-a]pyrimidine (Chemical Formula 38)

[Chemical Formula 38]

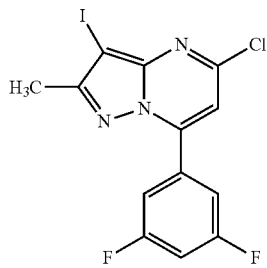

5-Chloro-7-(3,5-difluorophenyl)-2-methylpyrazolo[1,5-a]pyrimidine (327 mg) is dissolved in CH₂Cl₂ (50 mL). N-Iodosuccinimide (NIS, 304 mg) is added to the reaction solution. The reaction mixture is stirred at room temperature for about 16 hours. The reaction solvent is removed by distillation under reduced pressure. The remainder is extracted with ethyl acetate and water. The extracted organic layer is washed with 1 M NaHCO₃ aqueous solution and brine and dehydrated with anhydrous MgSO₄. The dehydrated organic layer is distilled under reduced pressure and purified by column chromatography to yield the target compound (301 mg).

Step 4: Preparation of (S)-(1-(7-(3,5-difluorophenyl)-3-iodo-2-methylpyrazolo[1,5-a]pyrimidin-5-yl)pyrrolidin-2-yl)methanol (Chemical Formula 39)

[Chemical Formula 39]

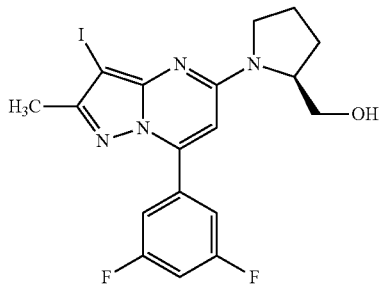

5-Chloro-7-(3,5-difluorophenyl)-3-iodo-2-methylpyrazolo[1,5-a]pyrimidine obtained in Step 3, DIPEA (0.35 mL) and (S)-2-pyrrolidinemethanol (401 mg) are stirred in an acetonitrile (60 mL) solvent for 2.5 hours at 90° C. The reaction solvent is removed by distillation under reduced pressure. The remainder is purified by column chromatography to yield the target compound. $^1$H NMR (CDCl$_3$, 300 MHz); δ 7.46 (m, 2H), 6.98 (m, 1H), 6.13 (s, 1H), 4.45 (br, 1H), 3.85-3.57 (m, 5H), 2.38 (s, 3H), 2.08-2.04 (m, 3H), 1.77 (m, 1H).

Step 5: Preparation of (S)-(1-(3-(3,4-methylenedioxyphenyl)-7-(3,5-difluorophenyl)-2-methylpyrazolo[1,5-a]pyrimidin-5-yl)pyrrolidin-2-yl)methanol (S)-(1-(7-(3,5-Difluorophenyl)-3-iodo-2-methylpyrazolo[1,5-a]pyrimidin-5-yl)pyrrolidin-2-yl)methanol (40 mg), 3,4-methylenedioxyphenylboronic acid (23 mg) and tetrakis(triphenylphosphine)palladium (10 mg) are added to toluene (5 mL), ethanol (3 mL) and 1 N NaHCO$_3$ aqueous solution (1.5 mL) and stirred at 85° C. for 4 hours under argon atmosphere. After cooling to room temperature, the reaction solvent is removed by distillation under reduced pressure. The remainder is extracted with ethyl acetate and water. The organic layer is washed with brine and dehydrated with anhydrous MgSO$_4$. The dehydrated organic layer is concentrated by distillation under reduced pressure and purified by column chromatography to yield the target compound (36 mg).

Chemical formula and NMR analysis data for the compounds of Examples 56-62 are shown in Chemical Formula 40 and Table 6.

[Chemical Formula 40]

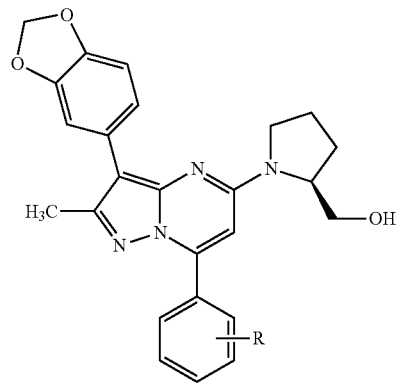

TABLE 6

| Ex. No. | R | $^1$H NMR (CDCl$_3$, 300 MHz) |
|---|---|---|
| 56 | H | 7.88 (m, 2H), 7.50 (m, 3H), 7.05 (s, 1H), 6.98 (m, 1H), 6.87 (d, J = 7.8 Hz, 1H), 6.10 (s, 1H), 5.94 (s, 2H), 4.36 (br, 1H), 3.78-3.52 (m, 4H), 2.40 (s, 3H), 2.15-1.99 (m, 3H), 1.78-1.69 (m, 1H) |
| 57 | 2-F | 8.10 (t, J = 7.8 Hz, 1H), 8.37 (s, 2H), 7.19 (m, 3H), 6.91 (d, J = 8.1 Hz, 1H), 6.45 (s, 1H), 5.98 (s, 2H), 5.75 (bs, 1H), 4.74 (bs, 1H), 3.82 (m, 2H), 3.69 (m, 2H), 2.57 (s, 3H), 2.11 (bs, 3H), 1.93 (m, 1H) |
| 58 | 3-OMe | 7.44 (m, 3H), 7.03 (m, 3H), 6.88 (d, J = 8.1 Hz, 2H), 6.12 (s, 1H), 5.96 (s, 2H), 4.38 (br, 1H), 3.85 (s, 3H), 3.81 (s, 3H), 3.69-3.50 (m, 4H), 2.42 (s, 3H), 2.15-1.99 (m, 3H), 1.78-1.69 (m, 1H) |
| 59 | 4-Me | 7.83 (d, J = 7.8 Hz, 2H), 7.34 (d, J = 7.8 Hz, 2H), 7.10 (s, 1H), 7.03 (d, J = 7.8 Hz, 1H), 6.91 (d, J = 7.8 Hz, 1H), 6.12 (s, 1H), 5.98 (s, 2H), 4.41 (br, 1H), 3.78-3.52 (m, 4H), 2.45 (s, 3H), 2.44 (s, 3H), 2.15-1.99 (m, 3H), 1.78-1.69 (m, 1H) |
| 60 | 3-Et | 7.73 (m, 2H), 7.44 (dd, J = 7.5, 7.2 Hz, 2H), 7.37 (d, J = 6.6 Hz, 1H), 7.10 (s, 1H), 7.03 (d, J = 7.8 Hz, 1H), 6.90 (d, J = 8.1 Hz, 1H), 6.12 (s, 1H), 5.98 (s, 2H), 5.61 (bs, 1H), 4.42 (m, 1H), 3.66 (m, 4H), 2.77 (m, 2H), 2.45 (s, 3H), 2.09 (m, 3H), 1.77 (m, 1H), 1.29 (m, 3H) |
| 61 | 3-F, 4-F | 7.89 (m, 1H), 7.70 (m, 2H), 7.45 (m, 2H), 7.03 (s, 1H), 7.01 (d, J = 8.4 Hz, 1H), 6.90 (d, J = 8.4 Hz, 1H), 6.12 (s, 1H), 5.99 (s, 2H), 5.74 (bs, 1H), 4.44 (br, 1H), 3.74-3.53 (m, 4H), 2.46 (s, 3H), 2.17-2.02 (m, 2H), 1.78 (m, 1H) |
| 62 | 3-F, 5-F | 7.54 (m, 2H), 7.09 (s, 1H), 7.01 (m, 2H), 6.92 (m, 1H), 6.14 (s, 1H), 5.99 (s, 2H), 4.42 (br, 1H), 3.75-3.56 (m, 4H), 2.47 (s, 3H), 2.17-2.00 (m, 2H), 1.87 (m, 1H) |

Example 63

Preparation of (S)-(1-(3-(4-methylphenyl)-7-(4-fluorophenyl)-2-methylpyrazolo[1,5-a]pyrimidin-5-yl)pyrrolidin-2-yl)methanol (Chemical Formula 41)

[Chemical Formula 41]

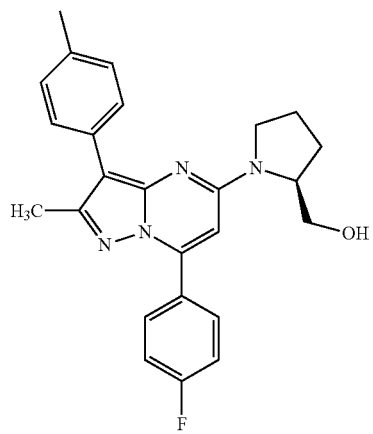

Step 1: Preparation of 3-(4-methylphenyl)-7-(4-fluorophenyl)-2-methylpyrazolo[1,5-a]pyrimidin-5(4H)-one (Chemical Formula 42)

[Chemical Formula 42]

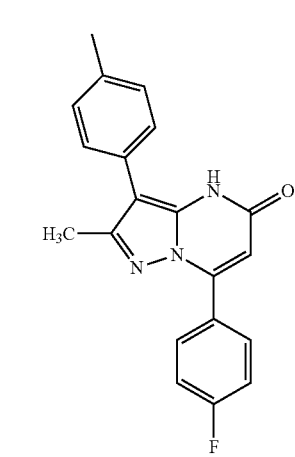

3-Methyl-4-(4-methylphenyl)-1H-pyrazol-5-amine and ethyl 3-(4-fluorophenyl)-3-oxopropanoate are stirred overnight in a pyridine (10 mL) solvent at 95° C. After cooling to room temperature, the reaction solvent is removed by distillation under reduced pressure. The remainder is extracted with ethyl acetate and water. The extracted organic layer is washed with brine and dehydrated with anhydrous MgSO$_4$. The dehydrated organic layer is distilled under reduced pressure and purified by column chromatography to yield the target compound.

Step 2: Preparation of 5-chloro-3-(4-methylphenyl)-7-(4-fluorophenyl)-2-methylpyrazolo[1,5-a]pyridine pyrimidine (Chemical Formula 43)

[Chemical Formula 43]

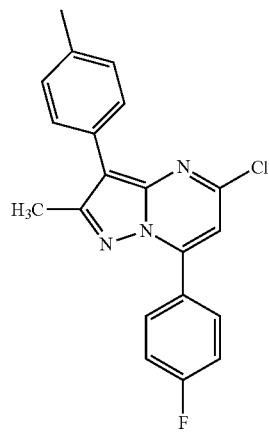

3-(4-Methylphenyl)-7-(4-fluorophenyl)-2-methylpyrazolo[1,5-a]pyrimidin-5(4H)-one is added to POCl$_3$ (3 mL) and pyridine (0.1 mL) and stirred for 2 hours while heating. After cooling to room temperature, POCl$_3$ is removed by distillation under reduced pressure. After the distillation, ethyl acetate (20 mL) and ice are added to the remainder. The organic layer is extracted and it is extracted once again with water and ethyl acetate. The organic layer is washed with 1 M NaHCO$_3$ aqueous solution and brine. The organic layer is dehydrated with anhydrous MgSO$_4$. The solvent is removed from the organic layer by distillation under reduced pressure. The remainder is purified by column chromatography to yield the target compound.

Step 3: Preparation of (S)-(1-(3-(4-methylphenyl)-7-(4-fluorophenyl)-2-methylpyrazolo[1,5-a]pyrimidin-5-yl)pyrrolidin-2-yl)methanol 5-Chloro-3-(4-methylphenyl)-7-(4-fluorophenyl)-2-methylpyrazolo[1,5-a]pyrimidine, (S)-pyrrolin-2-ylmethanol and DIPEA (0.2 mL) are added to acetonitrile (10 mL) and stirred overnight at 80° C. After cooling to room temperature, the solvent and volatile substance are removed by distillation under reduced pressure. The remainder is extracted 3 times with ethyl acetate (20 mL) and water. The collected organic layer is washed with brine. The organic layer is dehydrated with anhydrous MgSO$_4$ and the solvent is removed by distillation under reduced pressure. The remainder is purified by column chromatography to yield the target compound.

Example 64

Preparation of (S)-(1-(3-(4-methoxyphenyl)-7-(4-fluorophenyl)-2-methylpyrazolo[1,5-a]pyrimidin-5-yl)pyrrolidin-2-yl)methanol (Chemical Formula 44)

[Chemical Formula 44]

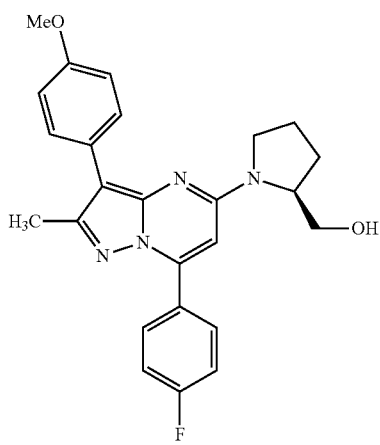

Step 1: Preparation of 7-(4-difluorophenyl)-2-methylpyrazolo[1,5-a]pyrimidin-5(4H)-one (Chemical Formula 45)

[Chemical Formula 45]

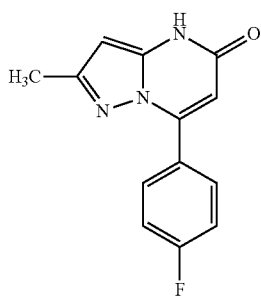

3-Methylpyrazol-5-amine (245 mg) and methyl 3-(4-fluorophenyl)-3-oxopropanoate (453 mg) are stirred overnight in a pyridine (10 mL) solvent at 95° C. After cooling to room temperature, the reaction solvent is removed by distillation under reduced pressure. The remainder is extracted with ethyl acetate and water. The extracted organic layer is washed with brine and dehydrated with anhydrous MgSO₄. The dehydrated organic layer is distilled under reduced pressure and purified by column chromatography to yield the target compound (151 mg). $^1$H NMR (CDCl₃, 300 MHz) δ 10.20 (br, 1H), 8.10 (m, 1H), 7.94 (m, 1H), 7.11 (m, 3H), 6.39 (s, 1H), 4.04 (s, 1H), 2.30 (s, 3H).

Step 2: Preparation of 5-chloro-7-(4-fluorophenyl)-2-methylpyrazolo[1,5-a]pyrimidine (Chemical Formula 46)

[Chemical Formula 46]

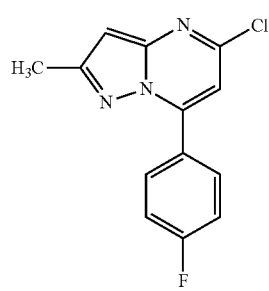

7-(4-Fluorophenyl)-2-methylpyrazolo[1,5-a]pyrimidin-5 (4H)-one (151 mg) is dissolved in POCl₃ (10 mL) and pyridine (0.1 mL) and stirred overnight while heating. After cooling to room temperature, the reaction solvent is removed by distillation under reduced pressure. The remainder is extracted with ethyl acetate and water. The extracted organic layer is washed with 1 M NaHCO₃ aqueous solution and brine and dehydrated with anhydrous MgSO₄. The dehydrated organic layer is distilled under reduced pressure and purified by column chromatography to yield the target compound (156 mg). $^1$H NMR (CDCl₃, 300 MHz); δ 8.07 (m, 2H), 7.26 (m, 2H), 6.78 (m, 1H), 6.48 (s, 1H), 2.50 (s, 3H).

Step 3: Preparation of 5-chloro-7-(4-difluorophenyl)-3-iodo-2-methylpyrazolo[1,5-a]pyrimidine (Chemical Formula 47)

[Chemical Formula 47]

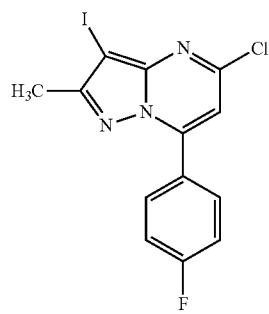

5-Chloro-7-(4-fluorophenyl)-2-methylpyrazolo[1,5-a]pyrimidine (128 mg) is dissolved in CH₂Cl₂ (50 mL). N-Iodosuccinimide (NIS, 165 mg) is added to the reaction solution. The reaction mixture is stirred at room temperature for about 16 hours. The reaction solvent is removed by distillation under reduced pressure. The remainder is extracted with ethyl acetate and water. The extracted organic layer is washed with 1 M NaHCO₃ aqueous solution and brine and dehydrated with anhydrous MgSO₄. The dehydrated organic layer is distilled under reduced pressure and purified by column chromatography to yield the target compound (182 mg). $^1$H NMR (CDCl₃, 300 MHz); δ 8.05 (m, 2H), 7.26 (m, 2H), 6.84 (s, 1H), 2.51 (s, 3H).

Step 4: Preparation of (S)-(1-(7-(4-fluorophenyl)-3-iodo-2-methylpyrazolo[1,5-a]pyrimidin-5-yl)pyrrolidin-2-yl)methanol (Chemical Formula 48)

[Chemical Formula 48]

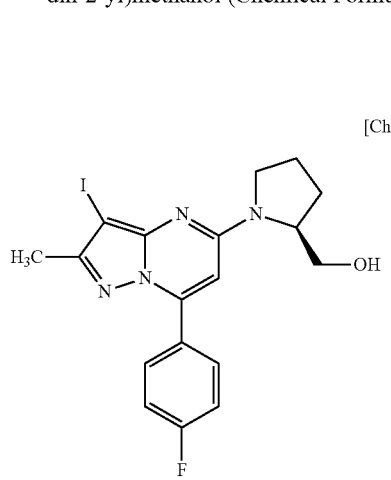

5-Chloro-7-(4-fluorophenyl)-3-iodo-2-methylpyrazolo[1,5-a]pyrimidine (241 mg), DIPEA (0.2 mL) and (S)-2-pyrrolidinemethanol (152 mg) are stirred at 90° C. for 16 hours in an acetonitrile (60 mL) solvent. The reaction solvent is removed by distillation under reduced pressure. The remainder is purified by column chromatography to yield the target compound (172 mg). $^1$H NMR (CDCl$_3$, 300 MHz); δ 7.92 (m, 2H), 7.22 (m, 2H), 6.10 (s, 1H), 4.45 (br, 1H), 3.85-3.57 (m, 4H), 2.38 (s, 3H), 2.08-2.01 (m, 3H), 1.72 (m, 1H).

Step 5: Preparation of (S)-(1-(3-(4-methoxyphenyl)-7-(4-fluorophenyl)-2-methylpyrazolo[1,5-a]pyrimidin-5-yl)pyrrolidin-2-yl)methanol (S)-(1-(7-(4-Fluorophenyl)-3-iodo-2-methylpyrazolo[1,5-a]pyrimidin-5-yl)pyrrolidin-2-yl)methanol (56 mg), 4-methoxyphenylboronic acid (30 mg) and tetrakis(triphenylphosphine)palladium (10 mg) are added to toluene (10 mL), ethanol (5 mL) and 1 N NaHCO$_3$ aqueous solution (1.5 mL) and stirred overnight at 90° C. under argon atmosphere. After cooling to room temperature, the reaction solvent is removed by distillation under reduced pressure. The remainder is extracted with ethyl acetate and water. The organic layer is washed with brine and dehydrated with anhydrous MgSO$_4$. The dehydrated organic layer is concentrated by distillation under reduced pressure and purified by column chromatography to yield the target compound (27 mg).

Examples 65-109

Compounds of Examples 65-109 are prepared in a similar manner as Examples 63 and 64.

Chemical formula and NMR analysis data for the compounds of Examples 63-109 are shown in Chemical Formula 49 and Table 7.

[Chemical Formula 49]

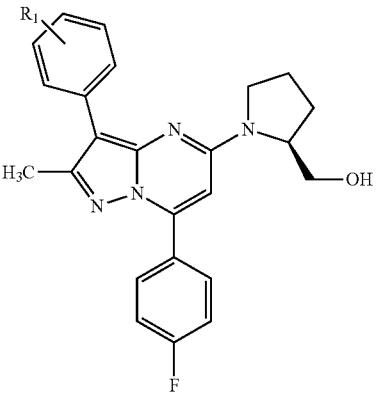

TABLE 7

| Ex. No. | R$_1$ | $^1$H NMR (CDCl$_3$, 300 MHz) |
|---|---|---|
| 63 | 4-Me | 7.96 (dd, J = 8.7, 8.4 Hz, 2H), 7.47 (d, J = 7.8 Hz, 2H), 7.26 (m, 4H), 6.10 (s, 1H), 5.54 (bs, 1H), 4.41 (m, 1H), 3.63 (m, 4H), 2.46 (s, 3H), 2.38 (s, 3H), 2.05 (m, 3H), 1.75 (m, 1H) |
| 64 | 4-MeO | 7.96 (m, 2H), 7.46 (m, 2H), 7.23 (m, 2H), 7.00 (m, 2H), 6.09 (s, 1H), 4.42 (br, 1H), 3.82 (s, 3H), 3.71-3.59 (m, 4H), 2.44 (s, 3H), 2.11-2.00 (m, 3H), 1.77 (m, 1H) |
| 65 | 4-EtO | 7.96 (dd, J = 8.7 Hz, 2H), 7.47 (d, J = 8.4 Hz, 2H), 7.26 (m, 2H), 6.99 (d, J = 8.7 Hz, 2H), 6.10 (s, 1H), 5.55 (bs, 1H), 4.41 (m, 1H), 4.07 (td, J = 6.9, 7.2 Hz, 2H), 3.63 (m, 4H), 2.45 (s, 3H), 2.05 (m, 3H), 1.75 (m, 1H), 1.42 (t, J = 6.9 Hz, 3H) |
| 66 | 3,4-methylenedioxy | 7.96 (m, 2H), 7.21 (d, J = 8.7 Hz, 2H), 7.09 (s, 1H), 7.00 (m, 1H), 6.90 (d, J = 8.4 Hz, 2H), 6.10 (s, 1H), 5.98 (s, 2H), 4.43 (br, 1H), 3.73-3.52 (m, 4H), 2.44 (s, 3H), 2.10-2.01 (m, 3H), 1.77 (m, 1H) |
| 67 | 4-CF$_2$H | 7.94 (m, 2H), 7.69 (d, J = 8.1 Hz, 2H), 7.55 (d, J = 8.1 Hz, 2H), 7.19 (d, J = 8.7 Hz, 2H), 6.64 (s, 1H), 6.10 (s, 1H), 4.44 (br, 1H), 3.72-3.50 (m, 4H), 2.47 (s, 3H), 2.38 (s, 3H), 2.15-1.99 (m, 3H), 1.78-1.69 (m, 1H) |
| 68 | 4-CH$_3$S | 7.96 (dd, J = 8.7 Hz, 2H), 7.53 (d, J = 8.4 Hz, 2H), 7.34 (d, J = 8.4 Hz, 2H), 7.20 (d, J = 9.0 Hz, 2H), 6.12 (s, 1H), 5.30 (bs, 1H), 4.44 (m, 1H), 3.63 (m, 4H), 2.51 (s, 3H), 2.47 (s, 3H), 2.06 (m, 3H), 1.78 (m, 1H) |
| 69 | 4-CF$_3$ | 7.97 (dd, J = 8.1 Hz, 2H), 7.77 (d, J = 8.4 Hz, 2H), 7.68 (d, J = 8.4 Hz, 2H), 7.21 (d, J = 8.4 Hz, 2H), 6.17 (s, 1H), 5.01 (bs, 1H), 4.49 (m, 1H), 3.62 (m, 4H), 2.51 (s, 3H), 2.05 (m, 3H), 1.83 (m, 1H) |
| 70 | 4-Et | 7.97 (dd, J = 8.7 Hz, 2H), 7.90 (m, 1H), 7.52 (d, J = 8.1 Hz, 2H), 7.25 (m, 4H), 6.10 (s, 1H), 5.41 (bs, 1H), 4.42 (m, 1H), 3.62 (m, 4H), 2.70 (q, J = 7.5 Hz, 2H), 2.48 (s, 3H), 2.05 (m, 3H), 1.78 (m, 1H), 1.28 (t, J = 7.8 Hz, 3H) |
| 71 | 4-vinyl | 7.96 (m, 2H), 7.58 (d, J = 8.4 Hz, 2H), 7.50 (d, J = 8.4 Hz, 2H), 7.20 (d, J = 8.4 Hz, 2H), 6.74 (m, 1H), 6.13 (s, 1H), 5.76 (d, J = 8.4 Hz, 1H), 5.21 (d, J = 8.1 Hz, 1H), 4.46 (br, 1H), 3.69-3.50 (m, 4H), 2.49 (s, 3H), 2.10-1.97 (m, 3H), 1.78-1.69 (m, 1H) |
| 72 | 4-propyl | 7.76 M, 2H), 7.50 (d, J = 7.8 Hz, 2H), 7.25 (m, 2H), 7.20 (d, J = 8.7 Hz, 2H), 6.11 (s, 1H), 4.43 (br, 1H), 3.78-3.49 (m, 4H), 2.62 (t, J = 7.8 Hz, 2H), 2.49 (s, 3H), 2.17-1.97 (m, 3H), 1.78-1.69 (m, 1H), 1.68 (m, 2H), 0.99 (t, J = 7.8 Hz, 3H) |
| 73 | 4-n-butyl | 7.98 (m, 2H), 7.50 (d, J = 8.4 Hz, 2H), 7.25 (m, 4H), 6.11 (s, 1H), 4.43 (br, 1H), 3.74-3.55 (m, 4H), 2.64 (t, J = 7.8 Hz, 2H), 2.48 (s, 3H), 2.13-1.99 (m, 3H), 1.77 (m, 1H), 1.65 (m, 2H), 1.44 (m, 2H), 0.95 (t, J = 6.9 Hz, 3H) |
| 74 | 4-n-PrO | 7.96 (dd, J = 8.7, 8.4 Hz, 2H), 7.47 (d, J = 8.7 Hz, 2H), 7.26 (m, 2H), 6.99 (d, J = 8.4 Hz, 2H) 6.10 (s, 1H), 5.52 (bs, 1H), 4.41 (m, 1H), 3.96 (t, J = 6.6 Hz, |

TABLE 7-continued

| Ex. No. | R₁ | ¹H NMR (CDCl₃, 300 MHz) |
|---|---|---|
| | | 2H), 3.63 (m, 4H), 2.45 (s, 3H), 2.05 (m, 3H), 1.75 (m, 3H), 1.05 (t, J = 7.2 Hz, 3H) |
| 75 | 4-n-BuO | 7.96 (m, 2H), 7.47 (d, J = 8.4 Hz, 2H), 7.25 (m, 2H), 6.98 (d, J = 8.7 Hz, 2H), 6.10 (s, 1H), 5.56 (bs, 1H), 4.42 (m, 1H), 3.99 (dd, J = 6.3, 6.6 Hz, 2H), 3.63 (m, 4H), 2.99 (m, 2H), 2.45 (s, 3H), 2.06 (m, 3H), 1.78 (m, 3H), 1.49 (m, 2H), 0.98 (dd, J = 7.2, 7.5 Hz, 3H) |
| 76 | 3,4-diF | 7.96 (m, 2H), 7.48 (m, 1H), 7.33 (m, 1H), 7.20 (m, 3H), 6.15 (s, 1H), 4.48 (br, 1H), 3.78-3.52 (m, 4H), 2.47 (s, 3H), 2.15-1.99 (m, 3H), 1.78-1.69 (m, 1H) |
| 77 | 2,4-diF | 7.96 (m, 2H), 7.23 (m, 4H), 6.66 (m, 1H), 6.15 (s, 1H), 4.48 (br, 1H), 3.78-3.52 (m, 4H), 2.47 (s, 3H), 2.15-1.99 (m, 3H), 1.78-1.69 (m, 1H) |
| 78 | 3,5-diF | 7.96 (m, 2H), 7.23 (m, 4H), 6.66 (m, 1H), 6.16 (s, 1H), 4.48 (br, 1H), 3.78-3.52 (m, 4H), 2.52 (s, 3H), 2.15-1.99 (m, 3H), 1.78-1.69 (m, 1H) |
| 79 | 3-F, 4-Me | 7.97 (m, 2H), 7.29 (m, 2H), 7.22 (m, 2H), 6.13 (s, 1H), 4.45 (br, 1H), 3.75-3.53 (m, 4H), 2.48 (s, 3H), 2.30 (s, 3H), 2.115-1.99 (m, 3H), 1.78 (m, 1H) |
| 80 | 3-F, 4-MeO | 7.96 (m, 2H), 7.38 (m, 2H), 7.20 (d, J = 8.4 Hz, 2H), 7.05 (m, 1H), 6.13 (s, 1H), 4.45 (br, 1H), 3.92 (s, 3H), 3.78-3.52 (m, 4H), 2.47 (s, 3H), 2.15-1.99 (m, 3H), 1.78-1.69 (m, 1H) |
| 81 | 4-EtO, 3-F | 7.96 (m, 2H), 7.38 (m, 1H), 7.30 (d, J = 8.7 Hz, 1H), 7.22 (m, 2H), 7.04 (m, 1H), 6.13 (s, 1H), 4.45 (br, 1H), 4.15 (q, J = 6.9 Hz, 2H), 3.78-3.52 (m, 4H), 2.47 (s, 3H), 2.17 (s, 3H), 2.15-1.99 (m, 3H), 1.78-1.69 (m, 1H), 1.47 (t, J = 7.2 Hz, 3H) |
| 82 | 4-F | 7.96 (m, 2H), 7.52 (m, 2H), 7.22 (m, 2H), 7.13 (m, 2H), 6.12 (s, 1H), 4.42 (br, 1H), 3.76-3.52 (m, 4H), 2.44 (s, 3H), 2.13-2.00 (m, 3H), 1.77 (m, 1H) |
| 83 | H | 7.97 (m, 2H), 7.59 (d, J = 7.8 Hz, 1H), 7.45 (t, J = 7.5 Hz, 2H), 7.26 (m, 3H), 6.12 (s, 1H), 5.35 (bs, 1H), 4.42 (m, 1H), 3.63 (m, 4H), 2.49 (s, 3H), 2.05 (m, 3H), 1.75 (m, 1H) |
| 84 | 4-CF₃O | 7.96 (m, 3H), 7.64 (d, J = 8.4 Hz, 2H), 7.22 (m, 3H), 6.14 (s, 1H), 5.07 (bs, 1H), 4.46 (m, 1H), 3.62 (m, 4H), 2.48 (s, 3H), 2.05 (m, 3H), 1.78 (m, 1H) |
| 85 | 4-iso-PrO | 7.94 (m, 1H), 7.87 (m, 1H), 7.44 (d, J = 7.8 Hz, 2H), 7.17 (d, J = 8.4 Hz, 2H), 6.93 (d, J = 8.4 Hz, 2H), 6.10 (s, 1H), 5.40 (bs, 1H), 4.58 (m, 1H), 4.44 (m, 1H), 3.62 (m, 4H), 2.43 (s, 3H), 2.01 (m, 3H), 1.73 (m, 1H), 1.34 (s, 3H), 1.32 (s, 3H) |
| 86 | 4-acetyl | 8.04 (d, J = 8.4 Hz, 2H), 7.95 (dd, J = 9.0, 8.7 Hz, 2H), 7.78 (d, J = 8.1 Hz, 2H), 7.21 (d, J = 8.7 Hz, 2H), 6.16 (s, 1H), 4.99 (bs, 1H), 4.50 (m, 1H), 3.62 (m, 4H), 2.62 (s, 3H), 2.52 (s, 3H), 2.05 (m, 3H), 1.83 (m, 1H) |
| 87 | 2-F | 7.98 (m, 2H), 7.45 (m, 1H), 7.30 (m, 1H), 7.21 (m, 4H), 6.11 (s, 1H), 4.43 (br, 1H), 3.63-3.54 (m, 4H), 2.36 (s, 3H), 2.13-2.04 (m, 3H), 1.80 (m, 1H) |
| 88 | 4-HOCH₂ | 7.96 (dd, J = 8.4, 9.0 Hz, 2H), 7.63 (m, 2H), 7.52 (m, 0.5H), 7.46 (m, 2.5H), 6.20 (d, J = 8.7 Hz, 2H), 6.12 (s, 1H), 5.48 (bs, 1H), 4.78 (s, 2H), 4.41 (m, 1H), 4.07 (td, J = 6.9, 7.2 Hz, 2H), 3.63 (m, 4H), 2.48 (s, 3H), 2.05 (m, 3H), 1.75 (m, 1H) |
| 89 | 4-tert-Bu | 7.96 (m, 2H), 7.56 (d, J = 8.1 Hz, 2H), 7.46 (d, J = 8.1 Hz, 2H), 7.20 (d, J = 8.4 Hz, 2H), 6.12 (s, 1H), 5.06 (bs, 1H), 4.47 (m, 1H), 3.62 (m, 4H), 2.49 (s, 3H), 2.05 (m, 3H), 1.78 (m, 1H), 1.36 (s, 9H) |
| 90 | 4-EtS | 7.96 (m, 2H), 7.54 (d, J = 7.2 Hz, 2H), 7.40 (d, J = 7.8 Hz, 2H), 7.22 (m, 2H), 6.12 (s, 1H), 5.16 (bs, 1H), 4.45 (m, 1H), 3.63 (m, 4H), 2.99 (m, 2H), 2.48 (s, 3H), 2.06 (m, 3H), 1.78 (m, 1H), 1.35 (t, J = 7.2 Hz, 3H), |
| 91 | 4-PhCH₂O | 7.96 (dd, J = 9.0, 8.7 Hz, 2H), 7.49 (m, 4H), 7.35 (m, 3H), 7.20 (d, J = 8.7 Hz, 2H), 7.08 (d, J = 8.4 Hz, 2H), 6.10 (s, 1H), 5.53 (bs, 1H), 5.09 (s, 2H), 4.43 (m, 1H), 3.63 (m, 4H), 2.45 (s, 3H), 2.06 (m, 3H), 1.78 (m, 1H) |
| 92 | 4-Ph | 7.98 (m, 2H), 7.70 (m, 6H), 7.43 (t, J = 7.8 Hz, 2H), 7.32 (d, J = 7.8 Hz, 1H), 7.21 (t, J = 8.4 Hz, 2H), 6.14 (s, 1H), 4.48 (br, 1H), 3.76-3.54 (m, 4H), 2.54 (s, 3H), 2.13-2.04 (m, 3H), 1.80 (m, 1H) |
| 93 | 3-Cl | 7.96 (m, 2H), 7.71 (bs, 1H), 7.53 (d, J = 7.8 Hz, 1H), 7.36 (m, 1H), 7.22 (m, 3H), 6.14 (s, 1H), 4.74 (bs, 1H), 4.46 (m, 1H), 3.75 (m, 2H), 3.57 (m, 2H), 2.50 (s, 3H), 2.06 (m, 3H), 1.83 (m, 1H) |
| 94 | 3-MeO | 7.96 (m, 2H), 7.59 (d, J = 8.1 Hz, 2H), 7.44 (m, 1H), 7.20 (d, J = 8.7 Hz, 2H), 7.07 (d, J = 7.8 Hz, 1H), 6.15 (s, 1H), 4.48 (br, 1H), 3.89 (s, 3H), 3.78-3.52 (m, 4H), 2.51 (s, 3H), 2.15-1.99 (m, 3H), 1.78-1.69 (m, 1H) |
| 95 | 3-CF₃O | 7.96 (m, 2H), 7.59 (d, J = 7.5 Hz, 2H), 7.44 (m, 1H), 7.20 (d, J = 7.5 Hz, 2H), 7.07 (d, J = 7.8 Hz, 1H), 6.15 (s, 1H), 4.48 (br, 1H), 3.78-3.52 (m, 4H), 2.51 (s, 3H), 2.15-1.99 (m, 3H), 1.78-1.69 (m, 1H) |
| 96 | 3,4-diCl | 7.95 (dd, J = 7.8, 8.1 Hz, 2H), 7.48 (m, 1H), 7.20 (d, J = 8.4 Hz, 2H), 6.15 (s, 1H), 5.64 (bs, 1H), 4.47 (m, 1H), 3.63 (m, 4H), 2.49 (s, 3H), 2.05 (m, 3H), 1.85 (m, 1H) |
| 97 | 2,4-diCl | 7.96 (m, 2H), 7.50 (s, 1H), 7.28 (s, 2H), 7.17 (m, 2H), 6.09 (s, 1H), 4.29 (m, 1H), 3.57 (m, 4H), 2.25 (s, 3H), 2.01 (m, 3H), 1.68 (m, 1H) |
| 98 | 2-CN | 7.97 (m, 2H), 7.80 (d, J = 7.8 Hz, 1H), 7.65 (t, J = 7.5 Hz, 1H), 7.50 (d, J = 7.8 Hz, 1H), 7.40 (t, J = 7.5 Hz, 1H), 7.22 (m, 2H), 6.15 (s, 1H), 4.43 (br, 1H), 3.66-3.55 (m, 4H), 2.48 (s, 3H), 2.30 (s, 3H), 2.15-1.99 (m, 3H), 1.77 (m, 1H) |
| 99 | 3-Cl, 4-F | 7.97 (m, 2H), 7.72 (m, 1H), 7.49 (m, 1H), 7.23 (m, 3H), 6.16 (s, 1H), 4.47 (br, 1H), 3.78-3.54 (m, 4H), 2.49 (s, 3H), 2.18-2.05 (m, 3H), 1.84 (m, 1H) |
| 100 | 3-F, 4-PrO | 7.96 (m, 2H), 7.36 (m, 2H), 7.22 (d, J = 8.7 Hz, 2H), 7.03 (t, J = 9.0 Hz, 1H), 6.13 (s, 1H), 4.45 (br, 1H), 4.03 (t, J = 6.6 Hz, 2H), 3.75-3.53 (m, 4H), 2.47 (s, 3H), 2.10-1.99 (m, 3H), 1.85 (m, 3H), 1.06 (t, J = 7.5 Hz, 3H) |
| 101 | 3-Me, 4-F | 7.97 (m, 2H), 7.29 (m, 2H), 7.22 (m, 3H), 6.13 (s, 1H), 4.45 (br, 1H), 3.75-3.55 (m, 4H), 2.49 (s, 3H), 2.30 (s, 3H), 2.08-2.01 (m, 3H), 1.80 (m, 1H) |
| 102 | 3-Me, 4-MeO | 7.96 (m, 2H), 7.36 (m, 2H), 7.22 (m, 2H), 6.93 (d, J = 8.4 Hz, 1H), 6.10 (s, 1H), 4.42 (br, 1H), 3.86 (s, 3H), 3.78-3.52 (m, 4H), 2.52 (s, 3H), 2.15-1.99 (m, 3H), 1.78-1.69 (m, 1H) |
| 103 | 3-MeO, 4-MeO | 7.97 (m, 2H), 7.21 (m, 3H), 7.09 (d, J = 8.1 Hz, 1H), 6.95 (d, J = 8.4 Hz, 1H), 6.11 (s, 1H), 5.35 (bs, 1H), 4.44 (m, 1H), 3.96 (s, 3H), 3.91 (s, 3H), 3.63 (m, 4H), 2.48 (s, 3H), 2.05 (m, 3H), 1.75 (m, 1H) |
| 104 | 2-F, 5-EtO | 7.96 (m, 2H), 7.22 (m, 2H), 7.08 (m, 1H), 6.96 (m, 1H), 6.82 (m, 1H), 6.11 (s, 1H), 4.37 (br, 1H), 4.08 (q, J = 7.2 Hz, 2H), 3.78-3.52 (m, 4H), 2.37 (s, 3H), 2.17 (s, 3H), 2.15-1.99 (m, 3H), 1.78-1.69 (m, 1H), 1.41 (t, J = 6.9 Hz, 3H) |
| 105 | 4-acetylamino | 7.96 (m, 2H), 7.54 (m, 4H), 7.21 (d, J = 8.4 Hz, 2H), 6.12 (s, 1H), 4.45 (br, 1H), 3.75-3.53 (m, 4H), 2.46 (s, 3H), 2.13 (s, 3H), 2.10-1.99 (m, 3H), 1.85 (m, 1H) |
| 106 | 4-CN | 7.90 (m, 3H), 7.77 (d, J = 7.8 Hz, 1H), 7.66 (d, J = 8.4 Hz, 1H), 7.17 (m, 3H), 6.15 (s, 1H), 4.37 (br, 1H), 3.78-3.52 (m, 4H), 2.49 (s, 3H), 2.15-1.99 (m, 3H), 1.78-1.69 (m, 1H) |
| 107 | 4-CH₃OSO₂ | 7.96 (m, 2H), 7.68 (d, J = 8.4 Hz, 2H), 7.36 (d, J = 8.4 Hz, 2H), 7.22 (d, J = 8.7 Hz, 2H), 6.15 (s, 1H), 5.08 (bs, 1H), 4.45 (bs, 1H), 3.66 (m, 4H), 3.16 (s, 3H), 2.49 (s, 3H), 2.09 (m, 3H), 1.80 (m, 1H) |
| 108 | 4-NH₂SO₂ | 7.96 (m, 2H), 7.94 (m, 1H), 7.67 (m, 1H), 7.48 (m, 1H), 7.46 (m, 2H), 7.23 (m, 1H), 6.18 (s, 1H), 4.95 (s, 2H), 4.45 (br, 1H), 3.75-3.53 (m, 4H), 2.51 (s, 3H), 2.13-1.99 (m, 3H), 1.87 (m, 1H) |
| 109 | 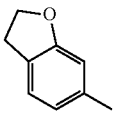 | 7.94 (m, 3H), 7.34 (s, 1H), 7.19 (m, 3H), 6.85 (d, J = 8.4 Hz, 1H), 6.07 (s, 1H), 4.56 (t, J = 8.7 Hz, 2H), 4.38 (br, 1H), 3.78-3.52 (m, 4H), 3.24 (t, J = 6.9 Hz, 2H), 2.41 (s, 3H), 2.15-1.99 (m, 3H), 1.78-1.69 (m, 1H) |

Example 110

Preparation of (S)-(1-(3-(4-methylphenyl)-7-(3-fluorophenyl)-2-methylpyrazolo[1,5-a]pyrimidin-5-yl)pyrrolidin-2-yl)methanol (Chemical Formula 50)

[Chemical Formula 50]

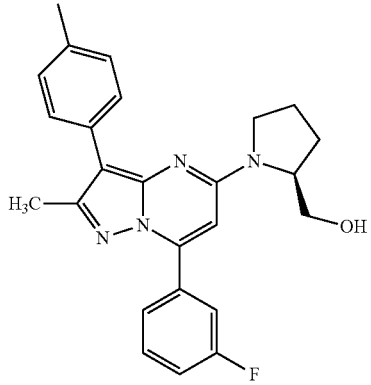

Step 1: Preparation of 3-(4-methylphenyl)-7-(3-fluorophenyl)-2-methylpyrazolo[1,5-a]pyrimidin-5(4H)-one (Chemical Formula 51)

[Chemical Formula 51]

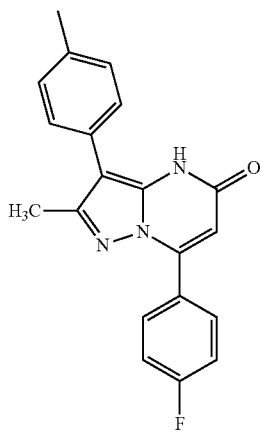

3-Methyl-4-(4-methylphenyl)-1H-pyrazol-5-amine and ethyl 3-(3-fluorophenyl)-3-oxopropanoate are stirred overnight in a pyridine (10 mL) solvent at 95° C. After cooling to room temperature, the reaction solvent is removed by distillation under reduced pressure. The remainder is extracted with ethyl acetate and water. The extracted organic layer is washed with brine and dehydrated with anhydrous MgSO$_4$. The dehydrated organic layer is distilled under reduced pressure and purified by column chromatography to yield the target compound.

Step 2: Preparation of 5-chloro-3-(4-methylphenyl)-7-(3-fluorophenyl)-2-methylpyrazolo[1,5-a]pyridine pyrimidine (Chemical Formula 52)

[Chemical Formula 52]

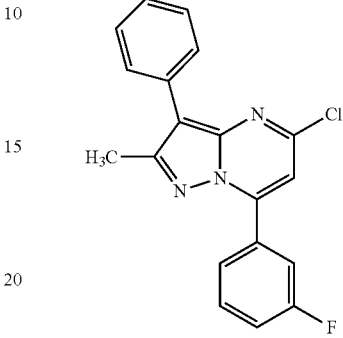

3-(4-Methylphenyl)-7-(3-fluorophenyl)-2-methylpyrazolo[1,5-a]pyrimidin-5(4H)-one is added to POCl$_3$ (3 mL) and pyridine (0.1 mL) and stirred for 2 hours while heating. After cooling to room temperature, POCl$_3$ is removed by distillation under reduced pressure. After the distillation, ethyl acetate (20 mL) and ice are added to the remainder. The organic layer is extracted and it is extracted once again with water and ethyl acetate. The organic layer is washed with 1 M NaHCO$_3$ aqueous solution and brine. The organic layer is dehydrated with anhydrous MgSO$_4$. The solvent is removed from the organic layer by distillation under reduced pressure. The remainder is purified by column chromatography to yield the target compound.

Step 3: Preparation of (S)-(1-(3-(4-methylphenyl)-7-(3-fluorophenyl)-2-methylpyrazolo[1,5-a]pyrimidin-5-yl)pyrrolidin-2-yl)methanol 5-Chloro-3-(4-methylphenyl)-7-(3-fluorophenyl)-2-methylpyrazolo[1,5-a]pyrimidine, (S)-pyrrolin-2-ylmethanol and DIPEA (0.2 mL) are added to acetonitrile (10 mL) and stirred overnight at 80° C. After cooling to room temperature, the solvent and volatile substance are removed by distillation under reduced pressure. The remainder is extracted 3 times with ethyl acetate (20 mL) and water. The collected organic layer is washed with brine. The organic layer is dehydrated with anhydrous MgSO$_4$ and the solvent is removed by distillation under reduced pressure. The remainder is purified by column chromatography to yield the target compound.

Examples 111-121

Compounds of Examples 111-121 are prepared in a similar manner as Example 110.

Chemical formula and NMR analysis data for the compounds of Examples 110-121 are shown in Chemical Formula 53 and Table 8.

[Chemical Formula 53]

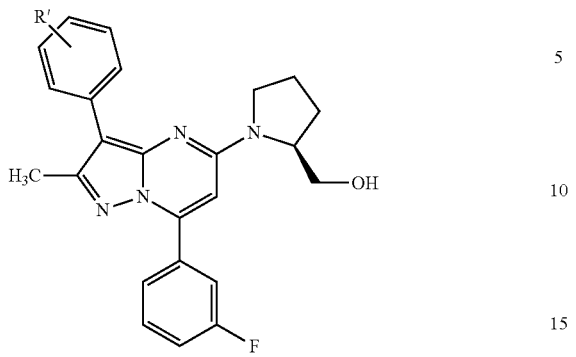

TABLE 8

| Ex. No. | R' | ¹H NMR (CDCl₃, 300 MHz) |
|---|---|---|
| 110 | 4-Me | 7.72 (d, J = 8.7 Hz, 2H), 7.48 (d, J = 7.8 Hz, 3H), 7.22 (m, 3H), 6.13 (s, 1H), 5.47 (bs, 1H), 4.40 (m, 1H), 3.63 (m, 4H), 2.48 (s, 3H), 2.38 (s, 3H), 2.06 (m, 3H), 1.76 (m, 1H) |
| 111 | 4-MeO | 7.70 (d, J = 8.4 Hz, 2H), 7.48 (m, 3H), 7.20 (m, 1H), 6.95 (d, J = 8.4 Hz, 2H), 6.11 (s, 1H), 4.37 (br, 1H), 3.81 (s, 3H), 3.78-3.52 (m, 4H), 2.43 (s, 3H), 2.15-1.99 (m, 3H), 1.78-1.69 (m, 1H) |
| 112 | 4-EtO | 7.69 (d, J = 7.8 Hz, 2H), 7.46 (m, 3H), 7.20 (m, 1H), 6.95 (d, J = 8.7 Hz, 2H), 6.11 (s, 1H), 4.39 (br, 1H), 4.04 (q, J = 7.2 Hz, 2H), 3.78-3.52 (m, 4H), 2.43 (s, 3H), 2.15-1.99 (m, 3H), 1.78-1.69 (m, 1H), 1.40 (t, J = 6.9 Hz, 3H) |
| 113 | 3,4-methylenedioxy | 7.68 (d, J = 8.1 Hz, 2H), 7.48 (m, 1H), 7.06 (s, 1H), 7.00 (m, 1H), 6.95 (d, J = 8.1 Hz, 2H), 6.12 (s, 1H), 5.95 (s, 2H), 4.37 (br, 1H), 3.78-3.52 (m, 4H), 2.43 (s, 3H), 2.15-1.99 (m, 3H), 1.78-1.69 (m, 1H) |
| 114 | 4-CF₂H | 7.70 (m, 4H), 7.55 (d, J = 8.1 Hz, 2H), 7.48 (m, 1H), 7.19 (m, 1H), 6.65 (s, 1H), 6.16 (s, 1H), 4.44 (br, 1H), 3.77-3.51 (m, 4H), 2.48 (s, 3H), 2.15-1.99 (m, 3H), 1.78-1.69 (m, 1H) |
| 115 | 4-CF₃ | 7.73 (m, 5H), 7.51 (m, 2H), 7.23 (m, 2H), 6.20 (s, 1H), 4.49 (br, 1H), 3.79-3.53 (m, 4H), 2.52 (s, 3H), 2.10-1.97 (m, 3H), 1.84 (m, 2H), 1.78-1.69 (m, 1H), 1.23 (t, J = 7.8 Hz, 3H) |
| 116 | 4-Et | 8.15 (d, J = 6.9 Hz, 2H), 7.73 (d, J = 8.1 Hz, 2H), 7.51 (d, J = 7.2 Hz, 2H), 7.32 (m, 2H), 6.15 (s, 1H), 4.43 (br, 1H), 3.79-3.53 (m, 4H), 2.70 (q, J = 7.8 Hz, 2H), 2.49 (s, 3H), 2.10-1.97 (m, 3H), 1.78-1.69 (m, 1H), 1.23 (t, J = 7.8 Hz, 3H) |
| 117 | 4-vinyl | 7.73 (d, J = 7.8 Hz, 2H), 7.58 (d, J = 7.8 Hz, 2H), 7.49 (d, J = 7.8 Hz, 2H), 7.48 (m, 1H), 7.23 (m, 1H), 6.74 (m, 1H), 6.16 (s, 1H), 5.76 (d, J = 8.7 Hz, 1H), 5.21 (d, J = 8.1 Hz, 1H), 4.46 (br, 1H), 3.69-3.50 (m, 4H), 2.50 (s, 3H), 2.10-1.97 (m, 3H), 1.78-1.69 (m, 1H) |
| 118 | 4-propyl | 7.70 (d, J = 7.8 Hz, 2H), 7.49 (m, 1H), 7.47 (d, J = 7.8, 2H), 7.23 (d, J = 6.0 Hz, 2H), 7.22 (m, 1H), 6.12 (s, 1H), 4.41 (br, 1H), 3.69-3.50 (m, 4H), 2.43 (s, 3H), 2.59 (t, J = 8.1 Hz, 2H), 2.10-1.97 (m, 3H), 1.84 (m, 2H), 1.78-1.69 (m, 1H), 1.65 (m, 2H), 0.96 (t, J = 7.2 Hz, 3H) |
| 119 | 4-n-PrO | 7.70 (d, J = 8.1 Hz, 2H), 7.49 (m, 1H), 7.44 (d, J = 8.7, 2H), 7.20 (m, 1H), 6.96 (d, J = 9.0 Hz, 2H), 6.11 (s, 1H), 4.38 (br, 1H), 3.92 (t, J = 7.2 Hz, 2H), 3.69-3.50 (m, 4H), 2.43 (s, 3H), 2.15-1.99 (m, 3H), 1.84 (m, 2H), 1.78-1.69 (m, 1H), 1.02 (t, J = 7.2 Hz, 3H) |
| 120 | H | 7.73 (d, J = 7.2 Hz, 2H), 7.60 (d, J = 7.5 Hz, 2H), 7.48 (m, 3H), 7.25 (m, 2H), 6.15 (s, 1H), 5.29 (bs, 1H), 4.42 (m, 1H), 3.63 (m, 4H), 2.49 (s, 3H), 2.06 (m, 3H), 1.77 (m, 1H) |
| 121 | 3-Cl | 7.71 (d, J = 6.9 Hz, 3H), 7.51 (m, 2H), 7.36 (m, 1H), 7.22 (m, 2H), 6.17 (s, 1H), 4.62 (bs, 1H), 4.44 (bs, 1H), 3.74 (bs, 2H), 3.62 (m, 1H), 3.54 (m, 1H), 2.51 (s, 3H), 2.06 (m, 3H), 1.84 (m, 1H) |

Example 122

Preparation of (S)-(1-(3-(4-methylphenyl)-7-(3-(trifluoromethyl)fluorophenyl)-2-methylpyrazolo[1,5-a]pyrimidin-5-yl)pyrrolidin-2-yl)methanol (Chemical Formula 54)

[Chemical Formula 54]

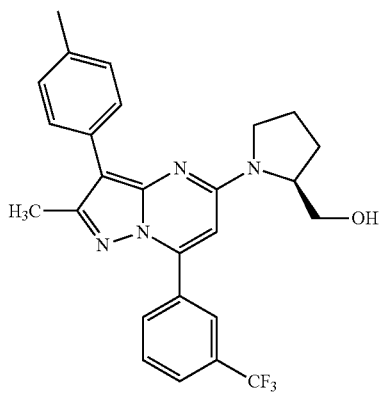

Step 1: Preparation of 3-(4-methylphenyl)-7-(3-(trifluoromethyl)phenyl)-2-methylpyrazolo[1,5-a]pyrimidin-5(4H)-one (Chemical Formula 55)

[Chemical Formula 55]

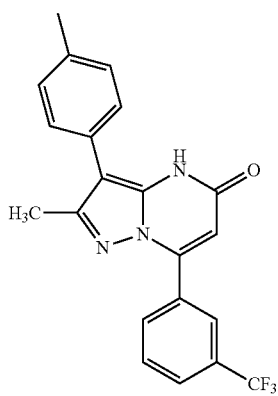

3-Methyl-4-(4-methylphenyl)-1H-pyrazol-5-a mine (300 mg) and ethyl 3-(3-(trifluoromethyl)phenyl)-3-oxopropanoate (500 mg) are stirred overnight in a pyridine (10 mL) solvent at 95° C. After cooling to room temperature, the reaction solvent is removed by distillation under reduced pressure. The remainder is extracted with ethyl acetate and water. The extracted organic layer is washed with brine and dehydrated with anhydrous MgSO₄. The dehydrated organic layer is distilled under reduced pressure and purified by column chromatography to yield 405 mg of the target compound.

Step 2: Preparation of 5-chloro-3-(4-methylphenyl)-7-(3-(trifluoromethyl)phenyl)-2-methylpyrazolo[1,5-a]pyridine pyrimidine (Chemical Formula 56)

[Chemical Formula 56]

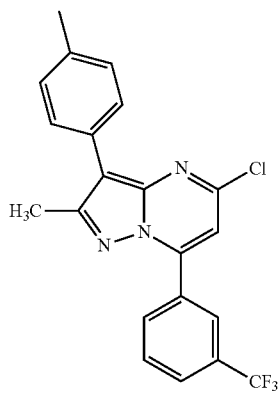

3-(4-Methylphenyl)-7-(3-(trifluoromethyl)phenyl)-2-methylpyrazolo[1,5-a]pyrimidin-5(4H)-one (150 mg) is added to POCl₃ (3 mL) and pyridine (0.1 mL) and stirred for 2 hours while heating. After cooling to room temperature, POCl₃ is removed by distillation under reduced pressure. After the distillation, ethyl acetate (20 mL) and ice are added to the remainder. The organic layer is extracted and it is extracted once again with water and ethyl acetate. The organic layer is washed with 1 M NaHCO₃ aqueous solution and brine. The organic layer is dehydrated with anhydrous MgSO₄. The solvent is removed from the organic layer by distillation under reduced pressure. The remainder is purified by column chromatography to yield 130 mg of the target compound. $^1$H NMR (CDCl₃, 300 MHz) δ 8.14 (m, 2H), 7.83 (m, 1H), 7.64 (m, 1H), 7.47 (m, 1H), 7.24 (m, 2H), 6.85 (s, 1H), 2.48 (s, 3H), 2.40 (s, 3H).

Step 3: Preparation of (S)-(1-(3-(4-methylphenyl)-7-(3-(trifluoromethyl)phenyl)-2-methylpyrazolo[1,5-a]pyrimidin-5-yl)pyrrolidin-2-yl)methanol 5-Chloro-3-(4-methylphenyl)-7-(3-(trifluoromethyl)phenyl)-2-methylpyrazolo[1,5-a]pyrimidine (50 mg), (S)-pyrrolin-2-ylmethanol (15 mg) and DIPEA (0.2 mL) are added to acetonitrile (10 mL) and stirred overnight at 80° C. After cooling to room temperature, the solvent and volatile substance are removed by distillation under reduced pressure. The remainder is extracted 3 times with ethyl acetate (20 mL) and water. The collected organic layer is washed with brine. The organic layer is dehydrated with anhydrous MgSO₄ and the solvent is removed by distillation under reduced pressure. The remainder is purified by column chromatography to yield 32 mg of the target compound.

Example 123

Preparation of (S)-(1-(3-(4-methoxyphenyl)-7-(3-(trifluoromethyl)fluorophenyl)-2-methylpyrazolo[1,5-a]pyrimidin-5-yl)pyrrolidin-2-yl)methanol (Chemical Formula 57)

[Chemical Formula 57]

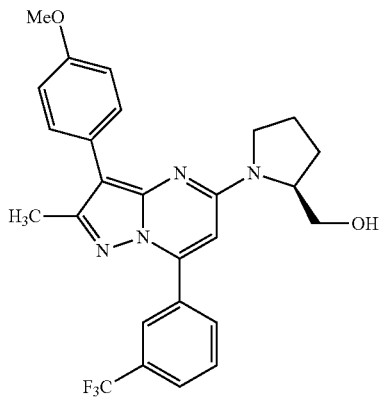

Step 1: Preparation of 3-(4-methoxyphenyl)-7-(3-(trifluoromethyl)phenyl)-2-methylpyrazolo[1,5-a]pyrimidin-5(4H)-one (Chemical Formula 58)

[Chemical Formula 58]

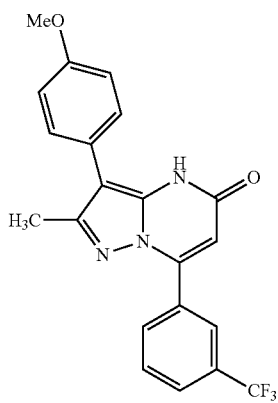

3-Methyl-4-(4-methoxyphenyl)-1H-pyrazol-5-amine (200 mg) and ethyl 3-(3-(trifluoromethyl)phenyl)-3-oxopropanoate (307 mg) are stirred overnight in a pyridine (10 mL) solvent at 95° C. After cooling to room temperature, the reaction solvent is removed by distillation under reduced pressure. The remainder is extracted with ethyl acetate and water. The extracted organic layer is washed with brine and dehydrated with anhydrous MgSO$_4$. The dehydrated organic layer is distilled under reduced pressure and purified by column chromatography to yield 270 mg of the target compound.

Step 2: Preparation of 5-chloro-3-(4-methoxyphenyl)-7-(3-(trifluoromethyl)phenyl)-2-methylpyrazolo[1,5-a]pyridine pyrimidine (Chemical Formula 59)

[Chemical Formula 59]

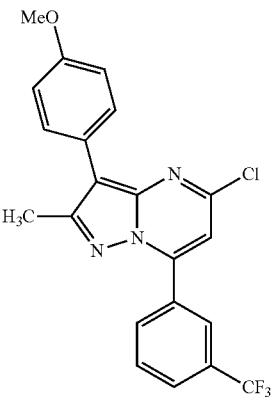

3-(4-Methoxyphenyl)-7-(3-(trifluoromethyl)phenyl)-2-methylpyrazolo[1,5-a]pyrimidin-5(4H)-one (150 mg) is added to POCl$_3$ (3 mL) and pyridine (0.1 mL) and stirred for 2 hours while heating. After cooling to room temperature, POCl$_3$ is removed by distillation under reduced pressure. After the distillation, ethyl acetate (20 mL) and ice are added to the remainder. The organic layer is extracted and it is extracted once again with water and ethyl acetate. The organic layer is washed with 1 M NaHCO$_3$ aqueous solution and brine. The organic layer is dehydrated with anhydrous MgSO$_4$. The solvent is removed from the organic layer by distillation under reduced pressure. The remainder is purified by column chromatography to yield 130 mg of the target compound. $^1$H NMR (CDCl$_3$, 300 MHz) δ 8.22 (m, 2H), 7.80 (m, 1H), 7.64 (m, 1H), 7.56 (m, 2H), 7.03 (m, 2H), 6.86 (s, 1H), 3.83 (s, 3H), 2.47 (s, 3H).

Step 3: Preparation of (S)-(1-(3-(4-methoxyphenyl)-7-(3-(trifluoromethyl)phenyl)-2-methylpyrazolo[1,5-a]pyrimidin-5-yl)pyrrolidin-2-yl)methanol 5-Chloro-3-(4-methoxyphenyl)-7-(3-(trifluoromethyl)phenyl)-2-methylpyrazolo[1,5-a]pyrimidine (50 mg), (S)-pyrrolin-2-ylmethanol (15 mg) and DIPEA (0.2 mL) are added to acetonitrile (10 mL) and stirred overnight at 80° C. After cooling to room temperature, the solvent and volatile substance are removed by distillation under reduced pressure. The remainder is extracted 3 times with ethyl acetate (20 mL) and water. The collected organic layer is washed with brine. The organic layer is dehydrated with anhydrous MgSO$_4$ and the solvent is removed by distillation under reduced pressure. The remainder is purified by column chromatography to yield 50 mg of the target compound.

Examples 124-155

Compounds of Examples 124-155 are prepared in a similar manner as Examples 122 and 123.

Chemical formula and NMR analysis data for the compounds of Examples 122-155 are shown in Chemical Formula 60 and Table 9.

[Chemical Formula 60]

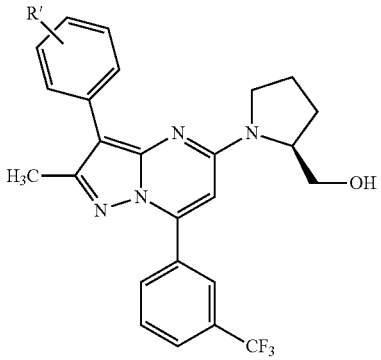

TABLE 9

| Ex. No. | R' | $^1$H NMR (CDCl$_3$, 300 MHz) |
|---|---|---|
| 122 | 4-Me | 8.12 (m, 2H), 7.76 (d, J = 7.5 Hz, 1H), 7.64 (m, 1H), 7.44 (d, J = 6.9 Hz, 1H), 7.24 (d, J = 6.3 Hz, 2H), 6.11 (s, 1H), 4.39 (br, 1H), 3.78-3.52 (m, 4H), 2.44 (s, 3H), 2.36 (s, 3H), 2.15-1.99 (m, 3H), 1.78-1.69 (m, 1H) |
| 123 | 4-MeO | 8.15 (m, 2H), 7.76 (d, J = 7.8 Hz, 1H), 7.64 (m, 1H), 7.46 (d, J = 9.0 Hz, 2H), 6.97 (d, J = 9.0 Hz, 2H), 6.12 (s, 1H), 4.39 (br, 1H), 3.81 (s, 3H), 3.78-3.52 (m, 4H), 2.43 (s, 3H), 2.15-1.99 (m, 3H), 1.78-1.69 (m, 1H) |
| 124 | 4-EtO | 8.15 (m, 2H), 7.78 (d, J = 7.5 Hz, 1H), 7.66 (m, 1H), 7.47 (d, J = 8.4 Hz, 2H), 6.97 (d, J = 8.1 Hz, 2H), 6.15 (s, 1H), 4.38 (br, 1H), 4.07 (q, J = 6.9 Hz, 2H), 3.78-3.52 (m, 4H), 2.44 (s, 3H), 2.15-1.99 (m, 3H), 1.78-1.69 (m, 1H), 1.41 (t, J = 6.9 Hz, 3H) |
| 125 | 3,4-methylenedioxy | 8.17 (m, 2H), 7.80 (d, J = 7.8 Hz, 1H), 7.66 (m, 1H), 7.10 (s, 1H), 7.03 (m, 1H), 6.90 (d, J = 8.1 Hz, 2H), 6.15 (s, 1H), 5.99 (s, 2H), 4.43 (br, 1H), 3.78-3.52 (m, 4H), 2.45 (s, 3H), 2.15-1.99 (m, 3H), 1.78-1.69 (m, 1H) |
| 126 | 4-CF$_2$H | 8.14 (m, 2H), 7.78 (d, J = 7.8 Hz, 2H), 7.68 (m, 3H), 7.54 (d, J = 7.8 Hz, 2H), 6.65 (s, 1H), 6.17 (s, 1H), 4.44 (br, 1H), 3.77-3.51 (m, 4H), 2.44 (s, 3H), 2.15-1.99 (m, 3H), 1.78-1.69 (m, 1H) |
| 127 | 3-CH$_3$S | 8.18 (m, 2H), 7.80 (d, J = 7.5 Hz, 1H), 7.54 (d, J = 7.8 Hz, 2H), 7.35 (d, J = 7.8 Hz, 2H), 6.17 (s, 1H), 4.47 (br, 1H), 3.69-3.50 (m, 4H), 2.52 (s, 3H), 2.47 (s, 3H), 2.15-1.99 (m, 3H), 1.78-1.69 (m, 1H) |
| 128 | 4-CF$_3$ | 8.22 (m, 2H), 7.76 (m, 2H), 7.49 (m, 2H), 7.20 (m, 2H), 6.20 (s, 1H), 4.44 (br, 1H), 3.69-3.50 (m, 4H), 2.37 (s, 3H), 2.15-1.99 (m, 3H), 1.78-1.69 (m, 1H) |
| 129 | 4-Et | 8.19 (m, 2H), 7.80 (d, J = 7.8 Hz, 1H), 7.68 (m, 1H), 7.52 (d, J = 7.8 Hz, 2H), 7.29 (d, J = 7.8 Hz, 2H), 6.16 (s, 1H), 4.45 (br, 1H), 3.69-3.50 (m, 4H), 2.68 (q, J = 7.8 Hz, 2H), 2.48 (s, 3H), 2.15-1.99 (m, 3H), 1.78-1.69 (m, 1H), 1.28 (t, J = 7.8 Hz, 3H) |
| 130 | 4-CF$_3$CH$_2$ | 8.19 (d, J = 7.8 Hz, 1H), 8.15 (s, 1H), 7.80 (d, J = 7.8 Hz, 1H), 7.68 (t, J = 7.8 Hz, 1H), 7.53 (d, J = 8.7 Hz, 2H), 7.03 (d, J = 8.7 Hz, 2H), 6.16 (s, 1H), 5.46 (bs, 1H), 4.40 (m, 3H), 3.68 (m, 4H), 2.45 (s, 3H), 2.04 (m, 3H), 1.78 (m, 1H) |
| 131 | 4-CH$_3$OCH$_2$ | 8.15 (m, 2H), 7.75 (m, 1H), 7.67 (m, 1H), 7.65 (m, 1H), 7.54 (m, 2H), 7.38 (m, 2H), 6.13 (s, 1H), 5.10 (br, 1H), 4.50 (s, 2H), 4.21 (br, 1H), 3.64 (m, 4H), 2.44 (s, 3H), 2.03 (m, 2H), 1.75 (m, 1H) |
| 132 | 4-EtOCH$_2$ | 8.17 (m, 2H), 7.75 (m, 1H), 7.65 (m, 1H), 7.54 (m, 2H), 7.42 (m, 2H), 6.14 (s, 1H), 4.51 (s, 2H), 4.42 (br, 1H), 3.73-3.52 (m, 4H), 2.45 (s,3H), 2.17-1.98 (m, 2H), 1.77 (m, 1H) |
| 133 | 4-n-PrO | 8.18 (m, 2H), 7.79 (d, J = 7.8 Hz, 1H), 7.67 (m, 1H), 7.48 (d, J = 8.4 Hz, 2H), 7.00 (d, J = 8.7 Hz, 2H), 6.14 (s, 1H), 4.41 (br, 1H), 3.98 (t, J = 6.9 Hz, 2H), 3.78-3.52 (m, 4H), 2.44 (s, 3H), 2.15-1.99 (m, 3H), 1.80 (m, 2H), 1.78-1.69 (m, 1H), 1.05 (t, J = 6.9 Hz, 3H) |
| 134 | 3,4-diF | 8.12 (m, 2H), 7.76 (m, 1H), 7.69 (m, 1H), 7.45 (m, 1H), 7.28 (m, 1H), 7.22 (m, 1H), 6.16 (s, 1H), 4.43 (br, 1H), 3.75-3.50 (m, 4H), 2.45 (s, 3H), 2.12-1.99 (m, 3H), 1.85-1.73 (m, 1H) |
| 135 | 2,4-diF | 8.18 (m, 2H), 7.80 (d, J = 7.8 Hz, 1H), 7.68 (m, 1H), 7.42 (m, 1H), 7.00 (m, 2H), 6.17 (s, 1H), 4.38 (br, 1H), 3.78-3.52 (m, 4H), 2.34 (s, 3H), 2.15-1.99 (m, 3H), 1.78-1.69 (m, 1H) |
| 136 | 3,5-diF | 8.12 (m, 2H), 7.76 (m, 1H), 7.65 (m, 1H), 7.25 (m, 2H), 6.66 (m, 1H), 6.19 (s, 1H), 4.47 (br, 1H), 3.75-3.50 (m, 4H), 2.47 (s, 3H), 2.12-1.99 (m, 3H), 1.85-1.73 (m, 1H) |
| 137 | 3-F, 4-Me | 8.18 (m, 2H), 7.80 (d, J = 7.5 Hz, 1H), 7.68 (m, 1H), 7.27 (m, 3H), 6.17 (s, 1H), 4.47 (br, 1H), 3.78-3.52 (m, 4H), 2.49 (s, 3H), 2.31 (s, 3H), 2.15-1.99 (m, 3H), 1.78-1.69 (m, 1H) |
| 138 | 3-F, 4-MeO | 8.18 (m, 2H), 7.80 (d, J = 7.5 Hz, 1H), 7.68 (m, 1H), 7.35 (m, 2H), 7.05 (m, 1H), 6.17 (s, 1H), 4.47 (br, 1H), 3.98 (s, 3H), 3.78-3.52 (m, 4H), 2.47 (s, 3H), 2.15-1.99 (m, 4H), 1.78-1.69 (m, 1H) |
| 139 | 4-F | 8.12 (m, 2H), 7.76 (m, 1H), 7.65 (m, 1H), 7.52 (m, 2H), 7.11 (m, 2H), 6.14 (s, 1H), 4.40 (br, 1H), 3.75-3.50 (m, 4H), 2.42 (s, 3H), 2.12-1.99 (m, 3H), 1.85-1.73 (m, 1H) |
| 140 | 4-MeO, 3-CF$_3$ | 8.19 (d, J = 7.5 Hz, 1H), 8.13 (d, J = 9.3 Hz, 1H), 7.94 (s, 1H), 7.73 (m, 3H), 7.10 (d, J = 8.4 Hz, 1H), 6.19 (s, 1H), 6.10 (s, 0.5H), 5.98 (s, 0.5H), 4.47 (bs, 1H), 3.94 (s, 3H), 3.74 (m, 4H), 2.48 (s, 3H), 2.08 (m, 3H), 1.80 (m, 1H) |
| 141 | 4-CH$_3$SO | 8.18 (m, 2H), 7.83 (m, 2H), 7.75-7.66 (m, 4H), 6.23 (s, 1H), 4.45 (br, 1H), 3.80-3.60 (m, 4H), |

TABLE 9-continued

| Ex. No. | R' | ¹H NMR (CDCl₃, 300 MHz) |
|---|---|---|
| 142 | 4-CH₃SO₂ | 2.79 (s, 3H), 2.52 (s, 3H), 2.17-1.99 (m, 3H), 1.85-1.73 (m, 1H) 8.12 (m, 2H), 8.01 (m, 1H), 7.92 (m, 2H), 7.79 (m, 1H), 7.45 (m, 2H), 6.25 (s, 1H), 4.45 (br, 1H), 3.75-3.50 (m, 4H), 3.08 (s, 3H), 2.52 (s, 3H), 2.12-1.99 (m, 3H), 1.85-1.73 (m, 1H) |
| 143 | 3-CH₃SO | 9.10 (s, 1H), 8.20 (m, 2H), 7.72 (m, 3H), 7.48 (m, 1H), 7.16 (d, J = 7.5 Hz, 1H), 6.17 (s, 1H), 5.10 (br, 1H), 4.59 (br, 1H), 4.22 (m, 1H), 3.62 (m, 1H), 3.45 (m, 1H), 3.24 (m, 1H), 2.82 (d, J = 3.9 Hz, 3H), 2.64 (s, 3H), 2.24 (m, 1H), 2.06 (m, 2H) |
| 144 | 4-CH₃OSO₂ | 8.19 (m, 2H), 7.81 (d, J = 7.8 Hz, 1H), 7.68 (m, 3H), 7.36 (d, J = 8.4 Hz, 2H), 6.20 (s, 1H), 5.00 (bs, 1H), 4.46 (m, 1H), 3.68 (m, 4H), 3.12 (s, 3H), 2.49 (s, 3H), 2.10 (m, 3H), 1.25 (m, 1H) |
| 145 | 4-CH₃OSO₂ | 8.13 (m, 4H), 7.74 (m, 4H), 6.20 (s, 1H), 4.85 (bs, 1H), 4.49 (bs, 1H), 3.91 (s, 3H), 3.69 (m, 4H), 2.52 (s, 3H), 2.10 (m, 3H), 1.84 (m, 1H), |
| 146 | 4-(CH₃)2N | 8.37 (s, 1H), 8.19 (d, J = 7.8 Hz, 1H), 8.14 (s, 1H), 7.78 (m, 1H), 7.67 (m, 1H), 7.54 (m, 1H), 7.48 (m, 1H), 6.65 (d, J = 8.4 Hz, 1H), 6.14 (s, 1H), 5.29 (bs, 1H), 4.45 (bs, 1H), 3.63 (m, 4H), 3.12 (s, 6H), 2.44 (s, 3H), 2.06 (m, 3H) 1.78 (m, 1H) |
| 147 | 3-(CH₃)2N | 8.12 (m, 2H), 7.78 (m, 1H), 7.68 (m, 1H), 7.32 (m, 2H), 7.04 (s, 1H), 6.69 (m, 1H), 6.15 (s, 1H), 4.45 (br, 1H), 3.75-3.50 (m, 4H), 3.08 (s, 6H), 2.50 (s, 3H), 2.12-1.99 (m, 3H), 1.85-1.73 (m, 1H) |
| 148 | (morpholinomethyl-4-methylphenyl) | 8.18 (m, 2H), 7.80 (m, 1H), 7.68 (m, 1H), 7.57 (d, J = 8.1 Hz, 2H), 7.40 (d, J = 8.1 Hz, 2H), 6.17 (s, 1H), 4.45 (br, 1H), 3.75-3.65 (m, 6H), 3.53 (s, 2H), 2.49 (s, 5H), 2.12-1.99 (m, 3H), 1.85-1.73 (m, 1H) |
| 149 | (cyclopropylsulfonamido-4-methylphenyl) | 8.12 (s, 1H), 7.75 (s, 1H), 7.62 (m, 2H), 7.48 (m, 2H), 7.43 (m, 2H), 6.15 (s, 1H), 4.43 (br, 1H), 4.01 (m, 1H), 3.76-3.50 (m, 4H), 2.48 (m, 2H), 2.43 (s, 3H), 2.15-1.99 (m, 4H), 1.78-1.69 (m, 1H) |
| 150 | 4-CH₃NHSO₂ | 8.12 (s, 1H), 7.83 (s, 1H), 7.62 (m, 3H), 7.48 (m, 3H), 6.20 (s, 1H), 4.46 (br, 1H), 3.72-3.50 (m, 4H), 2.68 (s, 3H), 2.49 (s, 3H), 2.15-1.99 (m, 4H) |
| 151 | 4-CH₃SO₂NH | 8.20 (m, 2H), 7.82 (m, 1H), 7.68 (m, 2H), 7.54 (m, 2H), 7.20 (m, 2H), 6.19 (s, 1H), 4.45 (br, 1H), 3.82-3.60 (m, 4H), 3.03 (s, 3H), 2.45 (s, 3H), 2.17-2.03 (m, 2H), 1.77 (m, 1H) |
| 152 | 4-(CH₃)2NCO | 8.16 (d, J = 11.0 Hz, 1H), 7.80 (d, J = 7.5 Hz, 0.5H), 7.65 (dd, J = 7.5, 7.2 Hz, 3.5H), 7.51 (d, J = 8.1 Hz, 3H), 6.20 (s, 1H), 4.86 (bs, 1H), 4.47 (bs, 1H), 3.69 (m, 4H), 3.10 (m, 6H), 2.50 (s, 3H), 2.08 (m, 3H), 1.83 (m, 1H) |
| 153 | 4-(CH₃CH₂)₂NCO | 8.18 (m, 1H), 7.80 (d, J = 7.8 Hz, 0.5H), 7.65 (m, 3.5H), 7.54 (m, 0.5H), 7.46 (d, J = 7.2 Hz, 2.5H), 6.19 (s, 1H), 4.71 (bs, 1H), 4.47 (bs, 1H), 3.69 (m, 8H), 2.50 (s, 3H), 2.08 (m, 3H), 1.82 (m, 1H), 1.23 (m, 6H) |
| 154 | (morpholinocarbonyl-2-fluoro-5-methylphenyl) | 8.26 (s, 1H), 8.18 (d, J = 12.3 Hz, 1H), 7.79 (d, J = 7.5 Hz, 1H), 7.67 (m, 2H), 7.55 (m, 1H), 7.47 (m, 1H), 7.13 (m, 1H), 6.87 (m, 1H), 6.16 (s, 1H), 4.92 (bs, 1H), 4.44 (bs, 1H), 4.05 (bs, 1H), 3.80 (m, 4H), 3.65 (m, 4H), 3.48 (bs, 2H), 3.36 (m, 2H), 2.54 (s, 3H), 2.08 (bs, 4H) |
| 155 | (piperidinocarbonyl-4-methylphenyl) | 8.19 (m, 2H), 7.80 (m, 2H), 7.67 (m, 4H), 6.19 (s, 1H), 4.47 (bs, 1H), 3.77-3.53 (m, 8H), 2.50 (s, 3H), 2.07 (m, 2H), 1.82-1.84 (m, 6H) |

Example 156

Preparation of (S)-(1-(3-(4-methylphenyl)-7-(3-methylfluorophenyl)-2-methylpyrazolo[1,5-a]pyrimidin-5-yl)pyrrolidin-2-yl)methanol (Chemical Formula 61)

[Chemical Formula 61]

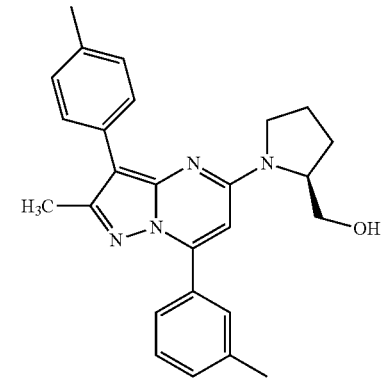

Step 1: Preparation of 3-(4-methylphenyl)-7-(3-methylphenyl)-2-methylpyrazolo[1,5-a]pyrimidin-5(4H)-one (Chemical Formula 62)

[Chemical Formula 62]

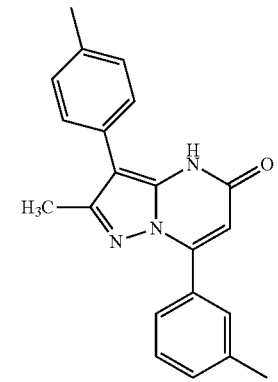

3-Methyl-4-(4-methylphenyl)-1H-pyrazol-5-amine and ethyl 3-(3-methylphenyl)-3-oxopropanoate are stirred overnight in a pyridine (10 mL) solvent at 95° C. After cooling to room temperature, the reaction solvent is removed by distillation under reduced pressure. The remainder is extracted with ethyl acetate and water. The extracted organic layer is washed with brine and dehydrated with anhydrous MgSO₄. The dehydrated organic layer is distilled under reduced pressure and purified by column chromatography to yield the target compound.

Step 2: Preparation of 5-chloro-3-(4-methylphenyl)-7-(3-methylphenyl)-2-methylpyrazolo[1,5-a]pyridine pyrimidine (Chemical Formula 63)

[Chemical Formula 63]

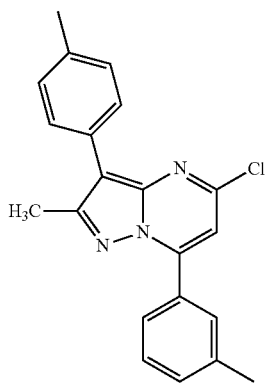

3-(4-Methylphenyl)-7-(3-methylphenyl)-2-methylpyrazolo[1,5-a]pyrimidin-5(4H)-one is added to POCl₃ (3 mL) and pyridine (0.1 mL) and stirred for 2 hours while heating. After cooling to room temperature, POCl₃ is removed by distillation under reduced pressure. After the distillation, ethyl acetate (20 mL) and ice are added to the remainder. The organic layer is extracted and it is extracted once again with water and ethyl acetate. The organic layer is washed with 1 M NaHCO₃ aqueous solution and brine. The organic layer is dehydrated with anhydrous MgSO₄. The solvent is removed from the organic layer by distillation under reduced pressure. The remainder is purified by column chromatography to yield the target compound.

Step 3: Preparation of (S)-(1-(3-(4-methylphenyl)-7-(3-methylphenyl)-2-methylpyrazolo[1,5-a]pyrimidin-5-yl)pyrrolidin-2-yl)methanol 5-Chloro-3-(4-methylphenyl)-7-(3-methylphenyl)-2-methylpyrazolo[1,5-a]pyrimidine, (S)-pyrrolin-2-ylmethanol and DIPEA (0.2 mL) are added to acetonitrile (10 mL) and stirred overnight at 80° C. After cooling to room temperature, the solvent and volatile substance are removed by distillation under reduced pressure. The remainder is extracted 3 times with ethyl acetate (20 mL) and water. The collected organic layer is washed with brine. The organic layer is dehydrated with anhydrous MgSO₄ and the solvent is removed by distillation under reduced pressure. The remainder is purified by column chromatography to yield the target compound.

Example 157

Preparation of (S)-(1-(3-(4-methoxyphenyl)-7-(3-methylphenyl)-2-methylpyrazolo[1,5-a]pyrimidin-5-yl)pyrrolidin-2-yl)methanol (Chemical Formula 64)

[Chemical Formula 64]

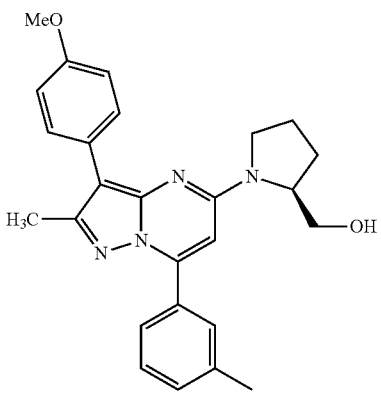

Step 1: Preparation of 7-(3-methylphenyl)-2-methylpyrazolo[1,5-a]pyrimidin-5(4H)-one (Chemical Formula 65)

[Chemical Formula 65]

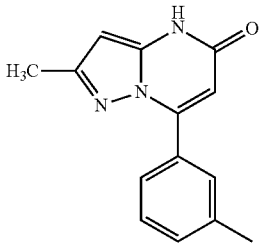

3-Methylpyrazol-5-amine (431 mg) and methyl 3-methylphenyl-3-oxopropanoate (812 mg) are stirred overnight at 93° C. in a pyridine (10 mL) solvent. After cooling to room temperature, the reaction solvent is removed by distillation under reduced pressure. The remainder is extracted with ethyl acetate and water. The extracted organic layer is washed with brine and dehydrated with anhydrous MgSO₄. The dehydrated organic layer is distilled under reduced pressure and purified by column chromatography to yield the target compound (673 mg).

Step 2: Preparation of 5-chloro-7-(3-methylphenyl)-2-methylpyrazolo[1,5-a]pyrimidine (Chemical Formula 66)

[Chemical Formula 66]

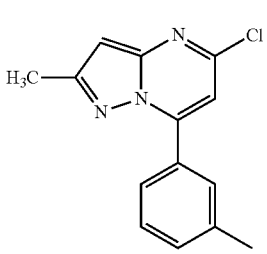

7-(3-Methylphenyl)-2-methylpyrazolo[1,5-a]pyrimidin-5 (4H)-one (673 mg) is dissolved in POCl$_3$ (15 mL) and pyridine (0.2 mL) and stirred overnight while heating. After cooling to room temperature, the reaction solvent is removed by distillation under reduced pressure. The remainder is extracted with ethyl acetate and water. The extracted organic layer is washed with 1 M NaHCO$_3$ aqueous solution and brine and dehydrated with anhydrous MgSO$_4$. The dehydrated organic layer is distilled under reduced pressure and purified by column chromatography to yield the target compound (381 mg). $^1$H NMR (CDCl$_3$, 300 MHz): δ 7.79 (m, 2H), 7.45 (m, 3H), 6.77 (m, 1H), 6.46 (s, 1H), 2.50 (s, 3H), 2.46 (s, 3H).

Step 3: Preparation of 5-chloro-7-(3-methylphenyl)-3-iodo-2-methylpyrazolo[1,5-a]pyrimidine (Chemical Formula 67)

[Chemical Formula 67]

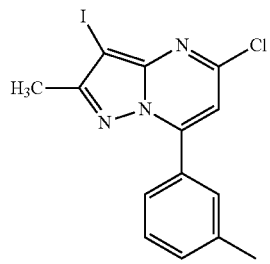

5-Chloro-7-(3-methylphenyl)-2-methylpyrazolo[1,5-a]pyrimidine (381 mg) is dissolved in CH$_2$Cl$_2$ (70 mL) and N-iodosuccinimide (NIS, 467 mg) is added to the reaction solution. The reaction mixture is stirred at room temperature for 16 hours. The reaction solvent is removed by distillation under reduced pressure. The remainder is extracted with ethyl acetate and water. The extracted organic layer is washed with 1 M NaHCO$_3$ aqueous solution and brine and dehydrated with anhydrous MgSO$_4$. The dehydrated organic layer is distilled under reduced pressure and purified by column chromatography to yield the target compound (580 mg). $^1$H NMR (CDCl$_3$, 300 MHz) δ 7.76 (m, 2H), 7.45 (m, 3H), 6.84 (s, 1H), 2.50 (s, 3H), 2.46 (s, 3H).

Step 4: Preparation of (S)-(1-(7-(3-methylphenyl)-3-iodo-2-methylpyrazolo[1,5-a]pyrimidin-5-yl)pyrrolidin-2-yl)methanol (Chemical Formula 68)

[Chemical Formula 68]

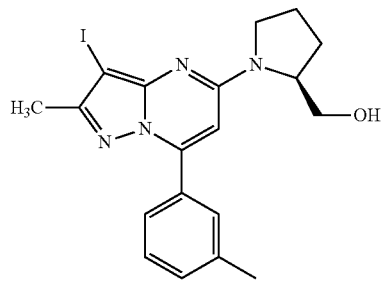

5-Chloro-7-(3-methylphenyl)-3-iodo-2-methylpyrazolo[1,5-a]pyrimidine (580 mg), DIPEA (0.4 mL) and (S)-2-pyrrolidinemethanol (400 mg) are stirred at 90° C. in an acetonitrile (60 mL) solvent for 6 hours. The reaction solvent is removed by distillation under reduced pressure. The remainder is purified by column chromatography to yield the target compound (360 mg). $^1$H NMR (CDCl$_3$, 300 MHz): δ 7.67 (m, 2H), 7.40 (m, 2H), 7.27 (s, 1H), 6.10 (s, 1H), 4.48 (br, 1H), 3.88-3.55 (m, 4H), 2.44 (s, 3H), 2.38 (s, 3H), 2.08-1.97 (m, 3H), 1.76 (m, 1H).

Step 5: Preparation of (S)-(1-(3-(4-methoxyphenyl)-7-(3-methylphenyl)-2-methylpyrazolo[1,5-a]pyrimidin-5-yl)pyrrolidin-2-yl)methanol (S)-(1-(7-(3-Methylphenyl)-3-iodo-2-methylpyrazolo[1,5-a]pyrimidin-5-yl)pyrrolidin-2-yl)methanol (22 mg), 4-methoxyphenylboronic acid (17 mg) and tetrakis(triphenylphosphine)palladium (10 mg) are added to toluene (10 mL), ethanol (3 mL) and 1 N NaHCO$_3$ aqueous solution (1.5 mL) and stirred overnight at 90° C. under argon atmosphere. After cooling to room temperature, the reaction solvent is removed by distillation under reduced pressure. The remainder is extracted with ethyl acetate and water. The organic layer is washed with brine and dehydrated with anhydrous MgSO$_4$. The dehydrated organic layer is concentrated by distillation under reduced pressure and purified by column chromatography to yield the target compound (12 mg).

Examples 158-168

Compounds of Examples 158-168 are prepared in a similar manner as Examples 156 and 157.

Chemical formula and NMR analysis data for the compounds of Examples 156-168 are shown in Chemical Formula 69 and Table 10.

[Chemical Formula 69]

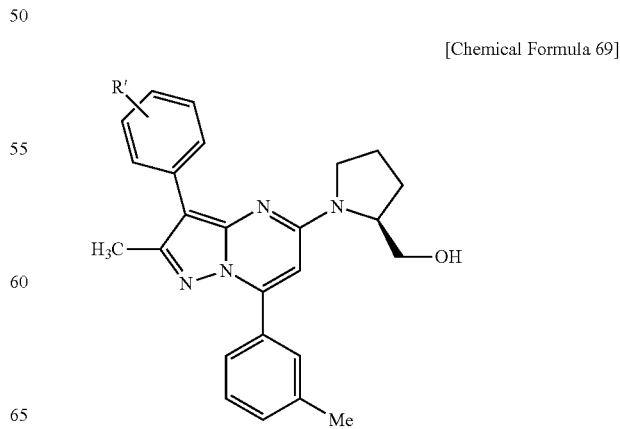

TABLE 10

| Ex. No. | R' | $^1$H NMR (CDCl$_3$, 300 MHz) |
|---|---|---|
| 156 | 4-Me | 7.72 (s, 2H), 7.48 (d, J = 7.8 Hz, 2H), 7.42 (m, 1H), 7.34 (d, J = 7.2 Hz, 1H), 7.26 (m, 2H), 6.12 (s, 1H), 5.65 (bs, 1H), 4.41 (m, 1H), 3.63 (m, 4H), 2.47 (s, 3H), 2.46 (s, 3H), 2.38 (s, 3H), 2.05 (m, 3H), 1.75 (m, 1H) |
| 157 | 4-MeO | 8.18 (d, J = 8.1 Hz, 1H), 7.71 (br, 2H), 7.48 (d, J = 8.7 Hz, 1H), 7.42 (m, 1H), 7.35 (m, 1H), 7.02 (m, 2H), 6.11 (s, 1H), 5.98 (s, 2H), 4.54 (br, 1H), 3.84 (s, 3H), 4.07 (q, J = 7.2 Hz, 2H), 3.73-3.50 (m, 4H), 2.46 (s, 3H), 2.15-1.99 (m, 3H), 1.78 (m, 1H) |
| 158 | 4-EtO | 7.72 (s, 2H), 7.48 (d, J = 8.4 Hz, 2H), 7.42 (m, 1H), 7.35 (m, 1H), 6.11 (s, 1H), 5.98 (s, 2H), 4.87 (br, 1H), 4.07 (q, J = 7.2 Hz, 2H), 3.76-3.50 (m, 4H), 2.46 (s, 3H), 2.15-1.99 (m, 3H), 1.70 (m, 1H) |
| 159 | 3,4-methylenedioxy | 7.70 (m, 2H), 7.42 (m, 1H), 7.395 (m, 1H), 7.05 (s, 1H), 7.02 (d, J = 7.8 Hz, 1H), 6.90 (d, J = 7.8 Hz, 1H), 6.11 (s, 1H), 5.98 (s, 2H), 4.46 (br, 1H), 3.76-3.52 (m, 4H), 2.46 (s, 3H), 2.09-1.99 (m, 3H), 1.78 (m, 1H) |
| 160 | 4-CF2H | 7.74 (m, 4H), 7.56 (d, J = 7.5 Hz, 2H), 7.44 (m, 1H), 7.36 (m, 1H), 6.76 (J = 56.4 Hz, 1H), 6.15 (s, 3H), 4.45 (br, 1H), 3.75-3.56 (m, 4H), 2.50 (s, 3H), 2.46 (s, 3H), 2.12-2.01 (m, 3H), 1.78 (m, 1H) |
| 161 | 4-CFH$_2$ | 7.68 (m, 2H), 7.43 (m, 2H), 7.34 (d, 2H), 7.25 (m, 1H), 6.06 (s, 3H), 5.98 (s, 3H), 4.43 (br, 1H), 3.78-3.62 (m, 4H), 2.44 (s, 3H), 2.37 (s, 3H), 2.12-2.04 (m, 3H), 1.78 (m, 1H) |
| 162 | 4-CH$_3$S | 7.70 (m, 2H), 7.54 (d, J = 8.4 Hz, 2H), 7.42 (m, 1H), 7.35 (d, J = 8.1 Hz, 2H), 6.13 (s, 1H), 4.47 (br, 1H), 3.75-3.55 (m, 4H), 2.52 (s, 3H), 2.47 (s, 3H), 2.45 (s, 3H), 2.12-2.00 (m, 2H), 1.77 (m, 1H) |
| 163 | 4-CF$_3$ | 7.78 (d, J = 8.4 Hz, 2H), 7.71 (m, 4H), 7.46 (m, 1H), 7.34 (d, J = 8.1 Hz, 1H), 6.17 (s, 1H), 4.49 (br, 1H), 3.79-3.57 (m, 4H), 2.51 (s, 3H), 2.47 (s, 3H), 2.14-2.02 (m, 3H), 1.81 (m, 1H) |
| 164 | 4-Et | 8.14 (d, J = 7.8 Hz, 1H), 7.67 (m, 2H), 7.63 (d, J = 8.1 Hz, 2H), 7.50 (m, 1H), 7.35 (m, 2H), 7.27 (m, 2H), 6.11 (s, 1H), 4.43 (br, 1H), 3.73-3.55 (m, 4H), 2.47 (s, 3H), 2.45 (s, 3H), 2.07-1.98 (m, 3H), 1.78 (m, 1H) |
| 165 | 4-vinyl | 7.70 (s, 2H), 7.58 (d, J = 8.1 Hz, 2H), 7.48 (d, J = 8.1 Hz, 2H), 7.42 (m, 1H), 7.34 (m, 1H), 6.74 (dd, J = 10.8, 17.4 Hz, 1H), 6.12 (s, 1H), 5.75 (d, J = 17.4 Hz, 1H), 5.20 (d, J = 11.1 Hz, 1H) 4.45 (br, 1H), 3.74-3.52 (m, 4H), 2.49 (s, 3H), 2.45 (s, 3H), 2.17-1.99 (m, 3H), 1.77 (m, 1H) |
| 166 | 4-propyl | 7.72 (m, 2H), 7.51 (d, J = 8.1 Hz, 2H), 7.45 (m, 1H), 7.35 (m,, 1H), 7.27 (m, 2H), 6.12 (s, 1H), 4.46 (br, 1H), 3.76-3.52 (m, 4H), 2.64 (t, J = 7.5 Hz, 2H), 2.48 (s, 3H), 2.46 (s, 3H), 2.09-1.99 (m, 3H), 1.78-1.66 (m, 3H), 0.98 (t, J = 7.5 Hz, 3H) |
| 167 | 4-F | 7.73 (m, 2H), 7.56 (m, 2H), 7.42 (m, 1H), 7.33 (m, 1H), 7.13 (m, 2H), 6.13 (s, 1H), 4.42 (br, 1H), 3.74-3.53 (m, 4H), 2.45 (s, 3H), 2.13-1.99 (m, 3H), 1.77 (m, 1H) |
| 168 | 4-CF$_3$O | 7.73 (m, 2H), 7.63 (d, J = 8.7 Hz, 2H), 7.45 (m, 1H), 7.36 (m, 1H), 7.27 (m, 2H), 6.15 (s, 1H), 4.46 (br, 1H), 3.75-3.53 (m, 4H), 2.48 (s, 3H), 2.46 (s, 3H), 2.12-2.01 (m, 3H), 1.78 (m, 1H) |

Example 169

Preparation of (S)-(1-(3-(4-methoxyphenyl)-7-(3-chlorophenyl)-2-methylpyrazolo[1,5-a]pyrimidin-5-yl)pyrrolidin-2-yl)methanol (Chemical Formula 70)

[Chemical Formula 70]

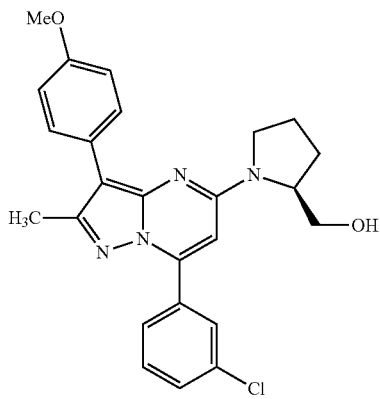

Step 1: Preparation of 5-chloro-7-(3-chlorophenyl)-2-methylpyrazolo[1,5-a]pyrimidine (Chemical Formula 71)

[Chemical Formula 71]

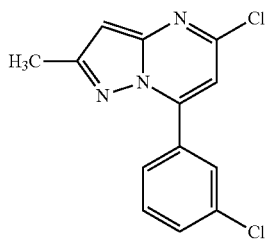

3-Methylpyrazol-5-amine (321 mg) and methyl 3-chlorophenyl-3-oxopropanoate (623 mg) are stirred overnight in a pyridine (10 mL) solvent at 95° C. After cooling to room temperature, the reaction solvent is removed by distillation under reduced pressure. The remainder is extracted with ethyl acetate and water. The extracted organic layer is washed with brine and dehydrated with anhydrous MgSO$_4$. The dehydrated organic layer is distilled under reduced pressure. The remainder is dissolved in POCl$_3$ (15 mL) and pyridine (0.2 mL) and stirred overnight while heating. After cooling to room temperature, the reaction solvent is removed by distillation under reduced pressure. The remainder is extracted with ethyl acetate and water. The extracted organic layer is washed with 1 M NaHCO$_3$ aqueous solution and brine and dehydrated with anhydrous MgSO$_4$. The dehydrated organic layer is distilled under reduced pressure and purified by column chromatography to yield the target compound (188 mg). $^1$H NMR (CDCl$_3$, 300 MHz): δ 8.03 (s, 1H), 7.91 (d, J=6.3 Hz, 1H), 7.52 (m, 2H), 7.42 (m, 1H), 6.79 (s, 1H), 6.49 (s, 1H), 2.51 (s, 3H).

Step 2: Preparation of 5-chloro-7-(3-chlorophenyl)-3-iodo-2-methylpyrazolo[1,5-a]pyrimidine (Chemical Formula 72)

[Chemical Formula 72]

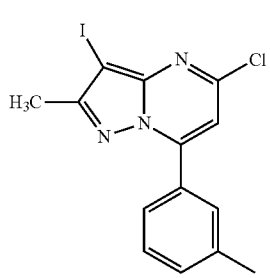

5-Chloro-7-(3-chlorophenyl)-2-methylpyrazolo[1,5-a]pyrimidine (186 mg) is dissolved in CH$_2$Cl$_2$ (40 mL) and N-iodosuccinimide (NIS, 323 mg) is added to the reaction solution. The reaction mixture is stirred at room temperature for 16 hours. The reaction solvent is removed by distillation under reduced pressure. The remainder is extracted with ethyl acetate and water. The extracted organic layer is washed with 1 M NaHCO$_3$ aqueous solution and brine and dehydrated with anhydrous MgSO$_4$. The dehydrated organic layer is distilled under reduced pressure and purified by column chromatography to yield the target compound (237 mg). $^1$H NMR (CDCl$_3$, 300 MHz) δ 7.99 (s, 1H), 7.89 (d, J=7.5 Hz, 1H), 7.53 (m, 3H), 6.85 (s, 1H), 2.51 (s, 3H).

Step 3: Preparation of (S)-(1-(7-(3-chlorophenyl)-3-iodo-2-methylpyrazolo[1,5-a]pyrimidin-5-yl)pyrrolidin-2-yl)methanol (Chemical Formula 73)

[Chemical Formula 73]

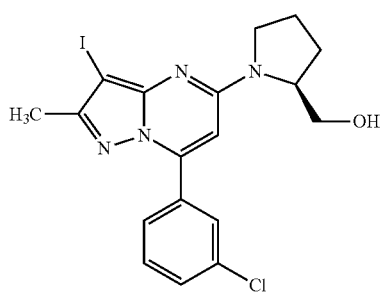

5-Chloro-7-(3-chlorophenyl)-3-iodo-2-methylpyrazolo[1,5-a]pyrimidine (237 mg), DIPEA (0.2 mL) and (S)-2-pyrrolidinemethanol (120 mg) are stirred at 90° C. for 2 hours in an acetonitrile (15 mL) solvent. The reaction solvent is removed by distillation under reduced pressure. The remainder is purified by column chromatography to yield the target compound (360 mg). $^1$H NMR (CDCl$_3$, 300 MHz): δ 7.84 (s, 1H), 7.76 (d, J=7.2 Hz, 1H), 7.45 (m, 3H), 6.10 (s, 1H), 4.47 (bs, 1H), 3.83-3.53 (m, 4H), 2.36 (s, 3H) 2.18-1.98 (m, 3H), 1.78 (m, 1H).

Step 4: Preparation of (S)-(1-(3-(4-methoxyphenyl)-7-(3-chlorophenyl)-2-methylpyrazolo[1,5-a]pyrimidin-5-yl)pyrrolidin-2-yl)methanol (S)-(1-(7-(3-Chlorophenyl)-3-iodo-2-methylpyrazolo[1,5-a]pyrimidin-5-yl)pyrrolidin-2-yl)methanol (30 mg), 4-methoxyphenylboronic acid (15 mg) and tetrakis(triphenylphosphine)palladium (10 mg) are added to toluene (10 mL), ethanol (3 mL) and 1 N NaHCO₃ aqueous solution (1.5 mL) and stirred overnight at 90° C. under argon atmosphere. After cooling to room temperature, the reaction solvent is removed by distillation under reduced pressure. The remainder is extracted with ethyl acetate and water. The organic layer is washed with brine and dehydrated with anhydrous MgSO₄. The dehydrated organic layer is concentrated by distillation under reduced pressure and purified by column chromatography to yield the target compound (21 mg).

Examples 170-176

Compounds of Examples 170-176 are prepared in a similar manner as Example 169.

Chemical formula and NMR analysis data for the compounds of Examples 170-176 are shown in Chemical Formula 74 and Table 11.

[Chemical Formula 74]

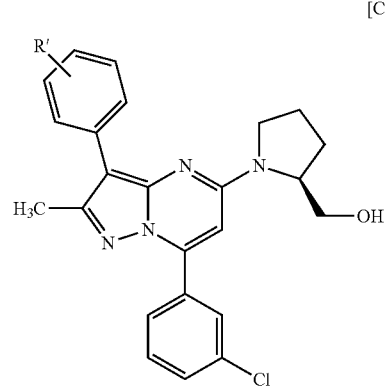

TABLE 11

| Ex. No. | R' | ¹H NMR (CDCl₃, 300 MHz) |
|---|---|---|
| 169 | 4-MeO | 7.92 (s, 1H), 7.86 (d, J = 7.2 Hz, 1H), 7.50 (m, 4H), 6.99 (d, J = 8.7 Hz, 2H), 6.13 (s, 1H), 4.43 (br, 1H), 3.85 (s, 3H), 3.73-3.56 (m, 4H), 2.46 (s, 3H), 2.09-2.00 (m, 3H), 1.78 (m, 1H) |
| 170 | 4-Me | 7.91 (s, 1H), 7.86 (d, J = 6.9 Hz, 1H), 7.47 (m, 3H), 7.25 (m, 3H), 6.13 (s, 1H), 5.47 (bs, 1H), 4.41 (m, 1H), 3.63 (m, 4H), 2.47 (s, 3H), 2.38 (s, 3H), 2.05 (m, 3H), 1.75 (m, 1H) |
| 171 | 4-EtO | 7.92 (s, 1H), 7.86 (d, J = 6.9 Hz, 1H), 7.49 (m, 4H), 7.20 (m, 2H), 6.12 (s, 1H), 4.40 (br, 1H), 4.11 (q, J = 7.2 Hz, 2H), 3.64-3.56 (m, 4H), 2.46 (s, 3H), 2.09-2.00 (m, 3H), 1.78 (m, 1H), 1.40 (t, J = 6.9 Hz, 3H) |
| 172 | 3,4-methylenedioxy | 7.92 (s, 1H), 7.86 (d, J = 7.2 Hz, 1H), 7.50 (m, 3H), 7.10 (s, 1H), 7.02 (m, 1H), 6.92 (d, J = 8.1 Hz, 1H), 6.13 (s, 1H), 5.99 (s, 2H), 4.46 (br, 1H), 3.75-3.54 (m, 4H), 2.46 (s, 3H), 2.14-2.00 (m, 3H), 1.78 (m, 1H) |
| 173 | 4-CF₃ | 7.92 (br, 1H), 7.86 (m, 1H), 7.84 (m, 2H), 7.70 (m, 2H), 7.48 (m, 2H), 6.18 (s, 1H), 4.49 (br, 1H), 3.79-3.58 (m, 4H), 2.52 (s, 3H), 2.15-2.05 (m, 3H), 1.83 (m, 1H) |
| 174 | 4-Et | 7.92 (s, 1H), 7.86 (d, J = 7.2 Hz, 1H), 7.50 (m, 4H), 7.27 (d, J = 7.2 Hz, 1H), 7.25 (m, 1H), 6.13 (s, 1H), 4.45 (br, 1H), 3.78-3.56 (m, 4H), 2.68 (q, J = 7.8 Hz, 2H), 2.49 (s, 3H), 2.10-2.00 (m, 3H), 1.69 (m, 1H), 1.28 (t, J = 8.1 Hz, 3H) |
| 175 | 4-propyl | 7.92 (s, 1H), 7.85 (d, J = 7.2 Hz, 1H), 7.53 (m, 4H), 7.27 (m, 2H), 6.13 (s, 1H), 4.44 (br, 1H), 3.76-3.53 (m, 4H), 2.62 (t, J = 7.2 Hz, 2H), 2.48 (s, 3H), 2.46 (s, 3H), 2.17-1.99 (m, 3H), 1.78-1.63 (m, 3H), 0.98 (t, J = 7.5 Hz, 3H) |
| 176 | 4-Me, 3-F | 7.92 (s, 1H), 7.85 (d, J = 7.2 Hz, 1H), 7.50 (m, 2H), 7.33 (m, 2H), 7.24 (m, 1H), 6.15 (s, 1H), 4.46 (br 1H), 3.75-3.56 (m, 4H), 2.49 (s, 3H), 2.30 (s, 3H), 2.15-2.04 (m, 4H), 1.78 (m, 1H) |

Example 177

Preparation of (S)-(1-(3-(4-(difluoromethyl)phenyl)-7-(3,5-difluorophenyl)-2-methylpyrazolo[1,5-a]pyrimidin-5-yl)pyrrolidin-2-yl)methanol (Chemical Formula 75)

[Chemical Formula 75]

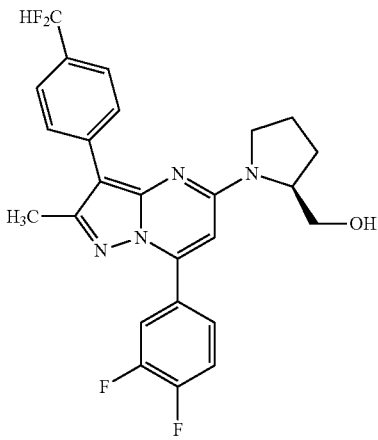

(S)-(1-(7-(3,5-Difluorophenyl)-3-iodo-2-methylpyrazolo[1,5-a]pyrimidin-5-yl)pyrrolidin-2-yl)methanol (55 mg), 4-(difluoromethyl)phenylboronic acid (34 mg) and tetrakis(triphenylphosphine)palladium (10 mg) are added to toluene (8 mL), ethanol (3 mL) and 1 N NaHCO$_3$ aqueous solution (1.5 mL) and stirred at 85° C. for 4 hours under argon atmosphere. After cooling to room temperature, the reaction solvent is removed by distillation under reduced pressure. The remainder is extracted with ethyl acetate and water. The organic layer is washed with brine and dehydrated with anhydrous MgSO$_4$. The dehydrated organic layer is concentrated by distillation under reduced pressure and purified by column chromatography to yield the target compound (51 mg).

Examples 178-195

Compounds of Examples 178-195 are prepared in a similar manner as Example 177.

Chemical formula and NMR analysis data for the compounds of Examples 177-195 are shown in Chemical Formula 76 and Table 12.

[Chemical Formula 76]

TABLE 12

| Ex. No. | R | R' | $^1$H NMR (CDCl$_3$, 300 MHz) |
|---|---|---|---|
| 177 | 3-F, 4F | 4-CHF$_2$ | 7.90 (m, 1H), 7.73 (m, 3H), 7.58 (d, J = 7.8 Hz, 2H), 7.40 (m, 1H), 7.35 (m, 1H), 7.68 (t, J = 56.7 Hz, 2H), 6.16 (s, 1H), 4.47 (br, 1H), 3.78-3.54 (m, 4H), 2.51 (s, 3H), 2.17-2.00 (m, 3H), 1.83 (m, 1H) |
| 178 | 3-OMe | 4-CHF$_2$ | 7.70 (d, J = 7.8 Hz, 2H), 7.55 (d, J = 7.8 Hz, 2H), 7.44 (m, 2H), 7.05 (d, J = 7.2 Hz, 2H), 6.64 (s, 1H), 6.16 (s, 1H), 4.44 (br, 1H), 3.86 (s, 3H), 3.72-3.50 (m, 4H), 2.47 (s, 3H), 2.15-1.99 (m, 3H), 1.78-1.69 (m, 1H) |
| 179 | 3-OMe | 4-CF$_3$ | 7.78 (d, J = 8.1 Hz, 2H), 7.68 (d, J = 8.4 Hz, 2H), 7.48 (m, 3H), 7.08 (m, 1H), 6.20 (s, 1H), 4.49 (br, 1H), 3.89 (s, 3H), 3.69-3.50 (m, 4H), 2.51 (s, 3H), 2.15-1.99 (m, 3H), 1.78-1.69 (m, 1H) |
| 180 | 4-Me | 4-CF$_3$ | 7.84 (d, J = 8.1 Hz, 2H), 7.77 (d, J = 8.1 Hz, 2H), 7.67 (d, J = 8.1 Hz, 2H), 7.33 (d, J = 8.1 Hz, 2H), 6.17 (s, 1H), 4.48 (br, 1H), 3.74-3.49 (m, 4H), 2.51 (s, 3H), 2.45 (s, 3H), 2.10-1.97 (m, 3H), 1.78-1.69 (m, 1H) |
| 181 | 3-OMe | 4-Et | 8.16 (m, 2H), 7.52 (d, J = 7.8 Hz, 2H), 7.44 (m, 1H), 7.31 (d, J = 7.8 Hz, 2H), 7.07 (m, 1H), 6.51 (s, 1H), 4.47 (br, 1H), 3.86 (s, 3H), 3.69-3.50 (m, 4H), 2.73 (q, J = 7.8 Hz, 2H), 2.48 (s, 3H), 2.15-1.99 (m, 3H), 1.78-1.69 (m, 1H), 1.26 (t, J = 7.8 Hz, 3H) |
| 182 | 4-Me | 4-Et | 7.84 (d, J = 8.1 Hz, 2H), 7.52 (d, J = 8.1 Hz, 2H), 7.33 (d, J = 7.8 Hz, 2H), 7.28 (d, J = 8.1 Hz, 2H), 6.12 (s, 1H), 4.43 (br, 1H), 3.74-3.49 (m, 4H), 2.68 (q, J = 7.5 Hz, 2H), 2.48 (s, 3H), 2.44 (s, 3H), 2.10-1.97 (m, 3H), 1.78-1.69 (m, 1H), 1.28 (t, J = 7.8 Hz, 3H) |

TABLE 12-continued

| Ex. No. | R | R' | ¹H NMR (CDCl₃, 300 MHz) |
|---|---|---|---|
| 183 | 3-OMe | 3-F, 4-Me | 7.50 (m, 3H), 7.32 (d, J = 9.0 Hz, 2H), 7.26 (m, 1H), 7.07 (m, 1H), 6.17 (s, 1H), 4.47 (br, 1H), 3.88 (s, 3H), 3.78-3.52 (m, 4H), 2.49 (s, 3H), 2.30 (s, 3H), 2.15-1.99 (m, 3H), 1.78-1.69 (m, 1H) |
| 184 | 3-F, 4-F | 3-F, 4-Me | 7.90 (m, 1H), 7.69 (m, 1H), 7.29 (m, 4H), 6.14 (s, 1H), 4.46 (br, 1H), 3.65 (m, 4H), 2.49 (s, 3H), 2.15 (s, 3H), 2.09 (m, 2H), 1.82 (m, 1H) |
| 185 | 3-Cl, 4-F | 3-F, 4-Me | 8.04 (m, 1H), 7.88 (m, 1H), 7.31 (m, 4H), 6.13 (s, 1H), 5.20 (br, 1H), 4.46 (br, 1H), 3.64 (m, 4H), 2.49 (s, 3H), 2.15 (s, 3H), 2.34 (m, 2H), 1.79 (m, 1H), |
| 186 | 3-OMe | 3-F, 4-MeO | 8.49 (m, 3H), 7.39 (m, 1H), 7.29 (m, 1H), 7.00 (m, 2H), 6.17 (s, 1H), 4.47 (br, 1H), 3.92 (s, 3H), 3.88 (s, 3H), 3.78-3.52 (m, 4H), 2.47 (s, 3H), 2.15-1.99 (m, 3H), 1.78-1.69 (m, 1H) |
| 187 | 3-F, 4-F | 3-F, 4-MeO | 7.90 (m, 1H), 7.70 (m, 1H), 7.37 (m, 3H), 7.05 (m, 1H), 6.14 (s, 1H), 4.46 (br, 1H), 3.92 (s, 3H), 3.65 (m, 4H), 2.48 (s, 3H), 2.09 (m, 2H), 1.82 (m, 1H) |
| 188 | 3-F, 5-F | 3-F, 4-MeO | 7.54 (m, 2H), 7.34 (m, 2H), 7.05 (m, 2H), 6.16 (s, 1H), 4.45 (br, 1H), 3.92 (s, 3H), 3.77-3.56 (m, 4H), 2.48 (s, 3H), 2.17-2.08 (m, 2H), 1.87 (m, 1H) |
| 189 | 3-Cl, 4-F | 3-F, 4-MeO | 8.02 (m, 1H), 7.87 (m, 1H), 7.65 (m, 1H), 7.46 (m, 1H), 7.32 (m, 1H), 7.05 (m, 1H), 6.13 (s, 1H), 4.38 (br, 1H), 3.92 (s, 3H), 3.78-3.52 (m, 4H), 2.47 (s, 3H), 2.09 (m, 2H), 1.80 (m, 1H) |
| 190 | 3-OMe | 2-F, 4-F | 7.54-7.38 (m, 3H), 7.00 (m, 1H), 6.94 (m, 2H), 6.79 (m, 1H), 6.16 (s, 1H), 4.35 (br, 1H), 3.89 (s, 3H), 3.78-3.52 (m, 4H), 2.40 (s, 3H), 2.15-1.99 (m, 4H), 1.78-1.69 (m, 1H) |
| 191 | 3-Et | 2-F, 4-F | 7.72 (d, J = 8.7 Hz, 2H), 7.40 (m, 3H), 7.25 (m, 1H), 6.28 (m, 1H), 6.07 (s, 1H), 5.96 (s, 1H), 4.44 (m, 1H), 3.67 (m, 4H), 2.75 (m, 2H), 2.37 (s, 3H), 2.08 (m, 3H), 1.75 (m, 1H), 1.30 (s, 3H) |
| 192 | 3-Cl, 4-F | 4-F | 8.04 (m, 1H), 7.87 (m, 1H), 7.52 (m, 2H), 7.28 (m, 2H), 7.11 (m, 2H), 6.12 (s, 1H), 4.43 (br, 1H), 3.66 (m, 4H), 2.45 (s, 3H), 2.11 (s, 2H), 1.77 (m, 1H) |
| 193 | 4-Me | 4-Pr | 7.82 (d, J = 7.8 Hz, 2H), 7.47 (d, J = 7.8 Hz, 2H), 7.30 (d, J = 7.8 Hz, 2H), 7.2 (d, J = 7.5 Hz, 2H), 6.09 (s, 1H), 4.40 (br, 1H), 3.69-3.50 (m, 4H), 2.58 (t, J = 7.8 Hz, 2H), 2.45 (s, 3H), 2.41 (s, 3H), 2.15-1.99 (m, 3H), 1.78-1.69 (m, 1H), 1.65 (m, 2H), 0.95 (t, J = 7.2 Hz, 3H) |
| 194 | 4-Me | 4-PrO | 7.82 (d, J = 8.1 Hz, 2H), 7.45 (d, J = 8.4 Hz, 2H), 7.30 (d, J = 7.8 Hz, 2H), 6.96 (d, J = 9.0 Hz, 2H), 6.08 (s, 1H), 4.38 (br, 1H), 3.93 (t, J = 8.4 Hz, 2H), 3.69-3.50 (m, 4H), 2.42 (s, 3H), 2.15-1.99 (m, 3H), 1.78 (m, 2H), 1.78-1.69 (m, 1H), 1.02 (t, J = 7.5 Hz, 3H) |
| 195 | H | 4-H | 7.94 (m, 2H), 7.60 (d, J = 7.5 Hz, 2H), 7.53 (bs, 3H), 7.44 (dd, J = 7.2, 7.5 Hz, 2H), 7.25 (m, 1H), 6.14 (s, 1H), 5.42 (bs, 1H), 4.41 (m, 1H), 3.63 (m, 4H), 2.49 (s, 3H), 2.06 (m, 3H), 1.76 (m, 1H) |

Example 196

Preparation of (S)-(1-(3-(4-chlorophenyl)-7-(4-fluorophenyl)-2-cyclopropylpyrazolo[1,5-a]pyrimidin-5-yl)pyrrolidin-2-yl)methanol (Chemical Formula 77)

[Chemical Formula 77]

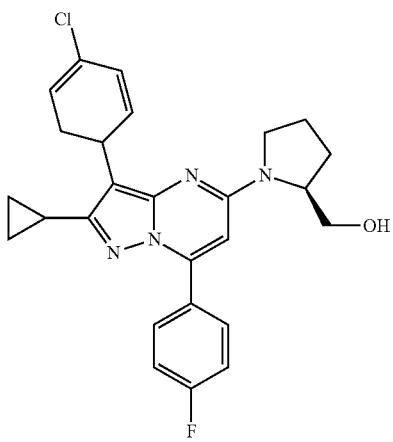

Step 1: Preparation of 2-(4-chlorophenyl)-3-cyclopropyl-3-oxopropanenitrile (Chemical Formula 78)

[Chemical Formula 78]

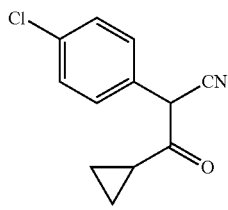

2-(4-Chlorophenyl)acetonitrile (5.74 g) is dissolved in 120 mL of THF at 0° C. After adding 60% NaH (4.2 g, 2.7 eq), the reaction mixture is stirred for 10 minutes. Ethylcyclopropane carboxylate is added and the mixture is stirred overnight. The reaction is stopped by adding acetic acid (5 mL) and water. The aqueous layer is extracted with ethyl acetate (50 mL×3). The collected organic layer is washed with brine and dehydrated with MgSO₄. The dehydrated organic layer is concentrated by distillation under reduced pressure and purified by column chromatography to yield 7.74 g of the target compound. ¹H NMR (CDCl₃, 300 MHz): δ 7.42 (d, J=8.7 Hz, 2H), 7.34 (d, J=8.7 Hz, 2H), 4.79 (s, 1H), 2.10 (m, 1H) 1.16 (m, 2H), 1.03 (m, 2H).

Step 2: Preparation of 4-(4-chlorophenyl)-3-cyclopropyl-1H-pyrazol-5-amine (Chemical Formula 79)

[Chemical Formula 79]

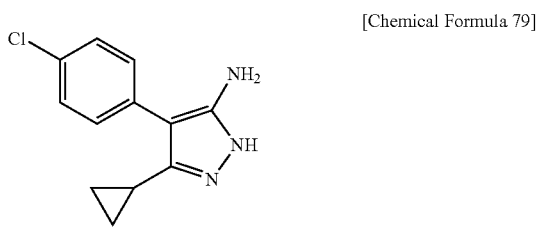 [SMILES: Nc1[nH]nc(C2CC2)c1-c1ccc(Cl)cc1]

2-(4-Chlorophenyl)-3-cyclopropyl-3-oxopropanenitrile (7.74 g), hydrazine hydrate (3.5 mL) and acetic acid (7.5 mL) are dissolved in a toluene solvent and stirred for 16 hours while heating. Upon completion of reaction, after cooling to room temperature, the solvent is removed by distillation under reduced pressure. The remainder is extracted with water and ethyl acetate. The extracted organic layer is dehydrated and distilled under reduced pressure. The remainder is purified by column chromatography to yield 5.2 g of the target compound. ¹H NMR (CDCl₃, 300 MHz): δ 7.40 (m, 4H), 3.75 (br, 2H), 1.86 (m, 1H) 0.93 (m, 2H), 0.65 (m, 2H).

Step 3: Preparation of 2-cyclopropyl3-(4-chlorophenyl)-7-(4-fluorophenyl)-pyrazolo[1,5-a]pyrimidin-5(4H)-one (Chemical Formula 80)

[Chemical Formula 80]

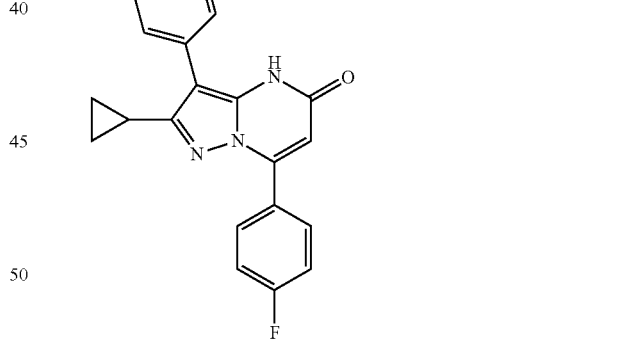

4-(4-Chlorophenyl)-3-cyclopropyl-1H-pyrazol-5-amine (121 mg) and ethyl 3-(4-fluorophenyl)-3-oxopropanoate (0.095 mL) are stirred overnight in a pyridine (7 mL) solvent at 95° C. After cooling to room temperature, the reaction solvent is removed by distillation under reduced pressure. The remainder is extracted with ethyl acetate and water. The extracted organic layer is washed with brine and dehydrated with anhydrous MgSO₄. The dehydrated organic layer is distilled under reduced pressure and purified by column chromatography to yield 75 mg of the target compound. ¹H NMR (CDCl₃, 300 MHz): δ 10.15 (br, 1H), 8.02 (m, 2H), 7.42 (m, 4H), 7.18 (m, 2H), 4.08 (br, 1H), 1.80 (m, 1H) 0.89 (m, 4H).

Step 4: Preparation of 5-chloro-2-cyclopropyl-3-(4-chlorophenyl)-7-(4-fluorophenyl)-pyrazolo[1,5-a]pyridine pyrimidine (Chemical Formula 81)

[Chemical Formula 81]

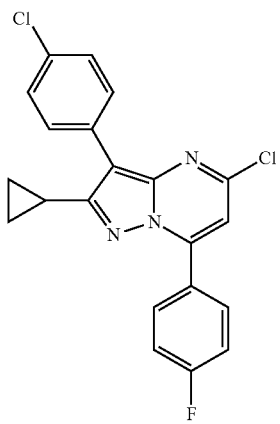

2-Cyclopropyl-3-(4-chlorophenyl)-7-(4-fluorophenyl)-pyrazolo[1,5-a]pyrimidin-5(4H)-one (257 mg) is added to POCl₃ (10 mL) and pyridine (0.2 mL) and stirred for 3 hours while heating. After cooling to room temperature, POCl₃ is removed by distillation under reduced pressure. After the distillation, ethyl acetate (20 mL) and ice are added to the remainder. The organic layer is extracted and it is extracted once again with water and ethyl acetate. The organic layer is washed with 1 M NaHCO₃ aqueous solution and brine. The organic layer is dehydrated with anhydrous MgSO₄. The solvent is removed from the organic layer by distillation under reduced pressure. The remainder is purified by column chromatography to yield the target compound (143 mg). $^1$H NMR (CDCl₃, 300 MHz): δ 8.09 (m, 2H), 7.79 (d, J=8.7 Hz, 2H), 7.46 (d, J=8.4 Hz, 2H), 7.26 (m, 2H), 6.83 (s, 1H), 2.17 (m, 1H), 1.13 (m, 2H), 1.06 (m, 2H).

Step 5: Preparation of (S)-(1-(3-(4-chlorophenyl)-7-(4-fluorophenyl)-2-cyclopropylpyrazolo[1,5-a]pyrimidin-5-yl)pyrrolidin-2-yl)methanol 5-Chloro-2-ethyl3-(4-methylphenyl)-7-(4-fluorophenyl)-pyrazolo[1,5-a]pyrimidine (48 mg), (S)-pyrrolin-2-ylmethanol (0.02 mL) and DIPEA (0.1 mL) are added to acetonitrile (15 mL) and stirred overnight at 80° C. After cooling to room temperature, the solvent and volatile substance are removed by distillation under reduced pressure. The remainder is extracted 3 times with ethyl acetate (20 mL) and water. The collected organic layer is washed with brine. The organic layer is dehydrated with anhydrous MgSO₄ and the solvent is removed by distillation under reduced pressure. The remainder is purified by column chromatography to yield the target compound (36 mg).

Example 197

A compound of Example 197 is prepared in a similar manner as Example 196.

Chemical formula and NMR analysis data for the compounds of Examples 196 and 197 are shown in Chemical Formula 82 and Table 13.

[Chemical Formula 82]

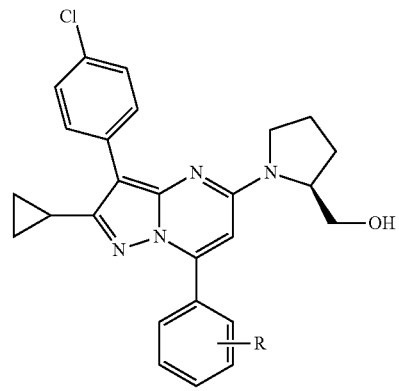

TABLE 13

| Ex. No. | R | $^1$H NMR (CDCl₃, 300 MHz) |
|---|---|---|
| 196 | 4-F | 7.98 (m, 2H), 7.70 (d, J = 8.4 Hz, 2H), 7.41 (d, J = 8.4 Hz, 2H), 7.23 (m, 2H), 6.13 (s, 1H), 4.44 (br, 1H), 3.75-3.55 (m, 4H), 2.13-2.03 (m, 3H), 1.79 (m, 1H), 1.05-0.93 (m, 5H). |
| 197 | 3-F | 7.75 (m, 4H), 7.48 (m, 1H), 7.41 (d, J = 8.4 Hz, 2H), 7.23 (m, 1H), 6.17 (s, 1H), 4.44 (br, 1H), 3.74-3.53 (m, 4H), 2.13-2.03 (m, 4H), 1.79 (m, 1H), 1.04-0.87 (m, 4H). |

Example 198

Preparation of (S)-(1-(3-(4-methylphenyl)-7-(4-fluorophenyl)-2-ethylpyrazolo[1,5-a]pyrimidin-5-yl)pyrrolidin-2-yl)methanol (Chemical Formula 83)

[Chemical Formula 83]

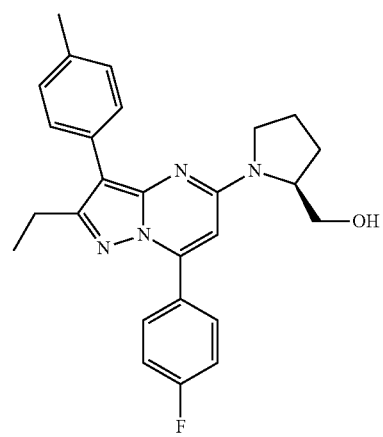

Step 1: Preparation of 2-ethyl3-(4-methylphenyl)-7-(4-fluorophenyl)-pyrazolo[1,5-a]pyrimidin-5(4H)-one (Chemical Formula 84)

[Chemical Formula 84]

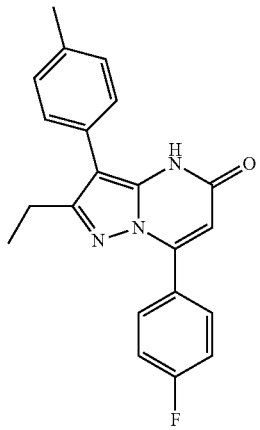

3-Ethyl-4-(4-methylphenyl)-1H-pyrazol-5-amine (200 mg) and ethyl 3-(4-fluorophenyl)-3-oxopropanoate (250 mg) are stirred overnight in a pyridine (10 mL) solvent at 95° C. After cooling to room temperature, the reaction solvent is removed by distillation under reduced pressure. The remainder is extracted with ethyl acetate and water. The extracted organic layer is washed with brine and dehydrated with anhydrous MgSO$_4$. The dehydrated organic layer is distilled under reduced pressure and purified by column chromatography to yield 280 mg of the target compound.

Step 2: Preparation of 5-chloro-2-ethyl-3-(4-methylphenyl)-7-(4-fluorophenyl)-pyrazolo[1,5-a]pyridine pyrimidine (Chemical Formula 85)

[Chemical Formula 85]

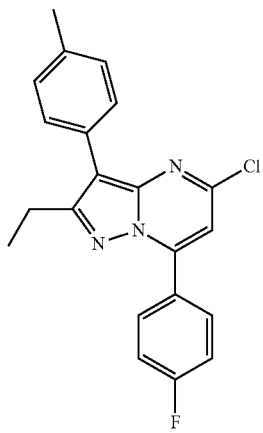

2-Ethyl-3-(4-methylphenyl)-7-(4-fluorophenyl)-pyrazolo[1,5-a]pyrimidin-5(4H)-one (150 mg) is added to POCl$_3$ (3 mL) and pyridine (0.1 mL) and stirred for 2 hours while heating. After cooling to room temperature, POCl$_3$ is removed by distillation under reduced pressure. After the distillation, ethyl acetate (20 mL) and ice are added to the remainder. The organic layer is extracted and it is extracted once again with water and ethyl acetate. The organic layer is washed with 1 M NaHCO$_3$ aqueous solution and brine. The organic layer is dehydrated with anhydrous MgSO$_4$. The solvent is removed from the organic layer by distillation under reduced pressure. The remainder is purified by column chromatography to yield 70 mg of the target compound. $^1$H NMR (CDCl$_3$, 300 MHz) δ 7.96 (m, 2H), 7.53 (m, 3H), 7.24 (m, 3H), 6.85 (s, 1H), 2.90 (q, J=7.8 Hz, 2H), 2.42 (s, 3H), 1.23 (t, J=7.8 Hz, 3H).

Step 3: Preparation of (S)-(1-(3-(4-methylphenyl)-7-(4-fluorophenyl)-2-ethylpyrazolo[1,5-a]pyrimidin-5-yl)pyrrolidin-2-yl)methanol 5-Chloro-2-ethyl3-(4-methylphenyl)-7-(4-fluorophenyl)-pyrazolo[1,5-a]pyrimidine (50 mg), (S)-pyrrolin-2-ylmethanol (17 mg) and DIPEA (0.2 mL) are added to acetonitrile (10 mL) and stirred overnight at 80° C. After cooling to room temperature, the solvent and volatile substance are removed by distillation under reduced pressure. The remainder is extracted 3 times with ethyl acetate (20 mL) and water. The collected organic layer is washed with brine. The organic layer is dehydrated with anhydrous MgSO$_4$ and the solvent is removed by distillation under reduced pressure. The remainder is purified by column chromatography to yield 48 mg of the target compound.

Examples 199 and 200

Compounds of Examples 199 and 200 are prepared in a similar manner as Example 198.

Chemical formula and NMR analysis data for the compounds of Examples 198-200 are shown in Chemical Formula 86 and Table 14.

[Chemical Formula 86]

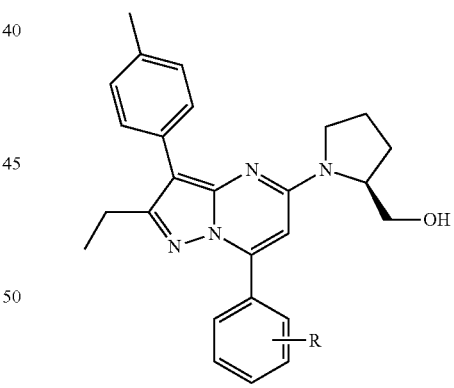

TABLE 14

| Ex. No. | R | $^1$H NMR (CDCl$_3$, 300 MHz) |
|---|---|---|
| 198 | 3-Cl | 7.76 (m, 2H), 7.51 (m, 1H), 7.42 (m, 2H), 7.24 (m, 3H), 6.15 (s, 1H), 5.54 (br, 1H), 4.38 (m, 1H), 3.61 (m, 4H), 2.88 (q, J = 7.8 Hz, 2H), 2.38 (s, 3H), 2.08 (m, 4H), 1.74 (m, 1H), 1.23 (m, 3H) |
| 199 | 4-F | 8.02 (m, 2H), 7.43 (d, J = 7.8 Hz, 2H), 7.25 (m, 2H), 7.20 (d, J = 7.8 Hz, 2H), 6.11 (s, 1H), 4.38 (m, 1H), 4.12 (q, J = 7.2 Hz, 2H), 3.78-3.50 (m, 3H), 2.38 (s, 3H), 2.15-1.99 (m, 3H), 1.75-1.69 (m, 1H), 1.23 (t, J = 6.9 Hz, 3H) |

TABLE 14-continued

| Ex. No. | R | $^1$H NMR (CDCl$_3$, 300 MHz) |
|---|---|---|
| 200 | 3-F | 7.96 (s, 1H), 7.91 (d, J = 7.2 Hz, 1H), 7.46 (m, 4H), 7.25 (d, J = 7.5 Hz, 2H), 6.13 (s, 1H), 5.56 (bs, 1H), 4.38 (m, 1H), 3.61 (m, 4H), 2.86 (dd, J = 7.5 Hz, 2H), 2.38 (s, 3H), 2.05 (m, 3H), 1.74 (m, 1H), 1.23 (dd, J = 7.5, 7.8 Hz) |

Example 201

Preparation of (S)-{1-[2-ethoxymethyl-7-(4-fluorophenyl)-3-(4-methylphenyl)-pyrazolo[1,5-a]pyrimidin-5-yl]pyrrolidin-2-yl}methanol (Chemical Formula 87)

[Chemical Formula 87]

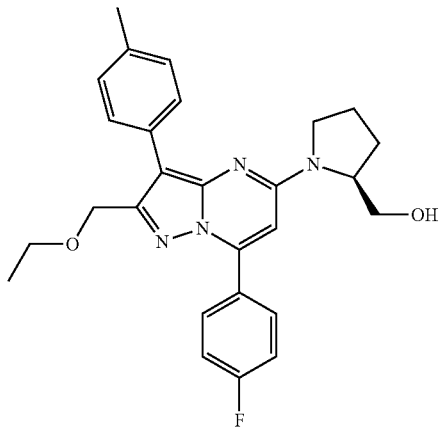

Step 1: Preparation of 4-ethoxy-2-(4-methylphenyl)-3-oxobutanenitrile (Chemical Formula 88)

[Chemical Formula 88]

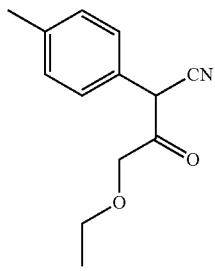

Sodium ethoxide (2 eq) is dissolved in ethanol (200 mL) and 4-methylphenylacetonitrile (10.0) and ethyl ethoxyacetate (1.5 eq) are slowly added. The reaction mixture is stirred for 1 hour under reflux. Upon completion of the reaction, ethanol is removed under reduced pressure and water (100 mL) and ethyl acetate are added. The organic layer is removed and the aqueous layer is acidified by adding acetic acid (10 mL) and extracted 3 times with ethyl acetate. The extracted organic layer is collected, washed with water and dehydrated with MgSO$_4$. After concentration under reduced pressure, the produced solid is recrystallized with Hx:EA=20:1 to obtain the target compound (70-95%).

Step 2: Preparation of 3-(ethoxymethyl)-4-(4-methylphenyl)-1H-pyrazol-5-amine (Chemical Formula 89)

[Chemical Formula 89]

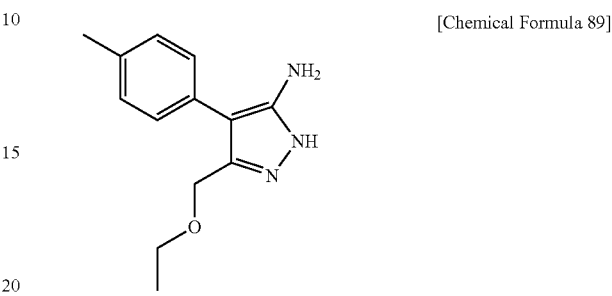

4-Ethoxy-2-(4-methylphenyl)-3-oxobutanenitrile (1.493 g) is dissolved in ethanol (50 mL). After adding hydrazine 2HCl (1.10 g), TEA (0.85 mL) and molecular sieve, the reaction mixture is heated to 80° C. After stirring for 15 hours and cooling to room temperature, the molecular sieve is removed by filtering. The reaction solvent is removed under reduced pressure. After the reaction is terminated by adding saturated aq. NaHCO$_3$, the reaction mixture is extracted 3 times with ethyl acetate. The organic layer is washed with water and dehydrated with MgSO$_4$. After concentration under reduced pressure, the produced solid is recrystallized to obtain the target compound (90%). $^1$H NMR (CDCl$_3$, 300 MHz): δ 7.26 (m, 2H), 7.02 (m, 2H), 6.80 (br, 2H), 4.20 (s, 2H), 3.38 (m, 2H), 2.24 (s, 3H), 1.06 (t, 3H).

Step 3: Preparation of 2-(ethoxymethyl)-7-(4-fluorophenyl)-3-(4-methylphenyl)pyrazolo[1,5-a]pyrimidin-5(4H)-one (Chemical Formula 90)

[Chemical Formula 90]

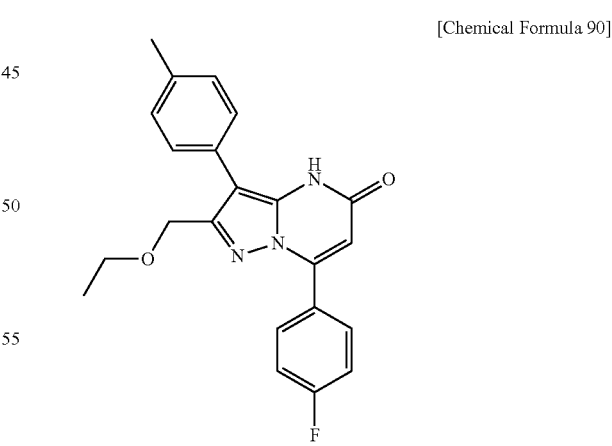

3-(Ethoxymethyl)-4-(4-methylphenyl)-1H-pyrazol-5-amine (133 mg) and ethyl 3-(4-fluorophenyl)-3-oxopropanoate (0.2 mL) are stirred at 84° C. for 14 hours in a pyridine (10 mL) solvent. After cooling to room temperature, the reaction solvent is removed by distillation under reduced pressure. The remainder is extracted with ethyl acetate and water. The extracted organic layer is washed with brine and dehydrated with anhydrous MgSO$_4$. The dehydrated organic layer is distilled under reduced pressure and purified by column chromatography to yield 132 mg of the target compound. $^1$H NMR (CDCl$_3$, 300 MHz): δ 10.08 (s, 1H), 7.98 (m, 2H), 7.28 (m, 4H), 7.13 (m, 2H), 4.43 (s, 2H), 4.04 (br, 1H), 3.50 (m, 2H), 2.35 (s, 3H), 1.06 (t, 3H).

Step 4: Preparation of 5-chloro-2-(ethoxymethyl)-7-(4-fluorophenyl)-3-(4-methylphenyl)pyrazolo[1,5-a]pyrimidine (Chemical Formula 91)

[Chemical Formula 91]

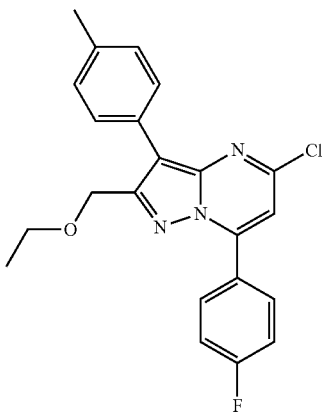

2-(Ethoxymethyl)-7-(4-fluorophenyl)-3-(4-methylphenyl)pyrazolo[1,5-a]pyrimidin-5(4H)-one (132 mg) is dissolved in POCl$_3$ (15 mL) and pyridine (0.2 mL) and stirred overnight while heating. After cooling to room temperature, the reaction solvent is removed by distillation under reduced pressure. The remainder is extracted with ethyl acetate and water. The extracted organic layer is washed with 1 M NaHCO$_3$ aqueous solution and brine and dehydrated with anhydrous MgSO$_4$. The dehydrated organic layer is distilled under reduced pressure and purified by column chromatography to yield the target compound (381 mg). $^1$H NMR (CDCl$_3$, 300 MHz): δ 8.11 (m, 2H), 7.73 (d, J=0.8.1 Hz, 2H), 7.26 (m, 4H), 6.87 (s, 1H), 4.70 (s, 2H), 6.66 (m, 2H), 2.41 (s, 3H), 1.26 (3H).

Step 5: Preparation of (S)-{1-[2-ethoxymethyl-7-(4-fluorophenyl)-3-(4-methylphenyl)-pyrazolo[1,5-a]pyrimidin-5-yl]pyrrolidin-2-yl}methanol 5-Chloro-2-(ethoxymethyl)-7-(4-fluorophenyl)-3-(4-methylphenyl)pyrazolo[1,5-a]pyrimidine (22 mg), DIPEA (0.1 mL) and (S)-2-pyrrolidinemethanol (0.1 mL) are stirred for 2 hours in an acetonitrile (7 mL) solvent at 84° C. The reaction solvent is removed by distillation under reduced pressure. The remainder is purified by column chromatography to yield the target compound (24 mg).

Examples 202-220

Compounds of Examples 202-220 are prepared in a similar manner as Example 201.

Chemical formula and NMR analysis data for the compounds of Examples 201-220 are shown in Chemical Formula 92 and Table 15.

[Chemical Formula 92]

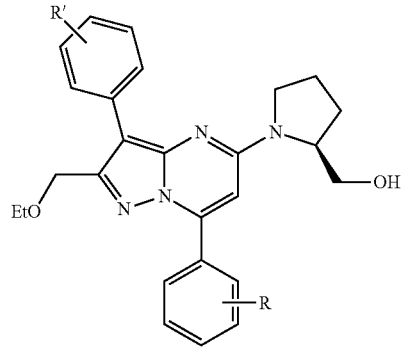

TABLE 15

| Ex. No. | R | R' | $^1$H NMR (CDCl$_3$, 300 MHz) |
|---|---|---|---|
| 201 | 4-F | 4-Me | 7.99 (m, 2H), 7.63 (m, 2H), 7.22 (m, 4H), 6.18 (s, 1H), 4.58 (s, 2H), 4.42 (br, 1H), 3.62 (m, 6H), 3.38 (s, 3H), 2.15 (m, 3H), 1.80 (m, 1H), 1.26 (t, J = 6.9 Hz, 3H) MS (M + 1): 461.4 |
| 202 | 3-F | 4-Me | 7.85 (m, 1H), 7.83 (m, 1H), 7.75 (m, 2H), 7.43 (m, 2H), 7.25 (m, 2H), 6.87 (s, 1H), 4.71 (s, 2H), 3.66 (q, J = 6.9 Hz, 2H), 2.47 (s, 3H), 2.41 (s, 3H), 1.26 (t, J = 6.9 Hz, 3H) |
| 203 | 3-OMe | 4-Me | 7.65 (m, 2H), 7.55 (s, 1H), 7.46 (m, 2H), 7.27 (m, 2H), 7.08 (m, 1H), 6.22 (s, 1H), 4.59 (s, 2H), 4.45 (br, 1H), 3.88 (s, 3H), 3.63 (m, 6H), 2.38 (s, 3H), 2.11 (m, 2H), 1.23 (m, 3H) |
| 204 | 3-CF$_3$ | 4-Me | 8.21 (m, 1H), 8.19 (m, 1H), 7.80 (m, 1H), 7.67 (m, 3H), 7.26 (m, 1H), 6.24 (s, 1H), 5.35 (br, 1H), 4.59 (s, 2H), 3.63 (m, 6H), 2.38 (s, 3H), 2.06 (m, 3H), 1.80 (m, 1H), 1.25 (t, J = 6.9 Hz, 3H) |
| 205 | 3-Me | 4-Me | 7.74 (m, 2H), 7.64 (m, 2H), 7.42 (m, 2H), 7.32 (m, 2H), 6.12 (s, 1H), 4.59 (s, 2H), 4.43 (m, 1H), 3.59 (m, 6H), 2.46 (s, 3H), 2.38 (m, 3H), 2.10 (m, 3H), 1.79 (m, 1H), 1.25 (t, J = 6.9 Hz, 3H) |

TABLE 15-continued

| Ex. No. | R | R' | $^1$H NMR (CDCl$_3$, 300 MHz) |
|---|---|---|---|
| 206 | 4-F | 4-Cl | 7.98 (m, 2H), 7.74 (d, J = 8.4 Hz, 2H), 7.40 (d, J = 8.4 Hz, 2H), 7.22 (t, J = 8.7 Hz, 2H), 6.21 (s, 1H), 5.06 (bs, 1H), 4.75 (s, 2H), 4.68 (m, 1H), 3.65 (m, 6H), 2.09 (m, 3H), 1.82 (m, 1H), 1.25 (dd, J = 6.9, 7.2 Hz, 3H) |
| 207 | 3-F | 4-Cl | 7.73 (m, 4H), 7.50 (m, 1H), 7.40 (d, J = 8.4 Hz, 2H), 7.06 (m, 1H) 6.25 (s, 1H), 4.99 (bs, 1H), 4.58 (s, 2H), 4.46 (bs, 1H), 3.63 (m, 6H), 2.09 (m, 3H), 1.82 (m, 1H), 1.24 (dd, J = 6.6, 7.2 Hz, 3H) |
| 208 | 3-CF$_3$ | 4-Cl | 8.18 (s, 1H), 8.16 (d, J = 9.6 Hz, 1H), 7.80 (d, J = 7.8 Hz, 2H), 7.74 (d, J = 8.4 Hz, 1H), 7.66 (t, J = 7.8 Hz, 1H), 7.40 (d, J = 8.7 Hz, 2H), 6.26 (s, 1H), 5.03 (bs, 1H), 4.57 (s, 2H), 4.45 (bs, 1H), 3.63 (m, 6H), 2.06 (m, 3H), 1.82 (m, 1H), 1.24 (m, 3H) |
| 209 | 4-F | 4-MeO | 7.95 (d, J = 8.7 Hz, 2H), 7.76 (m, 2H), 7.50 (m, 2H) 6.98 (d, J = 8.7 Hz, 2H), 6.27 (s, 1H), 4.65 (s, 2H), 4.44 (br, 1H), 3.85 (s, 3H), 3.66 (q, J = 7.2 Hz, 2H), 3.72-3.42 (m, 4H), 2.15-1.99 (m, 4H), 1.27 (t, J = 6.9 Hz, 3H) |
| 210 | 3-F | 4-MeO | 7.78 (m, 4H), 7.38 (m, 1H), 7.08 (m, 1H), 7.02 (d, J = 8.7 Hz, 2H), 6.23 (s, 1H), 5.70 (br, 1H), 4.73 (s, 2H), 3.84 (s, 3H), 3.73 (m, 5H), 3.65 (q, J = 8.1 Hz, 2H), 2.09 (m, 3H), 1.99 (m, 1H), 1.27 (t, J = 6.9 Hz, 3H) |
| 211 | 3-OMe | 4-MeO | 7.99 (m, 2H), 7.76 (m, 2H), 7.31 (m, 1H), 7.06 (m, 1H), 6.91 (d, J = 8.1 Hz, 1H), 6.30 (s, 1H), 4.60 (s, 2H), 4.45 (br, 1H), 3.87 (s, 3H), 3.78-3.50 (m, 5H), 3.45 (s, 3H), 3.63 (q, J = 6.9 Hz, 2H), 2.15-1.99 (m, 3H), 1.85-1.78 (m, 1H), 1.25 (t, J = 7.2 Hz, 3H) |
| 212 | 3-CF$_3$ | 4-MeO | 8.20 (m, 2H), 7.79 (m, 1H), 7.68 (m, 3H), 6.99 (d, J = 8.4 Hz, 2H), 6.24 (s, 1H), 4.58 (s, 2H), 4.45 (br, 1H), 3.85 (s, 3H), 3.78-3.50 (m, 5H), 3.63 (q, J = 6.9 Hz, 2H), 2.15-1.99 (m, 3H), 1.85-1.78 (m, 1H), 1.25 (t, J = 7.2 Hz, 3H) |
| 213 | 3-Cl | 4-MeO | 7.99 (s, 1H), 7.90 (m, 1H), 7.78 (d, J = 8.7 Hz, 2H), 7.35 (m, 2H), 7.00 (d, J = 8.7 Hz, 2H), 6.22 (s, 1H), 4.73 (s, 2H), 4.28 (br, 1H), 3.84 (s, 3H), 3.72 (m, 5H), 3.66 (q, J = 7.2 Hz, 2H), 2.09 (m, 3H), 1.99 (m, 1H), 1.27 (t, J = 6.9 Hz, 3H) |
| 214 | 3-F | 3,4-methylenedioxy | 7.73 (d, J = 8.4 Hz, 2H), 7.50 (m, 1H), 7.25 (m, 2H), 6.91 (d, J = 7.8 Hz, 2H), 6.23 (s, 1H), 5.98 (s, 2H), 4.58 (s, 2H), 4.47 (m, 1H), 3.72 (m, 5H), 2.04 (m, 3H), 1.79 (m, 1H), 1.25 (t, J = 6.9 Hz, 3H) |
| 215 | 3-OMe | 3,4-methylenedioxy | 7.54 (m, 1H), 7.47 (m, 3H), 7.31 (m, 1H), 7.06 (m, 1H), 6.91 (d, J = 8.1 Hz, 1H), 6.35 (s, 1H), 5.98 (s, 2H), 4.60 (s, 2H), 4.45 (br, 1H), 3.87 (s, 3H), 3.78-3.50 (m, 5H), 3.63 (q, J = 6.9 Hz, 2H), 2.15-1.99 (m, 3H), 1.85-1.78 (m, 1H), 1.25 (t, J = 7.2 Hz, 3H) |
| 216 | 3-CF$_3$ | 3,4-methylenedioxy | 8.26 (d, J = 7.5 Hz, 1H), 8.21 (s, 1H), 7.65 (d, J = 8.1 Hz, 1H), 7.55 (m, 1H), 7.44 (m, 1H), 7.29 (m, 1H), 6.91 (d, J = 8.1 Hz, 1H), 6.26 (s, 1H), 5.50 (br, 1H), 4.72 (s, 2H), 3.76 (m, 5H), 3.66 (q, J = 7.2 Hz, 2H), 2.09 (m, 3H), 2.00 (m, 1H), 1.27 (t, J = 6.9 Hz, 3H) |
| 217 | 3-Cl | 3,4-methylenedioxy | 7.97 (s, 1H), 7.92 (m, 1H), 7.43 (s, 1H), 7.36 (d, J = 4.5 Hz, 2H), 7.28 (d, J = 8.1 Hz, 1H), 6.91 (d, J = 8.1 Hz, 1H), 6.22 (s, 1H), 5.97 (s, 2H), 4.71 (s, 2H), 4.18 (br, 1H), 3.72 (m, 5H), 3.66 (q, J = 7.2 Hz, 2H), 2.09 (m, 3H), 2.00 (m, 1H), 1.27 (t, J = 6.9 Hz, 3H) |
| 218 | 3-F | 4-F | 8.25 (m, 2H), 7.77 (m, 2H), 7.39 (m, 1H), 7.14 (m, 3H), 6.25 (s, 1H), 4.71 (s, 2H), 4.15 (br, 1H), 3.75 (m, 5H), 3.65 (q, J = 6.9 Hz, 2H), 2.11 (m, 4H), 1.25 (t, J = 9.6 Hz, 3H) |
| 219 | 3-CF$_3$ | 4-F | 8.23 (m, 2H), 7.84 (m, 2H), 7.65 (d, J = 7.8 Hz, 1H), 7.55 (m, 1H), 7.14 (m, 2H), 6.27 (s, 1H), 4.71 (s, 2H), 4.15 (br, 1H), 3.75 (m, 5H), 3.68 (q, J = 7.2 Hz, 2H), 2.11 (m, 4H), 1.25 (t, J = 9.6 Hz, 3H) |
| 220 | 3-Me | 4-MeO | 7.74 (s, 2H), 7.68 (d, J = 8.7 Hz, 2H), 7.42 (m, 1H), 7.35 (m, 1H), 7.00 (d, J = 8.7 Hz, |

TABLE 15-continued

| Ex. No. | R | R' | $^1$H NMR (CDCl$_3$, 300 MHz) |
|---|---|---|---|
| | | | 2H), 6.20 (s, 1H), 5.40 (br, 1H), 4.58 (s, 2H), 4.44 (br, 1H), 3.84 (s, 3H), 3.60 (m, 5H), 2.45 (s, 2H), 2.02 (m, 4H), 1.72 (m, 1H), 1.24 (t, 3H) |

Example 221

Preparation of (S)-{1-[2-methoxymethyl-7-(3-(trifluoromethyl)phenyl)-3-(4-methoxyphenyl)-pyrazolo[1,5-a]pyrimidin-5-yl]pyrrolidin-2-yl}methanol (Chemical Formula 93)

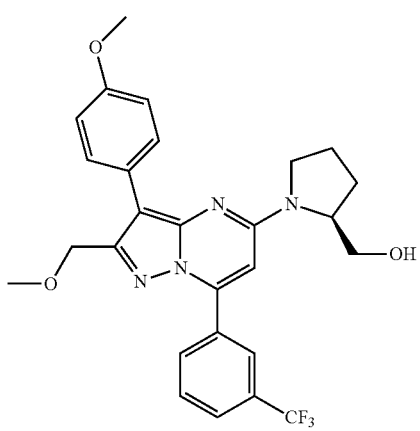

[Chemical Formula 93]

Step 1: Preparation of 4-ethoxy-2-(4-methoxyphenyl)-3-oxobutanenitrile (Chemical Formula 94)

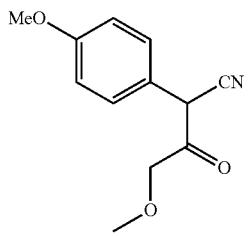

[Chemical Formula 94]

Sodium ethoxide (2 eq) is dissolved in ethanol (200 mL) and 4-methylphenylacetonitrile (10.0) and ethyl ethoxyacetate (1.5 eq) are slowly added. The reaction mixture is stirred for 1 hour under reflux. Upon completion of the reaction, ethanol is removed under reduced pressure and water (100 mL) and ethyl acetate are added. The organic layer is removed and the aqueous layer is acidified by adding acetic acid (10 mL) and extracted 3 times with ethyl acetate. The extracted organic layer is collected, washed with water and dehydrated with MgSO$_4$. After concentration under reduced pressure, the produced solid is recrystallized with Hx:EA=20:1 to obtain the target compound (70-95%).

Step 2: Preparation of 3-(methoxymethyl)-4-(4-methoxyphenyl)-1H-pyrazol-5-a mine (Chemical Formula 95)

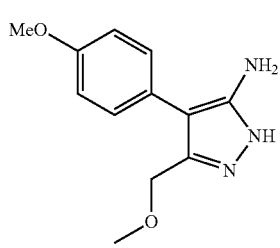

[Chemical Formula 95]

4-Ethoxy-2-(4-methylphenyl)-3-oxobutanenitrile (1.493 g) is dissolved in ethanol (150 mL) and hydrazine hydrate (~40%, 7.8 mL, 2 eq) and acetic acid (5.9 mL, 2 eq) are slowly added. The reaction mixture is stirred at 80° C.90° C. for 1 hour under reflux. Upon completion of the reaction, ethanol is removed under reduced pressure. After the reaction is terminated by adding saturated aq. NaHCO$_3$, the reaction mixture is extracted 3 times with ethyl acetate. The organic layer is washed with water and dehydrated with MgSO$_4$. After concentration under reduced pressure, the produced solid is recrystallized with Hx:EA:MC=20:1:0.1 to obtain the target compound (90%). $^1$H NMR (CDCl$_3$, 300 MHz): δ 7.25 (m, 2H), 6.95 (m, 2H), 4.43 (s, 3H), 3.82 (s, 3H), 3.38 (s, 3H).

Step 3: Preparation of 2-(methoxymethyl)-7-(3-(trifluoromethyl)phenyl)-3-(4-methylphenyl)pyrazolo[1,5-a]pyrimidin-5(4H)-one (Chemical Formula 96)

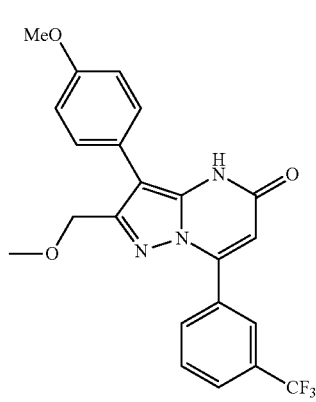

[Chemical Formula 96]

3-(Methoxymethyl)-4-(4-methoxyphenyl)-1H-pyrazol-5-amine (1.4 g, 6.0 mmol) and methyl 3-(trifluoromethyl)phenyloxopropanoate (2.2 g, 1.5 eq) are dissolved in pyridine (10 mL) and stirred at 95° C. for 12 hours under reflux. Upon completion of the reaction, 2.1 g of the target compound is obtained by purification by column chromatography (ethyl acetate 100%).

Step 4: Preparation of 5-chloro-2-(methoxymethyl)-7-(4-(trifluoromethylphenyl)-3-(4-methoxyphenyl)pyrazolo[1,5-a]pyrimidine (Chemical Formula 97)

[Chemical Formula 97]

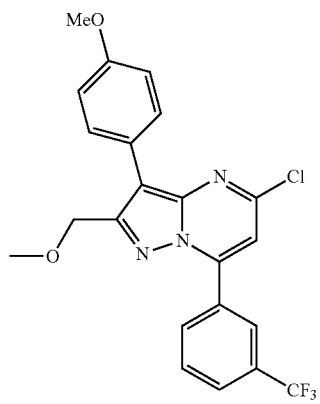

2-(Methoxymethyl)-7-(3-(trifluoromethyl)phenyl)-3-(4-methylphenyl)pyrazolo[1,5-a]pyrimidin-5(4H)-one (1.0 g, 2.33 mmol) is dissolved in POCl$_3$ (3 mL) and pyridine (0.03 mL) and stirred for 1 hour while refluxing at 95° C. Upon completion of the reaction, POCl$_3$ is removed under reduced pressure and ethyl acetate and ice water (5 mL) are added. The extracted organic layer is washed with saturated aq. NaHCO$_3$ and dehydrated with MgSO$_4$. 800 mg of the target compound is obtained by purification by column chromatography (ethyl acetate 10%). $^1$H NMR (CDCl$_3$, 300 MHz): δ 8.20 (m, 2H), 7.80 (m, 1H), 7.69 (m, 1H), 7.64 (m, 2H), 7.00 (d, J=8.4 Hz, 2H), 6.86 (s, 1H), 4.55 (s, 2H), 3.85 (s, 3H), 3.44 (s, 3H).

Step 5: Preparation of (S)-{1-[2-methoxymethyl-7-(3-(trifluoromethyl)phenyl)-3-(4-methoxyphenyl)-pyrazolo[1,5-a]pyrimidin-5-yl]pyrrolidin-2-yl}methanol (Chemical Formula 98)

[Chemical Formula 98]

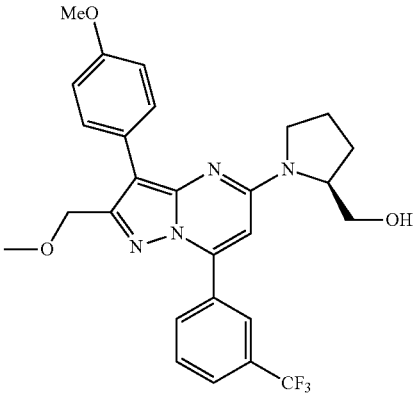

5-Chloro-2-(methoxymethyl)-7-(4-(trifluoromethylphenyl)-3-(4-methoxyphenyl)pyrazolo[1,5-a]pyrimidine (50 mg), DIPEA (0.2 mL) and (S)-2-pyrrolidinemethanol (0.02 mL) are stirred for 2 hours in an acetonitrile (7 mL) solvent at 84° C. The reaction solvent is removed by distillation under reduced pressure. The remainder is purified by column chromatography to yield 43 mg of the target compound.

Examples 222-238

Compounds of Examples 222-238 are prepared in a similar manner as Example 221.

Chemical formula and NMR analysis data for the compounds of Examples 222-238 are shown in Chemical Formula 99 and Table 16.

[Chemical Formula 99]

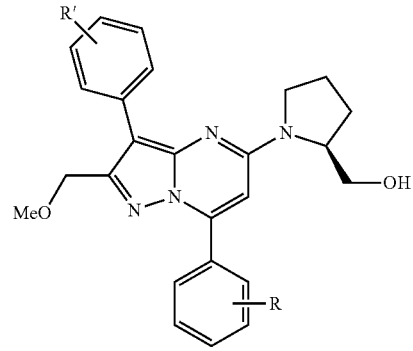

TABLE 16

| Ex. No. | R | R' | $^1$H NMR (CDCl$_3$, 300 MHz) |
|---|---|---|---|
| 221 | 3-CF$_3$ | 4-MeO | 8.20 (m, 2H), 7.80 (d, J = 7.8 Hz, 1H), 7.69 (d, J = 7.8 Hz, 1H), 7.64 (d, J = 8.4 Hz, 2H), 7.00 (d, J = 8.4 Hz, 2H), 6.25 (s, 1H), 4.55 (s, 2H), 4.46 (br, 1H), 3.85 (s, 3H), 3.62 (m, 5H), 3.44 (s, 3H), 2.09 (m, 3H), 1.82 (m, 1H) |
| 222 | 4-F | 4-MeO | 8.00 (m, 2H), 7.64 (d, J = 8.7 Hz, 2H), 7.26 (m, 2H), 7.00 (d, J = 8.7 Hz, 2H), 6.21 (s, 1H), 4.55 (s, 2H), 4.45 (br, 1H), 3.85 (s, 3H), 3.62 (m, 5H), 3.44 (s, 3H), 2.08 (m, 3H), 1.78 (m, 1H) |
| 223 | 3-F | 4-MeO | 7.75 (m, 2H), 7.65 (d, J = 8.7 Hz, 2H), 7.50 (m, 1H), 7.26 (s, 1H), 7.00 (d, J = 8.7 Hz, 2H), 6.24 (s, 1H), 4.56 (s, 2H), |

TABLE 16-continued

| Ex. No. | R | R' | $^1$H NMR (CDCl$_3$, 300 MHz) |
|---|---|---|---|
| 224 | 2-F | 4-MeO | 4.46 (br, 1H), 3.85 (s, 3H), 3.62 (m, 5H), 3.44 (s, 3H), 2.08 (m, 3H), 1.80 (m, 1H) 7.77 (t, J = 7.2 Hz, 1H), 7.65 (d, J = 6.9 Hz, 2H), 7.49 (m, 1H), 7.25 (m, 2H), 6.99 (d, J = 6.6 Hz, 2H), 6.26 (s, 1H), 5.38 (bs, 1H), 4.51 (s, 2H), 4.41 (bs, 1H), 3.83 (s, 3H), 3.60 (m, 4H), 3.39 (d, J = 1.8 Hz, 3H), 2.03 (m, 3H), 1.76 (m, 1H) |
| 225 | 4-MeO | 4-MeO | 7.93 (dd, J = 8.7 Hz, 2H), 7.61 (d, J = 6.9 Hz, 2H), 6.99 (m, 4H), 6.16 (d, J = 1.8 Hz, 1H), 5.42 (bs, 1H), 4.52 (s, 2H), 4.40 (m, 1H), 3.86 (s, 3H), 3.81 (s, 3H), 3.60 (m, 4H), 3.40 (d, J = 2.1 Hz, 3H), 2.03 (m, 3H), 1.73 (m, 1H) |
| 226 | 3-MeO | 4-MeO | 7.66 (d, J = 8.7 Hz, 2H), 7.56 (m, 1H), 7.52 (d, J = 7.8 Hz, 1H), 7.44 (d, J = 7.8 Hz, 1H), 7.09 (m, 1H), 7.02 (d, J = 8.7 Hz, 2H), 6.25 (s, 1H), 5.38 (bs, 1H), 4.56 (s, 2H), 4.45 (m, 1H), 3.89 (s, 3H), 3.85 (s, 3H), 3.64 (m, 4H), 3.44 (s, 3H), 2.06 (m, 3H), 1.79 (m, 1H) |
| 227 | 3-CH$_3$ | 4-MeO | 7.74 (d, J = 7.8 Hz, 2H), 7.65 (d, J = 9.0 Hz, 2H), 7.41 (dd, J = 7.8, 7.5 Hz, 1H), 7.34 (d, J = 7.8 Hz, 1H), 7.01 (d, J = 8.4 Hz, 2H), 6.20 (s, 1H), 5.41 (bs, 1H), 4.54 (s, 2H), 4.45 (m, 1H), 3.84 (s, 3H), 3.64 (m, 4H), 3.43 (s, 3H), 2.45 (s, 3H), 2.06 (m, 3H), 1.79 (m, 1H) |
| 228 | 3-CN | 4-MeO | 8.28 (m, 2H), 7.81 (m, 1H), 7.63 (m, 2H), 7.01 (m, 2H), 6.24 (ms, 1H), 5.11 (bs, 1H), 4.54 (s, 2H), 4.45 (s, 1H), 3.85 (s, 3H), 3.68 (m, 4H), 3.44 (s, 3H), 2.08 (m, 3H), 1.80 (m, 1H) |
| 229 | 4-Cl | 4-MeO | 7.89 (d, J = 7.8 Hz, 2H), 7.60 (d, J = 8.4 Hz, 2H), 7.46 (d, J = 7.5 Hz, 2H), 6.97 (d, J = 8.4 Hz, 2H), 6.19 (s, 1H), 5.25 (bs, 1H), 4.50 (s. 2H), 4.39 (m, 1H), 3.80 (s, 3H), 3.60 (m, 4H), 3.39 (s, 3H), 2.01 (m, 3H), 1.75 (m, 1H) |
| 230 | 3-Cl | 4-MeO | 7.92 (s, 1H), 7.86 (d, J = 7.5 Hz, 1H), 7.64 (d, J = 8.4 Hz, 2H), 7.47 (m, 2H), 7.00 (d, J = 8.7 Hz, 2H), 6.21 (s, 1H), 5.28 (bs, 1H), 4.56 (s, 2H), 4.29 (m, 1H), 3.83 (s. 3H), 3.66 (m, 4H), 3.43 (s, 3H), 2.06 (m, 3H), 1.78 (m, 1H) |
| 231 | 4-F | 4-Cl | 7.98 (m, 2H), 7.70 (d, J = 8.4 Hz, 2H), 7.41 (d, J = 8.4 Hz, 2H), 7.20 (d, J = 8.7 Hz, 2H), 6.23 (s, 1H), 4.54 (s, 2H), 4.48 (br, 1H), 3.62 (m, 5H), 3.44 (s, 3H), 2.08 (m, 3H), 1.78 (m, 1H) |
| 232 | 3-F | 4-Cl | 7.72 (m, 4H), 7.50 (m, 1H), 7.41 (d, J = 7.8 Hz, 2H), 7.26 (m, 1H), 6.26 (s, 1H), 4.54 (s, 2H), 4.47 (br, 1H), 3.62 (m, 5H), 3.44 (s, 3H), 2.08 (m, 3H), 1.80 (m, 1H) |
| 233 | 3-CF$_3$ | 4-Cl | 8.16 (m, 2H), 7.78 (d, J = 7.8 Hz, 1H), 7.66 (m, 3H), 7.38 (d, J = 8.7 Hz, 2H), 6.25 (s, 1H), 4.50 (s, 2H), 4.47 (br, 1H), 3.67 (m, 5H), 3.41 (s, 3H), 2.06 (m, 3H), 1.80 (m, 1H) |
| 234 | 3-CH$_3$ | 4-Cl | 7.72 (m, 4H), 7.42 (m, 4H), 6.23 (s, 1H), 4.55 (s, 2H), 4.47 (br, 1H), 3.86 (m, 4H), 3.43 (s, 3H), 2.46 (s, 3H), 2.08 (m, 3H), 1.80 (m, 1H) |
| 235 | 4-F | 3,4-methylenedioxy | 8.00 (m, 2H), 7.28-7.17 (m, 4H), 6.91 (d, J = 8.7 Hz, 1H), 6.21 (s, 1H), 5.99 (s, 2H), 4.55 (s, 2H), 4.45 (br, 1H), 3.78-3.50 (m, 5H), 3.44 (s, 3H), 2.15-1.99 (m, 3H), 1.83-1.78 (m, 1H) |
| 236 | 3-F | 3,4-methylenedioxy | 7.75 (s, 1H), 7.72 (s, 1H), 7.50 (m, 1H), 7.21 (m, 3H), 6.91 (d, J = 8.7 Hz, 1H), 6.24 (s, 1H), 5.99 (s, 2H), 4.55 (s, 2H), 4.45 (br, 1H), 3.78-3.50 (m, 5H), 3.44 (s, 3H), 2.17-2.02 (m, 3H), 1.83-1.78 (m, 1H) |

TABLE 16-continued

| Ex. No. | R | R' | $^1$H NMR (CDCl$_3$, 300 MHz) |
|---|---|---|---|
| 237 | 4-CF$_3$ | 3,4-methylenedioxy | 8.05 (d, J = 7.8 Hz, 2H), 7.76 (d, J = 7.2 Hz, 2H), 7.60 (d, J = 7.2 Hz, 2H), 6.96 (ds, J = 8.4 Hz, 2H), 6.20 (s, 2H), 5.12 (bs, 1H), 4.50 (s, 2H), 4.42 (m, 1H), 3.81 (s, 3H), 3.68 (m, 4H), 3.39 (s, 3H), 2.05 (m, 3H), 1.76 (m, 1H) |
| 238 | 3-CF$_3$ | 3,4-methylenedioxy | 8.20 (m, 2H), 7.80 (d, J = 7.8 Hz, 1H), 7.62 (m, 1H), 7.27 (d, J = 6.9 Hz, 1H), 7.20 (m, 1H), 6.91 (d, J = 7.8 Hz, 1H), 6.25 (s, 1H), 5.99 (s, 2H), 4.55 (s, 2H), 4.45 (br, 1H), 3.78-3.50 (m, 5H), 3.44 (s, 3H), 2.15-1.99 (m, 3H), 1.83-1.78 (m, 1H) |

Example 239

Preparation of 2-{[2-ethoxymethyl-7-(4-fluorophenyl)-3-(4-methylphenyl)-pyrazolo[1,5-a]pyrimidin-5-yl]methylamino}ethanol (Chemical Formula 100)

[Chemical Formula 100]

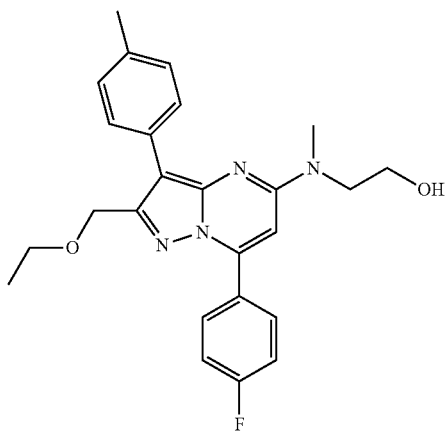

5-Chloro-2-(ethoxymethyl)-7-(4-fluorophenyl)-3-(4-methylphenyl)pyrazolo[1,5-a]pyrimidine (22 mg), DIPEA (0.1 mL) and N-methylaminoethanol (0.1 mL) are stirred for 12 hours in an acetonitrile (7 mL) solvent at 84° C. The reaction solvent is removed by distillation under reduced pressure. The remainder is extracted with ethyl acetate and water. The collected organic layer is washed with brine and dehydrated with anhydrous MgSO$_4$. The solvent is removed by distillation under reduced pressure and the remainder is purified by column chromatography to yield the target compound (18 mg).

Examples 240-256

Compounds of Examples 240-256 are prepared in a similar manner as Example 239.

Chemical formula and NMR analysis data for the compounds of Examples 240-256 are shown in Chemical Formula 101 and Table 17.

[Chemical Formula 101]

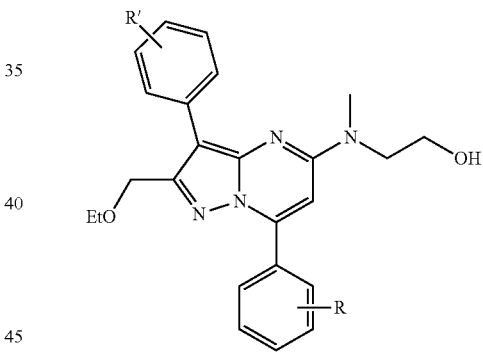

TABLE 17

| Ex. No. | R | R' | $^1$H NMR (CDCl$_3$, 300 MHz) |
|---|---|---|---|
| 239 | 4-F | 4-Me | 7.99 (m, 2H), 7.73 (m, 2H), 7.24 (m, 4H), 6.31 (s, 1H), 4.60 (s, 2H), 3.88 (m, 2H), 3.83 (m, 2H), 3.63 (q, J = 6.9 Hz, 2H), 3.23 (s, 3H), 2.39 (s, 3H), 1.26 (t, J = 6.9 Hz, 3H) |
| 240 | 3-F | 4-Me | 7.76-7.26 (m, 4H), 7.51 (m, 1H), 7.24 (m, 3H), 6.35 (s, 1H), 4.62 (s, 2H), 3.89 (m, 2H), 3.85 (m, 2H), 3.42 (br, 1H), 3.23 (s, 3H), 2.39 (s, 3H). |
| 241 | 3-CF$_3$ | 4-Me | 8.19 (m, 2H), 7.78-7.67 (m, 4H), 7.28 (m, 4H), 6.36 (s, 1H), 4.61 (s, 2H), 3.92 (m, 2H), 3.88 (m, 2H), 3.41 (br, 1H), 3.25 (s, 3H), 2.39 (s, 3H). |
| 242 | 4-F | 4-Cl | 7.96 (dd, J = 5.4 Hz, 2H), 7.83 (d, J = 8.4 Hz, 2H), 7.40 (d, J = 8.4 Hz, 2H), 7.22 (t, J = 8.7 Hz, 2H), 6.33 (s, 1H), 4.59 (s, 1H), 3.89 (m, 2H), 3.83 (m, 2H), 3.63 (dd, J = 6.9 Hz, 2H), 3.24 (s, 3H), 3.17 (m, 1H), 1.25 (dd, J = 6.9, 7.2 Hz, 3H) |

TABLE 17-continued

| Ex. No. | R | R' | $^1$H NMR (CDCl$_3$, 300 MHz) |
|---|---|---|---|
| 243 | 3-F | 4-Cl | 7.83 (d, J = 8.7 Hz, 2H), 7.73 (m, 1H), 7.71 (bs, 1H), 7.50 (m, 1H), 7.40 (d, J = 8.7 Hz, 2H), 7.24 (m, 1 H), 6.37 (s, 1 H), 4.60 (s, 2H), 3.91 (m, 2H), 3.84 (d, J = 4.5 Hz, 2H), 3.63 (dd, J = 7.2, 6.9 Hz, 2H), 3.25 (s, 3H), 3.08 (bs, 1H), 1.25 (dd, J = 7.2, 6.9 Hz, 3H) |
| 244 | 3-CF$_3$ | 4-Cl | 8.18 (s, 1H), 8.16 (d, J = 9.3 Hz, 1 H), 7.83 (d, J = 8.4 Hz, 2H), 7.79 (d, J = 8.7 Hz, 1 H), 7.66 (t, J = 7.8 Hz, 1 H), 7.40 (d, J = 8.4 Hz, 2H), 6.38 (s, 1H), 4.60 (s, 2H), 3.88 (m, 2H), 3.82 (m, 2H), 3.63 (dd, J = 7.2, 6.6 Hz, 2H), 3.25 (s, 3H), 1.25 (dd, J = 7.2, 6.9 Hz, 3H) |
| 245 | 4-F | 4-MeO | 8.06 (m, 2H), 7.86 (d, J = 9.0 Hz, 2H), 7.13 (m, 2H), 7.00 (d, J = 9.0 Hz, 2H), 6.50 (s, 1H), 4.71 (s, 2H), 4.00 (br, 4H), 3.84 (s, 3H), 3.63 (q, J = 6.9 Hz, 2H), 3.17 (s, 3H), 1.25 (t, J = 6.9 Hz, 3H) |
| 246 | 3-F | 4-MeO | 7.84 (m, 4H), 7.41 (m, 1H), 7.11 (m, 1H), 7.02 (d, J = 8.7 Hz, 2H), 6.52 (s, 1H), 4.71 (s, 2H), 4.01 (br, 4H), 3.84 (s, 3H), 3.63 (q, J = 6.9 Hz, 2H), 3.19 (s, 3H), 1.25 (t, J = 6.9 Hz, 3H) |
| 247 | 3-CF$_3$ | 4-MeO | 8.15 (m, 2H), 7.41 (m, 3H), 7.60 (m, 1H), 6.98 (d, J = 8.7 Hz, 2H), 6.08 (s, 1H), 5.22 (br, 1H), 4.57 (s, 2H), 3.84 (m, 2H), 3.83 (s, 3H), 3.65 (m, 2H), 3.63 (q, J = 6.6 Hz, 2H), 1.26 (t, J = 6.9 Hz, 3H) |
| 248 | 3-Cl | 4-MeO | 8.03 (s, 1 H), 7.96 (m, 1 H), 7.86 (d, J = 8.7 Hz, 2H), 7.40 (m, 2H), 7.00 (d, J = 8.7 Hz, 2H), 6.50 (s, 1H), 4.71 (s, 2H), 4.02 (br, 4H), 3.84 (s, 3H), 3.63 (q, J = 6.9 Hz, 2H), 3.20 (s, 3H), 1.25 (t, J = 6.9 Hz, 3H) |
| 249 | H | 3,4-methylenedioxy | 8.07 (m, 2H), 7.55 (s, 1H), 7.44 (m, 4H), 6.92 (d, J = 8.1 Hz, 1H), 6.57 (s, 1H), 5.97 (s, 2H), 5.84 (br, 1H), 4.69 (s, 2H), 3.99 (m, 4H), 3.63 (q, J = 6.9 Hz, 2H), 3.18 (s, 3H), 1.25 (t, J = 7.2 Hz, 3H) |
| 250 | 4-F | 3,4-methylenedioxy | 8.03 (m,2H), 7.51 (s, 1H), 7.37 (m, 1H), 7.13 (m, 2H), 6.91 (d, J = 7.8 Hz, 1H), 6.50 (s, 1H), 5.97 (s, 2H), 4.69 (s, 2H), 4.01 (m, 4H), 3.62 (q, J = 6.9 Hz, 2H), 3.18 (s, 3H), 1.25 (t, J = 6.9 Hz, 3H) |
| 251 | 3-F | 3,4-methylenedioxy | 7.54 (m, 1H), 7.45 (m, 3H), 7.31 (m, 1H), 7.07 (m, 1H), 6.90 (d, J = 8.7 Hz, 1H), 6.51 (s, 1H), 5.98 (s, 2H), 4.70 (s, 2H), 4.02 (m, 4H), 3.63 (q, J = 6.9 Hz, 2H), 3.20 (s, 3H), 1.27 (t, J = 7.2 Hz, 3H) |
| 252 | 3-OMe | 3,4-methylenedioxy | 7.54 (m, 1H), 7.47 (m, 3H), 7.31 (m, 1H), 7.06 (m, 1H), 6.91 (d, J = 8.1 Hz, 1H), 6.35 (s, 1H), 5.98 (s, 2H), 4.60 (s, 2H), 3.87 (s, 3H), 3.85 (m, 4H), 3.63 (q, J = 6.9 Hz, 2H), 3.23 (s, 3H), 1,25 (t, J = 7.2 Hz, 3H) |
| 253 | 3-CF$_3$ | 3,4-methylenedioxy | 8.29 (d, J = 7.8 Hz, 1H), 8.24 (s, 1H), 7.69 (d, J = 7.8 Hz, 1H), 7.59 (m, 1H), 7.50 (m, 1 H), 7.38 (m, 1H), 6.92 (d, J = 7.8 Hz, 1H), 6.53 (s, 1H), 5.98 (s, 2H), 5.61 (br, 1H), 4.70 (s, 2H), 4.05 (br, 4H), 3.64 (q, J = 6.9 Hz, 2H), 3.22 (s, 3H), 1.26 (t, J = 7.2 Hz, 3H) |
| 254 | 3-Cl | 3,4-methylenedioxy | 8.01 (s, 1H), 7.96 (m, 1H), 7.49 (s, 1H), 7.38 (m, 3H), 6.91 (d, J = 8.1 Hz, 1H), 6.50 (s, 1H), 5.98 (s, 2H), 5.66 (br, 1H), 4.70 (s, 2H), 4.02 (br, 4H), 3.63 (q, J = 7.2 Hz, 2H), 3.20 (s, 3H), 1.27 (t, J = 6.9 Hz, 3H) |
| 255 | 3-F | 4-F | 7.91 (m, 2H), 7.80 (m, 2H), 7.42 (m, 1H), 7.15 (m, 3H), 6.53 (s, 1H), 4.71 (s, 2H), 4.05 (br, 4H), 3.63 (q, J = 6.6 Hz, 2H), 3.20 (s, 3H), 1.25 (t, J = 6.9 Hz, 3H) |
| 256 | 3-CF$_3$ | 4-F | 8.28 (m, 2H), 7.91 (m, 2H), 7.68 (d, J = 7.8 Hz, 1H), 7.60 (m, 1H), 7.15 (m, 2H), 6.56 (s, 1H), 4.71 (s, 2H), 4.05 (br, 4H), 3.63 (q, J = 6.9 Hz, 2H), 3.23 (s, 3H), 1.25 (t, J = 7.2 Hz, 3H) |

Example 257

Preparation of 2-{[2-ethoxymethyl-7-[3-(trifluoromethyl)phenyl]-3-(4-methoxyphenyl)-pyrazolo[1,5-a]pyrimidin-5-yl]methylamino}ethanol (Chemical Formula 102)

[Chemical Formula 102]

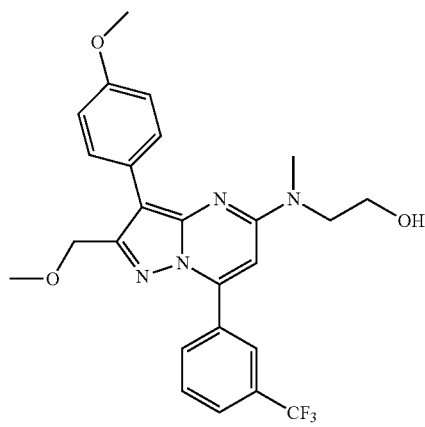

5-Chloro-2-(methoxymethyl)-7-[3-(trifluoromethyl)phenyl]-3-(4-methoxyphenyl)pyrazolo[1,5-a]pyrimidine (50 mg), DIPEA (0.2 mL) and N-methylaminoethanol (0.02 mL) are stirred for 12 hours in an acetonitrile (7 mL) solvent at 84° C. The reaction solvent is removed by distillation under reduced pressure. The remainder is extracted with ethyl acetate and water. The collected organic layer is washed with brine and dehydrated with anhydrous $MgSO_4$. The solvent is removed by distillation under reduced pressure and the remainder is purified by column chromatography to yield 37 mg of the target compound.

Examples 258-262

Compounds of Examples 258-262 are prepared in a similar manner as Example 257.

Chemical formula and NMR analysis data for the compounds of Examples 257-262 are shown in Chemical Formula 103 and Table 18.

[Chemical Formula 103]

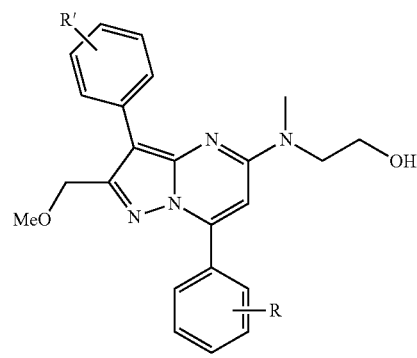

TABLE 18

| Ex. No. | R | R' | $^1$H NMR (CDCl$_3$, 300 MHz) |
|---|---|---|---|
| 257 | 3-CF$_3$ | 4-MeO | 8.20 (m, 2H), 7.30 (m, 2H), 7.29 (d, J = 8.4 Hz, 2H), 7.00 (d, J = 8.4 Hz, 2H), 6.38 (s, 1H), 4.58 (s, 2H), 3.91 (m, 2H), 3.86 (s, 3H), 3.85 (m, 2H), 3.45 (s, 3H), 3.26 (s, 3H) |
| 258 | 4-F | 4-MeO | 7.99 (m, 2H), 7.73 (d, J = 8.7 Hz, 2H), 7.21 (d, J = 8.7 Hz, 2H), 7.00 (d, J = 8.7 Hz, 2H), 6.33 (s, 1H), 4.57 (s, 2H), 3.91 (m, 2H), 3.85 (s, 3H), 3.83 (m, 2H), 3.45 (s, 3H), 3.25 (s, 3H) |
| 259 | 3-F | 4-MeO | 7.74 (m, 3H), 7.50 (m, 1H), 7.00 (d, J = 9.0 Hz, 2H), 6.37 (s, 1H), 4.58 (s, 2H), 3.91 (t, J = 4.2 Hz, 2H), 3.85 (s, 3H), 3.83 (m, 2H), 3.45 (s, 3H), 3.25 (s, 3H) |
| 260 | 4-F | 4-Cl | 7.99 (m, 2H), 7.78 (d, J = 7.2 Hz, 2H), 7.40 (d, J = 7.2 Hz, 2H), 7.20 (d, J = 7.4 Hz, 2H), 6.35 (s, 1H), 4.56 (s, 2H), 3.91 (m, 2H), 3.86 (m, 2H), 3.45 (s, 3H), 3.25 (s, 3H) |
| 261 | 3-F | 4-Cl | 7.79 (d, J = 7.2 Hz, 2H), 7.72 (d, J = 8.7 Hz, 2H), 7.50 (m, 1H), 7.40 (d, J = 7.2 Hz, 2H), 7.22 (m, 1H), 6.39 (s, 1H), 4.58 (s, 2H), 3.91 (m, 2H), 3.85 (m, 2H), 3.46 (s, 3H), 3.25 (s, 3H) |
| 262 | 3-Me | 4-Cl | 7.81 (d, J = 8.7 Hz, 2H), 7.72 (m, 2H), 7.38 (m, 4H), 6.34 (s, 1H), 4.58 (s, 2H), 3.88 (m, 2H), 3.83 (m, 2H), 3.44 (s, 3H), 3.23 (s, 3H), 2.46 (s, 3H) |

Example 263

Preparation of 2-[2-ethoxymethyl-7-(4-fluorophenyl)-3-(4-methylphenyl)-pyrazolo[1,5-a]pyrimidin-5-yl-amino]ethanol (Chemical Formula 104)

[Chemical Formula 104]

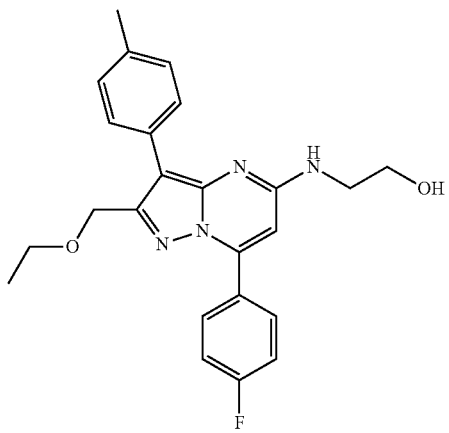

5-Chloro-2-(ethoxymethyl)-7-(4-fluorophenyl)-3-(4-methylphenyl)pyrazolo[1,5-a]pyrimidine (20 mg), DIPEA (0.1 mL) and aminoethanol (0.1 mL) are stirred for 12 hours in an acetonitrile (7 mL) solvent at 84° C. The solvent is removed by distillation under reduced pressure. The remainder is extracted with ethyl acetate and water. The collected organic layer is washed with brine and dehydrated with anhydrous MgSO$_4$. The solvent is removed by distillation under reduced pressure and the remainder is purified by column chromatography to yield the target compound (15 mg).

Examples 264-268

Compounds of Examples 264-268 are prepared in a similar manner as Example 263.

Chemical formula and NMR analysis data for the compounds of Examples 263-268 are shown in Chemical Formula 105 and Table 19.

[Chemical Formula 105]

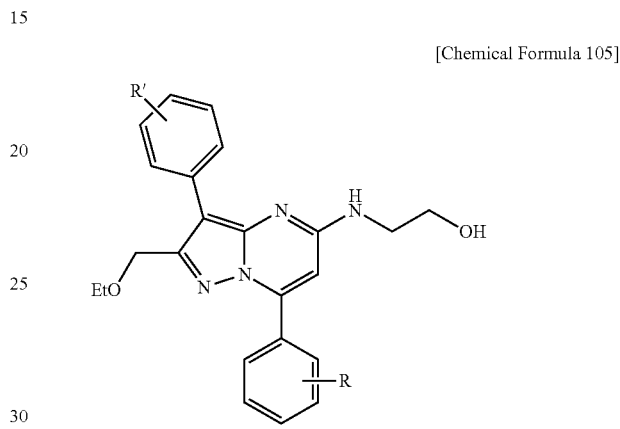

TABLE 19

| Ex. No. | R | R' | $^1$H NMR (CDCl$_3$, 300 MHz) |
|---|---|---|---|
| 263 | 4-F | 4-Me | 7.83 (m, 2H), 7.71 (m, 2H), 7.23 (m, 4H), 5.96 (s, 1H), 4.60 (s, 2H), 4.42 (br, 1H), 3.67 (m, 2H), 3.56 (m, 2H), 2.40 (s, 3H), 1.27 (t, J = 6.9 Hz, 3H) |
| 264 | 3-CF$_3$ | 4-OMe | 8.20 (m, 2H), 7.30 (m, 2H), 7.29 (d, J = 8.4 Hz, 2H), 7.00 (d, J = 8.4 Hz, 2H), 6.38 (s, 1H), 4.58 (s, 2H), 3.91 (m, 2H), 3.86 (s, 3H), 3.85 (m, 2H), 3.63 (q, J = 6.9 Hz, 2H), 3.26 (s, 3H), 1.26 (t, J = 6.9 Hz, 3H) |
| 265 | H | 3,4-methylenedioxy | 8.05 (m, 2H), 7.51 (s, 1H), 7.42 (m, 4H), 6.91 (d, J = 8.1 Hz, 1H), 6.66 (br, 1H), 6.42 (s, 1H), 5.97 (s, 2H), 4.69 (s, 2H), 3.96 (m, 2H), 3.67 (q, J = 7.2 Hz, 2H), 3.62 (m, 2H), 1.27 (t, J = 6.9 Hz, 3H) |
| 266 | 4-F | 3,4-methylenedioxy | 8.03 (m, 2H), 7.47 (s, 1H), 7.34 (d, J = 7.1 Hz, 1H), 7.10 (m, 2H), 6.91 (d, J = 8.1 Hz, 1H), 6.69 (br, 1H), 6.36 (s, 1H), 5.97 (s, 2H), 4.69 (s, 2H), 3.97 (m, 2H), 3.67 (q, J = 7.2 Hz, 2H), 3.64 (m, 2H), 1.27 (t, J = 6.9 Hz, 3H) |
| 267 | 3-F | 3,4-methylenedioxy | 7.80 (m, 2H), 7.47 (s, 1H), 7.36 (m, 2H), 7.06 (m, 1H), 6.91 (d, J = 8.1 Hz, 1H), 6.71 (br, 1H), 6.38 (s, 1H), 5.97 (s, 2H), 4.69 (s, 2H), 3.96 (m, 2H), 3.66 (q, J = 7.2 Hz, 2H), 3.62 (m, 2H), 1.27 (t, J = 6.9 Hz, 3H) |
| 268 | 3-OMe | 3,4-methylenedioxy | 7.52 (m, 1H), 7.39 (m, 3H), 7.31 (m, 1H), 7.06 (m, 1H), 6.91 (d, J = 8.1 Hz, 1H), 6.09 (s, 1H), 5.98 (s, 2H), 5.23 (br, 1H), 4.60 (s, 2H), 3.83 (s, 3H), 3.82 (m, 2H), 3.66 (q, J = 6.9 Hz, 2H), 3.62 (m, 2H), 3.37 (br, 1H), 1.25 (t, J = 7.2 Hz, 3H) |

Example 269

Preparation of (S)-(1-(3-(4-methylphenyl)-7-(4-fluorophenyl)-pyrazolo[1,5-a]pyrimidin-5-yl)pyrrolidin-2-yl)methanol (Chemical Formula 106)

[Chemical Formula 106]

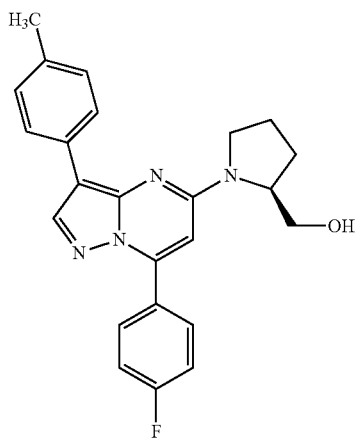

Step 1: Preparation of 3-(4-methylphenyl)-7-(4-fluorophenyl)-pyrazolo[1,5-a]pyrimidin-5(4H)-one (Chemical Formula 107)

[Chemical Formula 107]

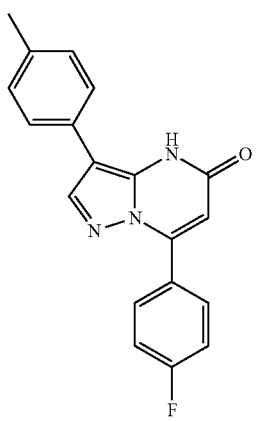

4-(4-Methylphenyl)-1H-pyrazol-5-amine (170 mg) and ethyl 3-(4-fluorophenyl)-3-oxopropanoate (250 mg) are stirred overnight in a pyridine (10 mL) solvent at 95° C. After cooling to room temperature, the reaction solvent is removed by distillation under reduced pressure. The remainder is extracted with ethyl acetate and water. The extracted organic layer is washed with brine and dehydrated with anhydrous MgSO$_4$. The dehydrated organic layer is distilled under reduced pressure and purified by column chromatography to yield 180 mg of the target compound.

Step 2: Preparation of 5-chloro-3-(4-methylphenyl)-7-(4-fluorophenyl)-pyrazolo[1,5-a]pyridine pyrimidine (Chemical Formula 108)

[Chemical Formula 108]

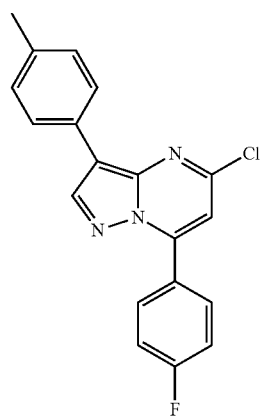

3-(4-Methylphenyl)-7-(4-fluorophenyl)-pyrazolo[1,5-a]pyrimidin-5(4H)-one (180 mg) is added to POCl$_3$ (3 mL) and pyridine (0.1 mL) and stirred for 2 hours while heating. After cooling to room temperature, POCl$_3$ is removed by distillation under reduced pressure. After the distillation, ethyl acetate (20 mL) and ice are added to the remainder. The organic layer is extracted and it is extracted once again with water and ethyl acetate. The organic layer is washed with 1 M NaHCO$_3$ aqueous solution and brine. The organic layer is dehydrated with anhydrous MgSO$_4$. The solvent is removed from the organic layer by distillation under reduced pressure. The remainder is purified by column chromatography to yield 170 mg of the target compound. $^1$H NMR (CDCl$_3$, 300 MHz) δ 8.15 (s, 1H), 7.92 (m, 2H), 7.80 (m, 2H), 7.33 (m, 4H), 6.91 (s, 1H), 2.45 (s, 3H).

Step 3: Preparation of (S)-(1-(3-(4-methylphenyl)-7-(4-fluorophenyl)-pyrazolo[1,5-a]pyrimidin-5-yl)pyrrolidin-2-yl)methanol (Chemical Formula 109)

[Chemical Formula 109]

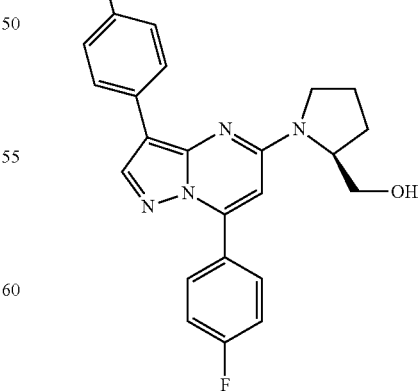

5-Chloro-3-(4-methylphenyl)-7-(4-fluorophenyl)-pyrazolo[1,5-a]pyrimidine (50 mg), (S)-pyrrolin-2-ylmethanol (15 mg) and DIPEA (0.2 mL) are added to acetonitrile (10 mL) and stirred overnight at 80° C. After cooling to room temperature, the solvent and volatile substance are removed by distillation under reduced pressure. The remainder is extracted 3 times with ethyl acetate (20 mL) and water. The collected organic layer is washed with brine. The organic layer is dehydrated with anhydrous MgSO$_4$ and the solvent is removed by distillation under reduced pressure. The remainder is purified by column chromatography to yield 32 mg of the target compound.

Examples 270-276

Compounds of Examples 270-276 are prepared in a similar manner as Example 269.

Chemical formula and NMR analysis data for the compounds of Examples 269-276 are shown in Chemical Formula 110 and Table 20.

[Chemical Formula 110]

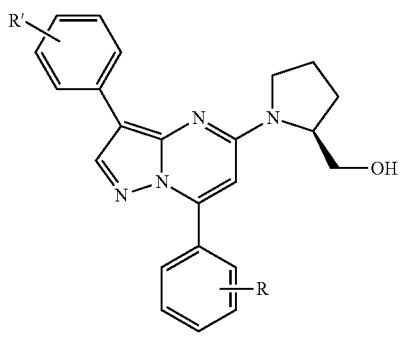

Example 277

Preparation of (S)-7-(4-fluorophenyl)-5-(2-(methoxymethyl)pyrrolidin-1-yl)-2-methyl-3-(4-methylphenyl)pyrazolo[1,5-a]pyrimidine (Chemical Formula 111)

[Chemical Formula 111]

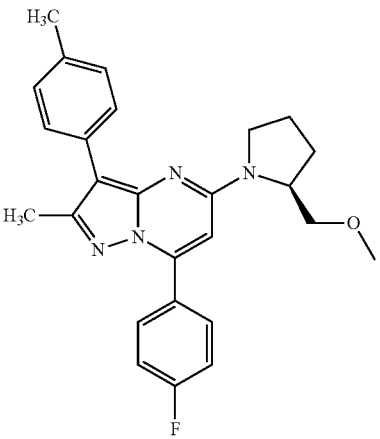

5-Chloro-3-(4-methylphenyl)-7-(3-fluorophenyl)-2-methylpyrazolo[1,5-a]pyrimidine (50 mg), (S)-2-methoxymethylpyrrolidine (0.02 mL) and DIPEA (0.2 mL) are added to acetonitrile (10 mL) and stirred overnight at 80° C. After cooling to room temperature, the solvent and volatile sub

TABLE 20

| Ex. No. | R | R' | $^1$H NMR (CDCl$_3$, 300 MHz) |
|---|---|---|---|
| 269 | 4-F | 4-Me | 8.15 (S, 1 H), 7.92 (m, 2H), 7.76 (d, J = 8.18 Hz, 2H), 7.23 (m, 4H), 6.21 (s, 1 H), 4.59 (br, 1 H), 3.87-3.57 (m, 4H), 2.36 (s, 3H), 2.13-1.99 (m, 3H), 1.85-1.73 (m, 1H) |
| 270 | 3-F | 4-Me | 8.16 (s, 1H), 7.76 (d, J = 7.8 Hz, 2H), 7.67 (m, 3H), 7.51 (m, 1H), 7.23 (d, J = 7.8 Hz, 2H), 6.23 (s, 1H), 4.57 (br, 1H), 3.87-3.57 (m, 4H), 2.36 (s, 3H), 2.13-1.99 (m, 3H), 1.85-1.73 (m, 1H) |
| 271 | 3-MeO | 4-Me | 8.15 (s, 1H), 7.75 (d, J = 7.2 Hz, 2H), 7.43 (m, 3H), 7.23 (d, J = 7.2 Hz, 2H), 7.06 (m, 1H), 6.23 (s, 1H), 4.55 (br, 1H), 3.87 (s, 3H), 3.87-3.57 (m, 4H), 2.36 (s, 3H), 2.13-1.99 (m, 3H), 1.85-1.73 (m, 1H) |
| 272 | 3-F, 4-F | 4-Me | 8.16 (s, 1H), 7.84 (m, 1H), 7.76 (d, J = 7.8 Hz, 2H), 7.70 (m, 1H), 7.34 (m, 1H), 7.25 (d, J = 7.8 Hz, 2H), 6.22 (s, 1H), 4.59 (br, 1H), 3.89-3.57 (m, 4H), 2.36 (s, 3H), 2.17-1.99 (m, 3H), 1.85-1.73 (m, 1H) |
| 273 | 3-F, 5-F | 4-Me | 8.18 (s, 1H), 7.76 (d, J = 7.8 Hz, 2H), 7.45 (m, 2H), 7.23 (s, 1H), 7.00 (s, 1 H), 6.25 (s, 1 H), 4.45 (br, 1 H), 3.85-3.57 (m, 4H), 2.36 (s, 3H), 2.17-1.99 (m, 3H), 1.85-1.73 (m, 1H) |
| 274 | 3-CF$_3$ | 4-MeO | 8.13 (m, 2H), 7.79 (m, 2H), 7.69 (m, 1H), 7.25 (m, 1H), 6.99 (d, J = 7.2 Hz, 2H), 6.25 (s, 1H), 4.60 (br, 1H), 3.85 (s, 3H), 3.80-3.50 (m, 5H), 2.15-1.99 (m, 3H), 1.85-1.78 (m, 1H) |
| 275 | 3-MeO | 4-F | 8.13 (m, 1H), 7.84 (m, 2H), 7.44 (m, 3H), 7.11 (m, 3H), 6.26 (s, 1H), 4.59 (br, 1H), 3.88 (s, 3H), 3.79-3.56 (m, 4H), 2.15-2.08 (m, 2H), 1.87 (m, 1H) |
| 276 | 3-CF$_3$ | 4-F | 8.15 (m, 3H), 7.82 (m, 3H), 7.69 (m, 1H), 7.11 (m, 2H), 6.27 (s, 1H), 4.59 (br, 1H), 3.80-3.50 (m, 4H), 2.15-2.04 (m, 2H), 1.89 (m, 1H) | stance are removed by distillation under reduced pressure. The remainder is extracted 3 times with ethyl acetate (20 mL) and water. The collected organic layer is washed with brine. The organic layer is dehydrated with anhydrous MgSO$_4$ and the solvent is removed by distillation under reduced pressure. The remainder is purified by column chromatography to yield 53 mg of the target compound.

Examples 278-284

Compounds of Examples 278-284 are prepared in a similar manner as Example 277.

Chemical formula and NMR analysis data for the compounds of Examples 278-284 are shown in Chemical Formula 112 and Table 21.

[Chemical Formula 112]

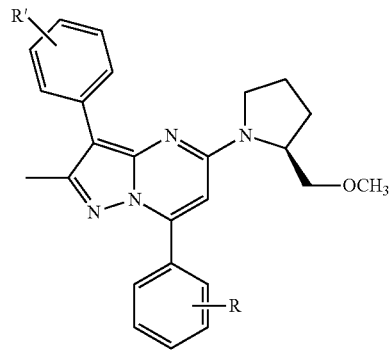

TABLE 21

| Ex. No. | R | R' | $^1$H NMR (CDCl$_3$, 300 MHz) |
|---|---|---|---|
| 277 | 4-F | Me | 7.95 (d, J = 8.4 Hz, 2H), 7.76-7.47 (m, 3H), 7.15 (m, 1H), 6.98 (d, J = 8.4 Hz, 2H), 6.30 (s, 1H), 4.44 (br, 1H), 3.85 (s, 3H), 3.72-3.60 (m, 2H), 3.56-3.43 (m, 2H), 3.39 (s, 3H), 2.38 (s, 3H), 2.15-1.99 (m, 4H) |
| 278 | 3-MeO | Me | 7.76 (d, J = 6.6 Hz, 2H), 7.53 (s, 1H), 7.44 (m, 2H), 7.22 (d, J = 7.2 Hz, 2H), 7.04 (d, J = 7.5 Hz, 1H), 6.18 (s, 1H), 4.42 (bs, 1H), 3.86 (s, 3H), 3.65 (m, 2H), 3.45 (m, 2H), 3.96 (s, 3H), 2.56 (s, 3H), 2.38 (s, 3H), 2.03 (m, 4H) |
| 279 | 3-Me | Me | 7.76 (s, 1H), 7.73 (d, J = 6.9 Hz, 2H), 7.75 (s, 1 H), 7.39 (t, J = 7.5 Hz, 1 H), 7.30 (d, J = 7.2 Hz, 1H), 7.20 (d, J = 7.8 Hz, 2H), 6.13 (s, 1H), 4.41 (bs, 1H), 3.65 (m, 2H), 3.48 (m, 2H), 3.90 (s, 3H), 2.55 (s, 3H), 2.46 (s, 3H), 2.37 (s, 3H), 2.03 (m, 4H) |
| 280 | 3-Cl | Me | 7.92 (s, 1H), 7.84 (d, J = 6.6 Hz, 1H), 7.71 (d, J = 6.6 Hz, 2H), 7.46 (m, 2H), 7.21 (d, J = 7.21 Hz, 2H), 6.16 (s, 1H), 4.41 (bs, 1H), 3.65 (m, 2H), 3.46 (m, 2H), 3.39 (s, 3H), 2.55 (s, 3H), 2.37 (s, 3H), 2.03 (m, 4H) |
| 281 | 3-F, 4-F | Me | 7.90 (dd, J = 8.7, 9.9 Hz, 1H), 7.72 (d, J = 7.8 Hz, 2H), 7.68 (s, 1H), 7.30 (t, J = 8.7 Hz, 1H), 7.21 (d, J = 7.8 Hz, 2H), 6.15 (s, 1H), 4.40 (bs, 1H), 3.63 (m, 2H), 3.46 (m, 2H), 3.38 (s, 3H), 2,55 (s, 3H), 2.37 (m, 3H), 2.03 (m, 4H) |
| 282 | 3-F | 3,4-methylenedioxy | 7.72 (d, J = 8.4 Hz, 2H), 7.50 (dd, J = 7.8, 7.5 Hz, 1H), 7.45 (s, 1H), 7.22 (m, 2H), 6.88 (d, J = 7.8 Hz, 1 H), 6.19 (s, 1H), 5.96 (s, 2H), 4.42 (bs, 1H), 3.66 (m, 2H), 3.47 (m, 2H), 3.40 (s, 3H), 2.54 (s, 3H), 2.07 (m, 4H) |
| 283 | 3-MeO | 3,4-methylenedioxy | 7.46 (m, 4H), 7.23 (d, J = 1.5 Hz, 1 H), 7.05 (d, J = 7.8 Hz, 1H), 6.87 (d, J = 8.1 Hz, 1H), 6.18 (s, 1 H), 5.96 (s, 2H), 4.30 (bs, 1 H), 3.87 (s, 3H), 3.65 (m, 2H), 3.45 (m, 2H), 3.40 (s, 3H), 2.54 (s, 3H), 2.07 (m, 4H) |
| 284 | 3-Cl | 3,4-methylenedioxy | 8.00 (s, 1H), 7.95 (m, 1H), 7.38 (m, 3H), 7.24 (m, 1H), 6.93 (d, J = 7.8 Hz, 1H), 6.24 (s, 1H), 5.99 (s, 2H), 3.96 (m, 1H), 3.72 (m, 1H), 3.63 (dd, J = 3.3, 3.6 Hz, 1H), 3.40 (m, 2H), 3.34 (s, 3H), 2.57 (s, 3H), 2.17 (bs, 3H), 2.04 (m, 1H) |

Example 285

Preparation of (S)-{1-(2-butyl-7-(3-fluorophenyl)-3-(p-tolyl)pyrazolo[1,5-a]pyrimidin-5-yl)methanol (Chemical Formula 113)

[Chemical Formula 113]

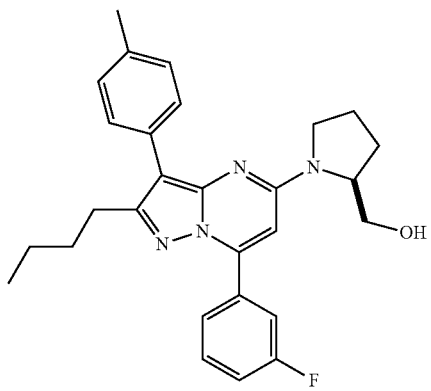

Step 1: Preparation of 2-butyl-3-(4-methylphenyl)-7-(4-fluorophenyl)-pyrazolo[1,5-a]pyrimidin-5(4H)-one (Chemical Formula 114)

[Chemical Formula 114]

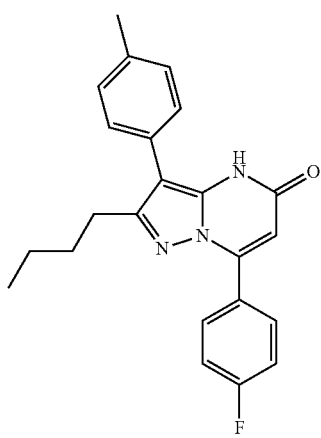

3-Butyl-4-(4-methylphenyl)-1H-pyrazol-5-amine (200 mg) and ethyl 3-(4-fluorophenyl)-3-oxopropanoate (250 mg) are stirred overnight in a pyridine (10 mL) solvent at 95° C. After cooling to room temperature, the reaction solvent is removed by distillation under reduced pressure. The remainder is extracted with ethyl acetate and water. The extracted organic layer is washed with brine and dehydrated with anhydrous MgSO$_4$. The dehydrated organic layer is distilled under reduced pressure and 215 mg of the target compound is yielded by column chromatography.

Step 2: Preparation of 5-chloro-2-butyl3-(4-methylphenyl)-7-(4-fluorophenyl)-pyrazolo[1,5-a]pyridine pyrimidine (Chemical Formula 115)

[Chemical Formula 115]

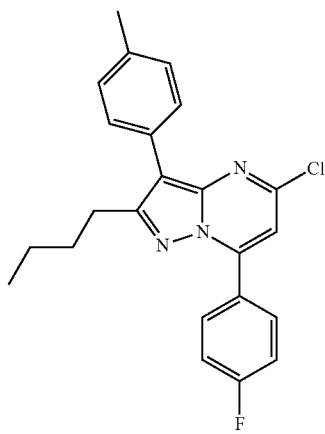

2-Butyl-3-(4-methylphenyl)-7-(4-fluorophenyl)-pyrazolo[1,5-a]pyrimidin-5(4H)-one (150 mg) is added to POCl$_3$ (3 mL) and pyridine (0.1 mL) and stirred for 2 hours while heating. After cooling to room temperature, POCl$_3$ is removed by distillation under reduced pressure. After the distillation, ethyl acetate (20 mL) and ice are added to the remainder. The organic layer is extracted and it is extracted once again with water and ethyl acetate. The organic layer is washed with 1 M NaHCO$_3$ aqueous solution and brine. The organic layer is dehydrated with anhydrous MgSO$_4$. The solvent is removed from the organic layer by distillation under reduced pressure. The remainder is purified by column chromatography to yield 100 mg of the target compound. $^1$H NMR (CDCl$_3$, 300 MHz) δ 7.96 (m, 2H), 7.47 (m, 2H), 7.39 (d, J=8.1 Hz, 2H), 7.21 (m, 2H), 6.85 (s, 1H), 2.81 (q, J=8.4 Hz, 2H), 2.44 (s, 3H), 1.62 (m, 2H), 1.32 (m, 2H), 0.84 (t, J=7.2 Hz, 3H).

Step 3: Preparation of (S)-(1-(3-(4-methylphenyl)-7-(4-fluorophenyl)-2-butylpyrazolo[1,5-a]pyrimidin-5-yl)pyrrolidin-2-yl)methanol 5-Chloro-2-butyl-3-(4-methylphenyl)-7-(4-fluorophenyl)-pyrazolo[1,5-a]pyridine pyrimidine (50 mg), (S)-pyrrolin-2-ylmethanol (17 mg) and DIPEA (0.2 mL) are added to acetonitrile (10 mL) and stirred overnight at 80° C. After cooling to room temperature, the solvent and volatile substance are removed by distillation under reduced pressure. The remainder is extracted 3 times with ethyl acetate (20 mL) and water. The collected organic layer is washed with brine. The organic layer is dehydrated with anhydrous MgSO$_4$ and the solvent is removed by distillation under reduced pressure. The remainder is purified by column chromatography to yield 58 mg of the target compound.

Examples 288-293

Compounds of Examples 288-293 are prepared in a similar manner as Example 287.

Chemical formula and NMR analysis data for the compounds of Examples 288-293 are shown in Chemical Formula 116 and Table 22.

[Chemical Formula 116]

Example 294

Preparation of (S)-(1-(7-(4-fluorophenyl)-2-propyl-3-(p-tolyl)pyrazolo[1,5-a]pyrimidin-5-yl)pyrrolidin-2-yl)methanol (Chemical Formula 117)

[Chemical Formula 117]

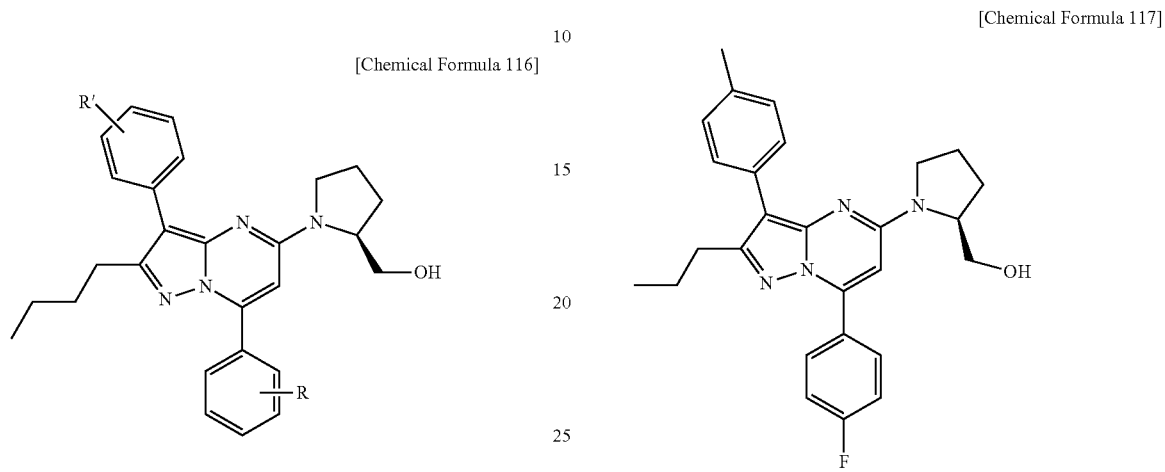

TABLE 22

| Ex. No. | R | R' | $^1$H NMR (CDCl$_3$, 300 MHz) |
|---|---|---|---|
| 287 | 3-F | 4-Me | δ 7.30 (m, 2H), 7.47 (m, 2H), 7.39 (d, J = 8.1 Hz, 2H), 7.21 (m, 2H), 6.11 (s, 1 H), 4.34 (m, 1 H), 3.67-3.48 (m, 5H), 2.78 (t, J = 7.8 Hz, 2H), 2.35 (s, 3H), 2.22-1.95 (m, 3H), 1.77-1.70 (m, 1H), 1.60 (m, 2H), 1.32 (m, 2H), 0.84 (t, J = 7.2 Hz, 3H) |
| 288 | 3-CF$_3$ | 4-Me | 8.22 (m, 2H), 7.78 (m, 1H), 7.67 (m, 1H), 7.43 (m, 2H), 7.25 (m, 2H), 6.16 (s, 1H), 5.60 (br, 1H), 4.38 (m, 1H), 3.67 (m, 4H), 2.82 (m, 2H), 2.38 (s, 3H), 2.06 (m, 4H), 1.65 (m, 2H), 1.37 (m, 2H), 0.89 (m, 3H) |
| 289 | 3-Me | 4-Me | δ 7.72 (m, 2H), 7.39 (d, J = 7.8 Hz, 2H), 7.35 (m, 2H), 7.21 (m, 2H), 6.08 (s, 1H), 4.33 (m, 1H), 3.81-3.53 (m, 5H), 2.80 (t, J = 7.8 Hz, 2H), 2.14 (s, 3H), 2.34 (s, 3H), 2.22-1.95 (m, 3H), 1.77-1.70 (m, 1H), 1.60 (m, 2H), 1.32 (m, 2H), 0.83 (t, J = 7.2 Hz, 3H) |
| 290 | 3-F | 4-Cl | δ 7.70 (m, 3H), 7.52 (d, J = 8.1 Hz, 2H), 7.44 (m, 1H), 7.36 (d, J = 8.1 Hz, 2H), 6.13 (s, 1H), 4.36 (br, 1H), 3.81-3.53 (m, 5H), 2.77 (t, J = 6.6 Hz, 2H), 2.22-1.95 (m, 3H), 1.77-1.70 (m, 1H), 1.58 (m, 2H), 1.32 (m, 2H), 0.85 (t, J = 7.2 Hz, 3H) |
| 291 | 3-CF$_3$ | 4-Cl | δ 8.22 (s, 1H), 8.15 (d, J = 7.8 Hz, 7.75 (d, J = 8.4 Hz, 1H), 7.64 (m, 1H), 7.45 (d, J = 8.4 Hz, 2H), 7.35 (d, J = 8.4 Hz, 2H), 6.15 (s, 1H), 4.37 (m, 1H), 3.69-3.40 (m, 5H), 2.80 (t, J = 7.8 Hz, 2H), 2.12-1.95 (m, 3H), 1.77-1.67 (m, 1H), 1.58 (m, 2H), 1.34 (m, 2H), 0.85 (t, J = 7.2 Hz, 3H) |
| 292 | 3-Me | 4-Cl | δ 7.71 (m, 2H), 7.46 (d, J = 8.4 Hz, 2H), 7.35 (m, 4H), 6.10 (s, 1H), 4.37 (m, 1H), 3.81-3.53 (m, 5H), 2.80 (t, J = 7.8 Hz, 2H), 2.39 (s, 3H), 2.22-1.95 (m, 3H), 1.77-1.70 (m, 1 H), 1.56 (m, 2H), 1.32 (m, 2H), 0.83 (t, J = 7.2 Hz, 3H) |
| 293 | 3-Me | 4-MeO | δ 7.72 (m, 2H), 7.40 (d, J = 8.7 Hz, 2H), 7.37 (m, 1H), 7.31 (m, 2H), 6.95 (d, J = 8,7 Hz, 2H), 6.08 (s, 1H), 4.35 (m, 1H), 3.80 (s, 3H), 3.67-3.48 (m, 5H), 2.76 (t, J = 8.1 Hz, 2H), 2.41 (s, 3H), 2.22-1.95 (m, 3H), 1.77-1.70 (m, 1 H), 1.60 (m, 2H), 1.32 (m, 2H), 0.83 (t, J = 7.2 Hz, 3H) |

Step 1: Preparation of 2-butyl-3-(4-methylphenyl)-7-(4-fluorophenyl)-pyrazolo[1,5-a]pyrimidin-5(4H)-one (Chemical Formula 118)

[Chemical Formula 118]

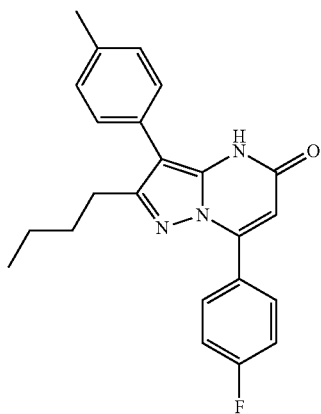

3-Butyl-4-(4-methylphenyl)-1H-pyrazol-5-amine (200 mg) and ethyl 3-(4-fluorophenyl)-3-oxopropanoate (250 mg) are stirred overnight in a pyridine (10 mL) solvent at 95° C. After cooling to room temperature, the reaction solvent is removed by distillation under reduced pressure. The remainder is extracted with ethyl acetate and water. The extracted organic layer is washed with brine and dehydrated with anhydrous $MgSO_4$. The dehydrated organic layer is distilled under reduced pressure and 215 mg of the target compound is yielded by column chromatography.

Step 2: Preparation of 5-chloro-2-butyl-3-(4-methylphenyl)-7-(4-fluorophenyl)-pyrazolo[1,5-a]pyridine pyrimidine (Chemical Formula 119)

[Chemical Formula 119]

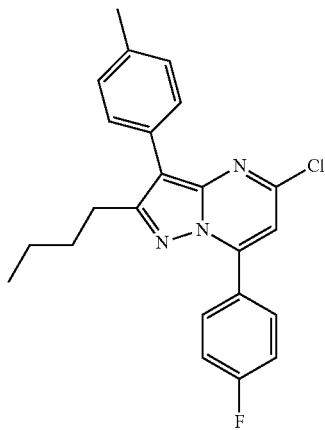

2-Butyl-3-(4-methylphenyl)-7-(4-fluorophenyl)-pyrazolo[1,5-a]pyrimidin-5(4H)-one (150 mg) is added to $POCl_3$ (3 mL) and pyridine (0.1 mL) and stirred for 2 hours while heating. After cooling to room temperature, $POCl_3$ is removed by distillation under reduced pressure. After the distillation, ethyl acetate (20 mL) and ice are added to the remainder. The organic layer is extracted and it is extracted once again with water and ethyl acetate. The organic layer is washed with 1 M $NaHCO_3$ aqueous solution and brine. The organic layer is dehydrated with anhydrous $MgSO_4$. The solvent is removed from the organic layer by distillation under reduced pressure. The remainder is purified by column chromatography to yield 100 mg of the target compound. $^1$H NMR ($CDCl_3$, 300 MHz) δ 7.96 (m, 2H), 7.47 (m, 2H), 7.39 (d, J=8.1 Hz, 2H), 7.21 (m, 2H), 6.85 (s, 1H), 2.81 (q, J=8.4 Hz, 2H), 2.44 (s, 3H), 1.62 (m, 2H), 1.32 (m, 2H), 0.84 (t, J=7.2 Hz, 3H).

Step 3: Preparation of (S)-(1-(3-(4-methylphenyl)-7-(4-fluorophenyl)-2-butylpyrazolo[1,5-a]pyrimidin-5-yl)pyrrolidin-2-yl)methanol 5-Chloro-2-butyl-3-(4-methylphenyl)-7-(4-fluorophenyl)-pyrazolo[1,5-a]pyridine pyrimidine (50 mg), (S)-pyrrolin-2-ylmethanol (17 mg) and DIPEA (0.2 mL) are added to acetonitrile (10 mL) and stirred overnight at 80° C. After cooling to room temperature, the solvent and volatile substance are removed by distillation under reduced pressure. The remainder is extracted 3 times with ethyl acetate (20 mL) and water. The collected organic layer is washed with brine. The organic layer is dehydrated with anhydrous $MgSO_4$ and the solvent is removed by distillation under reduced pressure. The remainder is purified by column chromatography to yield 58 mg of the target compound.

Examples 295-304

Compounds of Examples 295-304 are prepared in a similar manner as Example 294.

Chemical formula and NMR analysis data for the compounds of Examples 295-304 are shown in Chemical Formula 120 and Table 23.

[Chemical Formula 120]

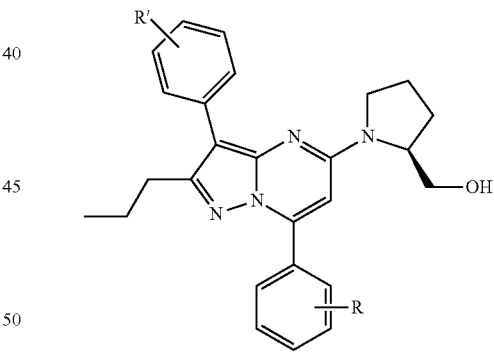

TABLE 23

| Ex. No. | R | R' | $^1$H NMR ($CDCl_3$, 300 MHz) |
|---|---|---|---|
| 294 | 4-F | 4-Me | δ 8.01 (m, 2H), 7.42 (d, J = 8.1Hz, 2H), 7.22 (m, 4H), 6.11 (s, 1H), 4.40 (m, 1H), 3.81-3.53 (m, 5H), 2.80 (t, J = 7.8 Hz, 2H), 2.39 (s, 3H), 2.22-1.95 (m, 3H), 1.77-1.70 (m, 3H), 0.93 (t, J = 7.2 Hz, 3H) |
| 295 | 3-F | 4-Me | δ 7.78 (d, J = 8.4 Hz, 2H), 7.51 (m, 1H), 7.44 (d, J = 8.4 Hz, 2H), 7.26 (m, 3H), 6.15 (s, 1H), 4.37 (m, 1H), 3.81-3.53 (m, 5H), 2.80 (t, J = 7.8 Hz, 2H), 2.39 (s, 3H), 2.22-1.95 (m, 3H), 1.77-1.70 (m, 3H), 0.93 (t, J = 7.2 Hz, 3H) |

TABLE 23-continued

| Ex. No. | R | R' | $^1$H NMR (CDCl$_3$, 300 MHz) |
|---|---|---|---|
| 296 | 3-CF$_3$ | 4-Me | δ 8.19 (s, 1H), 8.18 (d, J = 9.9 Hz, 1H), 7.75 (10.8 Hz, 1H), 7.63 (m, 1H), 7.40 (d, J = 6.9 Hz, 2H), 6.97 (d, J = 6.9 Hz, 2H), 6.13 (s, 1H), 4.33 (m, 1H), 3.81 (s, 3H), 3.72-3.51 (m, 5H), 2.73 (t, J = 7.2 Hz, 2H), 2.00 (s, 3H), 2.032-1.95 (m, 3H), 1.77-1.70 (m, 1H), 0.89 (t, J = 7.2 Hz, 3H) |
| 297 | 3-Me | 4-Me | 7.76 (m, 2H), 7.44 (m, 2H), 7.39 (m, 1H), 7.34 (m, 1H), 7.24 (m, 2H), 6.12 (s, 1H), 4.37 (br, 1H), 3.65 (m, 4H), 2.80 (t, J = 7.5 Hz, 2H), 2.45 (s, 3H), 2.39 (s, 3H), 2.02 (m, 3H), 1.70 (m, 4H), 0.93 (t, J = 6.6 Hz, 3H) |
| 298 | 4-F | 4-Cl | 8.00 (dd, J = 8.7 Hz, 2H), 7.49 (d, J = 8.4 Hz, 2H), 7.40 (d, J = 8.4 Hz, 2H), 7.21 (d, J = 8.7 Hz, 2H), 6.14 (s, 1H), 4.41 (m, 1H), 3.65 (m, 4H), 2.79 (dd, J = 7.5, 8.1Hz, 2H), 2.01 (m, 3H), 1.79 (m, 1H), 1.68 (m, 2H), 0.93 (dd, J = 7.5, 7.2 Hz, 3H) |
| 299 | 3-F | 4-Cl | 7.76 (s, 1H), 7.73 (m, 1H), 7.49 (m, 2H), 7.40 (d, J = 8.4 Hz, 2H), 7.22 (m, 2H), 6.18 (s, 1H), 4.42 (m, 1H), 3.65 (m, 4H), 2.79 (dd, J = 7.5, 7.8 Hz, 2H), 2.04 (m, 3H), 1.80 (m, 1H), 1.75 (m, 2H), 0.93 (dd, J = 7.5, 7.2 Hz, 3H) |
| 300 | 3-Me | 4-Cl | 7.73 (m, 4H), 7.40 (m, 4H), 6.23 (s, 1H), 4.55 (s, 2H), 4.50 (br, 1H), 3.69 (m, 4H), 3.57 (s, 3H), 2.46 (s, 3H), 2.07 (m, 3H), 1.80 (m, 1H), 0.93 (t, 3H) |
| 301 | 4-F | 4-MeO | 7.99 (m, 2H), 7.44 (d, J = 8.4 Hz, 2H), 7.20 (m, 2H), 6.99 (d, J = 8.7 Hz, 2H), 6.10 (s, 1H), 5.64 (bs, 1H), 4.36 (bs, 1H), 3.83 (s, 3H), 3.62 (m, 4H), 2.78 (dd, J = 7.8, 7.5 Hz, 2H), 1.99 (m, 3H), 1.68 (m, 3H), 0.92 (dd, J = 6.9, 7.5 Hz, 3H) |
| 302 | 3-F | 4-MeO | 7.71 (d. J = 7.8 Hz, 2H), 7.46 (m, 1H), 7.41 (s, 1H), 7.38 (s, 1H), 7.17 (m, 1H), 6.95 (d, J = 8.4 Hz, 2H), 6.10 (s, 1H), 5.54 (bs, 1H), 4.33 (m, 1H), 3.80 (s, 3H), 3.56 (m, 4H), 2.74 (dd, J = 7.5, 7.8 Hz, 2H), 2.00 (m, 3H), 1.67 (m, 3H), 0.88 (dd, J = 7.5, 7.2 Hz, 3H) |
| 303 | 3-CF$_3$ | 4-MeO | δ 8.19 (s, 1H), 8.18 (d, J = 9.9 Hz, 1H), 7.75 (10.8 Hz, 1H), 7.63 (m, 1H), 7.40 (d, J = 6.9 Hz, 2H), 6.97 (d, J = 6.9 Hz, 2H), 6.13 (s, 1H), 4.33 (m, 1H), 3.81 (s, 3H), 3.72-3.51 (m, 5H), 2.73 (t, J = 7.2 Hz, 2H), 2.00 (s, 3H), 2..32-1.95 (m, 3H), 1.77-1.70 (m, 1H), 0.89 (t, J = 7.2 Hz, 3H) |
| 304 | 3-Me | 4-MeO | 7.75 (m, 2H), 7.53 (m, 1H), 7.44 (m, 2H), 7.35 (m, 1H), 7.00 (m, 2H), 6.12 (s, 1H), 4.39 (br, 1H), 3.84 (s, 3H), 3.61 (m, 3H), 2.78 (t, J = 7.5 Hz, 2H), 2.45 (s, 3H), 2.02 (m, 3H), 1.68 (m, 3H), 0.93 (t, J = 7.8 Hz, 3H) |

Example 305

Preparation of (R)-(1-(3-(4-chlorophenyl)-7-phenyl-2-methylpyrazolo[1,5-a]pyrimidin-5-yl)pyrrolidin-yl)ethanol (Chemical Formula 121)

[Chemical Formula 121]

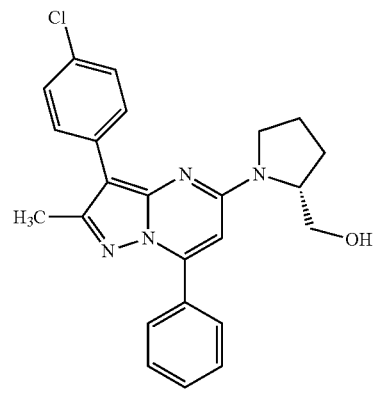

5-Chloro-3-(4-chlorophenyl)-7-phenyl-2-methylpyrazolo[1,5-a]pyrimidine (60 mg), (R)-pyrrolin-2-ylmethanol (17 mg) and DIPEA (0.2 mL) are added to acetonitrile (10 mL) and stirred overnight at 80° C. After cooling to room temperature, the solvent and volatile substance are removed by distillation under reduced pressure. The remainder is extracted 3 times with ethyl acetate (20 mL) and water. The collected organic layer is washed with brine. The organic layer is dehydrated with anhydrous MgSO$_4$ and the solvent is removed by distillation under reduced pressure. The remainder is purified by column chromatography to yield 40 mg of the target compound. $^1$H NMR (CDCl$_3$, 300 MHz) δ 7.94 (m, 2H), 7.55 (m, 5H), 7.40 (d, J=8.4 Hz, 2H), 6.17 (s, 1H), 4.46 (br, 1H), 3.78-3.52 (m, 4H), 2.47 (s, 3H), 2.15-1.99 (m, 3H), 1.78-1.69 (m, 1H).

Example 306

Preparation of (R)-{1-[2-methoxymethyl-7-(4-(fluoromethyl)phenyl)-3-(4-methoxyphenyl)-pyrazolo[1,5-a]pyrimidin-5-yl]pyrrolidin-2-yl}methanol (Chemical Formula 122)

[Chemical Formula 122]

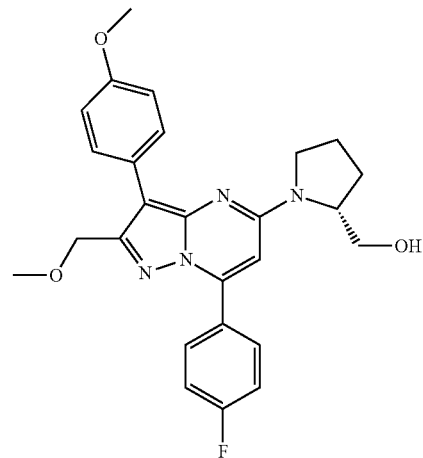

5-Chloro-3-(4-methoxyphenyl)-7-(4-fluorophenyl)-2-methoxymethylpyrazolo[1,5-a]pyrimidine (60 mg), (R)-pyrrolin-2-ylmethanol (18 mg) and DIPEA (0.2 mL) are added to acetonitrile (10 mL) and stirred overnight at 80° C. After cooling to room temperature, the solvent and volatile substance are removed by distillation under reduced pressure. The remainder is extracted 3 times with ethyl acetate (20 mL) and water. The collected organic layer is washed with brine. The organic layer is dehydrated with anhydrous $MgSO_4$ and the solvent is removed by distillation under reduced pressure. The remainder is purified by column chromatography to yield 56 mg of the target compound.

Test Example 2

CB1 Receptor Inhibition Effect

When cells in which the cannabinoid receptor 1 (CB1) is stably expressed are treated with a CB1 receptor agonist, the CB1 receptor is activated and influx of calcium ions into the cells increases. CB1 receptor inhibition effect of a test compound can be evaluated by measuring the degree of calcium influx inhibition after treating with the test compound.

First, Chem-1 cells (Chemicon International, #HTS019C) in which human CB1 cDNA is expressed stably were seeded onto a 96-well cell culture plate at a density of ~50,000 cells/well and incubated overnight in a 5% $CO_2$ incubator at 37° C. The next day, the culture medium was discarded and the cells were cautiously washed once using an assay buffer (HBSS containing 20 mM HEPES and 2.5 mM probenecid) with 200 μL/well. Calcium ion influx was measured using an assay kit (Fluo-4 NW calcium assay kit: Molecular Probes™, #F36206) according to the manufacturer's instructions. The compounds of Examples of desired concentration to be measured were comprised to 0.5% DMSO. For control, only 0.5% DMSO was used without the compounds of Examples. Reaction time was 10 minutes. After treating the Chem-1 cells stably expressing the CB1 receptor with 1 μM R-(+)-WIN55212-2 (Sigma, #W102), a CB1 receptor agonist, calcium ion ($Ca^{2+}$) flux induced thereby was measured for 80 seconds using Flex Station 3 (Molecular Device, USA).

The difference in calcium ion concentration of the cells treated with the compounds of Examples or those treated with 1 μM R-(+)-WIN55212-2 was obtained from the difference of the maximum and minimum values during the 80 seconds. Then, % inhibition of the compounds for the CB1 receptor was calculated using the following equation.

% inhibition={1−($\Delta RFU_{compound}$−$\Delta RFU_{Blank}$)/($\Delta RFU_{Control}$−$\Delta RFU_{Blank}$)}×100     [Equation]

wherein

ΔRFU: maximum relative fluorescence units−minimum relative fluorescence units $\Delta RFU_{Compound}$: difference in maximum and minimum RFUs in the well where the compounds of Examples dissolved in DMSO to a final concentration of 0.5% and 1 μM R-(+)-WIN55212-2 dissolved in DMSO to a final concentration of 0.5% were added $\Delta RFU_{Blank}$: difference in maximum and minimum RFUs in the well to which only 1% DMSO was added $\Delta RFU_{Control}$: difference in maximum and minimum RFUs in the well where 0.5% DMSO and 1 μM R-(+)-WIN55212-2 dissolved in DMSO to a final concentration of 0.5% were added $IC_{50}$ values of the compounds of Examples are given in Table 24.

TABLE 24

| Ex. No. | $IC_{50}$ (μM) |
|---|---|
| 2 | 0.10 |
| 3 | 0.093 |
| 4 | 0.36 |
| 5 | 0.096 |
| 6 | 0.2 |
| 9 | 0.12 |
| 11 | 0.27 |
| 12 | 0.21 |
| 13 | 0.30 |
| 14 | 0.09 |
| 15 | 0.35 |
| 21 | 0.051 |
| 22 | 0.11 |
| 25 | 0.039 |
| 26 | 0.053 |
| 27 | 0.24 |
| 28 | 0.12 |
| 30 | 0.16 |
| 31 | 0.13 |
| 32 | 0.14 |
| 33 | 0.082 |
| 34 | 0.22 |
| 35 | 0.41 |
| 36 | 0.10 |
| 37 | 0.14 |
| 38 | 0.10 |
| 39 | 0.25 |
| 40 | 0.35 |
| 41 | 0.26 |
| 42 | 0.35 |
| 43 | 0.21 |
| 44 | 0.16 |
| 45 | 0.12 |
| 46 | 0.19 |
| 47 | 0.13 |
| 48 | 0.18 |
| 51 | 0.25 |
| 53 | 0.39 |
| 55 | 0.2 |
| 56 | 0.09 |
| 57 | 0.24 |
| 58 | 0.3 |
| 60 | 0.21 |
| 62 | 0.07 |
| 63 | 0.041 |
| 64 | 0.17 |
| 65 | 0.10 |
| 66 | 0.14 |
| 67 | 0.094 |
| 68 | 0.170 |
| 69 | 0.22 |
| 70 | 0.230 |
| 71 | 0.210 |
| 72 | 0.35 |
| 74 | 0.16 |
| 77 | 0.35 |
| 79 | 0.10 |
| 81 | 0.30 |
| 83 | 0.22 |
| 84 | 0.53 |
| 85 | 0.470 |
| 87 | 0.43 |
| 96 | 0.31 |
| 100 | 0.31 |
| 101 | 0.16 |
| 106 | 0.25 |
| 110 | 0.08 |
| 111 | 0.06 |
| 112 | 0.13 |
| 113 | 0.049 |
| 114 | 0.077 |
| 115 | 0.14 |
| 116 | 0.160 |
| 117 | 0.24 |
| 119 | 0.45 |
| 122 | 0.045 |
| 123 | 0.076 |
| 124 | 0.07 |

TABLE 24-continued

| Ex. No. | IC$_{50}$ (μM) |
|---|---|
| 125 | 0.09 |
| 126 | 0.069 |
| 127 | 0.062 |
| 128 | 0.066 |
| 129 | 0.073 |
| 132 | 0.230 |
| 133 | 0.28 |
| 134 | 0.19 |
| 135 | 0.12 |
| 137 | 0.09 |
| 138 | 0.21 |
| 139 | 0.14 |
| 144 | 0.3 |
| 145 | 0.2 |
| 156 | 0.046 |
| 157 | 0.21 |
| 158 | 0.21 |
| 159 | 0.2 |
| 160 | 0.110 |
| 162 | 0.11 |
| 163 | 0.26 |
| 164 | 0.320 |
| 165 | 0.330 |
| 167 | 0.25 |
| 168 | 0.45 |
| 169 | 0.033 |
| 170 | 0.16 |
| 171 | 0.24 |
| 172 | 0.19 |
| 173 | 0.25 |
| 174 | 0.22 |
| 175 | 0.35 |
| 176 | 0.27 |
| 178 | 0.120 |
| 180 | 0.41 |
| 182 | 0.31 |
| 183 | 0.13 |
| 184 | 0.15 |
| 185 | 0.21 |
| 186 | 0.22 |
| 187 | 0.39 |
| 190 | 0.18 |
| 192 | 0.15 |
| 194 | 0.2 |
| 195 | 0.78 |
| 196 | 0.14 |
| 197 | 0.15 |
| 198 | 0.05 |
| 199 | 0.15 |
| 200 | 0.11 |
| 202 | 0.005 |
| 203 | 0.03 |
| 204 | 0.006 |
| 206 | 0.008 |
| 208 | 0.007 |
| 209 | 0.053 |
| 210 | 0.17 |
| 212 | 0.026 |
| 214 | 0.08 |
| 217 | 0.15 |
| 220 | 0.03 |
| 221 | 0.007 |
| 222 | 0.008 |
| 223 | 0.005 |
| 226 | 0.05 |
| 227 | 0.048 |
| 228 | 0.022 |
| 230 | 0.018 |
| 231 | 0.007 |
| 232 | 0.004 |
| 233 | 0.006 |
| 234 | 0.015 |
| 238 | 0.024 |
| 239 | 0.028 |
| 240 | 0.01 |
| 241 | 0.01 |
| 243 | 0.007 |
| 244 | 0.007 |
| 245 | 0.44 |
| 247 | 0.016 |
| 248 | 0.6 |
| 252 | 0.10 |
| 253 | 0.190 |
| 254 | 0.13 |
| 257 | 0.014 |
| 260 | 0.007 |
| 261 | 0.009 |
| 262 | 0.018 |
| 263 | 0.09 |
| 268 | 0.3 |
| 269 | 0.45 |
| 270 | 0.44 |
| 272 | 0.69 |
| 273 | 0.23 |
| 276 | 0.34 |
| 288 | 0.008 |
| 289 | 0.03 |
| 305 | 3 μM ~5% inhibition |
| 306 | 1 μM <5% inhibition |

As seen from Table 24, calcium flux was inhibited when the cells were treated with the compounds of Examples. Accordingly, the compounds of Examples have superior CB1 receptor inhibition effect.

The compounds of Examples 305 and 306, which are (R)-isomers of the compounds of Examples 5 and 222, respectively, showed lower CB1 receptor inhibition effect than the compounds of Examples 5 and 222. This means that (S)-isomers exhibit better CB1 receptor inhibition effect than (R)-isomers.

Test Example 3

Anti-Obesity Effect in High-Fat Diet-Induced Obese Mice

Obesity was induced for 4 weeks in 6-week-old C57/BL mice (Central Lab. Animal), 10 per group, using a high-fat diet (fat 60%). The mice were re-grouped such that each group had similar average body weight. The compounds of Examples 221 and 238 were homogeneously suspended in 1% methyl cellulose solution and orally administered for 4 weeks, once a day and five days a week, at a dosage of 10 mg/10 mL/kg. For control, only the 1% methyl cellulose solution was orally administered at 10 mL/kg. Change in body weight of the test and control groups was measured with 7-day intervals. The result is shown in FIG. 2.

Figure 2:
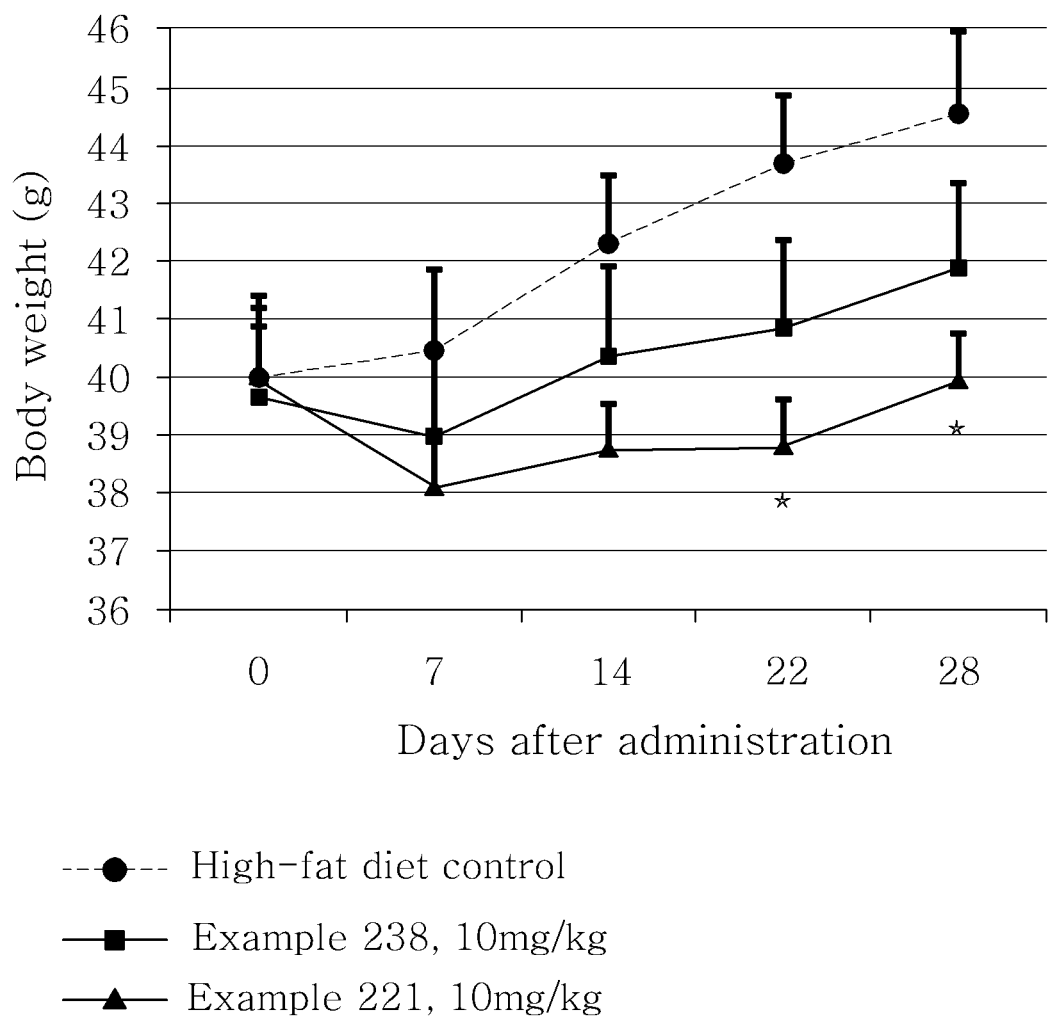
FIG. 2 shows change in the body weight of obese mice after administration of compounds according to exemplary embodiments.

As seen from FIG. 2, the administration of the compounds of Examples resulted in decreased body weight of the high-fat diet-induced obese mice. Accordingly, the compounds of Examples may exhibit excellent anti-obesity effect.

Hereinafter, formulation examples of a pharmaceutical composition containing the compound, the prodrug thereof, the isomer thereof, the pharmaceutically acceptable salt thereof, the hydrate thereof or the solvate thereof according to the present disclosure will be described in detail. However, the following formulation examples are for illustrative pur- Formulation Example 1

Preparation of Tablet

| Compound of Example | 50 mg |
|---|---|
| Cornstarch | 100 mg |
| Lactose | 100 mg |
| Magnesium stearate | 2 mg |
| Vitamin C | 50 mg |

The above ingredients are mixed and prepared into a tablet according to a commonly employed method.

Formulation Example 2

Preparation of Capsule

| Compound of Example | 50 mg |
|---|---|
| Cornstarch | 100 mg |
| Lactose | 100 mg |
| Magnesium stearate | 2 mg |
| Vitamin C | 50 mg |
| Serine | 50 mg |

The above ingredients are mixed and filled in a gelatin capsule according to a commonly employed method.

Formulation Example 3

Preparation of Liquid

| Compound of Example | 100 mg |
|---|---|
| High-fructose corn syrup | 10 g |
| Mannitol | 5 g |
| Vitamin C | 50 mg |
| Serine | 50 mg |
| Fat and oil | adequate |
| Purified water | balance |

According to a commonly employed method, the above ingredients are dissolved in purified water and an adequate amount of lemon flavor is added. The total volume is adjusted to 100 mL by adding purified water. The resulting liquid is filled in a brown bottle and sterilized.

Formulation Example 4

Preparation of Cream

A cream may be prepared according to a commonly employed method as described in Table 25.

TABLE 25

| Ingredients | wt % |
|---|---|
| Compound of Example | 2.0 |
| Polysorbate 60 | 1.5 |
| Sorbitan sesquioleate | 0.5 |
| PEG 60 hydrogenated castor oil | 2.0 |
| Liquid paraffin | 10 |
| Squalane | 5.0 |
| Caprylic/capric triglyceride | 5.0 |
| Glycerin | 5.0 |
| Butylene glycol | 3.0 |
| Propylene glycol | 3.0 |
| Triethanolamine | 0.2 |
| Antiseptic | adequate |
| Pigment | adequate |
| Flavor | adequate |
| Purified water | to 100 |

The invention claimed is:

1. A compound of Chemical Formula 1, a positional or optical isomer thereof, a pharmaceutically acceptable salt thereof, a hydrate thereof or a solvate thereof:

[Chemical Formula 1]

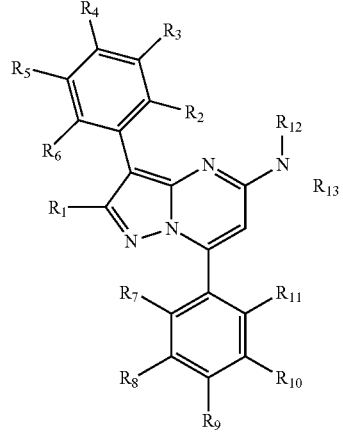

wherein $R_1$ is selected from a group consisting of hydrogen, $C_1$-$C_5$ alkyl, haloalkyl, $C_1$-$C_5$ cycloalkyl and $C_1$-$C_5$ alkoxyalkyl;

each of $R_2$ and $R_7$ is hydrogen;

each of $R_3$, $R_4$, $R_5$ and $R_6$ is independently selected from a group consisting of hydrogen, fluoro, chloro, bromo, iodo, nitro, cyano, $C_1$-$C_5$ alkyl, hydroxy $C_1$-$C_5$ alkyl, $C_1$-$C_5$ alkoxy, $C_1$-$C_5$ alkoxy alkyl, halo $C_1$-$C_3$ alkyl, halo $C_1$-$C_5$ alkoxy, haloalkoxy $C_2$-$C_5$ alkenyl, $C_2$-$C_5$ alkenyl, alkynyl, carboxyl, $C_1$-$C_5$ alkylcarbonyl, $C_1$-$C_5$ alkoxycarbonyl, $C_1$-$C_5$ alkylcarbonylamino, $C_1$-$C_{15}$ alkylamino carbonyl, $C_1$-$C_{15}$ alkylsulfanyl, $C_1$-$C_{15}$ alkylsulfonyl, $C_1$-$C_5$ alkoxysulfonyl, $C_1$-$C_5$ alkylsulfamoyl, aryl, aryl $C_1$-$C_3$ alkyl, aryl $C_1$-$C_5$ alkoxy, aminosulfonyl, $C_1$-$C_{15}$ alkylamino, $C_1$-$C_{15}$ alkylaminosulfonyl, $C_1$-$C_{15}$ alkylsulfonylamino, $C_1$-$C_5$ alkylthio, $C_3$-$C_7$ cycloalkylsulfonylaminophenyl,

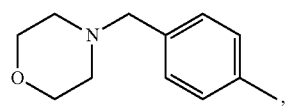,

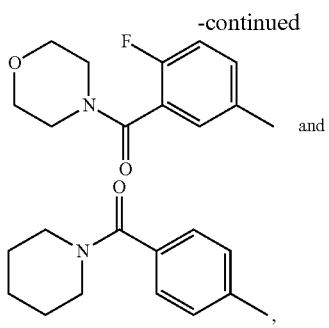

or two selected from $R_3$ through $R_6$ form a 5- to 7-membered ring fused with an aryl group together with the carbon atoms to which they are bound and the ring includes 0-2 double bonds and contains 0-2 N, O or S atoms;

each of $R_8$, $R_9$, $R_{10}$ and $R_{11}$ is independently selected from a group consisting of hydrogen, fluoro, chloro, bromo, iodo, nitro, cyano, $C_1$-$C_5$ alkyl, $C_1$-$C_5$ alkoxy, halo $C_1$-$C_3$ alkyl, haloalkoxy $C_2$-$C_5$ alkenyl, $C_2$-$C_5$ alkenyl and alkynyl; and each of $R_{12}$ and $R_{13}$ is independently selected from a group consisting of hydrogen, $C_1$-$C_5$ alkyl, hydroxy $C_1$-$C_5$alkyl, $C_3$-$C_7$ cycloalkyl and halo $C_1$-$C_5$ alkyl, or $R_{12}$ and $R_{13}$ form a 5- to 7-membered ring together with the nitrogen atom which they are bound and the ring contains 0-2 N, O or S atoms or at least one substituent selected from a group consisting of hydrogen, hydroxy, hydroxy $C_1$-$C_5$ alkyl, $C_1$-$C_5$ alkoxy, $C_1$-$C_5$ alkoxy alkyl, halo $C_1$-$C_5$ alkyl, halo $C_1$-$C_5$ alkoxy and carboxyl.

2. The compound, the isomer thereof, the pharmaceutically acceptable salt thereof, the hydrate thereof or the solvate thereof according to claim 1, wherein the compound is represented by Chemical Formula 2:

[Chemical Formula 2]

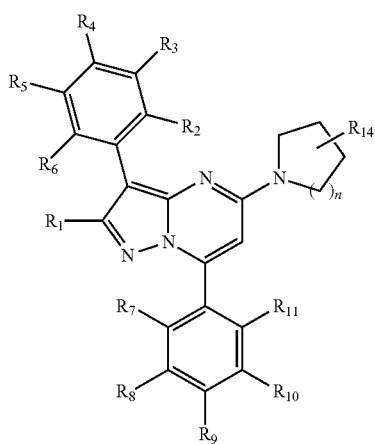

wherein $R_1$ is selected from a group consisting of hydrogen, $C_1$-$C_5$ alkyl, haloalkyl, $C_1$-$C_5$ cycloalkyl and $C_1$-$C_5$ alkoxyalkyl;

each of $R_2$ and $R_7$ is hydrogen;

each of $R_3$, $R_4$, $R_5$ and $R_6$ is independently selected from a group consisting of hydrogen, fluoro, chloro, bromo, iodo, nitro, cyano, $C_1$-$C_5$ alkyl, hydroxy $C_1$-$C_5$ alkyl, $C_1$-$C_5$ alkoxy, $C_1$-$C_5$ alkoxy alkyl, halo $C_1$-$C_3$ alkyl, halo $C_1$-$C_5$ alkoxy, haloalkoxy $C_2$-$C_5$ alkenyl, $C_2$-$C_5$ alkenyl, alkynyl, carboxyl, $C_1$-$C_5$ alkylcarbonyl, $C_1$-$C_5$ alkoxycarbonyl, $C_1$-$C_5$ alkylcarbonylamino, $C_1$-$C_{15}$ alkylamino carbonyl, $C_1$-$C_5$ alkylsulfanyl, $C_1$-$C_{15}$ alkylsulfonyl, $C_1$-$C_5$ alkoxysulfonyl, $C_1$-$C_5$ alkylsulfamoyl, aryl, aryl $C_1$-$C_3$ alkyl, aryl $C_1$-$C_5$ alkoxy, aminosulfonyl, $C_1$-$C_{15}$ alkylamino, $C_1$-$C_{15}$ alkylaminosulfonyl, $C_1$-$C_{15}$ alkylsulfonylamino, $C_1$-$C_5$ alkylthio, $C_3$-$C_7$ cycloalkylsulfonylaminophenyl,

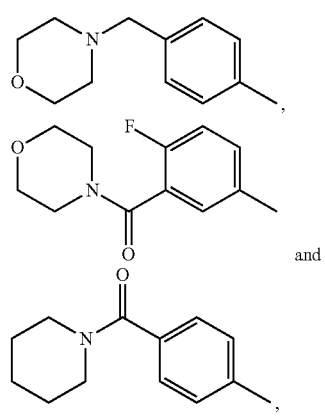

or two selected from $R_3$ through $R_6$ form a 5- to 7-membered ring fused with an aryl group together with the carbon atoms to which they are bound and the ring includes 0-2 double bonds and contains 0-2 N, O or S atoms;

each of $R_8$, $R_9$, $R_{10}$ and $R_{11}$ is independently selected from a group consisting of hydrogen, fluoro, chloro, bromo, iodo, nitro, cyano, $C_1$-$C_5$ alkyl, $C_1$-$C_5$ alkoxy, halo $C_1$-$C_3$ alkyl, haloalkoxy $C_2$-$C_5$ alkenyl, $C_2$-$C_5$ alkenyl and alkynyl;

$R_{14}$ is selected from a group consisting of hydrogen, hydroxy, hydroxy $C_1$-$C_5$ alkyl, $C_1$-$C_5$ alkoxy, $C_1$-$C_5$ alkoxy alkyl, halo $C_1$-$C_5$ alkyl, halo $C_1$-$C_5$ alkoxy and carboxyl; and n is an integer selected from 1 to 3.

3. The compound, the isomer thereof, the pharmaceutically acceptable salt thereof, the hydrate thereof or the solvate thereof according to claim 1, wherein the compound is represented by Chemical Formula 3:

[Chemical Formula 3]

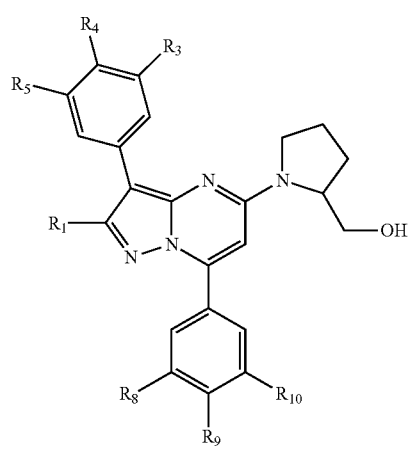

wherein

R₁ is selected from a group consisting of methyl, ethyl, propyl, butyl, isobutyl, difluoromethyl, trifluoromethyl, cyclopropyl, ethoxymethyl, methoxymethyl and ethoxyethyl;

each of $R_3$, $R_4$ and $R_5$ is independently selected from a group consisting of hydrogen, fluoro, chloro, bromo, iodo, nitro, cyano, methyl, ethyl, propyl, isopropyl, butyl, tert-butyl, methoxy, ethoxy, propoxy, isopropoxy, butoxy, hydroxymethyl, hydroxyethyl, trifluoromethyl, difluoromethyl, fluoromethyl, trifluoromethoxyvinyl, acetylenyl, carboxyl, methoxycarbonyl, ethoxycarbonyl, acetyl, methylsulfanyl, ethylsulfanyl, methylsulfonyl, methylsulfonylamino, cyclopropylaminosulfonyl, methylaminosulfonyl, ethylaminosulfonyl, dimethylaminocarbonyl, diethylaminocarbonyl, methylcarbonylamino, methylsulfamoyl, phenylmethyl, phenylethyl, phenylmethoxy, phenylacetyl, aminosulfonyl, methylaminosulfonyl, ethylaminosulfonyl, dimethylamino, diethylamino, cyclopropylamino and methylthio, or two selected from $R_3$ through $R_5$ form a 5- to 7-membered ring fused with an aryl group together with the carbon atoms to which they are bound and the ring includes 0-2 double bonds and contains 0-2 N, O or S atoms; and each of $R_8$, $R_9$ and $R_{10}$ is independently selected from a group consisting of hydrogen, fluoro, chloro, bromo, iodo, nitro, cyano, methyl, ethyl, propyl, butyl, isopropyl, methoxy, ethoxy, propoxy, isopropoxy, hydroxymethyl, trifluoromethyl, difluoromethyl, fluoromethyl, trifluoromethoxyvinyl and acetylenyl.

4. The compound, the isomer thereof, the pharmaceutically acceptable salt thereof, the hydrate thereof or the solvate thereof according to claim 3, wherein:

R₁ is selected from a group consisting of methyl, ethyl, propyl, butyl, isobutyl, trifluoromethyl, cyclopropyl, ethoxymethyl, methoxymethyl and ethoxyethyl;

each of $R_3$, $R_4$ and $R_5$ is independently selected from a group consisting of hydrogen, fluoro, chloro, nitro, cyano, methyl, ethyl, propyl, isopropyl, butyl, tert-butyl, methoxy, ethoxy, propoxy, methylenedioxy, isopropoxy, hydroxymethyl, hydroxyethyl, trifluoromethyl, difluoromethyl, fluoromethyl, trifluoromethoxyvinyl, acetylenyl, carboxyl, methoxycarbonyl, ethoxycarbonyl, acetyl, methylsulfonyl, methylsulfamoyl, phenylmethyl, phenylethyl and methylthio, or two selected from $R_3$ through $R_5$ form a 5- to 7-membered ring fused with an aryl group together with the carbon atoms to which they are bound and the ring includes 0-2 double bonds and contains 0-2 N, O or S atoms; and each of $R_8$, $R_9$ and $R_{10}$ is independently selected from a group consisting of hydrogen, fluoro, chloro, bromo, iodo, nitro, cyano, methyl, ethyl, propyl, butyl, isopropyl, methoxy, ethoxy, propoxy, isopropoxy, butoxy, hydroxymethyl, trifluoromethyl, difluoromethyl, fluoromethyl, trifluoromethoxyvinyl and acetylenyl.

5. The compound, the isomer thereof, the pharmaceutically acceptable salt thereof, the hydrate thereof or the solvate thereof according to claim 1, wherein the compound is selected from a group consisting of:

{1-[7-(3-chloro-4-fluorophenyl)-2-methyl-3-p-tolyl-pyrazolo[1,5-a]pyrimidin-5-yl]-pyrrolidin-2-yl}-methanol, {1-[7-(3-chloro-4-fluorophenyl)-3-(4-fluorophenyl)-2-methyl-pyrazolo[1,5-a]pyrimidin-5-yl]-pyrrolidin-2-yl}-methanol, {1-[3-(3-fluoro-4-methylphenyl)-7-(3-methoxyphenyl)-2-methyl-pyrazolo[1,5-a]pyrimidin-5-yl]-pyrrolidin-2-yl}-methanol, {1-[3-(2,4-difluorophenyl)-7-(3-methoxyphenyl)-2-methyl-pyrazolo[1,5-a]pyrimidin-5-yl]-pyrrolidin-2-yl}-methanol, {1-[3-(3-fluoro-4-methylphenyl)-2-methyl-7-(3-trifluoromethylphenyl)-pyrazolo[1,5-a]pyrimidin-5-yl]-pyrrolidin-2-yl}-methanol, {1-[3-(2,4-difluorophenyl)-2-methyl-7-(3-trifluoromethylphenyl)-pyrazolo[1,5-a]pyrimidin-5-yl]-pyrrolidin-2-yl}-methanol, {1-[7-(3-chloro-4-fluorophenyl)-3-(4-methoxyphenyl)-2-methyl-pyrazolo[1,5-a]pyrimidin-5-yl]-pyrrolidin-2-yl}-methanol, {1-[7-(3,4-difluorophenyl)-3-(3-fluoro-4-methyl-phenyl)-2-methyl-pyrazolo[1,5-a]pyrimidin-5-yl]-pyrrolidin-2-yl}-methanol, {1-[7-(3-ethylphenyl)-2-methyl-3-p-tolyl-pyrazolo[1,5-a]pyrimidin-5-yl]-pyrrolidin-2-yl}-methanol, {1-[3-(4-chlorophenyl)-7-(3-ethylphenyl)-2-methyl-pyrazolo[1,5-a]pyrimidin-5-yl]-pyrrolidin-2-yl}-methanol, {1-[7-(3,5-difluorophenyl)-3-(4-methoxyphenyl)-2-methyl-pyrazolo[1,5-a]pyrimidin-5-yl]-pyrrolidin-2-yl}-methanol, {1-[3-(3,4-difluorophenyl)-2-methyl-7-(3-trifluoromethylphenyl)-pyrazolo[1,5-a]pyrimidin-5-yl]-pyrrolidin-2-yl}-methanol, {1-[3-(4-fluorophenyl)-2-methyl-7-(3-trifluoromethylphenyl)-pyrazolo[1,5-a]pyrimidin-5-yl]-pyrrolidin-2-yl}-methanol, {1-[3-(3,4-difluorophenyl)-2-methyl-7-(3-trifluoromethylphenyl)-pyrazolo[1,5-a]pyrimidin-5-yl]-pyrrolidin-2-yl}-methanol, {1-[3-benzo-1,3]dioxol-5-yl-7-(3,5-difluorophenyl)-2-methyl-pyrazolo[1,5-a]pyrimidin-5-yl]-pyrrolidin-2-yl}-methanol, {1-[2-ethoxymethyl-3-(4-methoxyphenyl)-7-(3-trifluoromethylphenyl)-pyrazolo[1,5-a]pyrimidin-5-yl]-pyrrolidin-2-yl}-methanol, {1-[7-(3,5-difluorophenyl)-3-(4-methoxyphenyl)-2-methyl-pyrazolo[1,5-a]pyrimidin-5-yl]-pyrrolidin-2-yl}-methanol, {1-[3-(4-methoxyphenyl)-2-trifluoromethyl-7-(3-trifluoromethylphenyl)-pyrazolo[1,5-a]pyrimidin-5-yl]-pyrrolidin-2-yl}-methanol, {1-[2-ethoxymethyl-3-(4-methoxyphenyl)-7-(3-methoxyphenyl)-pyrazolo[1,5-a]pyrimidin-5-yl]-pyrrolidin-2-yl}-methanol, {1-[2-ethoxymethyl-7-(4-fluorophenyl)-3-(4-methoxyphenyl)-pyrazolo[1,5-a]pyrimidin-5-yl]-pyrrolidin-2-yl}-methanol, {1-[2-difluoromethyl-3-(4-methoxyphenyl)-7-(3-trifluoromethylphenyl)-pyrazolo[1,5-a]pyrimidin-5-yl]-pyrrolidin-2-yl}-methanol, {1-[3-benzo[1,3]dioxol-5-yl-2-ethoxymethyl-7-(3-fluorophenyl)-pyrazolo[1,5-a]pyrimidin-5-yl]-pyrrolidin-2-yl}-methanol, {1-[2-ethyl-7-(4-fluorophenyl)-3-p-tolyl-pyrazolo[1,5-a]pyrimidin-5-yl]-pyrrolidin-2-yl}-methanol, {1-[7-(3-chlorophenyl)-2-ethyl-3-p-tolyl-pyrazolo[1,5-a]pyrimidin-5-yl]-pyrrolidin-2-yl}-methanol, {1-[2-ethyl-7-(3-fluorophenyl)-3-p-tolylpyrazolo[1,5-a]pyrimidin-5-yl]-pyrrolidin-2-yl}-methanol, {1-[3-benzo[1,3]dioxol-5-yl-2-ethoxymethyl-7-(3-trifluoromethylphenyl)-pyrazolo[1,5-a]pyrimidin-5-yl]-pyrrolidin-2-yl}-methanol, {1-[3-benzo[1,3]dioxol-5-yl-7-(3-chlorophenyl)-2-ethoxymethyl-pyrazolo[1,5-a]pyrimidin-5-yl]-pyrrolidin-2-yl}-methanol,
{1-[2-ethoxymethyl-3-p-tolyl-7-(3-trifluoromethylphenyl)-pyrazolo[1,5-a]pyrimidin-5-yl]-pyrrolidin-2-yl}-methanol,
{1-[2-ethoxymethyl-7-(3-fluorophenyl)-3-p-tolyl-pyrazolo[1,5-a]pyrimidin-5-yl]-pyrrolidin-2-yl}-methanol,
{1-[2-ethoxymethyl-3-p-tolyl-7-(3-trifluoromethylphenyl)-pyrazolo[1,5-a]pyrimidin-5-yl]-pyrrolidin-2-yl}-methanol,
{1-[2-ethoxymethyl-7-m-tolyl-3-p-tolyl-pyrazolo[1,5-a]pyrimidin-5-yl]-pyrrolidin-2-yl}-methanol,
{1-[2-ethoxymethyl-7-(3-fluorophenyl)-3-(4-methoxyphenyl)-pyrazolo[1,5-a]pyrimidin-5-yl]-pyrrolidin-2-yl}-methanol,
{1-[2-ethoxymethyl-7-(4-fluorophenyl)-3-(4-methoxyphenyl)-pyrazolo[1,5-a]pyrimidin-5-yl]-pyrrolidin-2-yl}-methanol,
{1-[2-methoxymethyl-3-(4-methoxyphenyl)-7-(3-trifluoromethylphenyl)-pyrazolo[1,5-a]pyrimidin-5-yl]-pyrrolidin-2-yl}-methanol,
{1-[2-butyl-3-p-tolyl-7-(3-trifluoromethylphenyl)-pyrazolo[1,5-a]pyrimidin-5-yl]-pyrrolidin-2-yl}-methanol,
{1-[2-ethoxymethyl-7-(3-methoxyphenyl)-3-p-tolyl-pyrazolo[1,5-a]pyrimidin-5-yl]-pyrrolidin-2-yl}-methanol,
{1-[3-(4-chlorophenyl)-2-ethoxymethyl-7-(3-trifluoromethylphenyl)-pyrazolo[1,5-a]pyrimidin-5-yl]-pyrrolidin-2-yl}-methanol,
{1-[3-(4-chlorophenyl)-2-ethoxymethyl-7-(4-fluorophenyl)-pyrazolo[1,5-a]pyrimidin-5-yl]-pyrrolidin-2-yl}-methanol,
{1-[3-(4-chlorophenyl)-2-ethoxymethyl-7-(3-fluorophenyl)-pyrazolo[1,5-a]pyrimidin-5-yl]-pyrrolidin-2-yl}-methanol,
{1-[3-(4-chlorophenyl)-2-ethoxymethyl-7-(3-trifluoromethylphenyl)-pyrazolo[1,5-a]pyrimidin-5-yl]-pyrrolidin-2-yl}-methanol,
2-{[3-(4-chlorophenyl)-2-methoxymethyl-7-(3-trifluoromethylphenyl)-pyrazolo[1,5-a]pyrimidin-5-yl]-pyrrolidin-2-yl}-methanol,
{1-[3-(4-chlorophenyl)-7-(4-fluorophenyl)-2-methoxymethyl-pyrazolo[1,5-a]pyrimidin-5-yl]-pyrrolidin-2-yl}-methanol,
{1-[3-(4-chlorophenyl)-7-(3-fluorophenyl)-2-methoxymethyl-pyrazolo[1,5-a]pyrimidin-5-yl]-pyrrolidin-2-yl}-methanol,
2-{[2-methoxymethyl-3-(4-methoxyphenyl)-7-(3-trifluoromethyl-phenyl)-pyrazolo[1,5-a]pyrimidin-5-yl]-pyrrolidin-2-yl}-methanol,
{1-[7-(4-fluorophenyl)-2-methoxymethyl-3-(4-methoxyphenyl)-pyrazolo[1,5-a]pyrimidin-5-yl]-pyrrolidin-2-yl}-methanol,
{1-[3-benzo[1,3]dioxol-5-yl-7-(3-fluorophenyl)-2-methoxymethyl-pyrazolo[1,5-a]pyrimidin-5-yl]-pyrrolidin-2-yl}-methanol,
{1-[3-benzo[1,3]dioxol-5-yl-7-(4-fluorophenyl)-2-methoxymethyl-pyrazolo[1,5-a]pyrimidin-5-yl]-pyrrolidin-2-yl}-methanol,
{1-[3-benzo[1,3]dioxol-5-yl-2-methoxymethyl-7-(3-trifluoromethyl-phenyl)-pyrazolo[1,5-a]pyrimidin-5-yl]-pyrrolidin-2-yl}-methanol,
(S)-3-(5-(2-hydroxymethyl)pyrrolidin-1-yl)-2-(methoxymethyl)-3-(4-methoxyphenyl)-pyrazolo[1,5-a]pyrimidin-7-yl)benzonitrile,
(S)-[{1-(2-methoxymethyl)-3-(methoxyphenyl)-7-(m-tolyl)-pyrazolo[1,5-a]-pyrimidin-5-yl}-pyrrolidin-2-yl]-methanol,
(S)-{[1-(2-methoxymethyl)-7-(3-methoxyphenyl)-3-(4-methoxyphenyl)-pyrazolo[1,5-a]pyrimidin-5-yl]-pyrrolidin-2-yl}-methanol,
{1-[3-(4-chlorophenyl)-7-(2,4-difluorophenyl)-2-methyl-pyrazolo[1,5-a]pyrimidin-5-yl]-pyrrolidin-2-yl}-methanol,
[1-(3-benzo[1,3]dioxol-5-yl-2-methyl-7-phenyl-pyrazolo[1,5-a]pyrimidin-5-yl)-pyrrolidin-2-yl]-methanol,
{1-[3-(4-ethoxyphenyl)-2-methyl-7-phenyl-pyrazolo[1,5-a]pyrimidin-5-yl]-pyrrolidin-2-yl}-methanol,
{1-[3-(4-methoxyphenyl)-2-methyl-7-phenyl-pyrazolo[1,5-a]pyrimidin-5-yl]-pyrrolidin-2-yl}-methanol,
(S)-(1-(7-(3,4-difluorophenyl)-3-(4-ethoxyphenyl)-2-methyl-pyrazolo[1,5-a]pyrimidin-5-yl)-pyrrolidin-2-yl)-methanol,
{1-[2-methyl-3-(4-methylsulfanylphenyl)-7-(3-trifluoromethylphenyl)-pyrazolo[1,5-a]pyrimidin-5-yl]-pyrrolidin-2-yl}-methanol,
{1-[7-(3,4-difluorophenyl)-3-(4-methoxyphenyl)-2-methyl-pyrazolo[1,5-a]pyrimidin-5-yl]-pyrrolidin-2-yl}-methanol,
{1-[7-(3,4-difluorophenyl)-2-methyl-3-p-tolyl-pyrazolo[1,5-a]pyrimidin-5-yl]-pyrrolidin-2-yl}-methanol,
{1-[7-(3,4-difluorophenyl)-2-methyl-3-p-tolyl-pyrazolo[1,5-a]pyrimidin-5-yl]-pyrrolidin-2-yl}-methanol,
{1-[7-(3,4-difluorophenyl)-2-methyl-3-p-tolyl-pyrazolo[1,5-a]pyrimidin-5-yl]-pyrrolidin-2-yl}-methanol,
{1-[3-(4-chlorophenyl)-7-(3,4-difluorophenyl)-2-methyl-pyrazolo[1,5-a]pyrimidin-5-yl]-pyrrolidin-2-yl}-methanol,
{1-[7-(4-fluorophenyl)-2-methyl-3-p-tolyl-pyrazolo[1,5-a]pyrimidin-5-yl]-pyrrolidin-2-yl}-methanol,
[1-(2-methyl-7-phenyl-3-p-tolyl-pyrazolo[1,5-a]pyrimidin-5-yl]-pyrrolidin-2-yl]-methanol,
[1-[3-(4-difluoromethylphenyl)-7-(3-fluorophenyl)-2-methyl-pyrazolo[1,5-a]pyrimidin-5-yl]-pyrrolidin-2-yl}-methanol,
{1-[3-(4-difluoromethylphenyl)-7-(3-methoxyphenyl)-2-methyl-pyrazolo[1,5-a]pyrimidin-5-yl]-pyrrolidin-2-yl}-methanol,
{1-[3-(4-difluoromethylphenyl)-2-methyl-7-(3-trifluoromethylphenyl)-pyrazolo[1,5-a]pyrimidin-5-yl]-pyrrolidin-2-yl}-methanol,
{1-[3-(4-difluoromethylphenyl)-7-(4-fluorophenyl)-2-methyl-pyrazolo[1,5-a]pyrimidin-5-yl]-pyrrolidin-2-yl}-methanol,
{1-[3-(4-difluoromethylphenyl)-2-methyl-7-m-tolyl-pyrazolo[1,5-a]pyrimidin-5-yl]-pyrrolidin-2-yl}-methanol,
{1-[7-(4-chlorophenyl)-3-(4-methoxyphenyl)-2-methyl-pyrazolo[1,5-a]pyrimidin-5-yl]-pyrrolidin-2-yl}-methanol,
{1-[7-(3-methoxyphenyl)-2-methyl-3-(4-trifluoromethylphenyl)-pyrazolo[1,5-a]pyrimidin-5-yl]-pyrrolidin-2-yl}-methanol,
{1-[3-(4-ethylphenyl)-2-methyl-7-(3-trifluoromethylphenyl)-pyrazolo[1,5-a]pyrimidin-5-yl]-pyrrolidin-2-yl}-methanol,
{1-[3-(4-ethylphenyl)-2-methyl-7-(3-trifluoromethylphenyl)-pyrazolo[1,5-a]pyrimidin-5-yl]-pyrrolidin-2-yl}-methanol,
{1-[2-methyl-3-(4-trifluoromethylphenyl)-7-(3-trifluoromethylphenyl)-pyrazolo[1,5-a]pyrimidin-5-yl]-pyrrolidin-2-yl}-methanol, {1-[7-(4-chlorophenyl)-2-methyl-3-p-tolyl-pyrazolo[1,5-a]pyrimidin-5-yl]-pyrrolidin-2-yl}-methanol,
[1-(2-methyl-3,7-d]-p-tolyl-pyrazolo[1,5-a]pyrimidin-5-yl)-pyrrolidin-2-yl]-methanol,
{1-[7-(3-chlorophenyl)-2-methyl-3-p-tolyl-pyrazolo[1,5-a]pyrimidin-5-yl]-pyrrolidin-2-yl}-methanol,
{1-[7-(3-chlorophenyl)-2-methyl-3-p-tolyl-pyrazolo[1,5-a]pyrimidin-5-yl]-pyrrolidin-2-yl}-methanol
[1-(2-methyl-7-m-tolyl-3-p-tolyl-pyrazolo[1,5-a]pyrimidin-5-yl)-pyrrolidin-2-yl]-methanol,
{1-[7-(3-methoxyphenyl)-2-methyl-3-p-tolyl-pyrazolo[1,5-a]pyrimidin-5-yl]-pyrrolidin-2-yl}-methanol,
{1-[7-(4-methoxyphenyl)-2-methyl-3-p-tolyl-pyrazolo[1,5-a]pyrimidin-5-yl]-pyrrolidin-2-yl}-methanol,
{1-[7-(2-fluorophenyl)-2-methyl-3-p-tolyl-pyrazolo[1,5-a]pyrimidin-5-yl]-pyrrolidin-2-yl}-methanol,
{1-[3-benzo[1,3]dioxol-5-yl-7-(3-fluorophenyl)-2-methyl-pyrazolo[1,5-a]pyrimidin-5-yl]-pyrrolidin-2-yl}-methanol,
{1-[7-(3-fluorophenyl)-3-(4-methoxyphenyl)-2-methyl-pyrazolo[1,5-a]pyrimidin-5-yl]-pyrrolidin-2-yl}-methanol,
{1-[3-(4-ethoxyphenyl)-7-(3-fluoromethylphenyl)-2-methyl-pyrazolo[1,5-a]pyrimidin-5-yl]-pyrrolidin-2-yl}-methanol,
{1-[2-methyl-3-p-tolyl-7-(3-trifluoromethylphenyl)-pyrazolo[1,5-a]pyrimidin-5-yl]-pyrrolidin-2-yl}-methanol,
{1-[3-(4-methoxyphenyl)-2-methyl-7-(3-trifluoromethylphenyl)-pyrazolo[1,5-a]pyrimidin-5-yl]-pyrrolidin-2-yl}-methanol,
{1-[7-(3-chlorophenyl)-3-(4-methoxyphenyl)-2-methyl-pyrazolo[1,5-a]pyrimidin-5-yl]-pyrrolidin-2-yl}-methanol,
{1-[3-benzo[1,3]dioxol-5-yl-7-(3-chlorophenyl)-2-methyl-pyrazolo[1,5-a]pyrimidin-5-yl]-pyrrolidin-2-yl}-methanol,
{1-[7-(4-fluorophenyl)-2-methyl-3-(4-vinylphenyl)-pyrazolo[1,5-a]-pyrrolidin-2-yl}-methanol,
{1-[3-(4-ethoxyphenyl)-2-methyl-7-(3-trifluoromethylphenyl)-pyrazolo[1,5-a]pyrimidin-5-yl]-pyrrolidin-2-yl}-methanol,
{1-[3-benzo[1,3]dioxol-5-yl-2-methyl-7-(3-trifluoromethylphenyl)-pyrazolo[1,5-a]pyrimidin-5-yl]-pyrrolidin-2-yl}-methanol,
{1-[3-(4-fluoro-3-methylphenyl)-7-(4-fluorophenyl)-2-methyl-pyrazolo[1,5-a]pyrimidin-5-yl]-pyrrolidin-2-yl}-methanol,
{1-[3-(3-fluoro-4-methylphenyl)-7-(4-fluorophenyl)-2-methyl-pyrazolo[1,5-a]pyrimidin-5-yl]-pyrrolidin-2-yl}-methanol,
{1-[3-(4-ethoxyphenyl)-7-(4-fluorophenyl)-2-methyl-pyrazolo[1,5-a]pyrimidin-5-yl]-pyrrolidin-2-yl}methanol,
{1-[7-(4-fluorophenyl)-2-methyl-3-p-tolyl-pyrazolo[1,5-a]pyrimidin-5-yl]-pyrrolidin-2-yl}methanol,
{1-[7-(4-fluorophenyl)-2-methyl-3-(4-propoxyphenyl)-pyrazolo[1,5-a]pyrimidin-5-yl]-pyrrolidin-2-yl}methanol,
{1-[3-biphenyl-4-yl-7-(4-fluorophenyl)-2-methyl-pyrazolo[1,5-a]pyrimidin-5-yl]-pyrrolidin-2-yl}methanol,
{1-[3-(2,4-difluorophenyl)-7-(4-fluorophenyl)-2-methyl-pyrazolo[1,5-a]pyrimidin-5-yl]-pyrrolidin-2-yl}methanol,
{1-[3-(4-ethylsulfanylphenyl)-7-(4-fluorophenyl)-2-methyl-pyrazolo[1,5-a]pyrimidin-5-yl]-pyrrolidin-2-yl}methanol,
{1-[3-(4-butoxyphenyl)-7-(4-fluorophenyl)-2-methyl-pyrazolo[1,5-a]pyrimidin-5-yl]-pyrrolidin-2-yl}methanol,
{1-[7-(4-fluorophenyl)-2-methyl-3-(4-methylsulfanylphenyl)-pyrazolo[1,5-a]pyrimidin-5-yl]-pyrrolidin-2-yl}methanol,
{1-[3-(4-benzoyloxyphenyl)-7-(4-fluorophenyl)-2-methyl-pyrazolo[1,5-a]pyrimidin-5-yl]-pyrrolidin-2-yl}methanol,
{1-[7-(4-fluorophenyl)-2-methyl-3-(3-trifluoromethoxyphenyl)-pyrazolo[1,5-a]pyrimidin-5-yl]-pyrrolidin-2-yl}methanol,
{1-[7-(4-fluorophenyl)-2-methyl-3-(4-trifluoromethoxyphenyl)-pyrazolo[1,5-a]pyrimidin-5-yl]-pyrrolidin-2-yl}methanol,
{1-[3-(4-ethylphenyl)-7-(4-fluorophenyl)-2-methyl-pyrazolo[1,5-a]pyrimidin-5-yl]-pyrrolidin-2-yl}methanol,
{1-[7-(4-fluorophenyl)-2-methyl-3-(4-trifluoromethylphenyl)-pyrazolo[1,5-a]pyrimidin-5-yl]-pyrrolidin-2-yl}methanol,
1-{4-[7-(4-fluorophenyl)-5-(2-hydroxymethyl-pyrrolidin-1-yl)-2-methyl-pyrazolo[1,5-a]pyrimidin-3-yl]phenyl}-ethanol,
{1-[3-(4-tert-butylphenyl)-7-(4-fluorophenyl)-2-methyl-pyrazolo[1,5-a]pyrimidin-5-yl]pyrrolidin-2-yl}-methanol,
[1-(2-methyl-7-phenyl-3-p-tolyl-pyrazolo[1,5-a]pyrimidin-5-yl)-pyrrolidin-2-yl}-methanol,
{1-[7-(3-fluorophenyl)-2-methyl-3-p-tolyl-pyrazolo[1,5-a]pyrimidin-5-yl]-pyrrolidin-2-yl}-methanol,
{1-[3-(4-chlorophenyl)-2-methyl-7-m-tolyl-pyrazolo[1,5-a]pyrimidin-5-yl]-pyrrolidin-2-yl}-methanol,
{1-[3-benzo[1,3]dioxol-5-yl-7-(4-fluorophenyl)-2-methyl-pyrazolo[1,5-a]pyrimidin-5-yl]-pyrrolidin-2-yl}-methanol,
{1-[7-(4-fluorophenyl)-3-(4-methoxyphenyl)-2-methyl-pyrazolo[1,5-a]pyrimidin-5-yl]-pyrrolidin-2-yl}-methanol,
{1-[3-(4-chlorophenyl)-7-(4-fluorophenyl)-2-methyl-pyrazolo[1,5-a]pyrimidin-5-yl]-pyrrolidin-2-yl}methanol,
{1-[3-(4-chlorophenyl)-2-cyclopropyl-7-(3-fluorophenyl)-pyrazolo[1,5-a]pyrimidin-5-yl]-pyrrolidin-2-yl}-methanol,
{1-[3-(4-chlorophenyl)-2-methyl-7-(3-trifluoromethylphenyl)-pyrazolo[1,5-a]pyrimidin-5-yl]-pyrrolidin-2-yl}-methanol,
{1-[3-(4-chlorophenyl)-7-(3-fluorophenyl)-2-methyl-pyrazolo[1,5-a]pyrimidin-5-yl]-pyrrolidin-2-yl}-methanol,
{1-[3-(4-chlorophenyl)-7-(3-chlorophenyl)-2-methyl-pyrazolo[1,5-a]pyrimidin-5-yl]-pyrrolidin-2-yl}-methanol,
{1-[3,7-bis-(4-chlorophenyl)-2-methyl-pyrazolo[1,5-a]pyrimidin-5-yl]-pyrrolidin-2-yl}-methanol,
{1-[3-(2,4-dichlorophenyl)-2-cyclopropyl-7-(2-fluorophenyl)-pyrazolo[1,5-a]pyrimidin-5-yl]-pyrrolidin-2-yl}-methanol,
{1-[3-(2,4-dichlorophenyl)-2-cyclopropyl-7-(4-fluorophenyl)-pyrazolo[1,5-a]pyrimidin-5-yl]-pyrrolidin-2-yl}-methanol,
(S)-{1-[3-(4-chlorophenyl)-2-methyl-7-phenyl-pyrazolo[1,5-a]pyrimidin-5-yl]-pyrrolidin-2-yl}methanol,
(S)-{1-[7-(2-fluorophenyl)-2-(methoxymethyl)-3-(4-methoxyphenyl)-pyrazolo[1,5-a]pyrimidin-5-yl]-pyrrolidin-2-yl}-methanol, (S)-{1-[2-ethoxymethyl-3-(4-methoxyphenyl)-7-(3-tolyl)-pyrazolo[1,5-a]pyrimidin-5-yl]-pyrrolidin-2-yl}-methanol, (S)-{1-[7-(3-chlorophenyl)-2-(methoxymethyl)-3-(4-methoxyphenyl)-pyrazolo[1,5-a]pyrimidine-5-yl]-pyrrolidin-2-yl}-methanol, (S)-{1-[7-(4-chlorophenyl)-2-(methoxymethyl)-3-(4-methoxyphenyl)-pyrazolo[1,5-a]pyrimidin-5-yl]-pyrrolidin-2-yl}-methanol, (S)-{1-[3-(4-chlorophenyl)-2-(methoxymethyl)-7-(3-fluorophenyl)-pyrazolo[1,5-a]pyrimidin-5-yl]-pyrrolidin-2-yl}-methanol, (S)-{1-[3-(4-chlorophenyl)-2-(methoxymethyl)-7-(3-methylphenyl)-pyrazolo[1,5-a]pyrimidin-5-yl]-pyrrolidin-2-yl}-methanol, (S)-{1-[2-butyl-7-(3-tolyl)-3-(4-tolyl)-pyrazolo[1,5-a]pyrimidin-5-yl]-pyrrolidin-2-yl}-methanol, (S)-{1-[2-butyl-3-(p-tolyl)-7-(3-trifluoromethylphenyl)-pyrazolo[1,5-a]pyrimidin-5-yl]-pyrrolidin-2-yl}-methanol, (S)-{1-[2-propyl-3-(p-tolyl)-7-(3-trifluoromethylphenyl)-pyrazolo[1,5-a]pyrimidine-5-yl]-pyrrolidin-2-yl}-methanol and (S)-{1-[2-propyl-7-(m-tolyl)-3-(p-tolyl)-pyrazolo[1,5-a]pyrimidin-5-yl]-pyrrolidin-2-yl}-methanol.

6. The compound, the isomer thereof, the pharmaceutically acceptable salt thereof, the hydrate thereof or the solvate thereof according to claim 1, wherein the compound is represented by Chemical Formula 4:

[Chemical Formula 4]

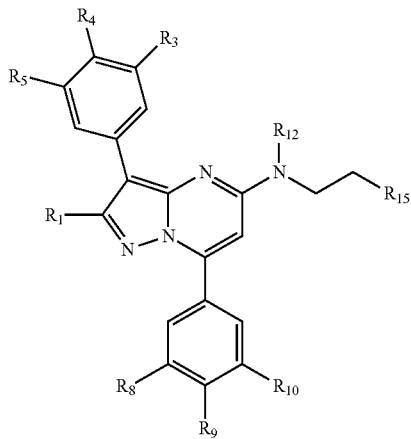

wherein $R_1$ is selected from a group consisting of methyl, ethyl, propyl, butyl, isobutyl, difluoromethyl, trifluoromethyl, cyclopropyl, ethoxymethyl, methoxymethyl and ethoxyethyl;

each of $R_3$, $R_4$ and $R_5$ is independently selected from a group consisting of hydrogen, fluoro, chloro, bromo, iodo, nitro, cyano, methyl, ethyl, propyl, isopropyl, butyl, tert-butyl, methoxy, ethoxy, propoxy, isopropoxy, butoxy, hydroxymethyl, hydroxyethyl, trifluoromethyl, difluoromethyl, fluoromethyl, trifluoromethoxyvinyl, vinyl, acetylenyl, carboxyl, methoxycarbonyl, ethoxycarbonyl, acetyl, methylsulfanyl, ethylsulfanyl, methylsulfonyl, methylsulfonylamino, cyclopropylaminosulfonyl, methylaminosulfonyl, ethylaminosulfonyl, dimethylaminocarbonyl, diethylaminocarbonyl, methylcarbonylamino, methylsulfamoyl, phenylmethyl, phenylethyl, phenylmethoxy, phenylacetyl, amino sulfonyl, methylaminosulfonyl, ethylaminosulfonyl, dimethylamino, diethylamino, cyclopropylamino and methylthio, or two selected from $R_3$ through $R_5$ form a 5- to 7-membered ring fused with an aryl group together with the carbon atoms to which they are bound and the ring includes 0-2 double bonds and contains 0-2 N, O or S atoms;

each of $R_8$, $R_9$ and $R_{10}$ is independently selected from a group consisting of hydrogen, fluoro, chloro, bromo, iodo, nitro, cyano, methyl, ethyl, propyl, butyl, isopropyl, methoxy, ethoxy, propoxy, isopropoxy, hydroxymethyl, trifluoromethyl, difluoromethyl, fluoromethyl, trifluoromethoxyvinyl and acetylenyl; and each of $R_{12}$ and $R_{15}$ is independently selected from a group consisting of hydrogen, methyl, ethyl, propyl, methoxy, ethoxy and hydroxy.

7. The compound, the isomer thereof, the pharmaceutically acceptable salt thereof, the hydrate thereof or the solvate thereof according to claim 6, wherein:

$R_1$ is selected from a group consisting of methyl, ethyl, propyl, butyl, isobutyl, trifluoromethyl, cyclopropyl, ethoxymethyl, methoxymethyl and ethoxyethyl;

each of $R_3$, $R_4$ and $R_5$ is independently selected from a group consisting of hydrogen, fluoro, chloro, nitro, cyano, methyl, ethyl, propyl, isopropyl, butyl, tert-butyl, methoxy, ethoxy, propoxy, methylenedioxy, isopropoxy, hydroxymethyl, hydroxyethyl, trifluoromethyl, difluoromethyl, fluoromethyl, trifluoromethoxyvinyl, acetylenyl, carboxyl, methoxycarbonyl, ethoxycarbonyl, acetyl, methylsulfonyl, methylsulfamoyl, phenylmethyl, phenylethyl and methylthio, or two selected from $R_3$ through $R_5$ form a 5- to 7-membered ring fused with an aryl group together with the carbon atoms to which they are bound and the ring includes 0-2 double bonds and contains 0-2 N, O or S atoms; and each of $R_8$, $R_9$ and $R_{10}$ is independently selected from a group consisting of hydrogen, fluoro, chloro, bromo, iodo, nitro, cyano, methyl, ethyl, propyl, butyl, isopropyl, methoxy, ethoxy, propoxy, isopropoxy, butoxy, hydroxymethyl, trifluoromethyl, difluoromethyl, fluoromethyl, trifluoromethoxyvinyl and acetylenyl.

8. The compound, the isomer thereof, the pharmaceutically acceptable salt thereof, the hydrate thereof or the solvate thereof according to claim 6, wherein the compound is selected from a group consisting of:

2-{[3-(4-methoxyphenyl)-2-methyl-7-(3-trifluoromethylphenyl)-pyrazolo[1,5-a]pyrimidin-5-yl]-methylamino}-ethanol, 2-{[3-benzo[1,3]dioxol-5-yl-2-ethoxymethyl-7-(3-methoxyphenyl)-pyrazolo[1,5-a]pyrimidin-5-yl]-methylamino}-ethanol, 2-{[7-(3-fluorophenyl)-2-methyl-3-p-tolyl-pyrazolo[1,5-a]pyrimidin-5-yl]-methylamino}-ethanol, 2-{[7-(4-fluorophenyl)-2-methyl-3-p-tolyl-pyrazolo[1,5-a]pyrimidin-5-yl]-methylamino}-ethanol, 2-{[7-(3-chlorophenyl)-2-methyl-3-p-tolyl-pyrazolo[1,5-a]pyrimidin-5-yl]-amino}-ethanol, 2-[2-ethoxymethyl-3-(4-methoxyphenyl)-7-(3-trifluoromethylphenyl)-pyrazolo[1,5-a]pyrimidin-5-yl]-methylamino}-ethanol, 2-{[2-ethoxymethyl-7-(4-fluorophenyl)-3-p-tolyl-pyrazolo[1,5-a]pyrimidin-5-yl]-amino}-ethanol, 2-{3-benzo[1,3]dioxol-5-yl-2-ethoxymethyl-7-(3-trifluoromethylphenyl)-pyrazolo[1,5-a]pyrimidin-5-yl]-methylamino}-ethanol, 2-{[3-benzo[1,3]dioxol-5-yl-7-(3-chlorophenyl)-2-ethoxymethyl-pyrazolo[1,5-a]pyrimidin-5-yl]-methylamino}-ethanol, 2-{[2-ethoxymethyl-7-(3-fluorophenyl)-3-p-tolyl-pyrazolo[1,5-a]pyrimidin-5-yl]-methylamino}-ethanol, 2-{[2-ethoxymethyl-3-p-tolyl-7-(3-trifluoromethylphenyl)-pyrazolo[1,5-a]pyrimidin-5-yl]-methylamino}-ethanol, 2-{[2-butyl-3-p-tolyl-7-(3-trifluoromethylphenyl)-pyrazolo[1,5-a]pyrimidin-5-yl]-methylamino}-ethanol, 2-{[3-(4-chlorophenyl)-2-ethoxymethyl-7-(4-fluorophenyl)-pyrazolo[1,5-a]pyrimidin-5-yl]-methylamino}-ethanol, 2-{[3-(4-chlorophenyl)-2-ethoxymethyl-7-(3-fluorophenyl)-pyrazolo[1,5-a]pyrimidin-5-yl]-methylamino}-ethanol, 2-{[3-(4-chlorophenyl)-2-ethoxymethyl-7-(3-trifluoromethylphenyl)-pyrazolo[1,5-a]pyrimidin-5-yl]-methylamino}-ethanol, 2-{[3-(4-chlorophenyl)-2-methoxymethyl-7-(3-trifluoromethylphenyl)-pyrazolo[1,5-a]pyrimidin-5-yl]-methylamino}-ethanol, 2-{[3-(4-chlorophenyl)-7-(4-fluorophenyl)-2-methoxymethyl-pyrazolo[1,5-a]pyrimidin-5-yl]-methylamino}-ethanol, 2-{[3-(4-chlorophenyl)-7-(3-fluorophenyl)-2-methoxymethyl-pyrazolo[1,5-a]pyrimidin-5-yl]-methylamino}-ethanol, 2-{[2-methoxymethyl-3-(4-methoxyphenyl)-7-(3-trifluoromethylphenyl)-pyrazolo[1,5-a]pyrimidin-5-yl]-methylamino}-ethanol, 2-{[3-(4-chlorophenyl)-2-ethoxymethyl-7-(4-fluorophenyl)-pyrazolo[1,5-a]pyrimidin-5-yl]-ethylamino}-ethanol and 2-{[3-(4-chlorophenyl)-2-methoxymethyl-7-(m-tolyl)-pyrazolo[1,5-a]pyrimidin-5-yl]-methylamino}-ethanol.

9. A method for inhibiting cannabinoid receptor-1, comprising:
administering to a subject in need thereof, the compound, the isomer thereof, the pharmaceutically acceptable salt thereof, the hydrate thereof or the solvate thereof according to claim 1.

10. The method according to claim 9, wherein the compound, the isomer thereof, the pharmaceutically acceptable salt thereof, the hydrate thereof, or the solvate thereof suppresses or treats a disease mediated by the cannabinoid receptor-1.

11. The method according to claim 10, wherein the disease mediated by the cannabinoid receptor-1 is obesity.

12. The method according to claim 11, wherein the method prevents or treats obesity through control of appetite, facilitation of energy metabolism or regulation of processes related with fat metabolism.

13. A method for preparing pyrazolo[1,5-a]pyrimidine having an aryl substituent bound at 7-position accord to claim 1, comprising reacting aminopyrazole and a diketoester in a pyridine solvent, wherein at least one of the aminopyrazole and the diketoester contains an aryl group.

14. The method according to claim 10, wherein the disease mediated by the cannabinoid receptor-1 is at least one selected from a group consisting of inflammatory pain, psycopathy, anxiety, depression, attention deficiency, memory or cognitive disorder, neuropathic pain disorder, sexual dysfunction, impulse control disorder, obesity, neurological or obsessive eating disorder, cancer, morning sickness, nausea, gastric ulcer, diabetes, hypertension, hyperlipidemia, valvular heart disease, myocardial infarction, cardiomegaly and congestive heart failure.

* * * * *